A United States Patent

(12) United States Patent
Dhar et al.

(10) Patent No.: US 7,078,420 B2
(45) Date of Patent: Jul. 18, 2006

(54) SPIRO-HYDANTOIN COMPOUNDS USEFUL AS ANTI-INFLAMMATORY AGENTS

(75) Inventors: T. G. Murali Dhar, Newtown, PA (US); Dominique Potin, Epone (FR); Magali Jeannine Blandine Maillet, Suresnes (FR); Michele Launay, Rueil Malmaison (FR); Eric Antoine Nicolai, Rueil Malmaison (FR); Edwin J. Iwanowicz, Cranbury, NJ (US)

(73) Assignees: Bristol-Myers Squibb Company, Princeton, NJ (US); Cerep SA, Rueil-Malmaison (FR)

( * ) Notice: Subject to any disclaimer, the term of this patent is extended or adjusted under 35 U.S.C. 154(b) by 210 days.

(21) Appl. No.: 10/852,576

(22) Filed: May 24, 2004

(65) Prior Publication Data

US 2004/0248920 A1     Dec. 9, 2004

Related U.S. Application Data

(62) Division of application No. 10/262,182, filed on Oct. 1, 2002.

(60) Provisional application No. 60/400,259, filed on Aug. 1, 2002, provisional application No. 60/354,113, filed on Feb. 4, 2002, provisional application No. 60/326,361, filed on Oct. 1, 2001.

(51) Int. Cl.
*A61K 31/4439* (2006.01)
*C07D 401/04* (2006.01)

(52) U.S. Cl. .................... 514/341; 546/274.4; 514/341

(58) Field of Classification Search ................ 514/341; 546/274.4
See application file for complete search history.

(56) References Cited

U.S. PATENT DOCUMENTS

| 4,931,444 | A | | 6/1990 | Wauwe et al. |
| 5,346,913 | A | | 9/1994 | Hsu et al. |
| 5,434,176 | A | | 7/1995 | Claussner et al. |
| 5,750,553 | A | | 5/1998 | Claussner et al. |
| 6,087,509 | A | * | 7/2000 | Claussner et al. ....... 548/307.1 |

FOREIGN PATENT DOCUMENTS

WO     WO 02/096426     12/2002

* cited by examiner

*Primary Examiner*—Kamal A. Saeed
*Assistant Examiner*—Janet L Coppins
(74) *Attorney, Agent, or Firm*—Laurelee A. Duncan

(57) ABSTRACT

Compounds having the formula (I), and pharmaceutically-acceptable salts, hydrates, enantiomers, and diastereomers, and prodrugs thereof,

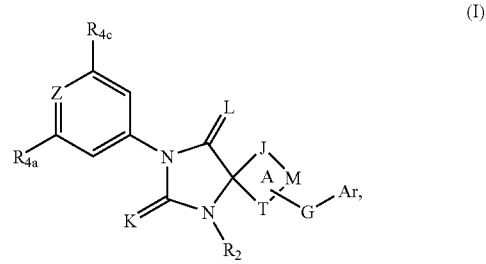

are useful as inhibitors of LFA-1/ICAM and as anti-inflammatory agents, wherein L and K are O or S; Z is N or $CR_{4b}$; Ar is an optionally-substituted aryl or heteroaryl; G is a linker attached to T or M or is absent; J, M and T are selected to define a three to six membered saturated or partially unsaturated non-aromatic ring; and $R_2$, $R_{4a}$, $R_{4b}$, and $R_{4c}$ are as defined in the specification.

22 Claims, No Drawings

SPIRO-HYDANTOIN COMPOUNDS USEFUL AS ANTI-INFLAMMATORY AGENTS

RELATED APPLICATIONS

This application is a Divisional of U.S. application Ser. No. 10/262,182, filed Oct. 1, 2002, which claims priority from U.S. Provisional Application Nos. 60/326,361, 60/354,113, and 60/400,259 filed Oct. 1, 2001, Feb. 4, 2002 and Aug. 1, 2002, respectively.

FIELD OF THE INVENTION

The present invention relates to spiro-hydantoin compounds, pharmaceutical compositions containing them, and methods of using such compounds in treating inflammatory or immune disease.

BACKGROUND OF THE INVENTION

Cells adhere to other cells and to substrates through specific, regulated processes that are critical to various biological functions. The proper functioning of the immune system is dependent upon adhesive interactions and cell migration. A key event in an immune response involves the migration of leukocytes to a disease site. During an inflammatory response, leukocytes are recruited to the site of injury and extravasated by a series of cellular interactions involving cell—cell and cell-substrate adhesion.

One family of molecules that serves an important adhesive function is integrins. Integrins are expressed on cell surfaces and function in cell—cell and cell-substrate adhesion. Integrins are alpha-beta heterodimers: each integrin has an alpha ($\alpha$) subunit non-covalently bound to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and to migrate among cells and tissue.

There are four known integrins having a $\beta_2$ or CD18 subunit which comprise the CD11/CD18 integrin sub-family, namely, Lymphocyte Function-associated Antigen 1 (LFA-1) (CD11a/CD 18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins is also referred to as Leukointegrins as they are expressed on the surface of various leukocyte cells, and they mediate a number of inflammation-related cellular interactions. See Diamond et al., "*The Dynamic Regulation of Integrin Adhesiveness*," Current Biology, Vol. 4 (1994) at pp. 506–532.

Ligands to LFA-1 and Mac-1 comprise the intercellular adhesion molecule (ICAM) ICAM-1. The primary CD11/CD18 integrin is LFA-1, which also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a deficiency in CD18 integrins. These patients are unable to mount a normal inflammatory or immune response; they suffer from disorders such as recurrent infections, poor wound healing, granulocytosis, progressive periodontitis, and umbilical cord separation. See Anderson et al., "*Leukocyte LFA-1, OKMI, p150,95 Deficiency Syndrome: Functional and Biosynthesis Studies of Three Kindreds*," Fed. Proc., Vol. 44 (1985), at pp. 2671–2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "*The Role of Cell Adhesion Molecules in Immunopathology,*" Immunology Today, Vol. 15 (1994), at pp. 251–255.

Compounds inhibiting CD18 integrins, ICAMs, and/or the LFA-1:ICAM interaction could potentially demonstrate a wide range of utilities in treating inflammatory or immune diseases. Blocking LFA-1 reportedly inhibits the influx of leukocytes in almost every system, including the skin, peritoneum, synovium, lung, kidney, and heart, and blocking ICAM-1 would be expected to have similar effects. Also, present therapies for many inflammatory and immune diseases have drawbacks. For example, current treatments for asthma include $\beta_2$-agonists, inhaled corticosteroids, and LTD$_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of these therapies raise toxicity issues over long-term (e.g., 6–9 month) use, whereas topical treatments have limited efficacy. Additionally, these treatments typically are applied only in response to flares and not as a prophylaxis measure.

Compounds that reportedly inhibit LFA-1/ICAM for use as anti-inflammatory agents include thiadiazole-based compounds (see Intern. Pub. No. WO 99/20,618, "*Thiadiazole Amides Useful as Anti-Inflammatory Agents*" filed by Pharmacia & Upjohn Co.; and WO 99/20,617, also to Pharmacia and Upjohn); and thiazole compounds linked to phenyl and pyrazole rings (Sanfilippo et al., "*Novel Thiazole Based Heterocycles as Inhibitors of LFA-1/ICAM-1 Mediated Cell Adhesion,*" J. Med. Chem., Vol. 38 (1995) at pp. 1057–1059). Small molecules that reportedly are antagonists to the binding of ICAMs with CD18 integrins include various benzylamines and 2-bromobenzoyltryptophan compounds (see Intern. Pub. No. WO99/49,856, "*Antagonists for Treatment of CD11/CD18 Adhesion Receptor Mediated Disorders,*" filed by Genentech, Inc.), and 1-(3,5 dichlorophenyl) imidazolidines (see Intern. Pub. No. WO98/39303, "*Small Molecules Useful in the Treatment of Inflammatory Disease,*" filed by Boehringer Ingelheim Pharmaceuticals, Inc. See also Boehringer patent applications WO 01/07052, WO 01/07048, WO 01/07044, WO 01/06984, and WO 01/07440). Hydantoin compounds are disclosed in Intern. Pub. No's WO 00/59880, WO 00/39081, WO 02/02522, WO 02/02539 (all to Abbott Laboratories). LFA-1 antagonist compounds are also claimed in WO 02/059114 (to Genentech), WO 02/42294 (to Celltech), WO 01/51508 (to Science and Technology corporation), WO 00/21920 and WO 01/58853 (both to Hoffmann-LaRoche), WO 99/11258, WO 00/48989 and WO 02/28832 (all to Novartis). Hydantoin compounds are disclosed in Intern. Pub. No. WO 01/30781 A2 (published May 3, 2001) to Tanabe Seiyaku Co. Ltd, "Inhibitors of $\alpha_L\beta_2$-Mediated Cell Adhesion," and in Intern. Pub. No. WO 02/44181 (published Jun. 6, 2002), "Hydantoin Compounds Useful as Anti-Inflammatory Agents", to the present assignee and having common inventors herewith.

As may be appreciated, those in the field of pharmaceutical research continue to develop new compounds and compositions for treating inflammatory and immune disease such as inhibitors of Leukointegrins and/or ICAMs. Particularly in the area of immune response, many individuals respond differently to different drugs. Thus, there is an interest in providing consumers not only with pharmaceutical compositions demonstrating increased effectiveness and reduced side-effects but also different structures or mechanisms of action to provide consumers with a choice of options. The instant invention is directed to aryl or heteroaryl substituted spiro-hydantoin compounds that are effective as antagonists of Leukointegrins and/or ICAMs. Diazaspiroheptane compounds are disclosed in Park et al., "Preparation of a 990 Member Chemical Compound Library of Hydantoin and Isoxazoline-Containing Heterocycles Using Multipin Technology," J. Comb. Chem., Vol. 3(2) (2001), at pp. 171–76. Spiro heterocycles are also disclosed in Couture et al., "Chemistry of Cyclic Aminooxycarbenes," Can. J. Chem., Vol. 75(9) (1997) at pp. 1281–1294; Brandstetter et al., "Glucofuranose Analogs of Hydantocidin," Tetrahedron, Vol. 52(32) (1996), at pp. 10721–10736; Brandstetter et al., "Spirohydantoins of Glucofuranose: Analogs of Hydantocidin," Tetrahedron Lett., Vol. 36(12) (1995) at pp. 2149–52; in US Pat. Nos. 6,022, 875, 4,241,208, 4,066,615, and 3,941,744, and International patent application WO 01/45704. WO 01/94346 discloses 1,3,8-triaza-spiro'4,5 decan-4-one derivatives as neurokinin receptor antagonists.

Each of the patents, patent applications and publications referenced above and hereinafter is incorporated herein by reference.

SUMMARY OF THE INVENTION

The present invention provides compounds useful in treating inflammatory or immune disease having the formula (I):

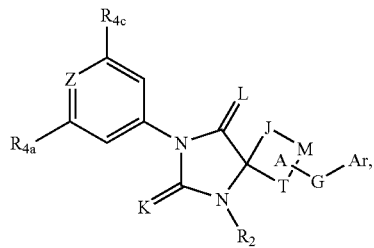

(I)

their enantiomers, diastereomers, and pharmaceutically-acceptable salts, hydrates, solvates, and prodrugs thereof, in which:

L and K, taken independently, are O or S;

Z is N or $CR_{4b}$;

Ar is aryl or heteroaryl;

G is attached to ring A at T or M; and (i) when attached to a carbon atom of ring A, G is selected from a bond, —O—, —N—, —S—, $C_{1-4}$alkylene, $C_{1-4}$substituted alkylene, or bivalent alkoxy, alkylthio, aminoalkyl, sulfonyl, sulfonamidyl, acyl, and alkoxycarbonyl; or (ii) when attached to a nitrogen atom of ring A, G is selected from a bond, $C_{1-4}$alkylene, $C_{1-4}$substituted alkylene, and bivalent acyl or alkoxycarbonyl, or bivalent alkoxy, alkylthio, aminoalkyl, sulfonyl, or sulfonamidyl wherein in (ii), each of said G groups have at least one carbon atom directly attached to ring A;

J is —O—, —S—, —NR$_3$—, —N=, —S(=O)—, —SO$_2$—, —NHSO$_2$—, a substituted or unsubstituted $C_{1-3}$alkylene, a substituted or unsubstituted $C_{2-3}$alkenylene, an unsubstituted $C_{1-2}$heteroalkylene, a substituted heteroalkylene having from one to two carbon atoms in the heteroalkylene straight chain, or J is absent so that ring A is a three-membered ring;

T is $T_1$ when G-Ar is attached to T, and $T_2$ when G-Ar is attached to M;

M is $M_1$ when G-Ar is attached to M, and $M_2$ when G-Ar is attached to T;

$T_1$ and $M_1$ are selected from —N— and —C(R$_5$)—;

$T_2$ and $M_2$ are selected from —O—, —S—, —N(R$_6$)—, —N=, —S(=O)—, —SO$_2$—, —NHSO$_2$—, and —C(R$_7$R$_8$)—, provided that J, M, and T are selected so that ring A defines a three to six membered saturated or partially unsaturated cycloalkyl or heterocyclic ring having 1 to 4 heteroatoms, wherein no two adjacent heteroatoms of said heterocyclic ring A are simultaneously selected from —O— and —S—;

R$_2$ is selected from hydrogen, alkyl, substituted alkyl, OR$_{12}$, NR$_{12}$R$_{13}$, C(=O)R$_{12}$, CO$_2$R$_{12}$, C(=O)NR$_{12}$R$_{13}$, NR$_{12}$C(=O)R$_{13}$, NR$_{12}$C(=O)OR$_{13}$, S(O)$_p$R$_{13a}$, NR$_{12}$SO$_2$R$_{13a}$, SO$_2$NR$_{12}$R$_{13}$, cycloalkyl, heterocyclo, aryl, and heteroaryl;

R$_{4a}$, R$_{4b}$ and R$_{4c}$ are independently selected from hydrogen, halogen, alkyl, substituted alkyl, alkenyl, substituted alkenyl, nitro, cyano, SR$_{14}$, OR$_{14}$, NR$_{14}$R$_{15}$, NR$_{14}$C(=O) R$_{15}$, CO$_2$R$_{14}$, C(=O)R$_{14}$, —C(=O)NR$_{14}$R$_{15}$, aryl, heterocyclo, cycloalkyl, and heteroaryl;

R$_3$ and R$_6$ are independently selected from hydrogen, alkyl, substituted alkyl, hydroxy, alkoxy, alkenyl, substituted alkenyl, aminoalkyl, alkylthio, C(=O)H, acyl, amide, alkoxycarbonyl, sulfonyl, sulfonamidyl, cycloalkyl, heterocyclo, aryl, and heteroaryl;

R$_5$, R$_7$, and R$_8$ are (i) independently selected from hydrogen, alkyl, substituted alkyl, halogen, nitro, cyano, hydroxy, alkoxy, alkenyl, substituted alkenyl, aminoalkyl, alkylthio, C(=O)H, acyl, CO$_2$H, amide, alkoxycarbonyl, sulfonyl, sulfonamidyl, cycloalkyl, heterocyclo, aryl, and heteroaryl; or (ii) R$_7$ with R$_8$ may form a cycloalkyl or heterocyclic ring or a double bond to an oxygen atom to define a keto (=O) group; or (iii) one of R$_5$ or R$_8$ may be a bond so that there is a double bond between T and M, or between M and J, respectively, so that ring A is partially unsaturated;

R$_{12}$, R$_{13}$, R$_{14}$ and R$_{15}$ (i) are selected independently of each other from hydrogen, alkyl, substituted alkyl, cycloalkyl, aryl, heteroaryl, and heterocyclo; or (ii) R$_{12}$ is taken together with R$_{13}$, and/or R$_{14}$ is taken together with R$_{15}$, to form a heteroaryl or heterocyclo ring;

R$_{13a}$ is selected from alkyl, substituted alkyl, cycloalkyl, aryl, heteroaryl, and heterocyclo; and p is 1 or 2.

The present invention is also directed to pharmaceutical compositions useful in treating immune or inflammatory diseases comprising compounds of formula (I), or pharmaceutically-acceptable salts thereof, and pharmaceutically-acceptable carriers or diluents. The invention further relates to methods of treating immune or inflammatory diseases comprising administering to a patient in need of such treatment a therapeutically-effective amount of a compound according to formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$ —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

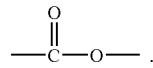

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$—Q—$A_2$—$R_h$, wherein $A_1$ is a bond, $C_{1-2}$alkylene, or $C_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, $C_{1-3}$alkylene, $C_{2-3}$alkenylene, —$C_{1-4}$alkylene-NR$_d$—, —$C_{1-4}$ alkylene-NR$_d$C(=O)—, —$C_{1-4}$alkylene-S—, —$C_{1-4}$ alkylene-SO$_2$—, or —$C_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteralkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$ alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-2}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

It should be understood that the selections for alkoxy, thioalkyl, and aminoalkyl will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "acyl" refers to a carbonyl group linked to an organic radical, more particularly, the group C(=O)R$_e$, as well as the bivalent groups —C(=O)— or —C(=O)R$_e$, which are linked to organic radicals or ring A in compounds of formula (I). The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula (I), when it is recited that G can be "acyl," this is intended to encompass a selection for G of —C(=O)— and also the groups —C(=O)R$_e$— or —R$_e$C(=O)—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" refers to a carboxy group

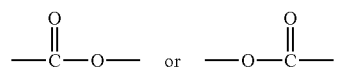

linked to an organic radical (CO$_2$Re), as well as the bivalent groups —CO$_2$—, —CO$_2$R$_e$— which are linked to organic radicals in compounds of formula (I), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula (I), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" refers to the group C(=O)NR$_a$R$_b$, wherein the groups R$_a$ and R$_b$ are defined as recited above in the definition for substituted alkyl groups.

The term "sulfonyl" refers to a sulphoxide group linked to an organic radical in compounds of formula (I), more particularly, the monovalent group S(O)$_{1-2}$—Re, or the bivalent group —S(O)$_{1-2}$— linked to organic radicals in compounds of formula (I). Accordingly, in compounds of formula (I), when it is recited that G can be "sulfonyl," this is intended to encompass a selection for G of —S(=O)— or —SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" refers to the group —S(O)$_2$NR$_a$R$_b$, wherein R$_a$ and Rb are as defined above for substituted alkyl groups. Additionally, the sulfonamidyl group may be bivalent, in which case one of the groups R$_a$ and R$_b$ will be a bond. Thus, in compounds of formula (I), when it is stated that G may be sulfonamidyl, it is intended to mean that G is a group —S(O)$_2$NR$_a$—.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$ ($C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon—carbon bridge of 3 to 4 carbon atoms. When a cycloalkyl is substituted with a further ring (or has a second ring fused thereto), said ring in turn is optionally substituted with one to two of ($C_{1-4}$)alkyl, ($C_{2-4}$)alkenyl, halogen, hydroxy, cyano, nitro, $CF_3$, $O(C_{1-4}$alkyl), $OCF_3$, C(=O)H, C(=O)($C_{1-4}$alkyl), $CO_2$H, $CO_2$($C_{1-4}$alkyl), $NHCO_2$($C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

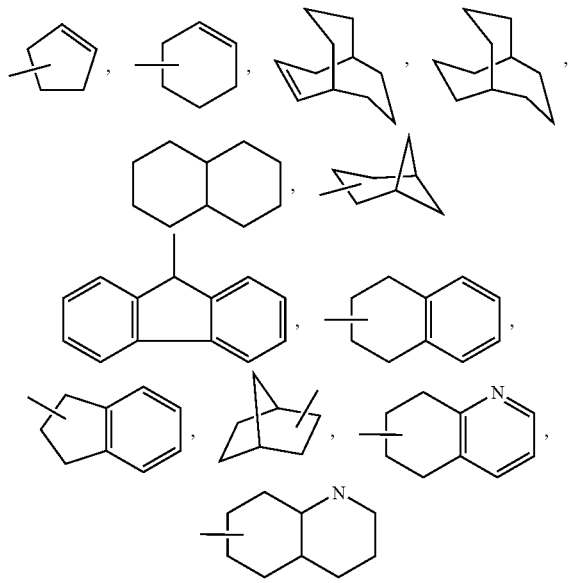

and the like, which optionally may be substituted at any available atoms of the ring(s). Preferred cycloalkyl groups include cyclopropyl, cyclobutyl, cyclopentyl, cyclohexyl,

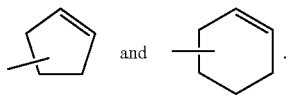

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —N(alkyl)$_3^+$, —$NR_aSO_2$, —$NR_aSO_2R_c$, —$SO_2R_c$ —$SO_2NR_aR_b$, —$SO_2NR_aC$(=O)$R_b$, $SO_3$H, —PO(OH)$_2$, —C(=O)$R_a$, —$CO_2R_a$, —C(=O)$NR_aR_b$, —C(=O)($C_{1-4}$alkylene)$NR_aR_b$, —C(=O)$NR_a(SO_2)R_b$, —$CO_2$($C_{1-4}$alkylene)$NR_aR_b$, —$NR_aC$(=O)$R_b$, —$NR_aCO_2R_b$, —$NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of ($C_{1-4}$)alkyl, ($C_{2-4}$)alkenyl, halogen, hydroxy, cyano, nitro, $CF_3$, $O(C_{1-4}$alkyl), $OCF_3$, C(=O)H, C(=O)($C_{1-4}$alkyl), $CO_2$H, $CO_2$($C_{1-4}$alkyl), $NHCO_2$($C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Thus, examples of aryl groups include:

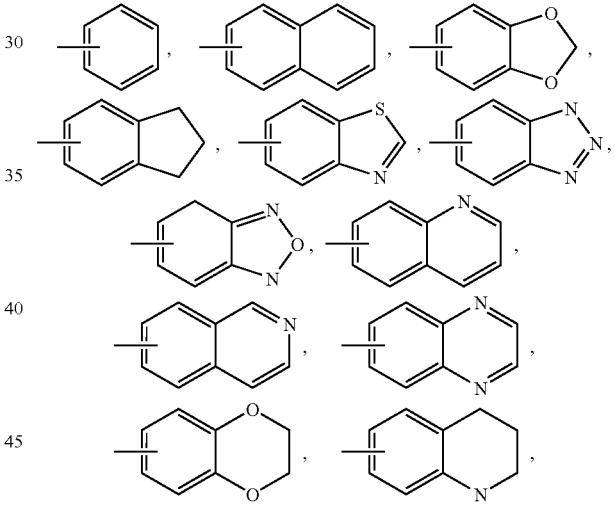

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, $NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}$alkylene$)NR_aR_b$, —$C(=O)NR_a(SO_2)R_b$, —$CO_2(C_{1-4}$alkylene$)NR_aR_b$, —$NR_aC(=O)R_b$, —$NR_aCO_2R_b$, —$NR_a(C_{1-4}$alkylene$)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}$ alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$ alkyl), $C(=O)(C_{1-4}$alkylene$)NH_2$, $C(=O)(C_{1-4}$alkylene$)NH(alkyl)$, and/or $C(=O)(C_{1-4}$alkylene$)N(C_{1-4}$alkyl$)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

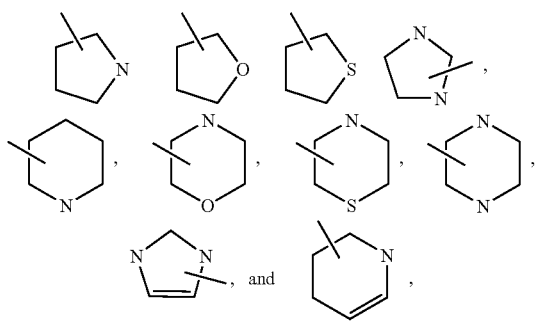

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, $SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}$alkylene$)NR_aR_b$, —$C(=O)NR_a(SO_2)R_b$, —$CO_2(C_{1-4}$alkylene$)NR_aR_b$, —$NR_aC(=O)R_b$, —$NR_aCO_2R_b$, —$NR_a(C_{1-4}$alkylene$)CO_2R_b$, aryl, cycloalkyl, heterocyclo, and/or heteroaryl, wherein $R_a$, $R_b$ and Rc are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}$ alkyl), $OCF_3$, $C(=O)H$, $C(=O)(C_{1-4}$alkyl), $CO_2H$, $CO_2(C_{1-4}$alkyl), $NHCO_2(C_{1-4}$alkyl), —$S(C_{1-4}$alkyl), —$NH_2$, $NH(C_{1-4}$alkyl), $N(C_{1-4}$alkyl$)_2$, $N(C_{1-4}$alkyl$)_3^+$, $SO_2(C_{1-4}$ alkyl), $C(=O)(C_{1-4}$alkylene$)NH_2$, $C(=O)(C_{1-4}$alkylene$)NH(alkyl)$, and/or $C(=O)(C_{1-4}$alkylene$)N(C_{1-4}$alkyl$)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

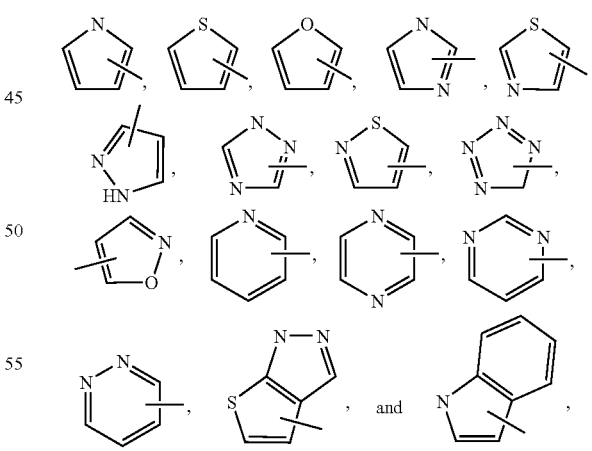

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0–2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds. For example, in compounds of formula (I), below, the groups J, M, and T are selected so that no two adjacent members of the ring A (defined by J, M and T) are simultaneously selected from S and O. As a further example, J is defined as being selected from groups including heteroalkylene optionally substituted by $R_9$. One skilled in the field may make the appropriate selections for $R_9$ as substituents for the heteroalkylene to provide stable compounds.

According to the foregoing definitions, the instant invention provides compounds having the formula (Ia) or (Ib):

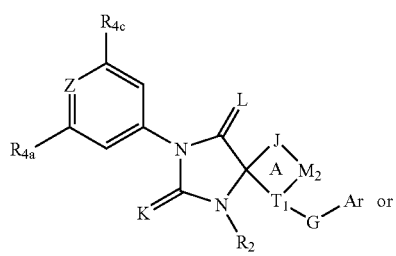
(Ia)

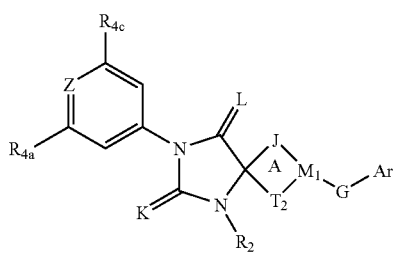
(Ib)

wherein the groups Ar, G, L, K, Z, $T_1$, $M_1$, $T_2$, $M_2$, $R_2$, $R_{4a}$, and $R_{4c}$, are as defined herein, and the group J may be selected from alkylene or heteroalkylene groups, including, without limitation, the following specific examples:

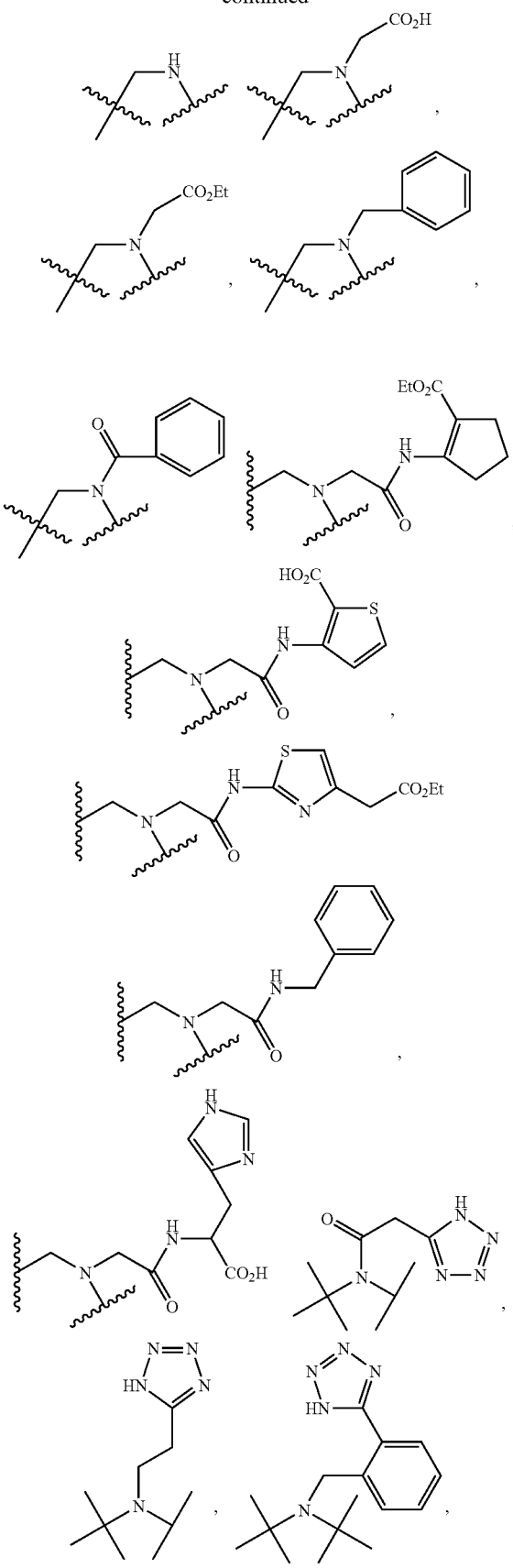

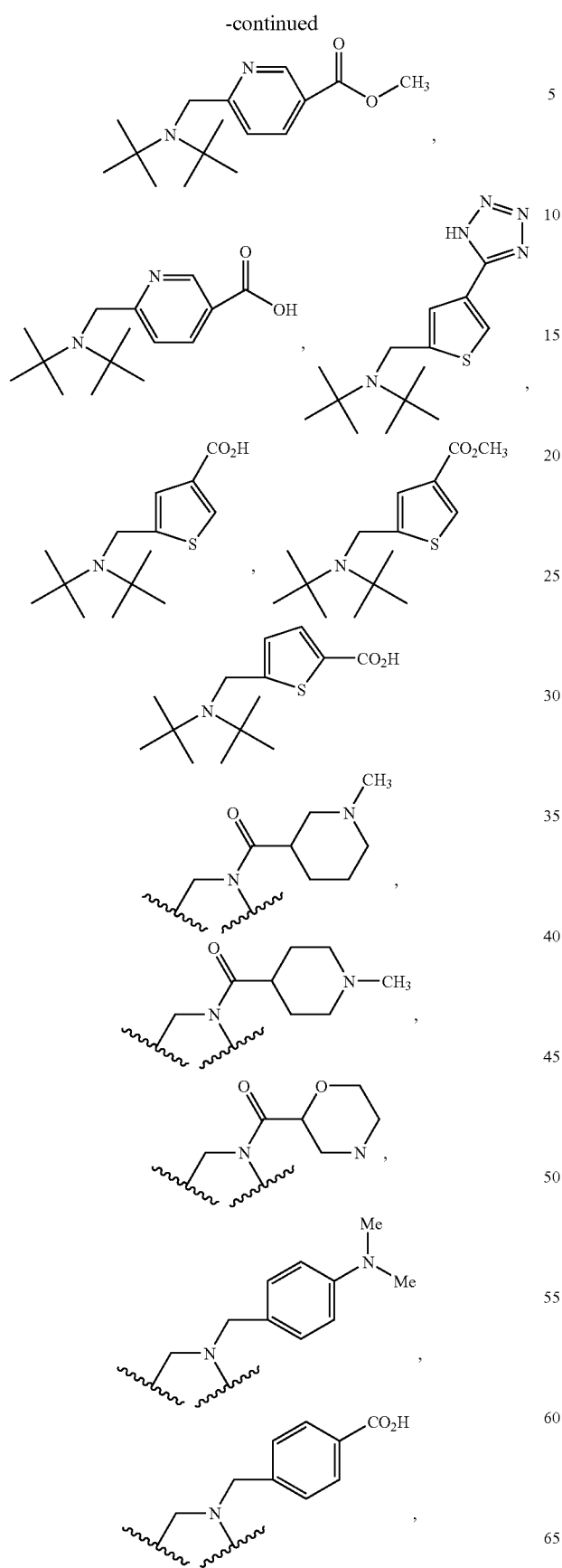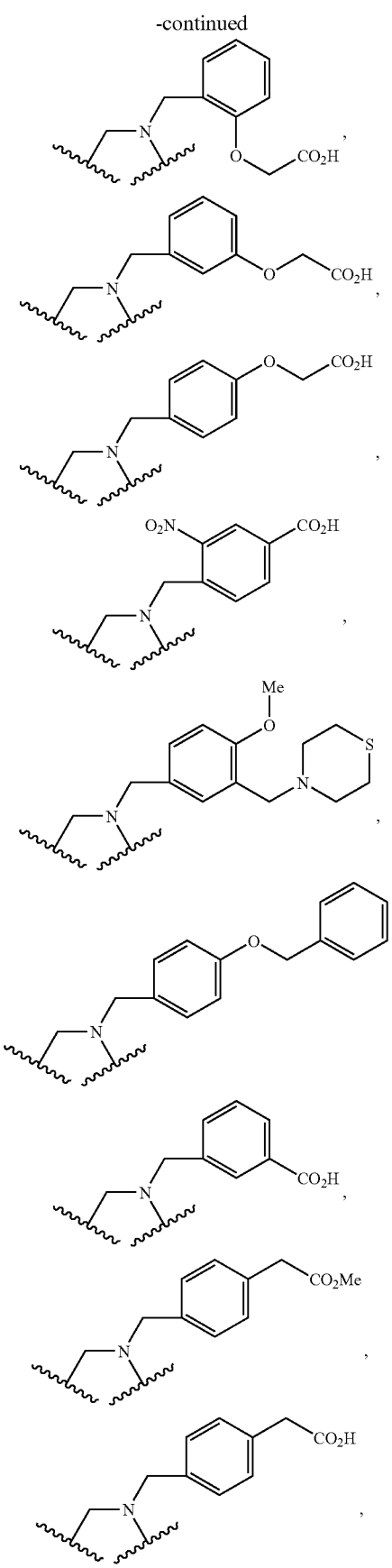

-continued
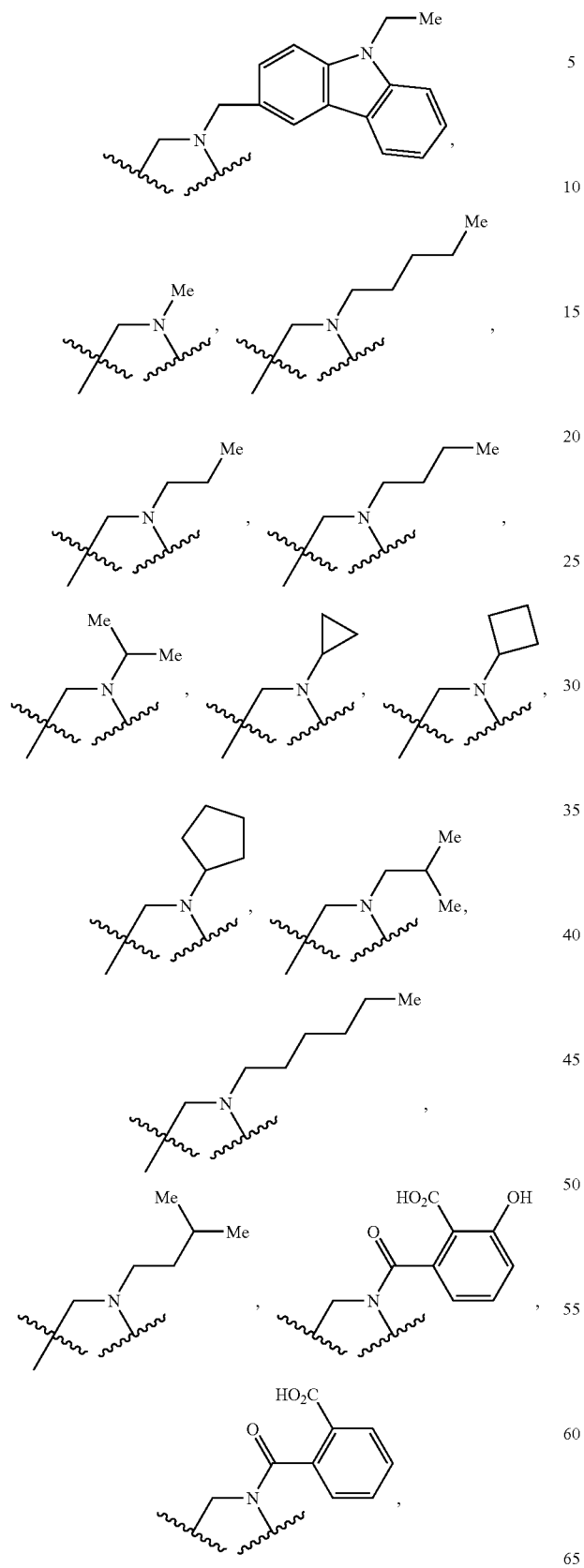
-continued
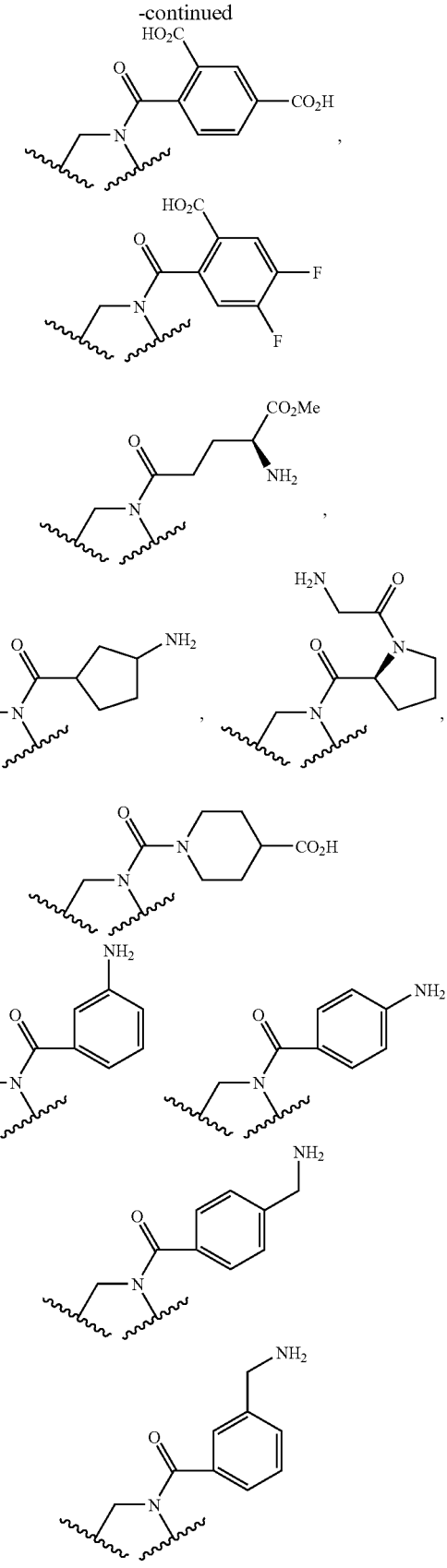

-continued
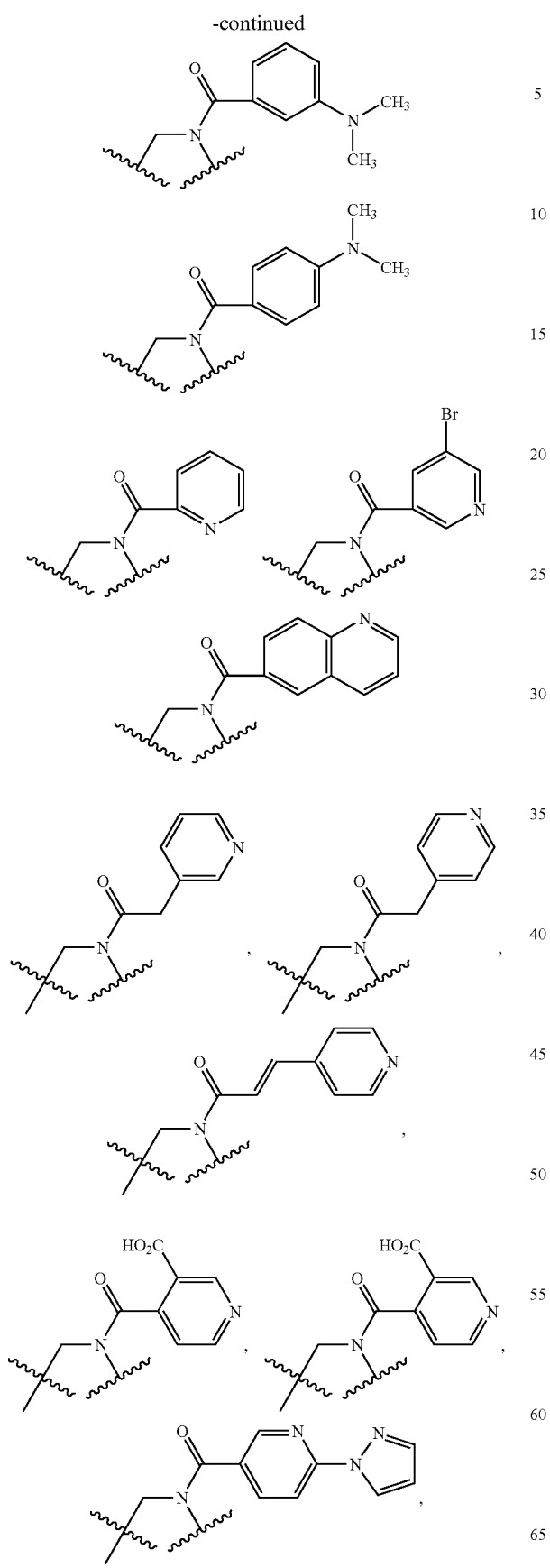
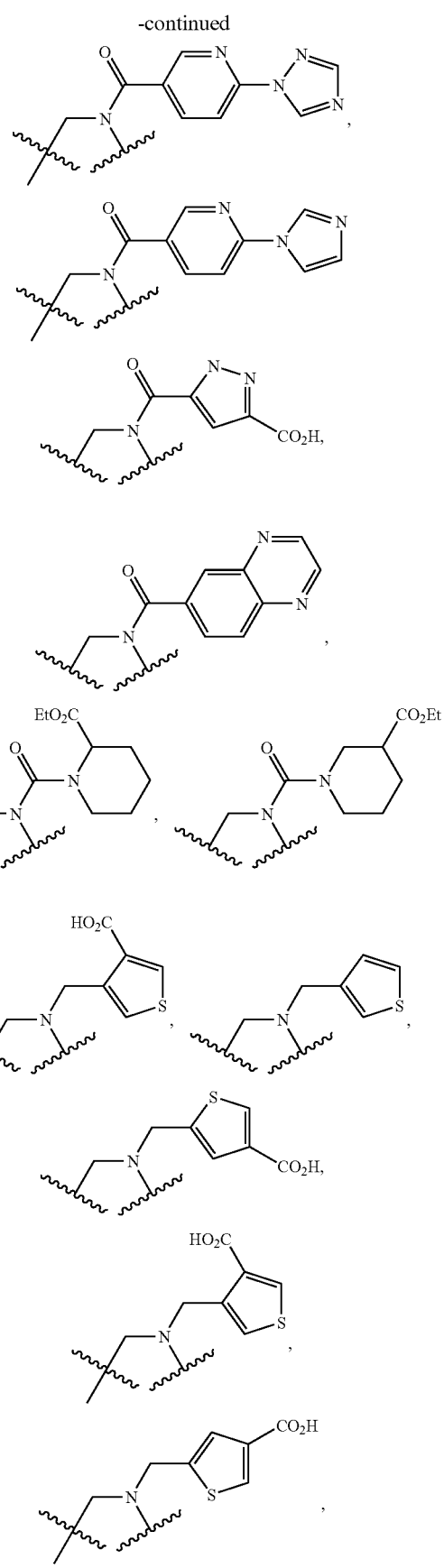

-continued
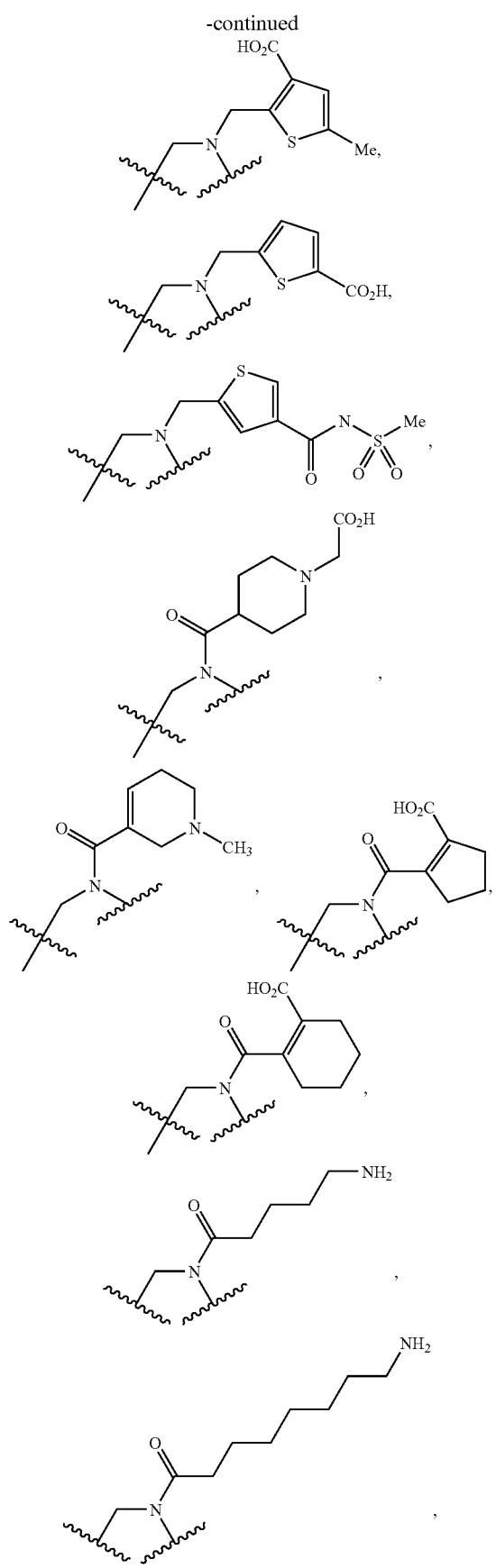
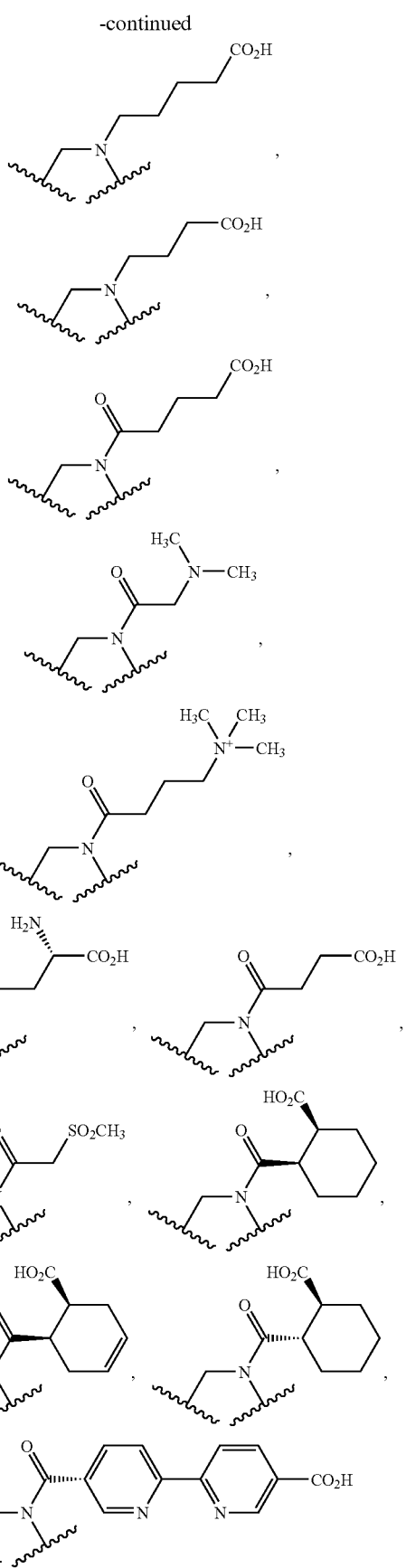

-continued
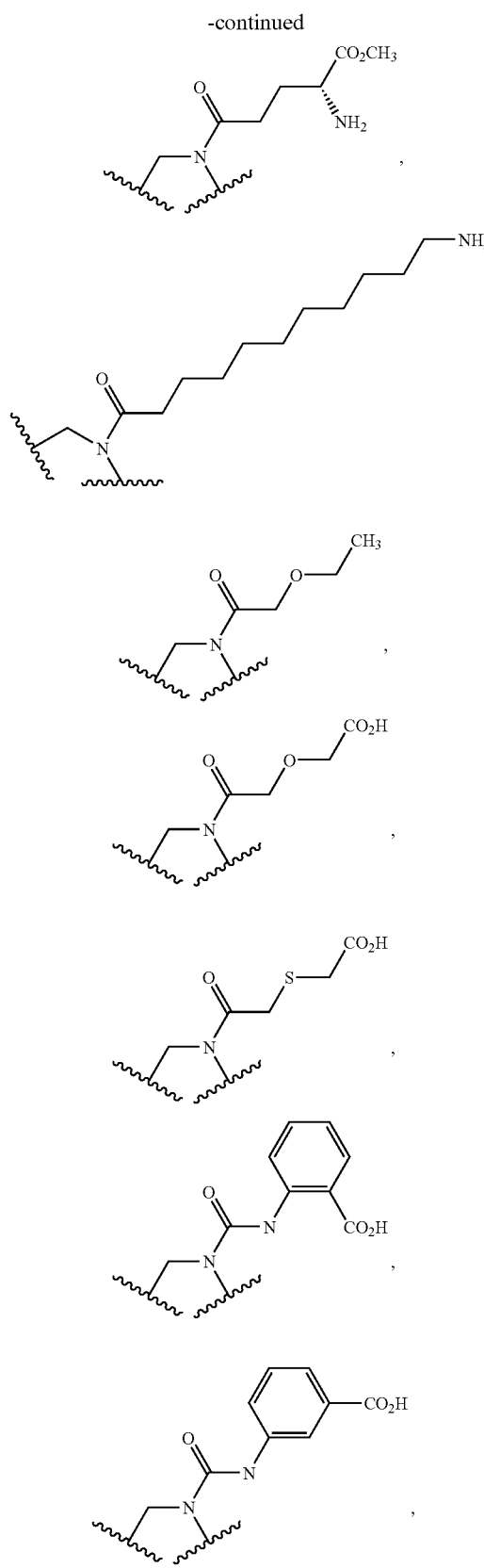
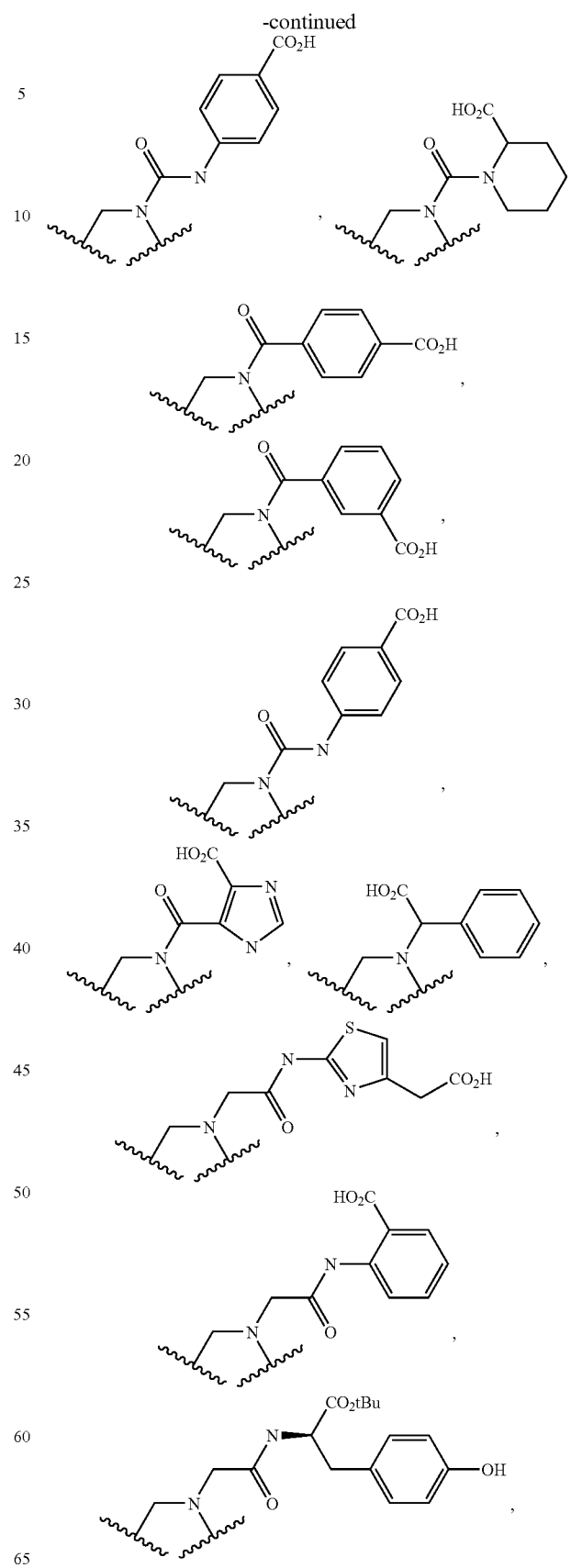

-continued
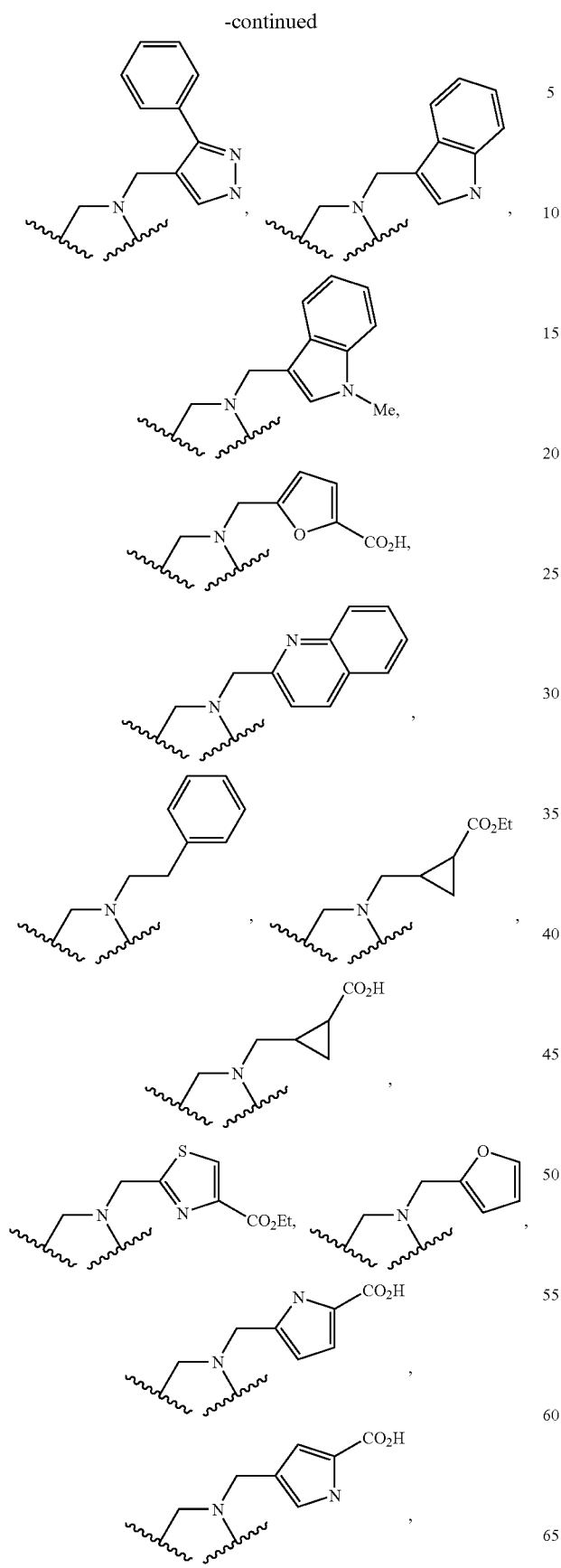
-continued
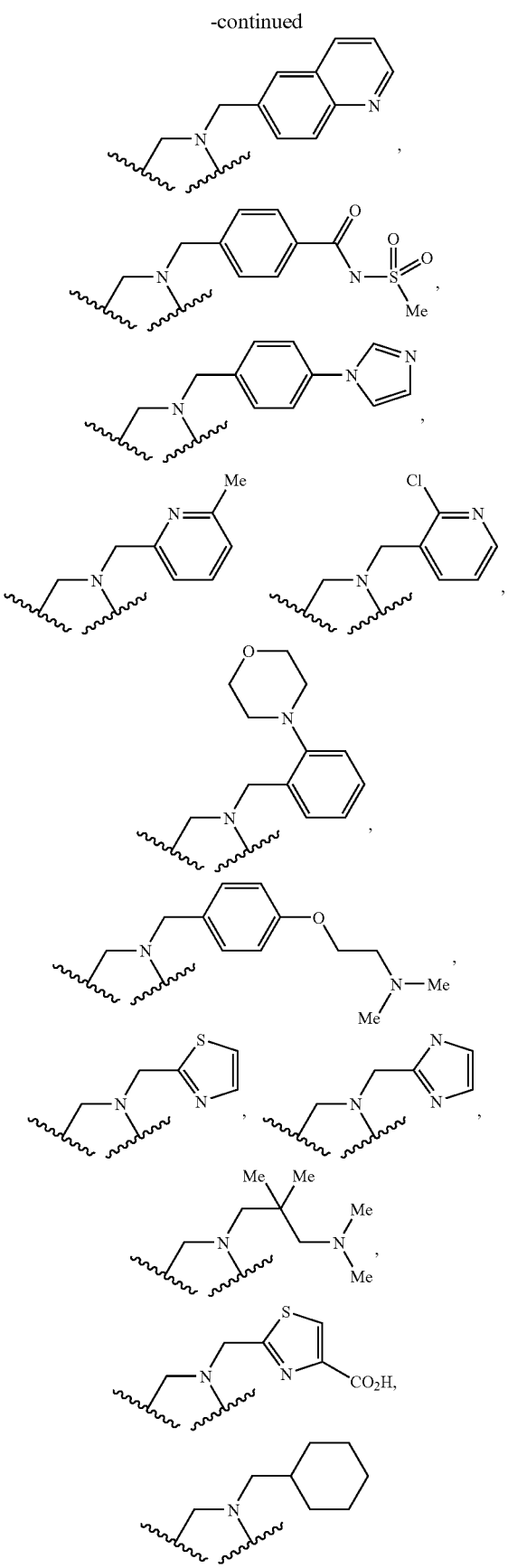

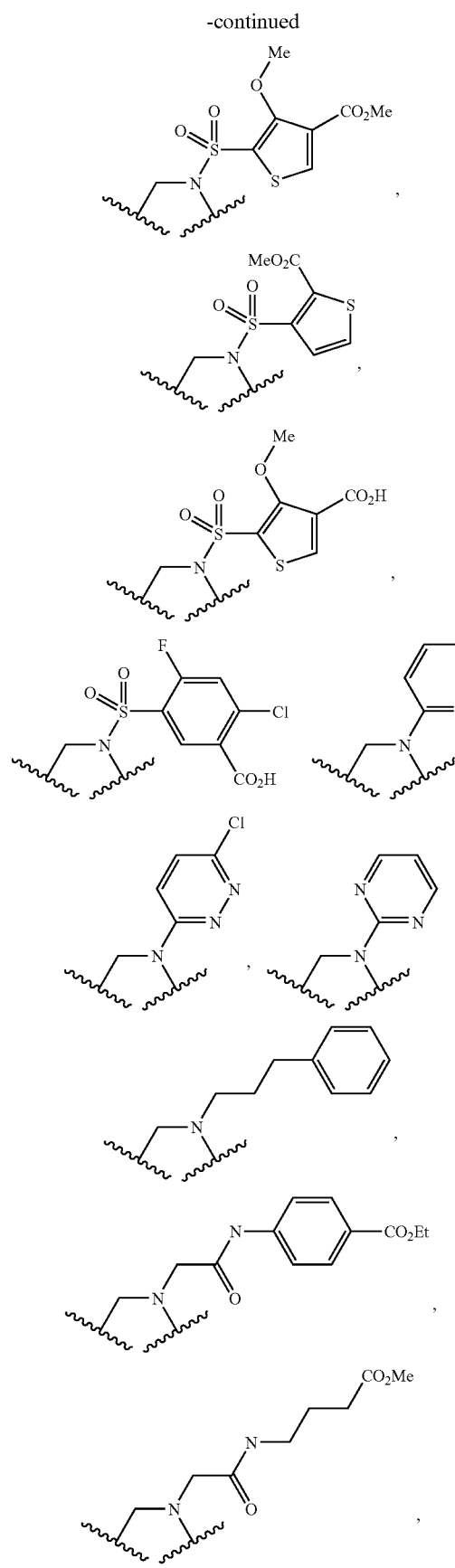
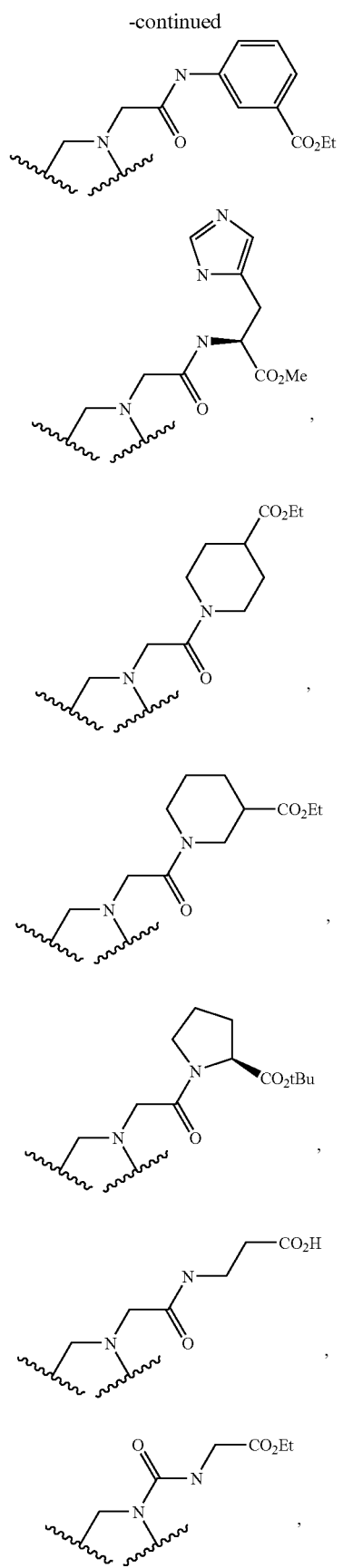

-continued
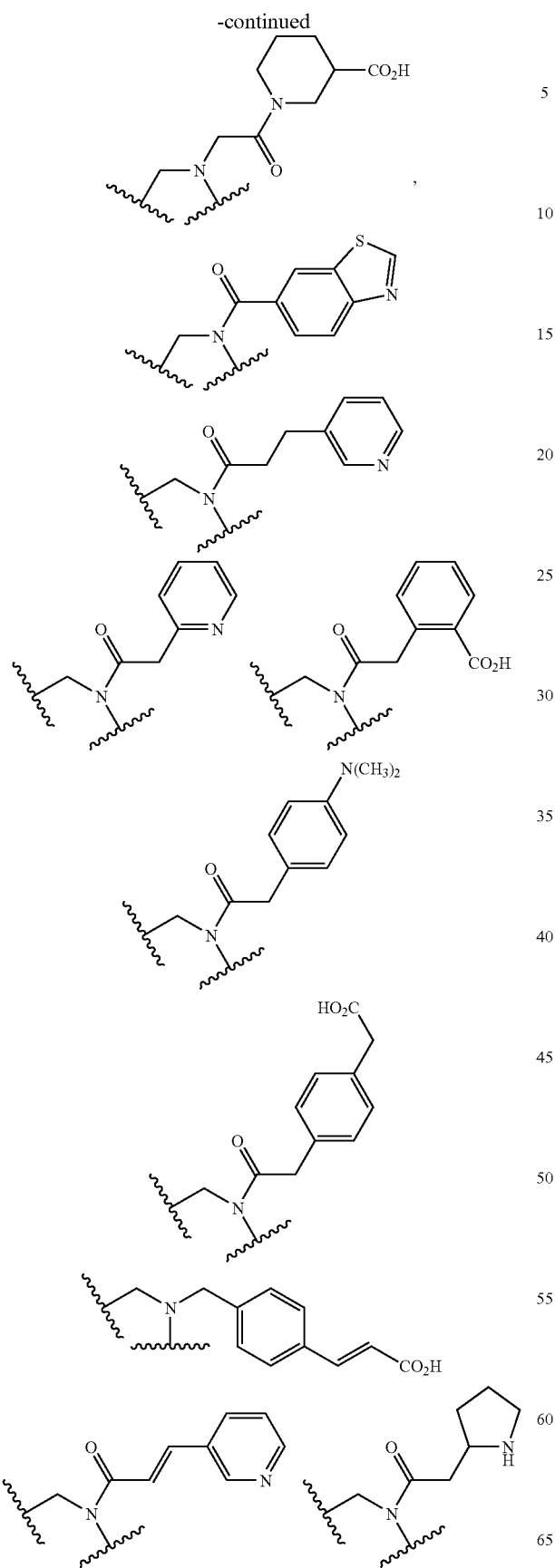
-continued
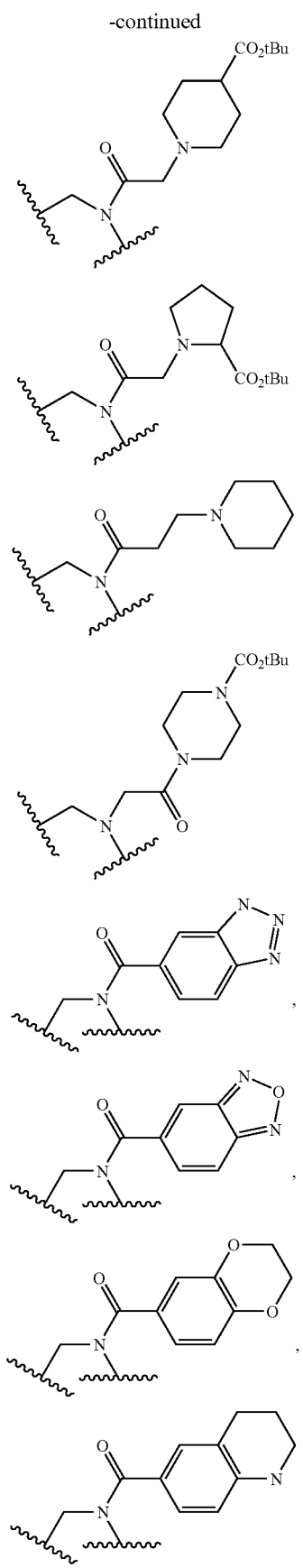

-continued
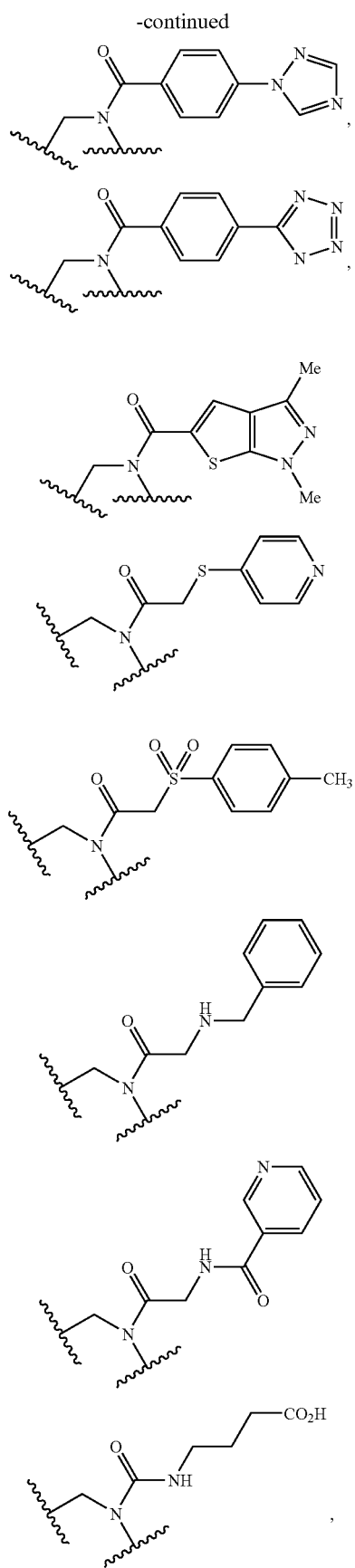
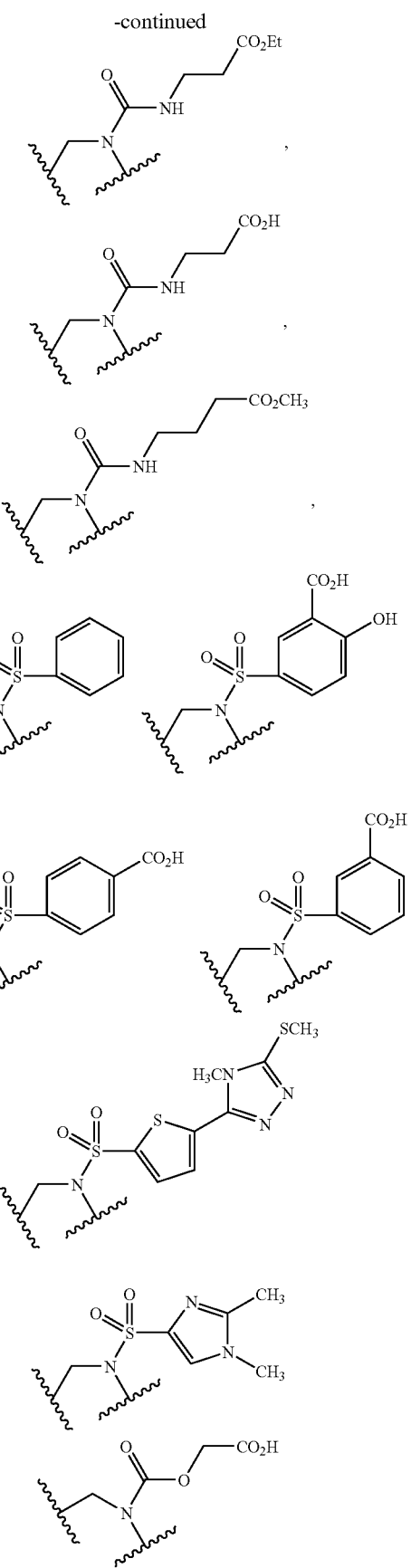

-continued
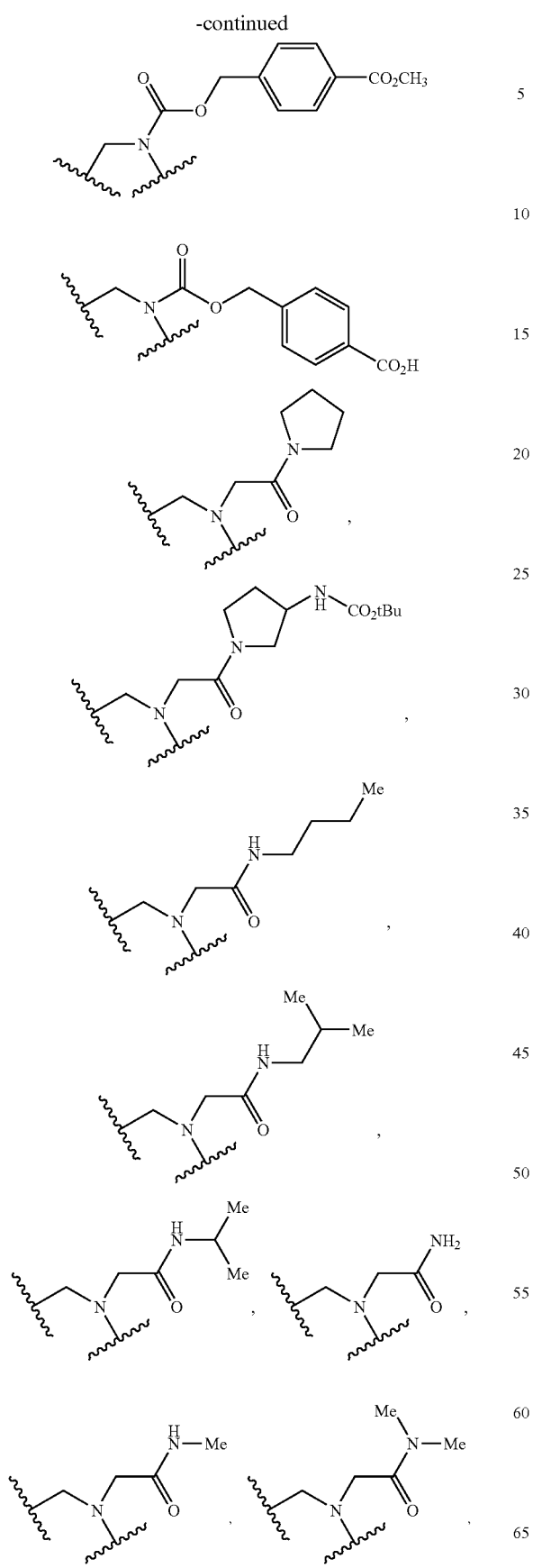
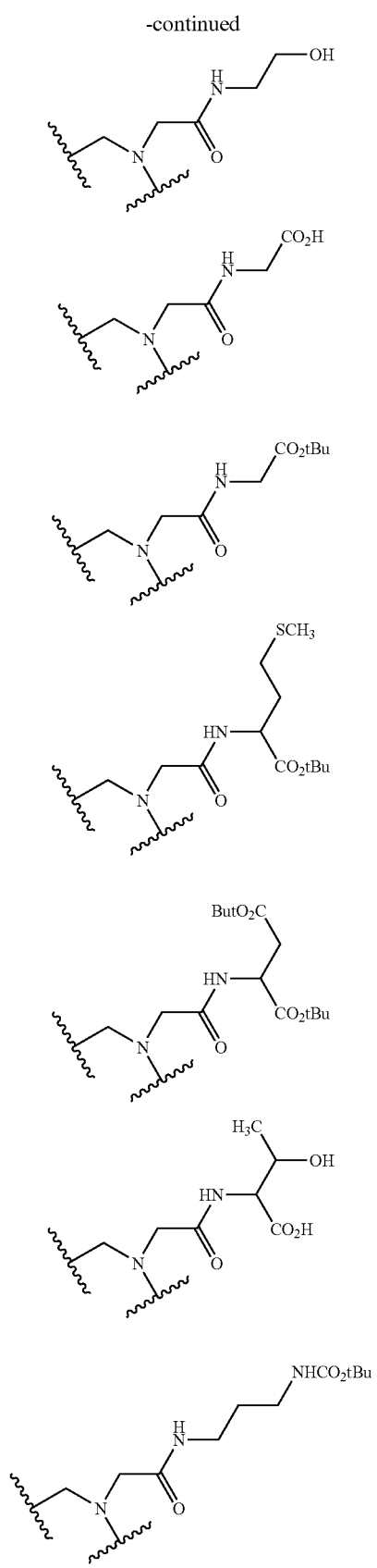

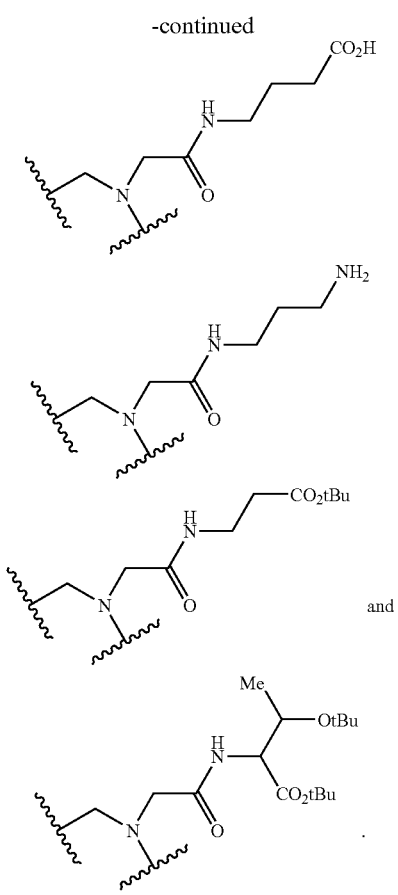

The compounds of formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., nontoxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

Compounds of the Formula (I) may also have prodrug forms. Any compound that will be converted in vivo to provide the bioactive agent (i.e., the compound for formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, pp. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, Vol. 8, pp. 1–38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred compounds are those having formula (I),

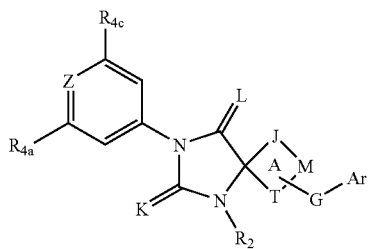

(I)

including enantiomers, diastereomers, and pharmaceutically-acceptable salts, hydrates, solvates, and prodrugs thereof, in which:

L and K, taken independently, are O or S;
Z is N or $CR_{4b}$;
G is a bond;
Ar is directly attached to T or M and is

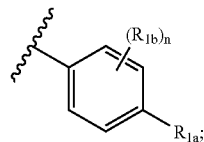

J is —O—, —S—, —NH—, —S(=O)—, —SO$_2$—, —NHSO$_2$—, a $C_{1-3}$ alkylene optionally substituted with one to two $R_9$, or a $C_{2-3}$alkenylene or $C_{1-2}$heteroalkylene optionally substituted with one to two $R_9$;

T is $T_1$ when Ar is attached to T and $T_2$ when Ar is attached to M;

M is $M_1$ when Ar is attached to M and $M_2$ when Ar is attached to T;

$T_1$ and $M_1$ are selected from —N— and —CH—, and $T_2$ and $M_2$ are selected from —O—, —S—, —NH—, —S(=O)—, —SO$_2$—, —NHSO$_2$—, —C(=O)— and —CH$_2$—;

provided that J, M, and T are selected to define a four to six membered saturated or partially unsaturated cycloalkyl or heterocyclo ring having from 1 to 2 heteroatoms wherein no two adjacent heteroatoms of said heterocyclo ring are simultaneously selected from —O— and —S—;

$R_{1a}$ and $R_{1b}$ are independently selected from halogen, $C_{1-4}$alkyl, hydroxy, alkoxy, haloalkyl, haloalkoxy, cyano, nitro, —CO$_2$H, —C(=O)H, —CO$_2$alkyl, C(=O)alkyl, —C(=O)NH(CH$_2$)$_r$CO$_2$H, —C(=O)NH(CH$_2$)$_r$CO$_2$(alkyl), and S(O)$_2$alkyl; or from phenyl, benzyl, phenyloxy, benzyloxy, and heteroaryl; wherein each group $R_{1a}$ and $R_{1b}$ in turn is optionally substituted at any available carbon or nitrogen atom with one to two of $C_{1-4}$alkyl, halogen, hydroxy, alkoxy, haloalkyl, haloalkoxy, cyano, nitro, —CO$_2$H, —C(=O)H, —CO$_2$alkyl, and/or —C(=O)alkyl; or alternatively, two $R_{1b}$ groups join together with each other or one $R_{1b}$ joins together with $R_{1a}$ to form a fused-benzo ring;

$R_2$ is selected from hydrogen, alkyl, substituted alkyl, OR$_{12}$, NR$_{12}$R$_{13}$, C(=O)R$_{12}$, CO$_2$R$_{12}$, C(=O)NR$_{12}$R$_{13}$, NR$_{12}$C(=O)R$_{13}$, NR$_{12}$C(=O)OR$_{13}$, SR$_{12}$, S(O)$_p$R$_{13a}$, NR$_{12}$SO$_2$R$_{13a}$, SO$_2$NR$_{12}$R$_{13}$, cycloalkyl, heterocycle, aryl, and heteroaryl;

$R_{4a}$ and $R_{4c}$ are halogen, alkyl, cyano, haloalkyl, haloalkoxy, or nitro;

$R_{4b}$ is hydrogen, halogen, alkyl, substituted alkyl, nitro, cyano, hydroxy, alkoxy, haloalkoxy, phenyloxy, —CO$_2$H, —C(=O)H, NH(alkyl), N(alkyl)$_2$, CO$_2$alkyl, C(=O)alkyl, alkylthio, —C(=O)NH(CH$_2$)$_r$CO$_2$H, —C(=O)NH(CH$_2$)$_r$CO$_2$(alkyl), aryl, heteroaryl, or heterocycle, wherein each of the aryl, heteroaryl, and heterocycle groups are optionally substituted with one to two of halogen, $C_{1-4}$alkyl, OMe, CF$_3$, CN, OCF$_3$, CO$_2$H, —C(=O)H, CO$_2$alkyl, and/or C(=O)alkyl;

$R_9$ is —A$_1$—Q—A$_2$—R$_{16}$;
A$_1$ is a bond, $C_{1-2}$alkylene, or $C_{2-3}$alkenylene;
Q is a bond, —C(=O)—, —C(=O)NR$_{17}$—, —C(=S)NR$_{17}$—, —SO$_2$—, —SO$_2$NR$_{17}$—, —CO$_2$—, or —NR$_{17}$CO$_2$—;

A$_2$ is a bond, $C_{1-3}$alkylene, $C_{2-3}$alkenylene, —$C_{1-4}$alkylene-NR$_{17}$—, —$C_{1-4}$alkylene-NR$_{17}$C(=O)—, —$C_{1-4}$alkylene-S—, —$C_{1-4}$alkylene-SO$_2$—, or —$C_{1-4}$alkylene-O—, wherein said A$_2$ alkylene groups are branched or straight chain and optionally substituted with a group selected from —CO$_2$H, —CO$_2$($C_{1-4}$alkyl), —S($C_{1-4}$alkyl), NH$_2$, —NH($C_{1-4}$alkyl), or —N($C_{1-4}$alkyl)$_2$;

$R_{12}$ and $R_{13}$ (i) are selected independently of each other from hydrogen, alkyl, substituted alkyl, cycloalkyl, aryl, heteroaryl, and heterocyclo; or (ii) taken together form a heteroaryl or heterocyclo;

$R_{13a}$ is alkyl, substituted alkyl, cycloalkyl, aryl, heteroaryl, or heterocyclo;

$R_{16}$ is selected from (i) hydrogen or a $C_{1-8}$alkyl or $C_{2-8}$alkenyl optionally substituted with up to three of OR$_{23}$, SR$_{23}$, —CO$_2$R$_{23}$, —SO$_2$(alkyl), and/or NR$_{23a}$R$_{23b}$, or from (ii) phenyl, napthyl, five to ten membered monocyclic or bicyclic heteroaryl, four to eleven membered monocyclic or bicyclic heterocyclo, and three to nine membered monocyclic or bicyclic cycloalkyl, wherein each of said $R_{16}$ cyclic groups in turn is optionally substituted with up to three $R_{18}$;

$R_{17}$ is selected from hydrogen, lower alkyl, and substituted lower alkyl;

$R_{18}$ is selected from —$(CH_2)_q$halogen, —$(CH_2)_q$nitro, —$(CH_2)_q$cyano, —$(CH_2)_q$haloalkyl, —$(CH_2)_q$haloalkoxy, —$(CH_2)_q SR_{24}$, $C_{3-7}$cycloalkyl, —$SO_2R_{24}$, —$OR_{24}$, —$(CH_2)_q CO_2R_{24}$, —$(CH_2)_q NR_{24}R_{25}$, —$(CH_2)_q NHCO_2R_{24}$, —$C(=O)NH$—$SO_2R_{24}$, $C(=O)(CH_2)_q NR_{24}R_{25}$, —$O(CH_2)_r NR_{24}R_{25}$, —$C(=O)R_{24}$, —$(CH_2)_q R_{24}$ and —$C_{1-4}$alkyl or —$C_{2-4}$alkenyl optionally substituted with $CO_2R_{24}$;

$R_{23}$, $R_{23a}$, and $R_{23b}$ are independentely selected from hydrogen and alkyl;

$R_{24}$ is selected from hydrogen, alkyl, phenyl, benzyl, $C_{3-7}$cycloalkyl, five or six membered heteroaryl, and four to seven membered heterocyclo, in turn optionally substituted with one to two $C_{1-4}$alkyl, halogen, hydroxy, trifluoromethyl, trifluoromethoxy, —$CO_2H$, $CO_2C_{1-4}$alkyl, $C_{1-4}$alkoxy, —$S(C_{1-4}$alkyl), amino, and/or amino$C_{1-4}$alkyl, provided that when $R_{24}$ is attached to a sulfonyl group as in —$SO_2R_{24}$, then $R_{24}$ is not hydrogen;

$R_{25}$ is selected from hydrogen and alkyl; and n is 0, 1, or 2;

p is 1 or 2;

q is 0, 1, 2, 3, or 4; and r is 1, 2, 3, or 4.

In compounds of formula (I), the group Ar is preferably

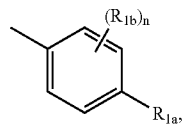

wherein $R_{1a}$ is preferably halogen, cyano, haloalkyl, haloalkoxy, or optionally substituted phenyl or heteroaryl, and $R_{1b}$ is absent or selected from halogen, $C_{1-4}$alkyl, hydroxy, alkoxy, haloalkyl, haloalkoxy, cyano, nitro, —$CO_2H$, —$C(=O)H$, —$CO_2$alkyl, —$C(=O)$alkyl, —$C(=O)NH(CH_2)_{1-4}CO_2H$, and —$C(=O)NH(CH_2)_{1-4}CO_2$(alkyl). Alternatively, two $R_{1b}$ groups may join together with each other or one $R_{1b}$ may join together with $R_{1a}$ to form a fused benzo ring.

In compounds of formula (I), the groups $R_{4a}$ and $R_{4c}$ are preferably selected from halogen, alkyl, cyano, nitro, haloalkyl, haloalkyl, aryloxy, and arylthio, and more preferably, $R_{4a}$ and $R_{4c}$, are both chlorine.

In compounds of formula (I), the group G is preferably a bond; the groups L and K are preferably oxygen; and Z is preferably CH.

In compounds of formula (I), the group T is preferably $T_1$ and is CH, M is preferably $M_2$ and is $CH_2$, and J is preferably an optionally-substituted $C_1$heteroalkylene so that A is a five-membered ring, more preferably J is a group $CH_2$—$NR_9$—.

In compounds of formula (I), the group $R_2$ is preferably $C(=O)$lower alkyl or $C_{1-6}$alkyl optionally substituted with $CO_2H$ or $CO_2$(alkyl), more preferably $R_2$ is methyl.

Also preferred are compounds according to formula (Ic),

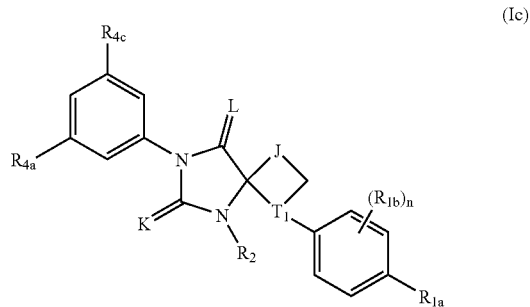

and pharmaceutically-acceptable salts, hydrates, and prodrugs thereof, in which:

L and K, taken independently, are O or S;

J is —O—, —S—, —NH—, —S(=O)—, —$SO_2$—, —$NHSO_2$—, an optionally substituted $C_{1-3}$alkylene, an optionally substituted $C_{2-3}$ alkenylene, or an optionally-substituted $C_{1-2}$heteroalkylene;

$T_1$ is —N— or —CH—;

$R_{1a}$ is halogen, cyano, or optionally-substituted phenyl or heteroaryl;

$R_{1b}$ is selected from halogen, $C_{1-4}$alkyl, hydroxy, alkoxy, haloalkyl, haloalkoxy, cyano, nitro, —$CO_2H$, —$C(=O)H$, —$CO_2$alkyl, —$C(=O)$alkyl, —$C(=O)NH(CH_2)_{1-4}CO_2H$, and —$C(=O)NH(CH_2)_{1-4}CO_2$(alkyl); or from phenyl, benzyl, phenyloxy, benzyloxy, and heteroaryl in turn optionally substituted with one to two of $C_{1-4}$alkyl, halogen, hydroxy, alkoxy, haloalkyl, haloalkoxy, cyano, nitro, —$CO_2H$, —$C(=O)H$, —$CO_2$alkyl, and/or —$C(=O)$alkyl;

$R_2$ is selected from hydrogen, alkyl, substituted alkyl, $O(C_{1-4}$ alkyl), amino, $NH(C_{1-4}$alkyl), $N(alkyl)_2$, $C(=O)H$, $C(=O)$alkyl, $CO_2$(alkyl), $SO_2$alkyl, $C_{3-6}$cycloalkyl, heterocycle, aryl, and heteroaryl;

$R_{4a}$ and $R_{4c}$ are halogen, alkyl, cyano, trifluoromethyl, or nitro; and n is 0, 1, or 2.

In compounds of formula (Ic), as immediately defined above, more preferably J is —$CH_2$—, —$CH_2$—$CH(R_9)$—, or —$CH_2$—$N(R_9)$—, wherein:

$R_9$ is —$A_1$—Q—$A_2$—$R_{16}$;

$A_1$ is a bond, $C_{1-2}$alkylene, or $C_{2-3}$alkenylene;

Q is a bond, —$C(=O)$—, —$C(=O)NR_{17}$—, —$SO_2$—, —$CO_2$—, or —$NR_{17}CO_2$—;

$A_2$ is a bond, $C_{1-2}$alkylene, $C_{2-3}$alkenylene, —$C_{1-4}$alkylene-$NR_{17}$—, —$C_{1-4}$alkylene-$NR_{17}C(=O)$—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted with a group selected from —$CO_2H$, —$CO_2(C_{1-4}$alkyl), —$S(C_{1-4}$alkyl), $NH_2$, —$NH(C_{1-4}$alkyl), or —$N(C_{1-4}$alkyl)$_2$;

$R_{16}$ is selected from (a) hydrogen and $C_{1-6}$alkyl or $C_{2-6}$alkenyl optionally substituted with one to two of OH, $O(C_{1-4}$alkyl), —$CO_2H$, —$CO_2(C_{1-4}$alkyl), $NH_2$, —$NH(C_{1-4}$alkyl), and/or $N(C_{1-4}$alkyl)$_2$, or from (b) furanyl, indolyl, carbazolyl, pyrazolyl, pyrrolyl, thienyl, pyridyl, pyrimidinyl, benzofuranyl, isoxazolyl, imidazolyl, triazolyl, tetrazolyl, phenyl, piperidyl, pyrrolidinyl, pyridazinyl, $C_{3-7}$cycloalkyl, piperazinyl, thiazolyl, morpholinyl, 1,2,5,6-tetrahydropyridyl, quinoxalinyl, benzothiazolyl, benzotriazolyl, benzodioxanyl, benzooxadiazolyl, thienopyrazolyl, tetrahydroquinolinyl, and quinolinyl, wherein each of said cyclic $R_{16}$ groups in turn is optionally substituted with up to three $R_{18}$;

$R_{17}$ is selected from hydrogen, lower alkyl, and substituted lower alkyl;

$R_{18}$ is selected from —$C_{1-4}$alkyl, —$S(C_{1-4}$alkyl), $C_{3-7}$cycloalkyl, —$SO_2(C_{1-4}$alkyl), —$O(C_{1-4}$alkyl), —$SO_2$-phenyl, halogen, hydroxy, nitro, cyano, —$(CH_2)_qCO_2H$, —$(CH_2)_qCO_2C_{1-4}$alkyl, —$(CH_2)_qNH_2$, —$O(CH_2)_q$ $CO_2H$, —CH=CH—$CO_2H$, —CH=CH—$CO_2$(alkyl), —$(CH_2)_qNH$(alkyl), —$(CH_2)_qNHCO_2$alkyl, —(C=O) NH—$SO_2$alkyl, —$(CH_2)_qNH$(benzyl), —$(CH_2)_qN$ (alkyl)$_2$, —$O(CH_2)_rN$(alkyl)$_2$, —Obenzyl, —C(=O) $(CH_2)_qNH_2$, —C(=O)$(CH_2)_qNH$(alkyl), —C(=O) $(CH_2)_qN$(alkyl)$_2$, —$O(CH_2)_rNH_2$, —$O(CH_2)_rNH$(alkyl), —$O(CH_2)_rN$(alkyl)$_2$, —C(=O)pyridyl, —$(CH_2)_q$phenyl, —$(CH_2)_q$ pyridyl, —$(CH_2)_q$triazolyl, —$(CH_2)_q$tetrazolyl, —$(CH_2)_q$imidazolyl, —$(CH_2)_q$pyrazolyl, —$(CH_2)_q$thiamorpholinyl, —$(CH_2)_q$morpholinyl, —$(CH_2)_q$thienyl, —$(CH_2)_q$pyrazinyl, wherein each alkyl or cyclic group of each $R_{18}$ in turn is optionally substituted with one to two $C_{1-4}$alkyl, halogen, hydroxy, trifluoromethyl, trifluoromethoxy, —$CO_2H$, $CO_2C_{1-4}$alkyl, $C_{1-4}$alkoxy, —$S(C_{1-4}$ alkyl), amino, and/or amino$C_{1-4}$alkyl;

q is 0, 1, 2, 3, or 4; and r is 1, 2, 3 or 4.

Further preferred are compounds as immediately defined above wherein $R_9$ is —$C_{1-4}$alkylene-$R_{16}$, —C(=O)$R_{16}$, or —C(=O)$C_{1-4}$alkylene-$R_{16}$, more preferably —$CH_2R_{16}$, and $R_{16}$ is as immediately defined above, more preferably thienyl, phenyl, or pyridyl, optionally substituted with one to two $R_{18}$.

Also preferred are compounds according to formula (Id),

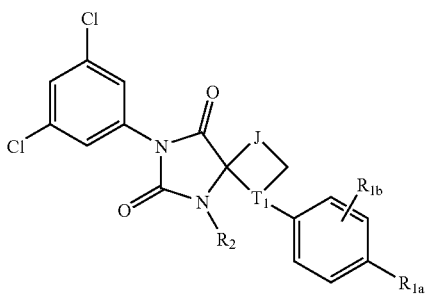

(Id)

and pharmaceutically-acceptable salts, hydrates, and prodrugs thereof, in which

J is —$(CR_{9a}R_{9b})_x$— or —$(CR_{9a}R_{9b})_y$—$NR_{9c}$—$(CR_{9a}R_{9b})_z$—, wherein x is 1, 2 or 3, y is 0, 1 or 2, and z is 0, 1 or 2, provided that y and z together are not greater than 2;

$T_1$ is —N— or —CH—;

$R_{1a}$ is halogen, cyano, nitro, trifluoromethyl, $OCF_3$, heterocyclo, or heteroaryl;

$R_{1b}$ is hydrogen, halogen, $C_{1-4}$alkyl, cyano, nitro, —$CO_2H$, —C(=O)H, —$CO_2$alkyl, or —C(=O)alkyl;

$R_2$ is selected from hydrogen, $C_{1-4}$alkyl, amino, NH($C_{1-4}$ alkyl), N(alkyl)$_2$, C(=O)H, C(=O)$C_{1-4}$alkyl, $CO_2(C_{1-4}$ alkyl), $SO_2C_{1-4}$alkyl, $C_{3-6}$cycloalkyl, heterocycle, aryl, and heteroaryl, or $C_{1-4}$alkyl substituted with one to three of amino, NH($C_{1-4}$alkyl), N(alkyl)$_2$, C(=O)H, C(=O) $C_{1-4}$alkyl, $CO_2H$, $CO_2(C_{1-4}$alkyl), $SO_2C_{1-4}$alkyl, $SO_3H$, and/or PO(OH)$_2$;

$R_{9a}$ and $R_{9b}$ at each occurrence are independently selected from hydrogen, halogen, $C_{1-4}$alkyl, substituted alkyl, hydroxy, alkoxy, haloalkyl, haloalkoxy, cyano, nitro, —$CO_2H$, —C(=O)H, —$CO_2$alkyl, —C(=O)alkyl, —C(=O)NH$(CH_2)_{1-4}CO_2H$, and/or —C(=O)NH $(CH_2)_{1-4}$ $CO_2$(alkyl); or $R_{9a}$ and $R_{9b}$ together form keto (=O);

$R_{9c}$ is selected from hydrogen, $C_{1-4}$alkyl, substituted alkyl, hydroxy, alkoxy, haloalkyl, haloalkoxy, $SO_2R_{16}$, C(=O) $R_{16}$, $SO_2NR_{16}R_{17}$, $CO_2R_{16}$, —C(=S)$NR_{16}R_{17}$, C(=O) C(=O)$R_{16}$, C(=O)NH$(CH_2)_{1-4}CO_2H$, —C(=O)NH $(CH_2)_{1-4}CO_2$(alkyl), phenyl, $C_{3-7}$cycloalkyl, and five to six membered heteroaryl or heterocyclo; and $R_{16}$ and $R_{17}$ are selected from hydrogen, lower alkyl, substituted alkyl, phenyl, $C_{3-7}$cycloalkyl, five to six membered heteroaryl, five to six membered heterocyclo, or nine to ten membered aryl or heteroaryl, in turn optionally substituted with one to two of $C_{1-4}$alkyl, halogen, nitro, cyano, amino, $C_{1-4}$aminoalkyl, $C_{1-4}$thioalkyl, hydroxy, $C_{1-4}$alkoxy, —$CO_2H$, —$CO_2$(alkyl), —C(=O)H, —C(=O)alkyl, —C(=O)$(CH_2)_qNH_2$, phenyl, $C_{3-7}$cycloalkyl, five to six membered heteroaryl, and/or five to six membered heterocyclo, provided that when $R_{16}$ is attached to a sulfonyl group as in —$SO_2R_{16}$, then $R_{16}$ is not hydrogen; and q is 0, 1 or 2.

In compounds of formula (Id) as defined above, preferably y is 1 or 2 and z is 0. $T_1$ is preferably —CH—, $R_2$ is preferably hydrogen or $C_{1-4}$ alkyl, and $R_{9a}$ and $R_{9b}$ are preferably hydrogen.

Also preferred are compounds of formula (Id), as defined above, where $R_{9c}$ is —$A_1$—Q—$A_2$—$R_{16}$, and $A_1$, Q, $A_2$, and $R_{16}$ are as defined above for compounds of formula (Ic).

According to another aspect of the invention, preferred compounds are those having the formula (Ie),

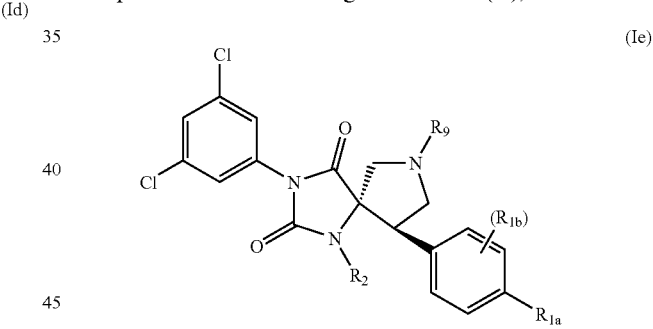

(Ie)

or an enantiomer, diastereomer, or salt thereof, in which:

$R_{1a}$ is halogen, cyano, nitro, trifluoromethyl, $OCF_3$, heteroaryl, or heterocyclo;

$R_{1b}$ is hydrogen, halogen, $C_{1-4}$alkyl, cyano, nitro, —$CO_2H$, —C(=O)H, —$CO_2$alkyl, or —C(=O)alkyl;

$R_2$ is hydrogen or $C_{1-4}$alkyl;

$R_9$ is selected from hydrogen, $C_{1-10}$alkyl, $C_{2-10}$alkenyl, hydroxy, alkoxy, alkylthio, haloalkyl, haloalkoxy, phenyl, $C_{3-6}$cycloalkyl, phenyl, pyridyl, pyridazinyl, pyrimidinyl, —$(CH_2)_s$phenyl, —$(CH_2)_s$tetrazolyl, —$(CH_2)_s$pyridyl, —$(CH_2)_s$thienyl, —$(CH_2)_s$carbazolyl, —$(CH_2)_s$indolyl, —$(CH_2)_s$furyl, —$(CH_2)_s$quinolyl, —$(CH_2)_sC_{3-6}$cycloalkyl, —$(CH_2)_s$thiazolyl, —$(CH_2)_s$pyrrolyl, —$(CH_2)_s$ imidazolyl, —$(CH_2)_s$isoxazolyl, —$(CH_2)_s$benzofuryl, —$(CH_2)_s$pyrazolyl, —C(=O)H, —C(=O)(alkyl), —C(=O)$C_{1-10}$alkyl, —C(=O)phenyl, —C(=O)piperidyl, —C(=O)morpholinyl, —C(=O)$C_{3-6}$cycloalkyl, —C(=O)pyrrolidinyl, —C(=O)quinolyl, —C(=O)imidazolyl, —C(=O)pyrazolyl, —C(=O)thiazolyl, —C(=O)quinoxalinyl, —C(=O)pyridyl, —C(=O)-1,2, 5,6-tetrahydropyridyl, —C(=O)benzothiazolyl, —C(=O)benzotriazolyl, —C(=O)benzodioxanyl, —C(=O)benzooxadiazolyl, —C(=O) 1,2,3,4-tetrahydroquinolyl, —C(=O)thienopyrazolyl, —C(=O)$(CH_2)_s$ tetrazolyl, —C(=O)$(CH_2)_s$pyridyl, —C(=O)$(CH_2)_s$ phenyl, —C(=O)$(CH_2)_s$pyrrolidinyl, —C(=O)$(CH_2)_s$ piperidyl, —C(=O)CH=CH(phenyl), —C(=O) CH=CH(pyridyl), —C(=O)$CH_2$O(alkyl), —C(=O) $CH_2$S(alkyl), —C(=O)$CH_2$S(pyridyl), —C(=O) $CH_2SO_2$(alkyl), —C(=O)$CH_2SO_2$(phenyl), —C(=O) $CH_2$NH(phenyl), —C(=O)$CH_2$NH(benzyl), —C(=O) $CH_2$NH(thiazolyl), —C(=O)$CH_2$NHC(=O)pyridyl, —C(=O)$CH_2$NHC(=O)phenyl, —$(CH_2)_n SO_2$(alkyl), —$(CH_2)_t SO_2$(phenyl), —$(CH_2)_t SO_2$(thienyl), —$(CH_2)_t$ $SO_2$(imidazolyl), —$(CH_2)_t SO_2$(furyl), $(CH_2)_t SO_2$(pyrrolyl), $SO_2$NH(phenyl), —C(=S)$NH_2$, —C(=S)NH (alkyl), —C(=S)NH(phenyl), —$(CH_2)$C(=O)pyrrolidinyl, —$(CH_2)$C(=O)piperidyl, —$(CH_2)$C(=O) piperazinyl, —$CO_2$(alkyl), —$CO_2$(phenyl), —$CO_2$ (benzyl), —$NHCO_2$(alkyl), —$(CH_2)_t$C(=O)NH(phenyl), —$(CH_2)_t$C(=O)NH(piperidyl), —$(CH_2)_t$C(=O)NH (thienyl), —$(CH_2)_t$C(=O)NH(thiazolyl), —$(CH_2)_t$C (=O)NH($C_{5-6}$cycloalkyl), —$(CH_2)_t$C(=O)NH(benzyl), —$(CH_2)_t$C(=O)NH(pyrrolidinyl), —$(CH_2)_t$C(=O)NH (piperazinyl), —$(CH_2)_t$C(=O)$NH_2$, —$(CH_2)_t$C(=O)NH (alkyl), —$(CH_2)_t$C(=O)N(alkyl)$_2$, —$(CH_2)_t$C(=O)N ($C_{1-4}$alkyl)(phenyl), —$(CH_2)_t$C(=O)N($C_{1-4}$alkyl) (thienyl), —$(CH_2)_t$C(=O)N($C_{1-4}$alkyl) (thiazolyl), —$(CH_2)_t$C(=O)N($C_{1-4}$alkyl)(benzyl), or —$(CH_2)_t$C (=O)N($C_{1-4}$alkyl)$CO_2$(alkyl);

wherein each alkyl, alkenyl, or cyclic group of each $R_9$ in turn is optionally substituted with up to three $R_{18}$;

$R_{18}$ is selected from —$C_{1-4}$alkyl, —S($C_{1-4}$alkyl), $C_{3-7}$cycloalkyl, —$SO_2$($C_{1-4}$alkyl), —O($C_{1-4}$alkyl), —$SO_2$-phenyl, halogen, hydroxy, nitro, cyano, —$(CH_2)_q CO_2$H, —$(CH_2)_q CO_2 C_{1-4}$alkyl, —$(CH_2)_q NH_2$, —O$(CH_2)_q$ $CO_2$H, —CH=CH—$CO_2$H, —CH=CH—$CO_2$(alkyl), —$(CH_2)_q$NH(alkyl), —$(CH_2)_q NHCO_2$alkyl, —C(=O) NH—$SO_2$alkyl, —$(CH_2)_q$NH(benzyl), —$(CH_2)_q$N (alkyl)$_2$, —O$(CH_2)_r$N(alkyl)$_2$, —Obenzyl, —C(=O) $(CH_2)_q NH_2$, —C(=O)$(CH_2)_q$NH(alkyl), —C(=O) $(CH_2)_q$N(alkyl)$_2$, —O$(CH_2)_r NH_2$, —O$(CH_2)_r$NH(alkyl), —O$(CH_2)_r$N(alkyl)$_2$, —C(=O)pyridyl, —$(CH_2)_q$phenyl, —$(CH_2)_q$ pyridyl, —$(CH_2)_q$triazolyl, —$(CH_2)_q$tetrazolyl, —$(CH_2)_q$imidazolyl, —$(CH_2)_q$pyrazolyl, —$(CH_2)_q$thiamorpholinyl, —$(CH_2)_q$morpholinyl, —$(CH_2)_q$thienyl, —$(CH_2)_q$pyrazinyl, wherein each alkyl or cyclic group of each $R_{18}$ in turn is optionally substituted with one to two $C_{1-4}$alkyl, halogen, hydroxy, trifluoromethyl, trifluoromethoxy, —$CO_2$H, $CO_2 C_{1-4}$alkyl, $C_{1-4}$alkoxy, —S($C_{1-4}$ alkyl), amino, and/or amino$C_{1-4}$alkyl;

n is 0, 1 or 2;
q is 0, 1, 2, 3, or 4;
r is 1, 2, 3 or 4.
s is 1, 2, 3 or 4; and
t is 0, 1, or 2.

Methods of Preparation

The compounds of the invention may be prepared by the exemplary processes described in the following reaction Schemes A–K. Exemplary reagents and procedures for these reactions appear hereinafter. Starting materials are commercially available or can be readily prepared by one of ordinary skill in the art. For all of the schemes, the groups Z, K, L, Ar, J, T, M, $R_1$, $R_2$, $R_3$, $R_{4a}$, $R_{4b}$, and $R_{4c}$, are as described herein for a compound of formula (I), unless otherwise indicated. Groups designated generally as R, R', X, and P as well as solvents, temperatures, pressures, starting materials having the desired groups, and other reaction conditions, may be readily selected as appropriate by one of ordinary skill in the art.

Scheme A:

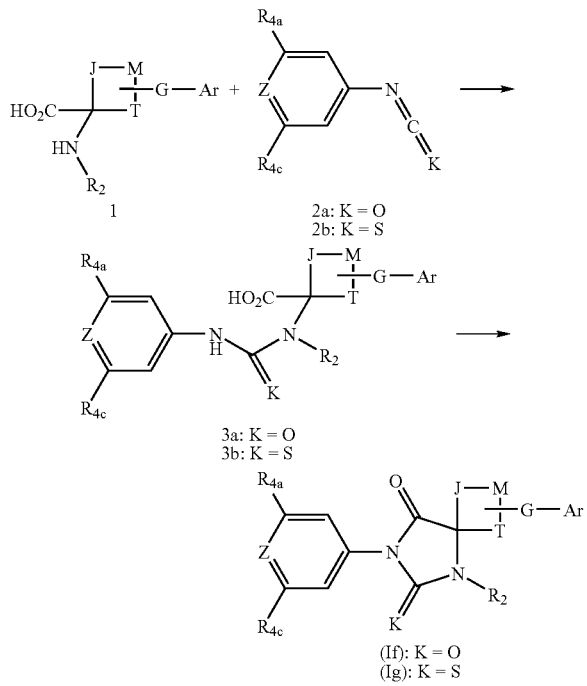

A suitably functionalized amino acid 1 is reacted with an isocyanate 2a or an isothiocyanate 2b in water in the presence of a base (such as NaOH, KOH, $K_2CO_3$, $KHCO_3$, $Na_2CO_3$ or $NaHCO_3$), to yield after acidification the ureidoacid 3a or the thioureidoacid 3b, respectively. This intermediate product is then cyclized in an organic or aqueous solvent in the presence of a catalytic amount of acid (such as hydrochloric acid, sulfuric acid, methanesulfonic acid, or toluenesulfonic acid) to give the spirohydantoin having the formula (If) or spiro-2-thiohydantoin having the formula (Ig). See, e.g., Espada et al., *Farmaco*, Vol. 45 (1990), at pp. 1237–1243, or Nicole et al., *Can. J. Chem.*, Vol. 40 (1962), at pp. 353–366. Alternatively, the ureido or thioureido acid can be cyclized in an organic solvent (such as DMF, THF, DCM) using a dehydrating agent (such as DCC or EDCI) in the presence of an activating agent (such as HOBT or 1-hydroxy-7-azabenzotriazole) and a non-nucleophilic base (such as TEA or DIPEA).

Scheme B:

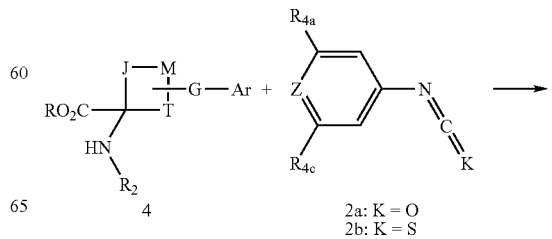

-continued

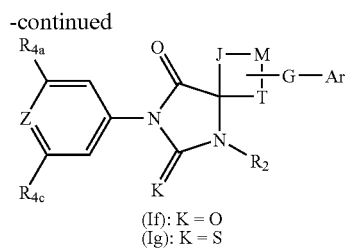

(If): K = O
(Ig): K = S

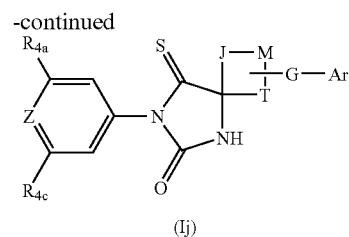

(Ij)

Compounds having the formula (If) or (Ig) can also be obtained in one step as depicted in Scheme B. Reaction of a suitably functionalized amino ester 4 with an isocyanate 2a or isothiocyanate 2b in an organic solvent (such as THF, methylene chloride or DMF) in the presence of a base (such as TEA, $K_2CO_3$ or KOH), yields the desired compound having the formula (If) or (Ig) respectively. See, e.g., Park et al. *J. Org. Chem.*, Vol. 63 (1998), at pp. 113–117; Johnson et al., *J. Am. Chem. Soc.*, Vol. 40 (1918), at p. 645; and Schollkopf et al., *Liebigs Ann. Chem.*, (1981), at pp 439–458.

Scheme C:

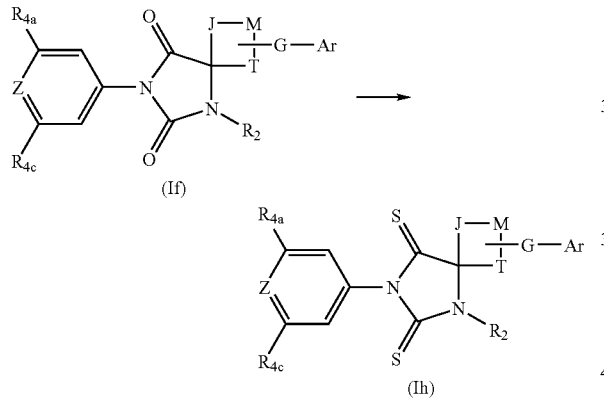

Treatment of hydantoins (If) with a reagent such as $P_2S_5$ or 2,4-bis(4-methoxyphenyl)-1,3-dithia-2,4-diphosphetane-2,4-disulfide (Lawesson's reagent) in an organic solvent such as toluene or dioxane, yields the corresponding dithio-hydantoins having the formula (Ih). See, e.g., Carrington et al., *J. Chem. Soc.*, (1950), at p. 354.

Scheme D:

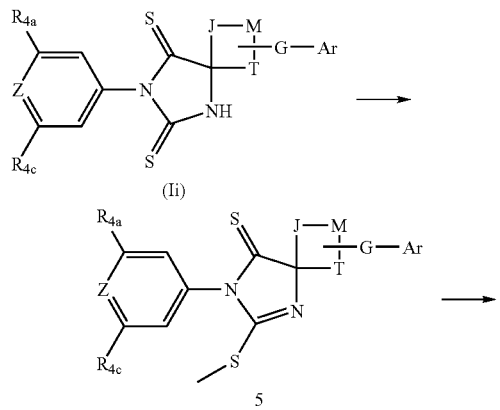

Dithio-hydantoins (Ii) can be converted into 4-thio-hydantoins by S-alkylating compounds (Ii) with a reagent such as methyl iodide to give intermediate 5, which is hydrolyzed under mild acidic conditions to the 4-thio-hydantoins having the formula (Ij). See, e.g., Carrington et al., *J. Chem. Soc.*, (1950), at p. 354.

Scheme E:

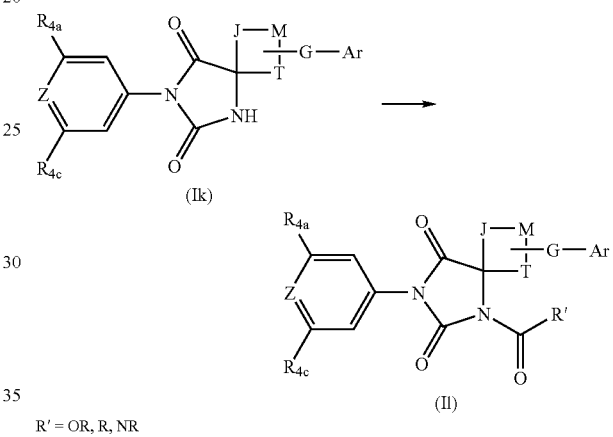

R′ = OR, R, NR

N-acylation of hydantoins having the formula (Ik) can be obtained by treatment with an acylating agent (such as an acyl chloride, an anhydride, a chloroformate or an isocyanate) in an organic solvent (such as THF or acetonitrile) in the presence of a base (such as TEA, DIPEA, DMAP or NaH) to give hydantoins having the formula (I). See, e.g., Link et al., *Eur. J. Med. Chem.*, Vol. 19 (1984), at pp. 261–266, and Ortin et al., *An. R. Soc. Esp. Fis. Quim. Ser. B*, (1958), at p. 69.

Scheme F:

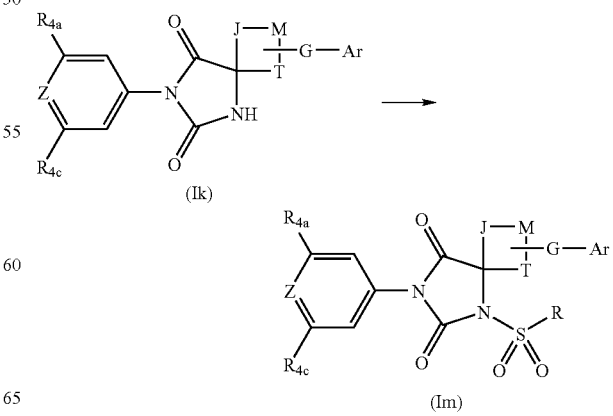

Sulfonylation of hydantoins having the formula (Ik) is obtained by treatment with a sulfonyl chloride in the presence of a base (such as such as TEA, DIPEA, pyridine or DMAP) in an organic solvent such as toluene to give the desired compounds having the formula (Im). See, e.g., Takayama et al., *Agric. Biol. Chem.*, Vol. 51 (1987), at pp. 1547–1552.

Scheme G:

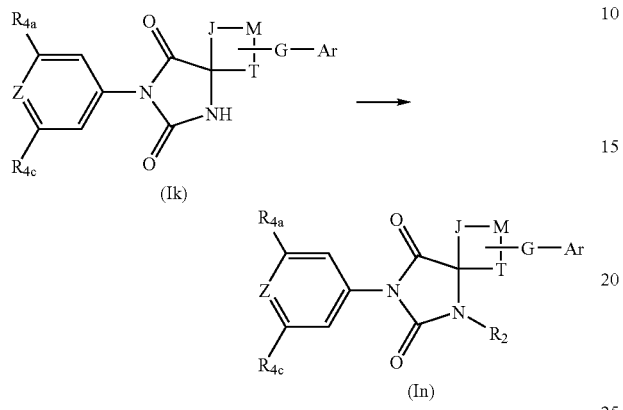

Hydantoins having the formula (Ik) can be N-alkylated in an aprotic solvent (such as DMF, THF or DMSO) by treatment with one equivalent of a base (such as NaH, NaHMDS, LDA, LiHMDS, KH, KHMDS or tBuOK) followed by addition of a suitable alkylating agent (such as an alkyl iodide, alkyl bromide, alkyl chloride, a tosylate or a mesylate) to yield hydantoins having the formula (In). See, e.g., Parmee et al., *Bioorg. Med. Chem. Lett.*, Vol. 9 (1999), at pp. 749–754.

Scheme H:

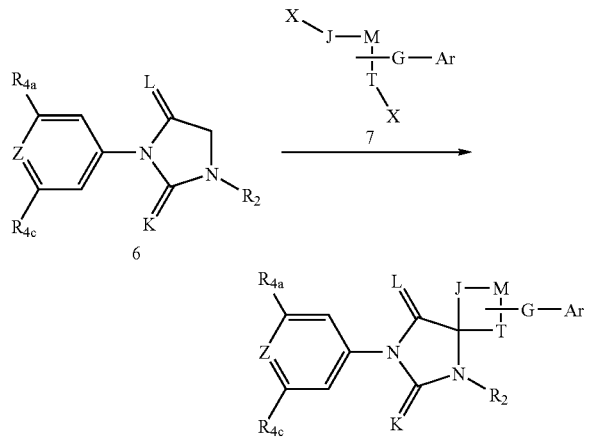

Spiro hydantoins can also be prepared as depicted in Scheme H. Hydantoin 6 is treated either sequentially or directly with two equivalents of a base (such as NaH, KH, LiHMDS, KHMDS, LDA, tBuOK, KOH, methylmagnesium carbonate or DBU) in an organic solvent (such as THF, DMF, DMSO) and reacted with compound 7 bearing two leaving groups X (such as Cl, Br, I, OMs or OTs) to yield the desired hydantoin having the formula (I). See, e.g., Collado et al., *Tetrahedron Lett.*, Vol. 37 (1996), at pp. 6193–6196; Fujiwara et al., *J. Chem. Soc. Perkin Trans.* 2, (1980), at pp. 1573–1577; and Belzecki et al., *J. Org. Chem.*, Vol. 45 (1980), at pp. 2215–2217.

Scheme I:

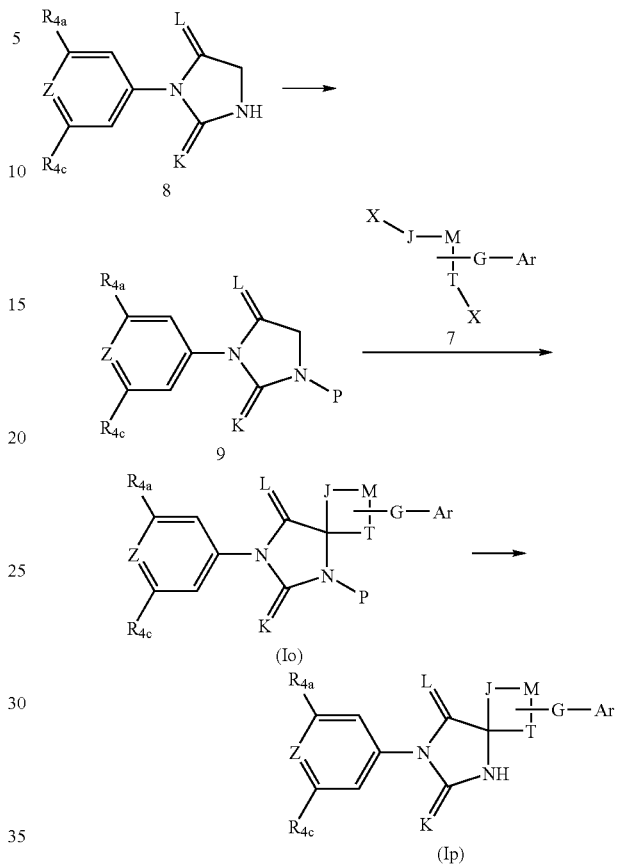

N-unsubstituted hydantoins having the formula (Ip) can be prepared using the same or similar procedure as for Scheme H, with the addition of a protection/deprotection sequence. Thus hydantoin 8 is protected on the nitrogen with a protecting group P, such as BOC (see, e.g., Nilsson et al., *J. Med. Chem.*, Vol. 35 (1992), at pp. 3270–3279) to give the intermediate 9, which is dialkylated as previously with 7 to yield the compound having the formula (Io). Deprotection gives the desired N-unsubstituted spirohydantoin having the formula (Ip).

Scheme J:

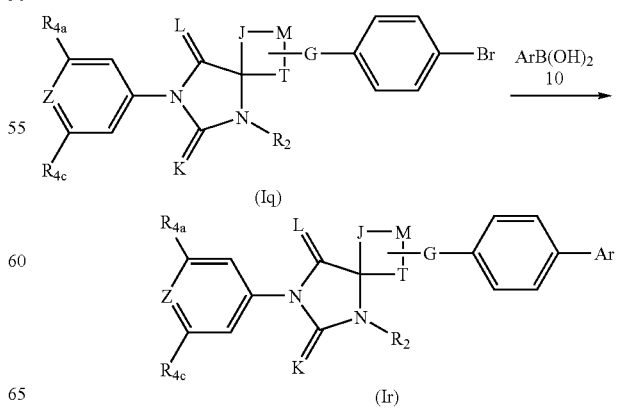

Bromo Spiro hydantoins having the formula (Iq) can be transformed into biaryl compounds having the formula (Ir) by reaction with an aromatic or heteroaromatic boronic acid 10 in the presence of a palladium catalyst (such as Pd (PPh$_3$)$_4$) and a base (such as K$_2$CO$_3$ or Na$_2$CO$_3$) in an appropriate solvent (such as toluene, DMF, DME or water), under conventional Suzuki coupling conditions. See, e.g., Suzuki et al., *Synth. Commun.*, Vol. 11 (1981), at p. 513.

Scheme K:

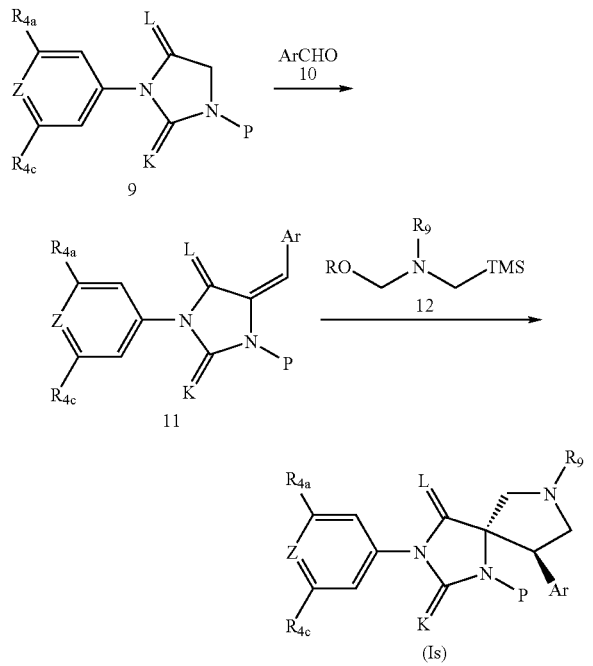

Hydantoins 9 can be submitted to a Knoevenagel condensation with an aromatic aldehyde 10 under classical conditions (e.g., sodium acetate in refluxing acetic anhydride) to obtain 11, which is reacted with amine 12 under acidic catalysis (such as trifluoroacetic acid) to yield spiropyrrolo hydantoins having the formula (Is).

Scheme L:

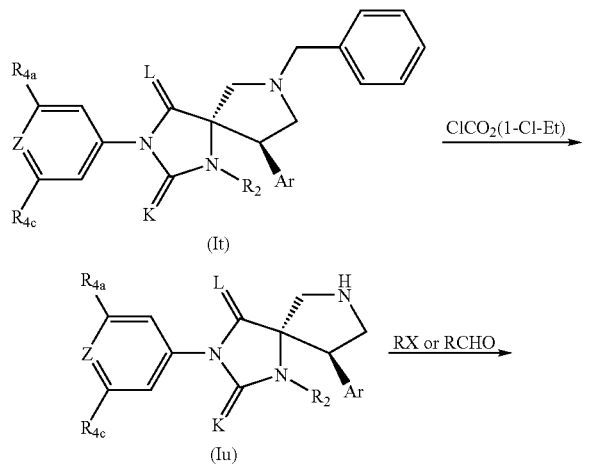

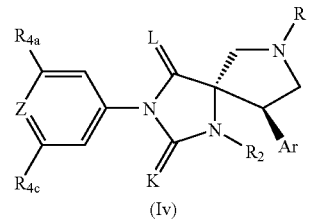

Hydantoins (It) can be debenzylated using, for example, 1-chloroethyl chloroformate in a solvent such as DCM or DCE, to yield the NH derivatives having the formula (Iu). Compounds of formula (Iu) can be alkylated by reaction with an alkyl halide RX (e.g., an alkyl iodide), in a solvent such as acetonitrile or acetone at temperature ranging from room temperature to reflux. Alternatively, alkylation can be achieved by reaction with an aldehyde in the presence of a reducing agent such as sodium triacetoxy borohydride or sodium cyanoborohydride in a solvent such as acetonitrile or DCE to yield compounds of formula (Iv).

Scheme M:

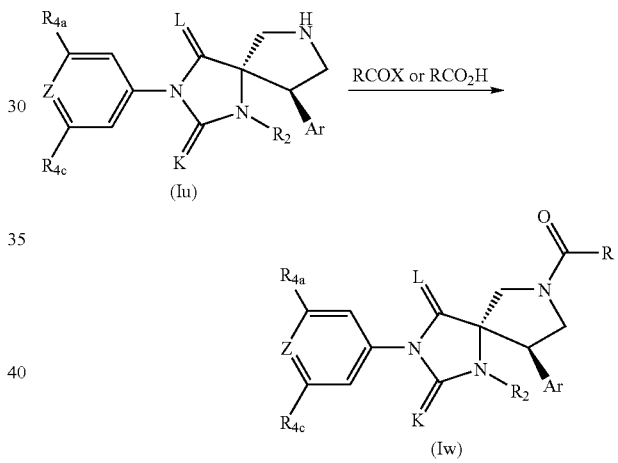

Compounds of formula (Iu) can also be acylated with an acyl halide (for example, an acyl chloride or acyl bromide) in the presence of an organic base (such as triethylamine or diisopropylethylamine) or an inorganic base (such as sodium carbonate) in a solvent such as DCM at a temperature ranging from −15° C. to room temperature to yield acylated derivatives of formula (Iw). Compounds (Iw) can also be obtained by reaction with an acid RCO$_2$H in the presence of a coupling agent such as dicyclohexylcarbodiimide in a solvent such as DCM.

Scheme N:

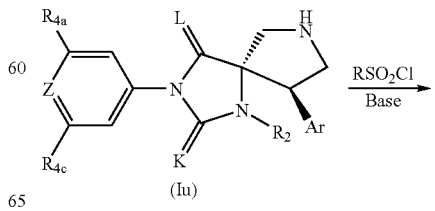

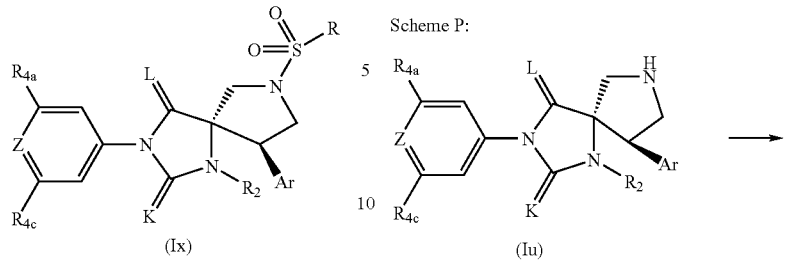

Sulfonamides of formula (Ix) can be obtained from compounds of formula (Iu) by reaction with a sulfonyl halide in the presence fo a base (such as triethylamine or sodium carbonate) in a solvent such as DCM or THF at temperature ranging from –15° C. to room temperature.

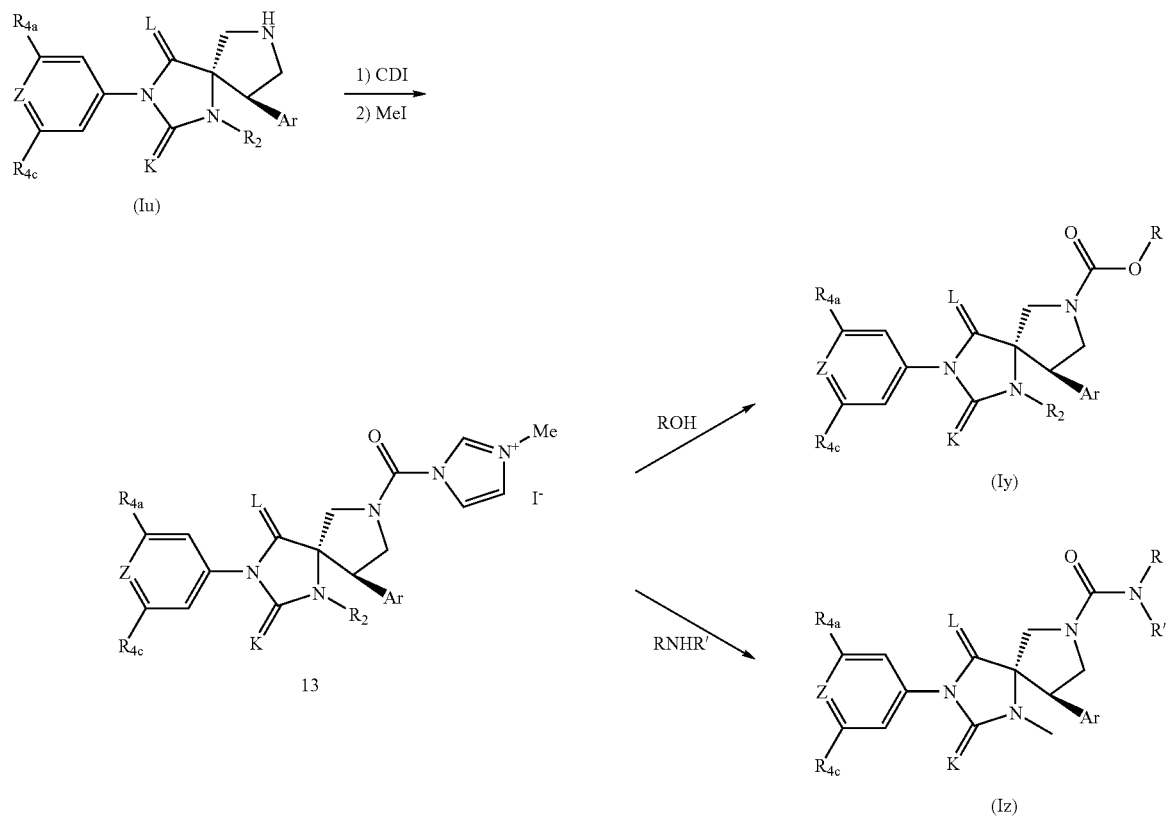

Compounds of formula (Iu) can also be transformed into the activated intermediates 13 by sequential reaction with carbonyl diimidazole and methyl iodide. See R. A. Batey et al. *Tetrahedron Lett.*, Vol. 39 (1998), at p. 6267. Compounds 13 can then be reacted with either an alcohol or an amine to give carbamates of formula (Iy) or ureas of formula (Iz), respectively.

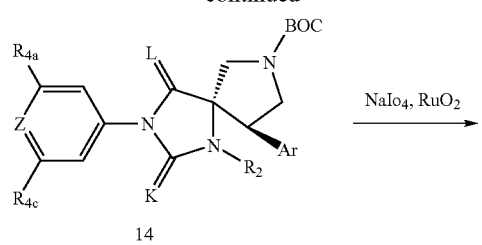

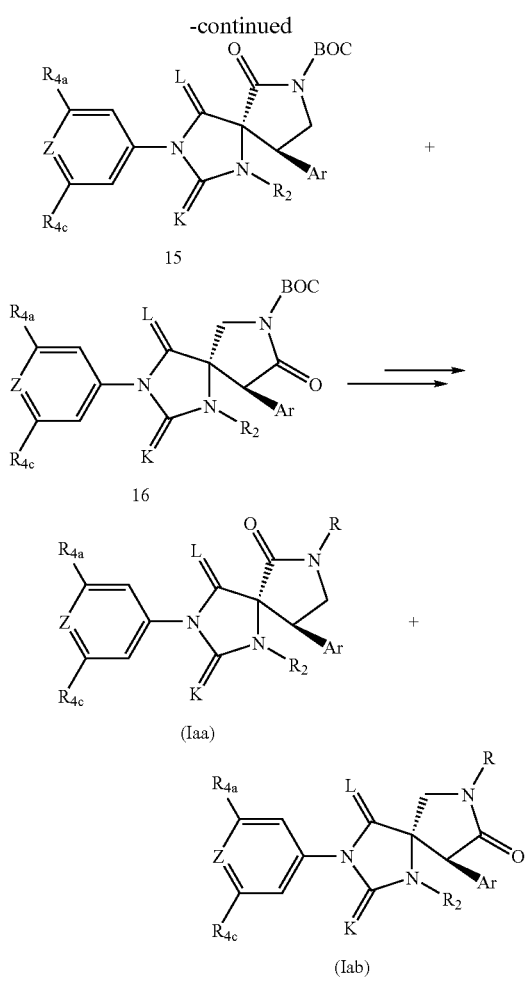

Compounds of formula (Iu) can be transformed into intermediates 14 by reaction with di tert-butyl dicarbonate in a solvent such as THF or DCM. Oxidation of 14 with, for example, sodium periodate in the presence of ruthenium oxide then gives a mixture of lactones 15 and 16, which can be transformed under standard conditions into compounds of formula (Iaa) and (Iab).

Utility

The compounds and compositions of this invention are antagonists and/or inhibitors of LFA-1, Mac-1, and/or ICAMs. They are useful in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1, Mac-1 and/or ICAM-1, ICAM-2, or ICAM-3. As used herein, the term "treating" includes prophylactic and therapeutic uses and thus includes the alleviation of symptoms of a Leukointegrin/ICAM-associated condition in a patient, the improvement of an ascertainable measurement associated with such a condition, or the prevention of such a condition or its symptoms. The term "patient" refers to a mammal, preferably a human.

In view of their inhibition activity, the compounds may be used to treat conditions involving the activation, co-stimulation, or infiltration of T-cells and/or leukocytes, including without limitation conditions involving the influx of leukocytes in the skin, peritoneum, synovium, lung, kidney, and heart. The inventive compounds may be used to treat conditions resulting from a response of the specific or nonspecific immune system in a patient.

Leukointegrin/ICAM-associated conditions that may be treated with the inventive compounds include acute or chronic graft vs host reactions (e.g., pancreatic islet allograft); and acute or chronic transplant rejection (e.g., kidney, liver, heart, lung, pancreas, bone marrow, cornea, small bowel, skin allografts, skin homografts, heterografts, and/or cells derived from such organs). Additionally, the compounds may be used to treat inflammatory conditions including, but not limited to, multiple sclerosis, rheumatoid arthritis, psoriatic arthritis, osteoarthritis, osteoporosis, diabetes (e.g., insulin dependent diabetes mellitus or juvenile onset diabetes), cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome.

The inventive compounds may be used to treat inflammatory conditions of the skin including eczema, atopic dermatitis, contact dermatitis, urticaria, schleroderma, psoriasis, and dermatosis with acute inflammatory components.

The compounds also may also be used to treat allergies and respiratory conditions, including asthma, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, the compounds of the invention may be used to treat autoimmune diseases and/or inflammation associated with autoimmune diseases such as organ-tissue autoimmune diseases (e.g., Raynaud's syndrome), autoimmune thyroiditis, uveitis, systemic lupus erythematosis, Addison's disease, autoimmune polyglandular disease (also known as autoimmune polyglandular syndrome), and Grave's disease.

The compounds of this invention also may be used to treat metastases or as an adjunct to minimize toxicity with cytokine therapy in the treatment of cancers.

The compounds of this invention further have utility in treating hypogonadism, frailty, sexual dysfunction, wasting, such as wasting syndromes associated with cancer and AIDS, and anemia. The compounds further have utility in treating cancers, including but not limited to cancers of the breast, brain, skin, ovary, endometrium, bladder, prostate, lung, colon, lymphatic system, liver and kidney. The inventive compounds are useful for conditions such as hirsutism, acne, seborrhea, alopecia, fibroids, hyperpilosity, cachexia, polycystic ovarian syndrome, anorexia, contraception, drug withdrawal syndrome, pregnancy termination, and benign prostate hypertrophy. The compounds are further useful as antiangiogenic agents. Additionally, the compounds may be useful as inhibitors of protein prenyltransferases, particularly farnesyltransferase and the prenylation of the oncogene protein Ras. As such, the inventive compounds may potentially be useful for treating and/or preventing the diseases and disorders referred to in WO 01/45704, incorporated herein by reference.

When used as anti-inflammatory agents, the compounds may be administered prior to the onset of, at, or after the initiation of inflammation. When used prophylactically, the compounds are preferably provided in advance of any inflammatory response or symptom (for example, prior to, at, or shortly after the time of an organ or tissue transplant but in advance of any symptoms of organ rejection). Administration of the compounds may prevent or attenuate inflammatory responses or symptoms.

The present invention thus provides methods for treating such conditions as those listed above, comprising administering to a patient in need thereof an effective amount of at least one compound of formula (I) or a salt thereof. Other therapeutic agents such as those described below may be employed in combination with the compounds of formula (I). In the methods of the present invention, such other therapeutic agent(s) may be administered prior to, simultaneously with, or following the administration of the inventive compounds.

The present invention also provides pharmaceutical compositions capable of treating the above-referenced diseases and disorders. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.), according to techniques such as those well known in the art of pharmaceutical formulation.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal administration via aerosol or inhalation include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating diseases and disorders referenced above, for example, where the second drug has the same or different mechanism of action than the present compounds. Exemplary of such other therapeutic agents include anti-inflammatory agents, antibiotics, anti-viral agents, anti-oxidants, and agents used to treat respiratory conditions such as COPD and asthma.

Examples of suitable other anti-inflammatory agents with which the inventive compounds may be used include aspirin, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), methotrexate (FK506), integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG).

The inventive compounds may be used in combination with other agents used to treat respiratory conditions such as asthma, COPD, and allergic rhinitis, such as adrenergic agonists (such as albuterol, terbutaline, formoterol, salbutamol, salmeterol, bitolterol, pilbuterol, and fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); Muscarinic M3 cholinergic antagonists (e.g., Spiriva®), PDE 4 inhibitors (e.g. rolipram, cilomilast [Ariflo®], piclamilast, or roflumilast), histamine $H_1$ antagonists, Allegra® (fexofenadine), Claritin® (loratidine), and/or Clarinex® (desloratidine).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, C-11294A, CDC-801, BAY-19-8004, cipamfylline, SCH351591, YM-976, PD-189659, mesiopram, pumafentrine, CDC-998, IC-485, and KW-4490.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, arniodarone, azirnilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also be useful in combination with antiangiogenic agents, such as compounds that are inhibitors of VEGF receptors, or in conjunction with antitumor agents such as paclitaxel, adriamycin, epithilones, cisplatin, and carboplatin. Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Compounds of formula (I), including the compounds described in the examples hereof, have been tested in assay(s) described below and have shown a measurable level of activity as inhibitors of LFA-1 and/or ICAM-1.

Assays

H1-HeLa Adhesion assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to $2\times10^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at $5\times10^7$/ml. Calcein-AM, 10 μM (Molecular Probes, Eugene, Oreg.) and 100 nM phorbol myristate acetate (SIGMA, St. Louis, Mo.) were added to the labeling and activation mix. Following incubation at 37° C. for 30 minutes, ten ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 μl of HBSS. An additional 50 μl of HBSS containing compound solution, DMSO, or anti-CD18 antibody was then added to each well. To the H1-HeLa cells were added 200,000 HSB-2 cells/well in 100 μl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC adhesion assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 μl/well of 2.5 μg/ml mouse Type IV collagen (Trevigen) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 μl/well for use four days later. Twenty hours prior to use, the medium was removed and cells were stimulated with 200 μl of 10 nM phorbol myristate acetate (PMA, Sigma, St. Louis, Mo.) in EGM. When the cells were 90% confluent (typically day 8), the PMA-containing medium was removed, the wells were washed with HBSS, and 50 μl of HBSS was added to the wells. An additional 50 μl containing compound solution, DMSO or blocking anti-CD18 was then added to each well.

On day 7, HSB-2 cells were then divided to $2\times10^5$/ml in RPMI 1640 (Gibco), 10% FCS (Hyclone, Logan, Utah), 1% Pen-Strep (Gibco), and 1% L-glutamine (Gibco). The following day, the cells were centrifuged at 534×G for 8 minutes, washed, and resuspended in HBSS at $5\times10^7$/ml. For activation and labeling, calcein-AM, 10 μM (Molecular Probes, Eugene, Oreg.) and 100 nM phorbol myristate acetate (Sigma, St. Louis, Mo.) were added and the cells incubated at 37° C. for 30 minutes. Following the addition of ten ml of HBSS, the cells were centrifuged, resuspended, and counted.

To the HUVEC cells were added 200,000 labeled and activated HSB-2 cells/well in 100 μl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

EXAMPLES

The following Examples illustrate embodiments of the inventive compounds and starting materials, and are not intended to limit the scope of the claims. For ease of reference, the following abbreviations are used herein:

Abbreviations $AlCl_3$=aluminum chloride
$Ac_2O$=acetic anhydride
AcONa=sodium acetate
bp=boiling point
$CH_3CN$=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DME=1,2-dimethoxyethane
DMF=dimethyl formamide
EDCI=1–3-dimethylaminopropyl)-3-ethylcarbodiimide
$Et_2O$=diethyl ether
HOBT=1-hydroxybenzotriazole
EtOAc=ethyl acetate
EtOH=ethanol
g=gram(s)
HCl=hydrochloric acid
KOH=potassium hydroxide
$K_2CO_3$=potassium carbonate
l=liter
$LiAlH_4$=lithium aluminum hydride
MeCN=acetonitrile
MeOH=methanol
$MgSO_4$=magnesium sulfate
NaH=sodium hydride
$Na_2SO_4$=sodium sulfate NaOH=sodium hydroxide
NMP=1-methyl-2-pyrrolidinone
PBr₃=phosphorus tribromide
(Ph₃P)₄Pd=tetrakis(triphenylphosphine)palladium(0)
PS=polystyrene
SOCl₂=thionyl chloride
TEA=triethylamine
mg=milligram(s)
ml=milliliter
μl=microliter
mmol=millimole
μmol=micromole
mol=mole
mp=melting point
RT=room temperature Preparation 1

4-(4-Bromophenyl)-4-oxobutyric acid

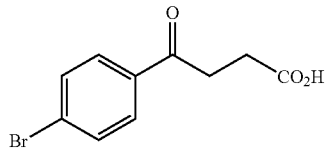

AlCl₃ (128.8 g, 0.97 mol) was added by portions within 20 min to a suspension of succinic anhydride (44.3 g, 0.44 mol) and bromobenzene (100 ml, 0.99 mol) in DCM (500 ml) while the reaction flask was cooled in a water bath. After 1 h 30 min at RT, the reaction mixture was refluxed for 2 h. After cooling, the reaction medium was slowly poured into a mixture of ice (1.5 l) and concentrated HCl (100 ml). The precipitate was washed twice with water, with isopropanol, and finally with pentane. After drying 4-(4-bromophenyl)-4-oxobutyric acid was obtained as an off-white solid (86.4 g, mp=148° C.). $^1$H NMR (CDCl₃): 7.85 (2H, d, J=8.5 Hz), 7.62 (2H, d, J=8.5 Hz), 3.28 (2H, t, J=6.5 Hz), 2.82 (2H, t, J=6.5 Hz).

Preparation 2

4-(4-Bromophenyl)-4-oxobutyric acid methyl ester

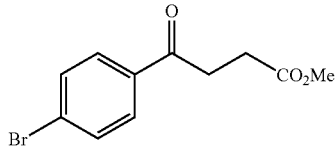

4-(4-Bromophenyl)-4-oxobutyric acid (86.4 g, 0.336 mol) (Preparation 1) in MeOH (1.7 l) containing H₂SO₄ (86 ml) was refluxed for 21 h. After cooling, the light precipitate was filtered off and the reaction mixture concentrated to dryness. The obtained solid was placed in water and extracted twice with EtOAc. The organic layer was washed with diluted NaOH and twice with brine, dried over Na₂SO₄ and concentrated to yield the desired 4-(4-bromophenyl)-4-oxobutyric acid methyl ester as a low melting point solid (87.5 g, mp=50° C.). $^1$H NMR (CDCl₃): 7.85 (2H, d, J=8.5 Hz), 7.60 (2H, d, J=8.5 Hz), 3.71 (3H, s), 3.28 (2H, t, J=6.5 Hz), 2.76 (2H, t, J=6.5 Hz).

Preparation 3

1-(4-Bromophenyl)-butane-1,4-diol

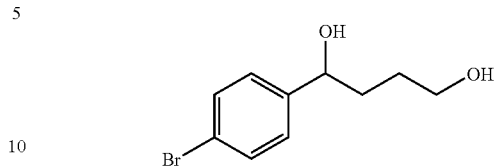

A solution of 4-(4-bromophenyl)-4-oxobutyric acid methyl ester (19 g, 70 mmol) (Preparation 2) in anhydrous diethyl ether (100 ml) was added dropwise to a suspension of LiAlH₄ (5.3 g, 140 mmol) in ether (100 ml), while the temperature was kept below 5° C. with an ice bath. After 2 h at RT, the reaction mixture was refluxed for 4 h. It was then cooled to 5° C. and hydrolyzed with a saturated Na₂SO₄ solution with the temperature kept below 15° C. The suspension was filtered over celite and concentrated to yield a yellow oil (16.1 g) which was chromatographed over silica gel (eluent: DCM/MeOH 90/10) to yield 1-(4-bromophenyl)-butane-1,4-diol as an oil (15 g). $^1$H NMR (CDCl₃): 7.40 (2H, d, J=8.4 Hz), 7.12 (2H, d, J=8.4 Hz), 4.65 (1H, br s), 4.50–4.60 (1H, m), 3.97 (1H, br s), 3.4–3.65 (2H, m), 1.6–1.85 (2H, m), 1.45–1.6 (2H, m).

Preparation 4

1-Bromo-4-(1,4-dibromobutyl)benzene

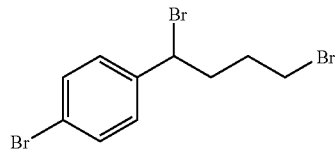

PBr₃ (4 ml, 40 mmol) was added dropwise in 10 min to a solution of 1-(4-bromophenyl)-butane-1,4-diol (15 g, 61 mmol) (Preparation 3) in diethyl ethyl (300 ml) maintained at −10° C. After 20 h at RT, the reaction mixture was cooled with an ice bath and water (100 ml) was added rapidly. The aqueous layer was extracted twice with ether. The combined organic layers were washed with a diluted aqueous Na₂CO₃ solution then three times with water until neutrality, dried over magnesium sulfate and concentrated to yield 1-bromo-4-(1,4-dibromobutyl)benzene (13 g) as a yellow oil. $^1$H NMR (CDCl₃): 7.47 (2H, d, J=8.5 Hz), 7.26 (2H, d, J=8.5 Hz), 4.8–5.0 (1H, m), 3.42 (2H, t, J=6.4 Hz), 2.2–2.45 (2H, m), 1.8–2.2 (2H, m).

Preparation 5

3-Bromo-1-(4-bromophenyl)propan-1-one

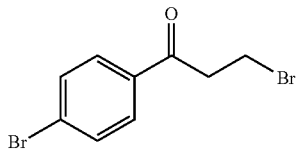

AlCl₃ (23.8 g, 178 mmol) was added by portions to bromobenzene (155 ml, 1.47 mol) at 0° C. 3-Bromopropionyl chloride (25 g, 146 mmol) was added dropwise to the red solution kept at 0° C. over 30 min. After 1 h at RT, the reaction mixture was heated to 50° C. for 1 h. After cooling, the mixture was poured over ice/water and extracted with DCM. The organic layer was dried over $Na_2SO_4$ and concentrated to yield 3-bromo-1-(4-bromophenyl)propan-1-one (36 g) which was crystallized from petroleum ether (mp=66° C.). $^1$H NMR ($CDCl_3$): 7.82 (2H, d, J=8.5 Hz), 7.62 (2H, d, J=8.5 Hz), 3.73 (2H, t, J=6.5 Hz), 3.55 (2H, t, J=6.5 Hz).

Preparation 6

3-Bromo-1-(4-bromophenyl)propan-1-ol

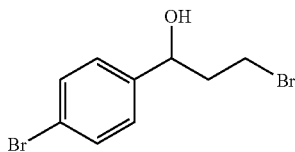

$NaBH_4$ (1.5 g, 39.7 mmol) was added by portions to a solution of 3-bromo-1-(4-bromophenyl)propan-1-one (11.7 g, 40 mmol) (Preparation 5) in MeOH while keeping the temperature below 10° C. After 1 h at RT, 1N aqueous hydrochloric acid was added at 5° C. to pH=1 and the mixture was concentrated in vacuum. The residue was dissolved in water and extracted three times with DCM. The organic layer was dried over $Na_2SO_4$ and concentrated to yield 3-bromo-1-(4-bromophenyl)propan-1-ol as a yellow oil (11.1 g). $^1$H NMR ($CDCl_3$): 7.47 (2H, d, J=8.3 Hz), 7.22 (2H, d, J=8.3 Hz), 4.87 (1H, br s), 3.50–3.62 (1H, m), 3.31–3.42 (1H, m), 2.35 (1H, OH, br s), 2–2.31 (2H, m).

Preparation 7

1-Bromo-4-(3-bromo-1-chloropropyl)benzene

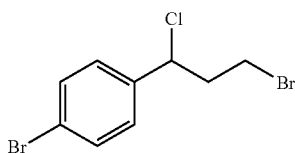

$SOCl_2$ (2.8 ml, 38.6 mmol) was added dropwise to a cooled (−20° C.) solution of 3-bromo-1-(4-bromophenyl)propan-1-ol (11.1 g, 37.8 mmol) (Preparation 6) in a mixture of DCM (110 ml) and pyridine (3 ml, 37.6 mmol). After 2 h at −20° C., the reaction mixture was poured over a mixture of ice and 10% HCl. The organic layer was washed with water, dried over $Na_2SO_4$ and concentrated to yield a yellow oil (12.8 g). Distillation under reduced pressure gave 1-bromo-4-(3-bromo-1-chloropropyl)benzene as a colorless oil (5.1 g, bp=128–130° C./0.5 mm Hg). $^1$H NMR ($CDCl_3$): 7.4–7.55 (2H, m), 7.15–7.3 (2H, m), 5.07 (1H, m), 3.45–3.6 (1H, m), 3.3–3.45 (1H, m), 2.35–2.65 (2H, m).

Preparation 8

3-(3,5-Dichlorophenyl)-2-thioxoimidazolidin-4-one

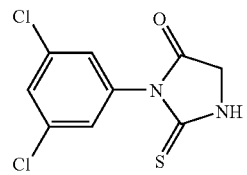

3,5-Dichlorophenylisothiocyanate (5 g, 24.5 mmol) was added by portion to a suspension of the HCl salt of ethyl glycinate (3.4 g, 24.5 mmol) in a mixture of TEA (7.5 ml, 53.9 mmol) and dry DCM (40 ml) while cooling the flask in a water bath. After 60 h at RT, the solution was concentrated to dryness and partitioned between EtOAc and aqueous HCl. The organic layer was washed with water and concentrated. The obtained amorphous solid was washed with $Et_2O$ to yield 3-(3,5-dichlorophenyl)-2-thioxoimidazolidin-4-one as an orange solid (5.3 g). $^1$H NMR ($CDCl_3$): 7.45 (1H, m), 7.25 (2H, m), 4.44 (2H, s).

Preparation 9

3-(3,5-Dichlorophenyl)-4-oxo-2-thioxoimidazolidine-1-carboxylic acid tert-butyl ester

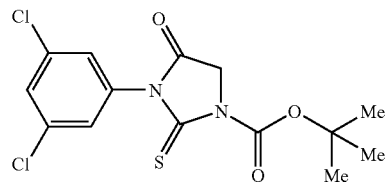

A solution of di-tert-butyldicarbonate (1.04 g, 4.6 mmol) in MeCN (1 ml) was added to a suspension of 3-(3,5-dichlorophenyl)-2-thioxoimidazolidin-4-one (1.04 g, 4 mmol) (Preparation 8) and DMAP (73 mg, 0.6 mmol) in MeCN (5 ml). After 2 h at RT, the mixture was evaporated, taken into EtOAc, washed twice with aqueous $KHSO_4$ and once with water, and finally concentrated to yield 3-(3,5-dichlorophenyl)-4-oxo-2-thioxoimidazolidine-1-carboxylic acid tert-butyl ester (1.04 g) as a brown solid. $^1$H NMR ($CDCl_3$): 7.46 (1H, m), 7.18 (2H, m), 4.54 (2H, s), 1.57 (9H, s).

Preparation 10

(5R*,6S*)-6-(4-Bromophenyl)-3-(3,5-dichlorophenyl)-4-oxo-2-thioxo-1,3-diazaspiro[4.4]nonane-1-carboxylic acid tert-butyl ester

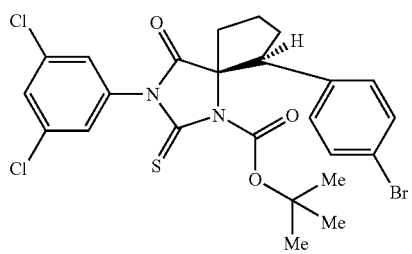

Using the same procedure as in Example 1 starting from 1-bromo-4-(1,4-dibromobutyl)benzene (423 mg, 1.1 mmol)

(Preparation 4) and 3-(3,5-dichlorophenyl)-4-oxo-2-thioxoimidazolidine-1-carboxylic acid tert-butyl ester (361 mg, 1 mmol) (Preparation 9), (5R*,6S*)-6-(4-bromophenyl)-3-(3,5-dichlorophenyl)-4-oxo-2-thioxo-1,3-diazaspiro[4.4]nonane-1-carboxylic acid tert-butyl ester was obtained (54 mg) as a white solid. $^1$H NMR (CDCl$_3$): 7.49 (2H, d, J=8.4 Hz), 7.33 (1H, m), 7.09 (2H, d, J=8.4 Hz), 6.22 (2H, m), 4.17 (1H, dd, J$_1$=13.2 Hz, J$_2$=5.4 Hz), 2.35–2.6 (3H, m), 2–2.35 (3H, m), 1.69 (9H, s).

Preparation 11

3-(3,5-Dichlorophenyl)-2,4-dioxoimidazolidine-1-carboxylic acid tert-butyl ester

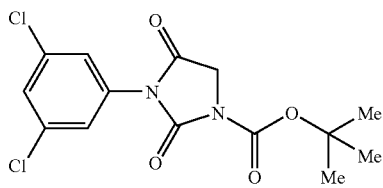

A solution of di-tert-butyldicarbonate (7.72 g, 35.4 mmol) in THF (100 ml) was added to a suspension of 3-(3,5-dichlorophenyl)-imidazolidin-2,4-dione (7.5 g, 30.6 mmol, prepared according to Fujinami et al. cited above) and DMAP (560 mg, 4.6 mmol) in THF (150 ml). After 3 h at RT, the mixture was evaporated, taken into DCM, washed twice with 1N aqueous HCl and once with brine, and finally concentrated to yield 3-(3,5-dichlorophenyl)-2,4-dioxoimidazolidine-1-carboxylic acid tert-butyl ester (10.17 g) as a white solid. $^1$H NMR (CDCl$_3$): 7.40 (1H, m), 7.37 (2H, m), 4.40 (2H, s), 1.58 (9H, s).

Preparation 12

5-(4-Bromophenyl)-5-oxopentanoic acid methyl ester

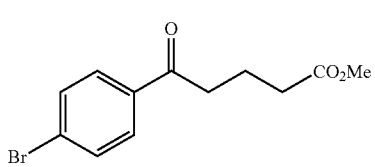

Using the procedure described in Preparations 1 and 2, the above above-titled compound was obtained from glutaric anhydride and bromobenzene. $^1$H NMR (CDCl$_3$): 7.83 (2H, d, J=8.5 Hz), 7.60 (2H, d, J=8.5 Hz), 3.68 (3H, s), 3.03 (2H, t, J=7.1 Hz), 2.45 (2H, t, J=7.1 Hz), 2.06 (2H, m).

Preparation 13

1-(4-Bromophenyl)-pentane-1,5-diol

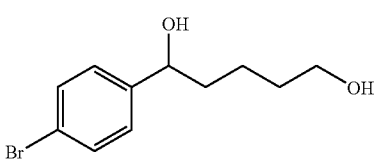

Using the procedure described in Preparation 3,5-(4-bromophenyl)-5-oxopentanoic acid methyl ester (12.8 g, 45 mmol) (Preparation 12) was reduced with LiAlH4 (3.4 g, 90 mmol) to yield 1-(4-bromophenyl)-pentane-1,5-diol (9.4 g) as a yellow oil. $^1$H NMR (CDCl$_3$): 7.42 (2H, d, J=8.3 Hz), 7.15 (2H, d, J=8.3 Hz), 4.56 (1H, m), 3.63 (1H, br s), 3.45–3.6 (2H, m), 2.96 (1H, br s), 1.25–1.9 (6H, m).

Preparation 14

1-Bromo-4-(1,5-dibromopentyl)benzene

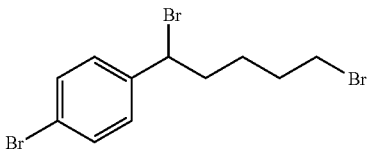

Using the procedure described in Preparation 4,1-(4-bromophenyl)-pentane-1,5-diol (9.4 g, 36.3 mmol) (Preparation 13) was treated with PBr$_3$ (3.4 ml, 36.2 mmol) to yield 1-bromo-4-(1,5-dibromopentyl)benzene (6.1 g) as a yellow oil. $^1$H NMR (CDCl$_3$): 7.47 (2H, d, J=8.5 Hz), 7.26 (2H, d, J=8.5 Hz), 4.88 (1H, t, J=7.5 Hz), 3.38 (2H, t, J=6.6 Hz), 2–2.3 (2H, m), 1.8–2.0 (2H, m), 1.55–1.8 (1H, m), 1.4–1.55 (1H, m).

Preparation 15

(E)-4-[3-Acetyl-1-(3,5-dichlorophenyl)-2,5-dioxoimidazolidin-4-ylidenemethyl]benzonitrile

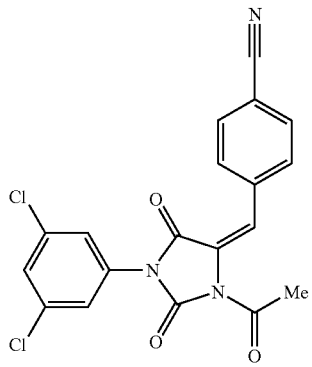

A mixture of 3-(3,5-dichlorophenyl)-2,4-dioxoimidazolidine-1-carboxylic acid tert-butyl ester (3.45 g, 10 mmol) (Preparation 11), 4-cyanobenzaldehyde (1.31 g, 10 mmol) and NaOAc (0.82 g, 10 mmol) was refluxed for 3 h in Ac$_2$O (50 ml). The solid obtained after concentration was taken into a mixture of ice/water and DCM. The organic layer was dried and concentrated to yield a solid (4.4 g) which was chromatographed over silica gel (eluent: DCM) to yield 4-[3-acetyl-1-(3,5-dichlorophenyl)-2,5-dioxoimidazolidin-4-ylidenemethyl]-benzonitrile as a white solid (1.25 g). mp=212° C. $^1$H NMR (CDCl$_3$): 8.52 (1H, s), 7.6–7.75 (4H, m), 7.43 (1H, m), 7.37 (2H, m), 2.78 (3H, s).

Preparation 16

(E)-1-Acetyl-5-(4-bromobenzylidene)-3-(3,5-dichlorophenyl)-imidazolidine-2,4-dione

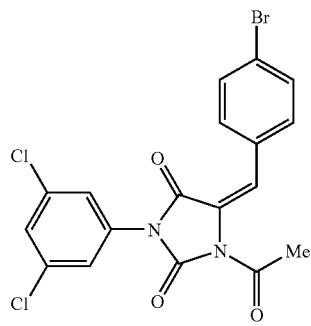

Using the same procedure as in Preparation 15, but starting with Preparation 11 (34.5 g, 0.1 mol) and 4-bromobenzaldehyde (18.5 g, 0.1 mol), the above-titled compound was obtained as a white solid (16.8 g). mp=222° C. $^1$H NMR (DMSO-$d_6$): 8.23 (1H, s), 7.79 (1H, m), 7.55–7.75 (6H, m), 2.65 (3H, s).

Preparation 17

(E)-4-[1-(3,5-dichlorophenyl)-3-methyl-2,5-dioxoimidazolidin-4-ylidenemethyl]-benzonitrile

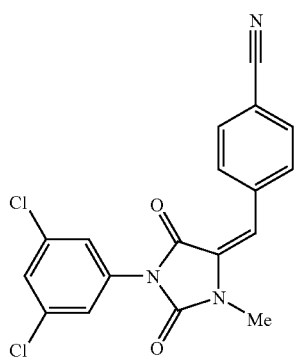

Preparation 17 was obtained via three alternative methods:
(1). A solution of 3-(3,5-dichlorophenyl)-1-methyl-imidazole-2,4-dione (70 g, 0.27 mol), 4-cyanobenzaldehyde (53 g, 0.404 mol), and β-alanine (16.1 g, 0.181 mol) in acetic acid (1 l) was heated for 32 h at reflux. The solution was cooled and kept at 50° C. for one hour. It was then allowed to cool to 35° C., and the insoluble material was recovered by filtration to yield 35.5 g (0.095 mol) of the above-titled compound. Yield 35%. mp=236° C.;
(2). A mixture of 3-(3,5-dichlorophenyl)-1-methyl-imidazole-2,4-dione (1.3 g, 5 mmol), 4-cyanobenzaldehyde (0.98 g, 7.5 mmol, 1.5 eq), pyrrolidine (0.3 ml), anhydrous MgSO$_4$ (0.9 g, 1.5 eq), and EtOH (35 ml) was heated at 78° C. for eighteen hours. The reaction mixture was filtered while hot, and the solid obtained was washed with hot EtOH (2×20 mL), water (2×20 mL), EtOH (2×20 mL) and dried. Yield: 1.58 g;
(3) A mixture of 3-(3,5-dichlorophenyl)-1-methyl-imidazole-2,4-dione (1.3 g, 5 mmol), 4-cyanobenzaldehyde (0.98 g, 7.5 mmol, 1.5 eq), pyrrolidine (0.3 ml) and EtOH (35 ml) was heated at 78° C. for eighteen hours. The reaction mixture was filtered while hot and the solid obtained was washed with hot EtOH (2×20 mL), water (2×20 mL), EtOH (2×20 mL), and dried. Yield: 2.78 g.

Preparation 18

(E)-5-(4-Bromobenzylidene)-3-(3,5-dichlorophenyl)-1-methyl-imidazolidine-2,4-dione

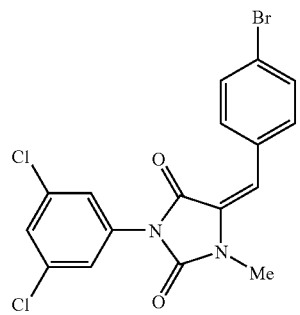

The same procedures as for Preparation 17 were followed, using 4-bromobenzaldehyde in place of 4-cyanobenzaldehyde. $^1$H NMR (DMSO-$d_6$): 7.90 (2H, d), 7.72 (1H, m), 7.58 (4H, m), 6.65 (1H, s), 3.24 (3H, s).

Preparation 19

3-(2,6-Dichloropyridin-4-yl)-1-methyl-imidazolidine-2,4-dione

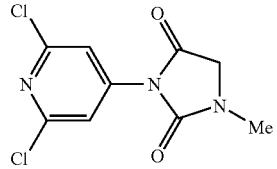

TEA (7.2 ml, 51 mmol) was added to a suspension of the HCl salt of sarcosine ethyl ester (3.4 g, 24.5 mmol) in dry DCM (80 ml). The formed triethylamine hydrochloride was filtered off and rinsed with DCM (20 ml). The filtrate was transferred into a 3-necked round bottom flask and cooled to 5° C. A solution of 2,6-dichloropyridin-4-yl isocyanate (10 g, 53 mmol) in DCM (25 ml) was added dropwise over 10 min while keeping the inner temperature below 10° C. After 96 h at RT, the reaction mixture was refluxed for 10 h. After cooling to RT, the solution was washed with brine, dried over MgSO$_4$ and concentrated. The obtained amorphous solid was chromatographed over silica gel (eluent: cyclohexane/EtOAc 80/20 to 50/50) to yield the above titled compound as a white solid (9.9 g). mp=134° C. $^1$H NMR (CDCl$_3$): 7.75 (2H, s), 4.07 (2H, s), 3.10 (3H, s).

Preparation 20

(E)-4-[1-(2,6-Dichloropyridin-4-yl)-3-methyl-2,5-dioxo-imidazolidin-4-ylidenemethyl]-benzonitrile

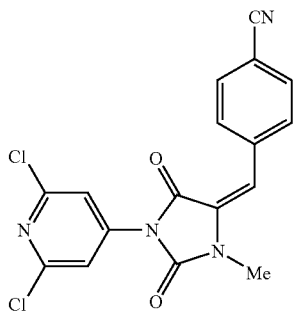

Using the third method described in Preparation 17, Preparation 19 (5 g, 19.2 mmol) was reacted with 4-cyanobenzaldehyde (3.78 g, 28.8 mmol) to yield the above-titled compound as a white solid (5.6 g). mp=230° C. $^1$H NMR (CDCl$_3$): 7.91 (2H, d, J=8.1 Hz), 7.65–7.75 (4H, m), 6.40 (1H, s), 3.37 (3H, s).

Preparation 21

2-Hydroxymethyl-thiazole-5-carboxylic acid

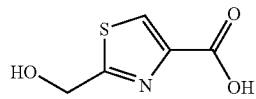

The above-titled compound was synthesized according to the procedure described in DE 2548505 to Roussel-Uclaf (1975) and Chem. Abstr., Vol. 85, #46650. $^1$H NMR (DMSO-d$_6$) 8.27 (1H, s), 4.77 (2H, s).

Preparation 22

Ethyl 2-hydroxymethyl-thiazole-5-carboxylate

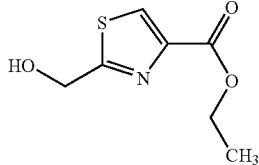

A solution of crude Preparation 21 (300 mg, 1.9 mmol) and concentrated sulfuric acid (2 ml) in EtOH (30 ml) was refluxed during 5 hours. The solvent was evaporated under reduced pressure and the residue was partitioned between aqueous Na$_2$CO$_3$ and EtOAc. The organic layer was washed with water, dried with sodium sulfate, and evaporated under reduced pressure to yield a brown oil (320 mg, 1.7 mmol). $^1$H NMR (CDCl$_3$): 8.28 (1H, s); 4.94 (2H, s); 4.33 (2H, q); 1.35 (3H, t).

Preparation 23

Ethyl 2-bromomethylthiazole 4-carboxylate

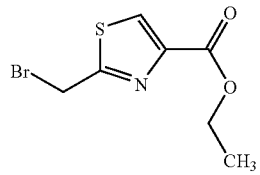

A mixture of ethyl-2-methylthiazole 4-carboxylate (500 mg, 2.9 mmol), N-bromosuccinimide (877 mg, 4.9 mmol), and benzoyl peroxide (5–10 mg) in 1,2-DCE (3 mL) was heated at 70° C. for 85 h. After cooling to room temperature, DCM (10 ml) was added and washed with water (3 times). The organic layer was dried over Na$_2$SO$_4$ and evaporated in vacuo. The residue was purified by preparative chromatography to yield the above-titled compound (58 mg). $^1$H NMR (CDCl$_3$): 8.23 (1H, s), 4.77 (2H, s), 4.43 (2H, q), 1.42 (3H, t).

Preparation 24

Ethyl 5-bromomethylisoxazole-3-carboxylate

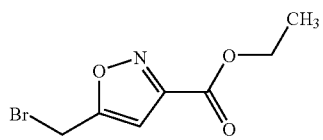

The above-titled compound was synthesized according to the procedure described in Heterocycles, Vol. 23, 3 (1985), at pp. 571–585. $^1$H NMR (CDCl$_3$) 6.74 (1H, s), 4.50 (2H, q), 1.42 (3H, t).

Preparation 25

4-[(5S*,9R*)-7-(2-Bromo-acetyl)-3-(3,5-dichloro-phenyl)-1-methyl-2,4-dioxo-1,3,7-triaza-spiro[4.4]non-9-yl]-benzonitrile

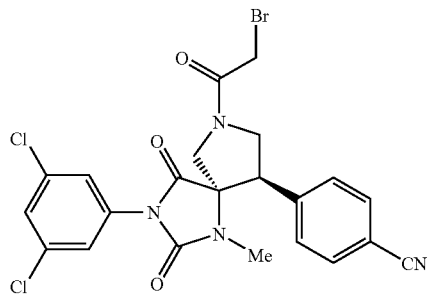

To a solution of Example 15 (373.5 mg, 0.9 mmol) in 7 ml THF, were added TEA (175 μl, 1.26 mmol) and bromoacetyl bromide (94 μl, 1.08 mmol). After 15 min. at RT, the reaction mixture was evaporated to dryness. The residue was partitioned between DCM (20 ml) and 1N HCl solution (10 ml). The DCM layer was washed with brine, dried over sodium sulfate and concentrated to yield 441.3 mg of crude compound. $^1$H NMR (CDCl$_3$): 7.75 (2H, d), 7.45–7.55 (3H, m), 6.7–6.9 (2H, m), 4.55–3.65 (7H, m), 3.25 (3H, m).

Preparation 26

4-Trifluoromethanesulfonyloxy-benzoic acid tert-butyl ester

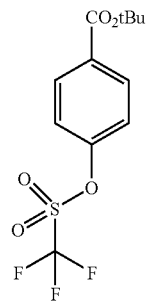

Trifluoromethanesulfonic anhydride (1.04 ml, 6.2 mmol) was added to a cooled (5° C.) solution of tert-butyl 4-hydroxybenzoate (1 g, 5.1 mmol) in a mixture of DCM (25 ml) and TEA (1.1 ml, 7.8 mmol). After 4 h at 5° C., water was added. The organic layer was separated, dried over MgSO$_4$ and concentrated in vacuo. The residue was chromatographed over silica gel (eluent: cyclohexane/iPr$_2$O 95/5) to yield the above-titled compound as a colorless oil (1.45 g). $^1$H NMR (CDCl$_3$): 8.09 (2H, d, J=8.6 Hz), 7.32 (2H, d, J=8.6 Hz), 1.60 (9H, s).

Preparation 27

4-[(5S*,9R*)-9-(4-Cyanophenyl)-3-(3,5-dichlorophenyl)-1-methyl-2,4-dioxo-1,3,7-triazaspiro[4.4]non-7-yl]-benzoic acid tert-butyl ester

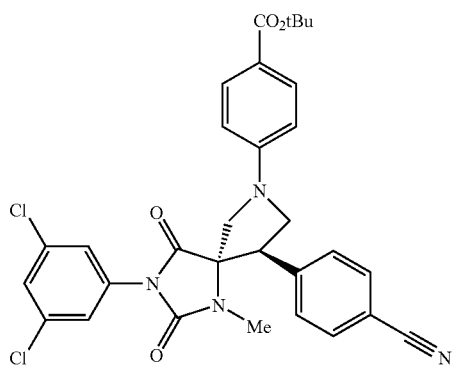

A mixture of Example 15 (300 mg, 0.72 mmol), Cs$_2$CO$_3$ (330 mg, 1 mmol), racemic BINAP (33.7 mg, 0.05 mmol), Pd(OAc)$_2$ (8.1 mg, 0.036 mmol) and Preparation 26 (283 mg, 0.87 mmol) was heated at 80° C. in dioxane (5 ml) for 24 h. After cooling to room temperature, the insoluble salts were removed. The filtrate was concentrated in vacuo and purified using chromatography on silica gel (eluent: DCM) to yield the above-titled compound (139 mg). $^1$H NMR (CDCl$_3$): 7.94 (2H, d, J=8.5 Hz), 7.69 (2H, d, J=8.1 Hz), 7.40 (2H, d, J=8.1 Hz), 6.63 (2H, d, J=8.5 Hz), 3.74.2 (6H, m), 3.26 (3H, s), 1.59 (9H, s).

Preparation 28

5-o-Tolyl-1-trityl-1H-tetrazole

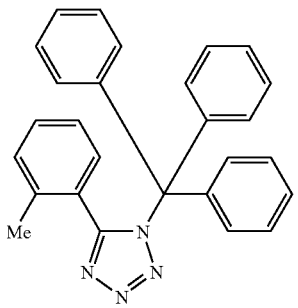

A solution of triphenylmethyl chloride (348 mg, 1.25 mmol, 2 ml DCM) was added dropwise to a mixture of 5-(2-methylphenyl)-1H-tetrazole (200.5 mg, 1.25 mmol) and TEA (174 μl, 1.25 mmol) in 8 ml DCM. The reaction mixture was stirred overnight at RT, then washed with water (10 ml). The organic layer was dried over sodium sulfate and evaporated in vacuo. The residue was purified by preparative chromatography (Cyclohexane/EtOAc 95:5) to yield the above-titled compound (159 mg). $^1$H NMR (CDCl$_3$): 8.1 (1H, d), 7.45–7.1 (18H, m), 2.5 (3H, s).

Preparation 29

5-(2-Bromomethyl-phenyl)-1-trityl-1H-tetrazole

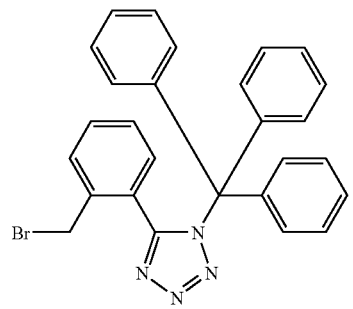

A mixture of preparation 28 (96.9 mg, 0.24 mmol), N-bromosuccinimide (42.7 mg, 0.24 mmol) and benzoyl peroxide (5.8 mg, 0.024 mmol) in 5 ml 1,2-dichloromethane was refluxed under nitrogen for 7 h. The crude titled compound was obtained after evaporation in vacuo and used without purification. $^1$H NMR (CDCl$_3$): 8.15 (1H, m), 7.45–7.1 (18H, m), 4.9 (2H, s).

Preparation 30

6-Hydroxymethyl-nicotinic acid methyl ester

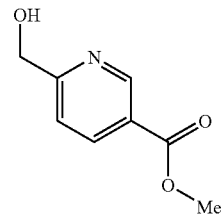

The above-titled compound was synthesized according to procedures described in the literature (see, Y. Langlois and P. Potier, *Tetrahedron*, Vol. 31 (1975), pp. 419422). ¹H NMR (DMSO-d$_6$): 8.98 (1H, s), 8.30 (2H,d), 7.63 (2H,d), 5.64 (1H, t), 4.64 (2H, d), 3.88 (3H, 1H).

Preparation 31

6-Bromomethyl-nicotinic acid methyl ester

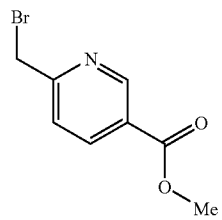

Phosphorus tribromide (1.4 g; 5.32 mmol) was added slowly to a cooled solution (ice/water/sodium chloride bath) of Preparation 30 (1 g, 5.7 mmol) in toluene (100 ml). The reaction mixture was allowed to warm to RT overnight and then refluxed for one hour. The reaction mixture was cooled to RT and DCM was added. The organic layer was washed with a saturated aqueous solution of sodium bicarbonate, then with water, dried over sodium sulfate, and concentrated under reduced pressure to yield an oil (m=0.99 g, yield 76%) which was used without further purification. ¹H NMR (CDCl$_3$):9.18(1H, s); 8.35 (1H,d); 7.56 (1H, d); 4.62 (2H, s); 4.00 (3H,s).

Preparation 32

4-(1H-Tetrazol-5-yl)-thiophene-2-carboxaldehyde

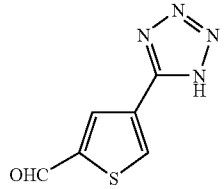

Sodium azide (2.9 g, 44.6 mmol) and TEA hydrochloride (4.13 g, 30 mmol) were added to a solution of 5-formyl-thiophene-3-carbonitrile (2 g, 15 mmol, prepared according to Intern. application WO 02126718) in DMF (50 ml). The solution was refluxed for 12 h. After cooling to RT, water was added and the solution was carefully acidified with HCl. The solution was extracted 3 times with EtOAc. The combined organic layers were dried over Na$_2$SO$_4$ and concentrated under reduced pressure to yield the desired product as a brown solid (540 mg) which was used without further purification.

Example 1

(5R*,6S*)-6-(4-Bromophenyl)-3-(3,5-dichlorophenyl)-1-methyl-1,3-diazaspiro[4.4]nonane-2,4-dione

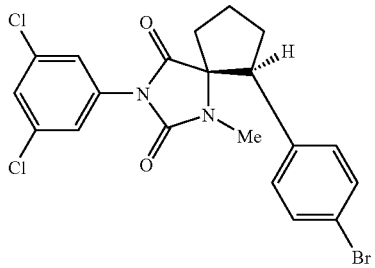

KOH flakes (1.3 g, 23.2 mmol) were added at RT to a solution of 1-bromo-4(1,4-dibromobutyl)benzene (4.08 g, 10.6 mmol) (Preparation 4) and 3-(3,5-dichlorophenyl)-1-methylimidazolidine-2,4-dione (2.5 g, 9.6 mmol, prepared according to Fujinami et al. cited above) in dry DMSO (40 ml). After 30 h at RT, the reaction mixture was poured into water and extracted with EtOAc. The organic layer was dried over Na$_2$SO$_4$ and concentrated to yield an orange oil (4.98 g) which was chromatographed over silica gel (DCM/pentane 50/50) to give 6-(4-bromophenyl)-3-(3,5-dichlorophenyl)-1-methyl-1,3-diazaspiro[4.4]nonane-2,4-dione (2.1 g) as a white solid having the relative stereochemistry depicted above. ¹H NMR (CDCl$_3$): 7.45 (2H, d, J=8.4 Hz), 7.25 (1H, m), 7.03 (2H, d, J=8.4 Hz), 6.65 (2H, m), 3.36 (1H, dd, J$_1$=12.9 Hz, J$_2$=6.2 Hz), 3.13 (3H, s), 2.4–2.65 (1H, m), 1.8–2.4 (5H, m).

Example 2

(1S*,4R*)-1-(4-Bromophenyl)-7-(3,5-dichlorophenyl)-5-methyl-5,7-diazaspiro[3.4]octane-6,8-dione

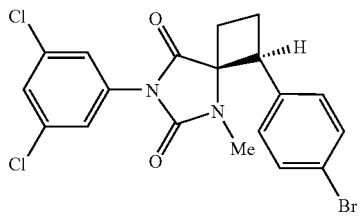

Using the same procedure as in Example 1 starting from 1-bromo-4-(3-bromo-1-chloropropyl)benzene (Preparation 7) and 3-(3,5-dichlorophenyl)-1-methylimidazolidine-2,4-dione, the above titled compound was obtained after reverse phase HPLC purification (gradient from CH$_3$CN/H$_2$O/TFA: 5/95/0.05 to CH$_3$CN/H$_2$O[[FA: 80/20/0.05). ¹H NMR (CDCl$_3$): 7.44 (2H, d, J=8.4 Hz), 7.25 (1H, m), 6.95–7 (4H, m), 4.05 (1H, t, J=10.1 Hz), 3.22 (3H, s), 2.65–2.85 (1H, br q), 2.4–2.65 (2H, m), 2.1–2.3 (1H, br q).

Example 3

(5R*,6S*)-6-(4-Bromophenyl)-3-(3,5-dichlorophenyl)-1-methyl-1,3-diazaspiro[4.5]decane-2,4-dione

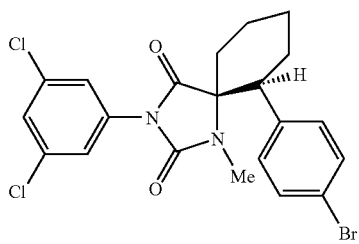

Using the same procedure as in Example 1 starting from 1-bromo-4-(1,5-dibromopentyl)benzene (4.2 g, 10.9 mmol) (Preparation 14) and 3-(3,5-dichlorophenyl)-1-methylimidazolidine-2,4-dione (2.59 g, 10 mmol), the above titled compound was obtained as a white solid (3.1 g, mp=118° C.). ¹H NMR (CDCl$_3$): 7.41 (2H, d, J=8.4 Hz), 7.30 (1H, m), 7.00 (2H, d, J=8.4 Hz), 6.90 (2H, m), 3.03 (3H, s), 2.91 (1H, dd, J$_1$=12.9 Hz, J$_2$=3.6 Hz), 2.55 (1H, dq), 2.1–2.3 (1H, m), 1.8–2.05 (5H, m), 1.3–1.6 (1H, m).

Example 4

(5R*,6S*)-6-(4-Bromophenyl)-3-(3,5-dichlorophenyl)-2,4-dioxo-1,3-diazaspiro[4.4]nonane-1-carboxylic acid tert-butyl ester

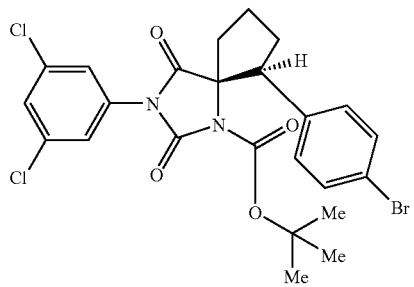

Using the same procedure as in Example 1 starting from 1-bromo-4-(1,4-dibromobutyl)benzene (153 mg, 0.4 mmol) (Preparation 4) and 3-(3,5-dichlorophenyl)-2,4-dioxoimidazolidine-1-carboxylic acid tert-butyl ester (113 mg, 0.33 mmol) (Preparation 11), the above-titled compound was obtained (33 mg) as a white solid. $^1$H NMR (CDCl$_3$): 7.48 (2H, d, J=8.3 Hz), 7.30 (1H, m), 7.07 (2H, d, J=8.3 Hz), 6.52 (2H, m), 4.06 (1H, dd, J$_1$=13.1 Hz, J$_2$=5.5 Hz), 2.35–2.6 (3H, m), 2–2.35 (3H, m), 1.66 (9H, s).

Example 5

(5R*,6S*)-6-(4-Bromophenyl)-3-(3,5-dichlorophenyl)-2-thioxo-1,3-diazaspiro[4.4]nonan-4-one

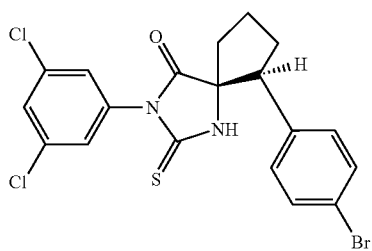

6-(4-Bromophenyl)-3-(3,5-dichlorophenyl)-4-oxo-2-thioxo-1,3-diazaspiro[4.4]nonane-1-carboxylic acid tert-butyl ester (42 mg, 74 μmol) (Preparation 10) was added to a TFA/DCM/H$_2$O (1/1/0.1) solution (1 ml) at RT. After 30 min the reaction mixture was concentrated to give a beige solid which was washed with pentane to yield 6-(4-Bromophenyl)-3-(3,5-dichlorophenyl)-2-thioxo-1,3-diazaspiro[4.4]nonan-4-one (21 mg, beige solid). $^1$H NMR (CDCl$_3$): 8.39 (1H, s), 7.51 (2H, d, J=8.4 Hz), 7.35 (1H, m), 7.19 (2H, d, J=8.4 Hz), 6.44 (2H, m), 3.36 (1H, dd, J$_1$=12.9 Hz, J$_2$=6.1 Hz), 2.45–2.65 (2H, m), 1.8–2.25 (4H, m).

Example 6

(5R*,6S*)-6-(4-Bromophenyl)-3-(3,5-dichlorophenyl)-1,3-diazaspiro[4.4]nonan-2,4-dione

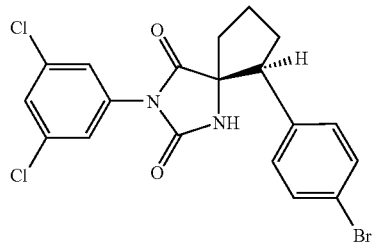

Using the same procedure as in Example 5, (5R*,6S*)-6-(4-bromophenyl)-3-(3,5-dichlorophenyl)-2,4-dioxo-1,3-diazaspiro[4.4]nonane-1-carboxylic acid tert-butyl ester (80 mg, 0.14 mmol) (Example 4) was converted into (5R*,6S*)-6-(4-bromophenyl)-3-(3,5-dichlorophenyl)-1,3-diazaspiro[4.4]nonan-2,4-dione (58 mg). $^1$H NMR (CDCl$_3$): 7.48 (2H, d, J=8.3 Hz), 7.32 (1H, m), 7.18 (2H, d, J=8.3 Hz), 6.68 (2H, m), 6.54 (1H, br s), 3.22 (1H, dd, J$_1$=12.7 Hz, J$_2$=6.2 Hz), 2.45–2.65 (2H, m), 1.9–2.25 (4H, m).

Example 7

4-[(5R*,6S*)-3-(3,5-Dichlorophenyl)-1-methyl-2,4-dioxo-1,3-diazaspiro[4.4]non-6-yl]benzonitrile

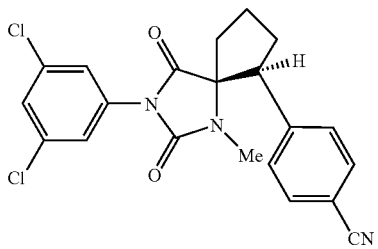

A mixture of 6-(4-bromophenyl)-3-(3,5-dichlorophenyl)-1-methyl-1,3-diazaspiro[4.4]nonane-2,4-dione (1 g, 2.1 mmol) (Example 1) and CuCN (0.45 g, 5 mmol) in NMP was heated to 180° C. for 6 h. After cooling, the reaction mixture was poured on a mixture of ice and ethylene diamine and extracted twice with DCM. The brown residue was chromatographed over silica gel to yield 4-[(5R*,6S*)-3-(3,5-dichlorophenyl)-1-methyl-2,4-dioxo-1,3-diazaspiro[4.4] non-6-yl]benzonitrile as a beige solid. $^1$H NMR (CDCl$_3$): 7.62 (2H, d, J=8.1 Hz), 7.25–7.3 (3H, m), 6.67 (2H, br s), 3.45 (1H, dd, J$_1$=12.8 Hz, J$_2$=6.4 Hz), 3.16 (3H, s), 2.4–2.7 (1H, m), 1.8–2.4 (5H, m).

Example 8

(5R*,6S*)-6-Biphenyl-4-yl-3-(3,5-dichlorophenyl)-1-methyl-1,3-diazaspiro[4.4]nonane-2,4-dione

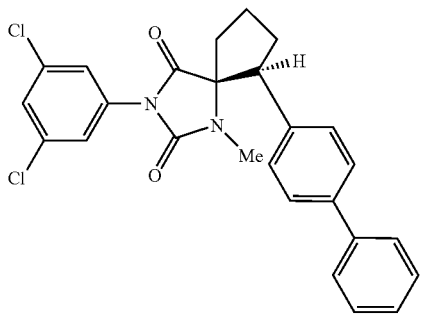

A solution of (5R*,6S*)-6-(4-bromophenyl)-3-(3,5-dichlorophenyl)-1-methyl-1,3-diazaspiro[4.4]nonane-2,4-dione (80 mg, 0.17 mmol) (Example 1), phenylboronic acid (73 mg, 0.6 mmol), (Ph$_3$P)$_4$Pd (20 mg, 0.02 mmol) and K$_2$CO$_3$ (80 mg, 0.6 mmol) in a mixture of DME (1.5 ml) and water (50 µl) was heated at 80° C. for 12 h. The insoluble material was filtered off and the filtrate concentrated. After chromatography, (5R*,6S*)-6-biphenyl-4-yl-3-(3,5-dichlorophenyl)-1-methyl-1,3-diazaspiro[4.4]nonane-2,4-dione (20 mg) was obtained as a white solid. $^1$H NMR (CDCl$_3$): 7.5–7.6 (4H, m), 7.3–7.5 (3H, m), 7.15–7.3 (3H, m), 6.64 (2H, m), 3.45 (1H, dd, J$_1$=12.4 Hz, J$_2$=6.1 Hz), 3.18 (3H, s), 2.5–2.75 (1H, m), 1.8–2.45 (5H, m).

Example 9

(5R*,6S*)-3-(3,5-Dichlorophenyl)-6-(4'-fluorobiphenyl-4-yl)-1-methyl-1,3-diazaspiro[4.4]nonane-2,4-dione

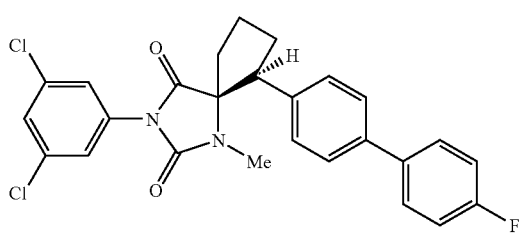

Using the procedure described in Example 8 (5R*,6S*)-6-(4-bromophenyl)-3-(3,5-dichlorophenyl)-1-methyl-1,3-diazaspiro[4.4]nonane-2,4-dione (80 mg, 0.17 mmol) (Example 1) was reacted with 4-fluorophenylboronic acid (71.4 mg, 0.51 mmol) to yield the above-titled compound (12 mg) as a white solid. $^1$H NMR (CDCl$_3$) δ 7.45–7.55 (4H, m), 7.05–7.25 (5H, m), 6.62 (2H, m), 3.46 (1H, dd, J$_1$=12.9 Hz, J$_{2=6.3}$ Hz), 3.18 (3H, s), 2.5–2.75 (1H, m), 1.85–2.45 (5H, m).

Example 10

4-[(5R*,6S*)-3-(3,5-Dichlorophenyl)-1-methyl-2,4-dioxo-1,3-diazaspiro[4.5]dec-6-yl]-benzonitrile

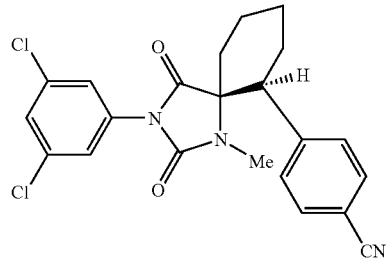

Using the same procedure as in Example 7 starting from (5R*,6S*)-6-(4-bromophenyl)-3-(3,5-dichlorophenyl)-1-methyl-1,3-diazaspiro[4.5]decane-2,4-dione (1 g, 2.3 mmol) (Example 3) and CuCN (0.38 g, 4.2 mmol), the above-titled compound was obtained as a white solid (0.8 g, mp=192° C.). $^1$H NMR (CDCl$_3$): 7.59 (2H, d, J=8.3 Hz), 7.25–7.35 (3H, m), 6.89 (2H, m), 3.04 (3H, s), 3.02 (1H, dd, J$_1$=12.9 Hz, J$_2$=3.5 Hz), 2.6 (1H, dq), 2.1–2.3 (1H, m), 1.8–2.05 (5H, m), 1.3–1.6 (1H, m).

Example 11

4-[(5S*,9R*)-1-Acetyl-7-benzyl-3-(3,5-dichlorophenyl)-2,4-dioxo-1,3,7-triazaspiro[4.4]non-9-yl]-benzonitrile

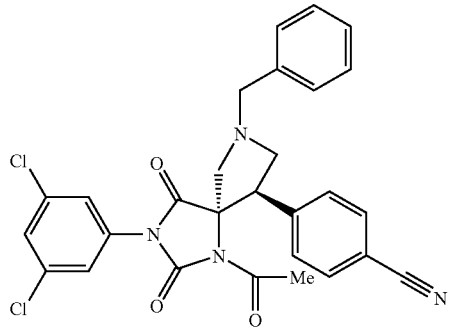

TFA (72 µl, 0.9 mmol) was added to a cooled solution (5° C.) of Preparation 15 (4.15 g, 10.4 mmol) and N-(methoxymethyl)-N-(trimethylsilylmethyl)benzylamine (2.9 g, 11.9 mmol) in DCM (200 ml). After 20 h at RT, the solution was washed with diluted ammonium hydroxide and water. The organic layer was dried over Na$_2$SO$_4$ and concentrated to yield a solid (7.5 g) which was chromatographed over silica gel (eluent: DCM/acetone 95/5) to yield the above-titled compound as a white solid (3.3 g). mp=224° C. $^1$H NMR (CDCl$_3$): 7.65 (2H, d, J=8.3 Hz), 7.45 (2H, d, J=6.9 Hz), 7.25–7.40 (6H, m), 6.53 (2H, d, J=1.5 Hz), 4.62 (1H, dd, J$_1$=10.3 Hz, J$_2$=7 Hz), 4.04 (1H, d, J=13.1 Hz), 3.79 (1H, d, J=1 Hz), 3.70 (1H, d, J=10.2 Hz), 3.40–3.50 (2H, m), 3.02 (1H, d, J=10.2 Hz), 2.71 (3H, s).

Example 12

4-[(5S*,9R*)-7-Benzyl-3-(3,5-dichlorophenyl)-2,4-dioxo-1,3,7-triazaspiro[4.4]non-9-yl]-benzonitrile

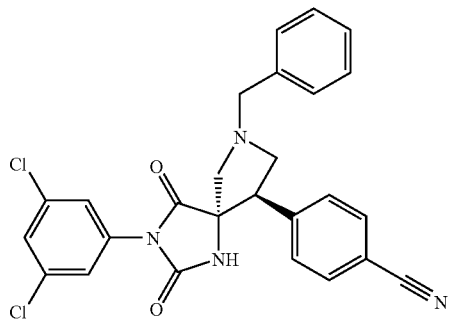

A mixture of Example 11 (8.9 g, 16.7 mmol), TEA (3.8 ml) and pyrrolidine (2.2 ml) in THF (270 ml) was refluxed for 2 h 30 min. The mixture was concentrated in vacuo and taken into DCM, then washed with water. The organic layer was dried over MgSO$_4$ and concentrated. The resulting solid was chromatographed over silica gel (eluent: DCM/MeOH 95/5) to yield the above-titled compound (9.3 g) as a white solid (mp=200° C.). $^1$H NMR (DMSO-d$_6$): 9.32 (1H, br s), 7.84 (2H, d, J=8.2 Hz), 7.60 (1H, m), 7.25–7.45 (7H, m), 6.74 (2H, d, J=1.9 Hz), 3.65–3.9 (3H, m), 3–3.3 (4H, m).

Example 13

(5S*,9R*)-7-Benzyl-9-(4-bromophenyl)-3-(3,5-dichlorophenyl)-1,3,7-triazaspiro[4.4]nonane-2,4-dione

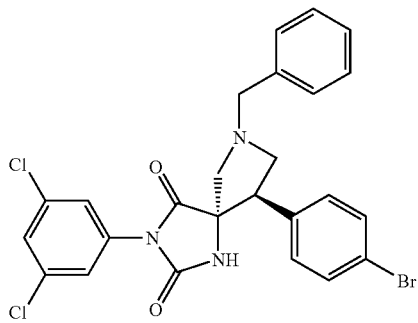

Using the same procedure as in Examples 11 and 12, but using Preparation 16 instead of Preparation 15, the above-titled compound was obtained as a white solid. $^1$H NMR (DMSO-d$_6$): 10.3 (1H, br s), 7.79 (2H, d), 7.62 (3H, m), 7.35–7.55 (3H, m), 7.20 (2H, d, J=8.4 Hz), 6.73 (2H, d, J=1.9 Hz), 4.6–4.9 (3H, m), 4.2–4.4 (2H, m), 3.65–3.8 (1H, m), 3.25–3.5 (1H, m).

Example 14

4-[(5S*,9R*)-7-Benzyl-3-(3,5-dichlorophenyl)-1-methyl-2,4-dioxo-1,3,7-triazaspiro[4.4]non-9-yl]-benzonitrile

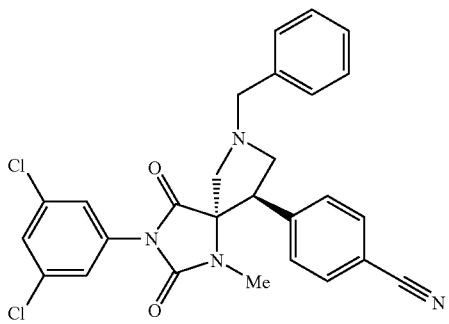

Example 12 (6.25 g, 12.7 mmol) was added to a suspension of NaH (60% in oil, 0.75 g, 18.8 mmol) in dry DMF (60 ml). After 2 h at RT, methyl iodide (1.2 ml, 19.2 mmol) was added. After 48 h, the mixture was concentrated in vacuo and taken into DCM and water. The organic layer was dried over MgSO$_4$ and concentrated to dryness. The residue was chromatographed over silica gel (DCM/acetone 95/5) to yield the above-titled compound (5.1 g) as a white solid (mp=164° C.). $^1$H NMR (CDCl$_3$): 7.61 (2H, d, J=8.1 Hz), 7.25–7.4 (8H, m), 6.65 (2H, d, J=1.6 Hz), 3.7–3.9 (3H, m), 3.1–3.35 (2H, m), 3.22 (3H, s), 2.98 (2H, d, J=10.9 Hz).

Example 15

4-[(5S*,9R*)-3-(3,5-Dichlorophenyl)-1-methyl-2,4-dioxo-1,3,7-triazaspiro[4.4]non-9-yl]-benzonitrile

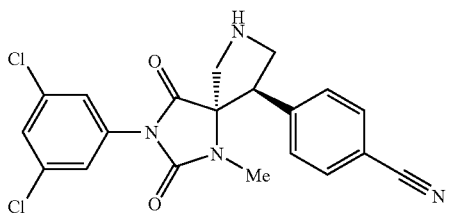

1-Chloroethyl chloroformate (4.4 ml, 40.3 mmol) was added to a cooled (5° C.) solution of Example 14 (5.1 g, 10.1 mmol) in DCM (250 ml). After 1 h at 5° C., the reaction mixture was stirred at RT for 20 h. The solution was concentrated to dryness and then refluxed in MeOH (350 ml) for 3 h. After concentration in vacuo, the oily residue was triturated in Et$_2$O to give the hydrochloride of the desired compound (4.9 g). After basification, the product was chromatographed over silica gel (DCM/MeOH 90/10) to yield the above-titled compound (3.35 g) as an amorphous solid. $^1$H NMR (CDCl$_3$): 7.64 (2H, d, J=8.4 Hz), 7.25–7.32 (3H, m), 6.72 (2H, d, J=2 Hz), 3.6–3.75 (2H, m), 3.35–3.55 (3H, m), 3.20 (3H, s), 2.16 (1H, br s).

Examples 15A and 15B

Compound 15 was resolved into its enantiomers Examples 15A and 15B, below, using HPLC, a Chiralpak-AD column, and solvent system of hexane: MeOH:EtOH or carbondioxide: MeOH. There are numerous alternative ways of resolving compounds of the present invention into their enantiomers.

Example 15a

4-[(5S,9R)-3-(3,5-Dichlorophenyl)-1-methyl-2,4-dioxo-1,3,7-triazaspiro[4.4]non-9-yl]-benzonitrile

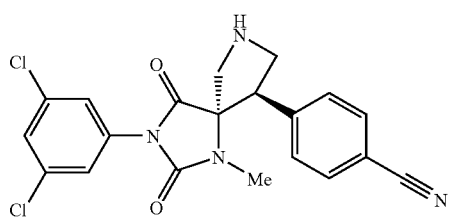

Retention time on a Chiralpak-AD column using carbondioxide: MeOH as eluent is 5.74 minutes. [α]$_D$=+95.2 (c=1, MeOH).

Example 15b

4-[(5R,9S)-3-(3,5-Dichlorophenyl)-1-methyl-2,4-dioxo-1,3,7-triazaspiro[4.4]non-9-yl]-benzonitrile

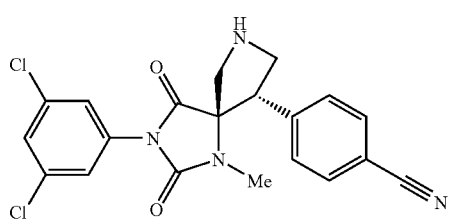

Retention time on a Chiralpak-AD column using carbondioxide: MeOH as eluent is 13.31 minutes. [α]$_D$=−96.5 (c=1, MeOH).

Examples 16–21

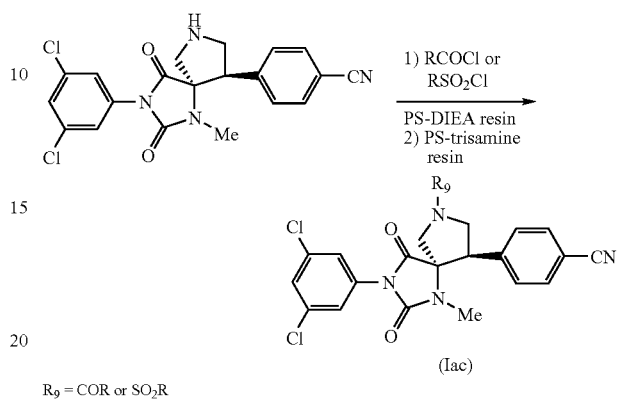

$R_9$ = COR or $SO_2R$

A solution of Example 15 (12.4 mg, 0.03 mmol) in 1 ml THF was added to the acid or sulfonyl chlorides (0.045 mmol). After addition of the supported base PS-DIEA (Argonaut, 3.56 mmol/g, 15 mg, 0.05 mmol), the suspensions were agitated overnight at RT. The scavenger PS-trisamine (Argonaut, 3.65 mmol/g, 36 mg, 0.13 mmol) was then added and the mixtures were filtered after overnight agitation. When necessary, the resulting solutions were treated with PS-Isocyanate (Argonaut, 1.44 mmol/g, 90 mg, 0.13 mmol) overnight. Compounds having the above formula (Iac), wherein $R_9$ has the values listed in Table 1, were obtained after filtration and evaporation to dryness. For each compound the purity and the LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 1

| Ex. | $R_9$ | Quan. (mg) | Purity (%) | Ret. time | Other |
|---|---|---|---|---|---|
| 16 | (sulfonyl-thiophene-triazole with SCH$_3$, N-CH$_3$) | 4.3 | 90 | 2.09 | 688(M + 1) |
| 17 | (phenylsulfonyl) | 13.7 | 100 | 2.24 | $^1$H NMR (CDCl3): 7.9 (2H, d), 7.7–7.5(5H, m), 7.3–7.1(3H, m), 6.6(2H, s), 4.0–3.65 (5H, m), 3.15 (3H, s) |

TABLE 1-continued

| Ex. | R$_9$ | Quan. (mg) | Purity (%) | Ret. time | Other |
|---|---|---|---|---|---|
| 18 | (phenyl ketone) | 9.9 | 87 | 2.07 | |
| 19 | (2-pyridyl ketone) | 11.7 | 74 | 2.08 | |
| 20 | (5-bromo-3-pyridyl ketone) | 1.8 | 95 | 2.1 | |
| 21 | (1,2-dimethylimidazol-4-yl sulfonyl) | 11.3 | 100 | 1.96 | 573(M + 1) |

Examples 22–24

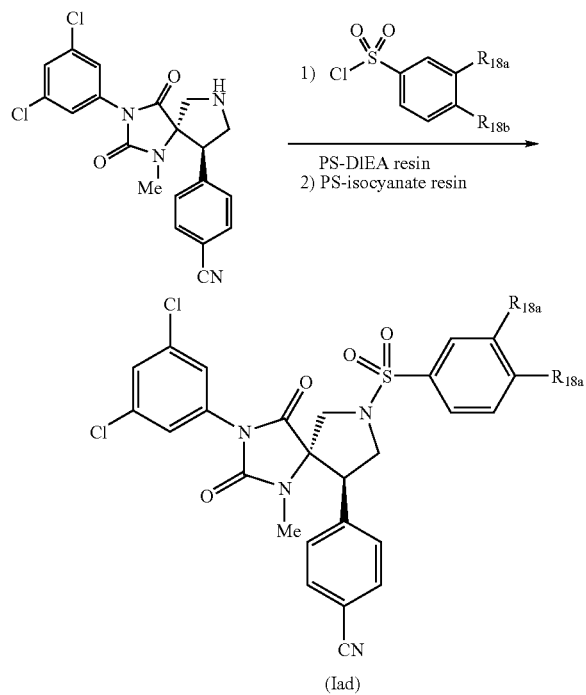

A solution of Example 15 (18.7 mg, 0.045 mmol) in 1 ml THF was added to the sulfonyl chlorides (0.03 mmol). After addition of the supported base PS-DIEA (Argonaut, 3.56 mmol/g, 15 mg, 0.05 mmol), the suspensions were agitated overnight at RT. The scavenger PS-isocyanante (Argonaut, 1.44 mmol/g, 90 mg, 0.13 mmol) was then added and the mixtures were agitated overnight at RT. The desired compounds having formula (Iad), wherein R$_{18a}$ and R$_{18b}$ have the values listed in Table 2, were obtained after filtration and evaporation to dryness. For each compound, the purity and the LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$/TFA (80/20/0.05)).

TABLE 2

| Ex. | R$_{18a}$ | R$_{18b}$ | Quan. (mg) | Purity (%) | Ret. time | Other |
|---|---|---|---|---|---|---|
| 22 | —CO$_2$H | —OH | 7.3 | 80 | 1.72 | |
| 23 | —H | —CO$_2$H | 15.1 | 80 | 2.15 | |
| 24 | —CO$_2$H | —H | 10.8 | 88 | 2.07 | $^1$H NMR (CDCl$_3$): 8.6(1H, s), 8.36(1H, d), 8.1(1H, d), 7.7 (1H, t), 7.6(2H, d), 7.3–7.12(3H, m), 6.7(2H, s), 4.1–3.5(5H, m), 3.2(3H, s) |

Example 24a

3-[(5S,9R)-9-(4-Cyanophenyl)-3-(3,5-dichlorophenyl)-1-methyl-2,4-dioxo-1,3,7-triazaspiro[4,4]nonane-7-sulfonyl]-benzoic acid

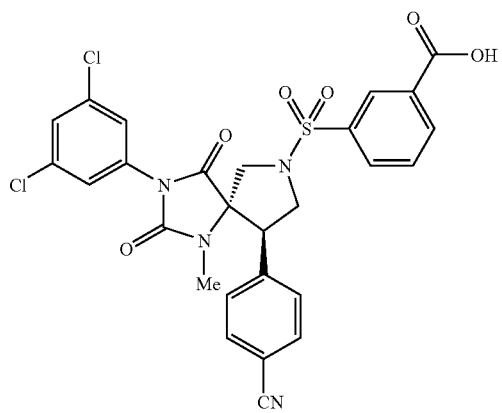

To a mixture of 4-[(5S,9R)-3-(3,5-Dichlorophenyl)-1-methyl-2,4-dioxo-1,3,7-triazaspiro[4.4]non-9-yl]-benzonitrile (Example 15a) (0.11 g, 0.26 mmol) and (3-(Chlorosulfonyl)benzoic acid (0.058 g, 0.26 mmol) in acetone and water (1:1 mL) was added sodium bicarbonate at room temperature. The reaction mixture was stirred at room temperature for forty minutes, quenched by the slow addition of 1N hydrochloric acid (1 mL) and partitioned between DCM (2×20 mL) and brine (25 mL). The DCM layer was dried over sodium sulfate, concentrated and column purified using silica gel chromatography using DCM and MeOH to yield the titled compound (0.12 g). Retention time: 3.39 min. YMC S5 Combiscreen ODS 4.6×50 mm (4 minute gradient). Solvent A=10% MeOH, 90% water and 0.2% phosphoric acid. Solvent B=90% MeOH, 10% water and 0.2% phosphoric acid.

Example 24b

3-[(5R,9S)-9-(4-Cyanophenyl)-3-(3,5-dichlorophenyl)-1-methyl-2,4-dioxo-1,3,7-triazaspiro[4.4]nonane-7-sulfonyl]-benzoic acid

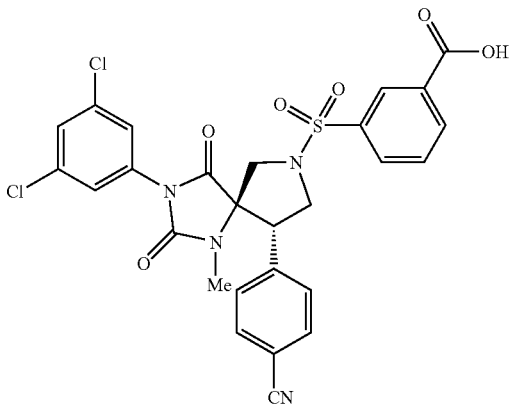

Example 24b was made in a similar fashion to what is described in Example 24a starting from 4-[(5R,9S)-3-(3,5-dichlorophenyl)-1-methyl-2,4-dioxo-1,3,7-triazaspiro[4.4]non-9-yl]-benzonitrile (0.404 g, 0.97 mmol) (Example 15b) to yield 0.331 g of the titled compound. Retention time: 3.36 min. YMC S5 ODS 4.6×50 mm (4 minute gradient). Solvent A=10% MeOH, 90% water and 0.2% phosphoric acid. Solvent B=90% MeOH, 10% water and 0.2% phosphoric acid.

Examples 25–36

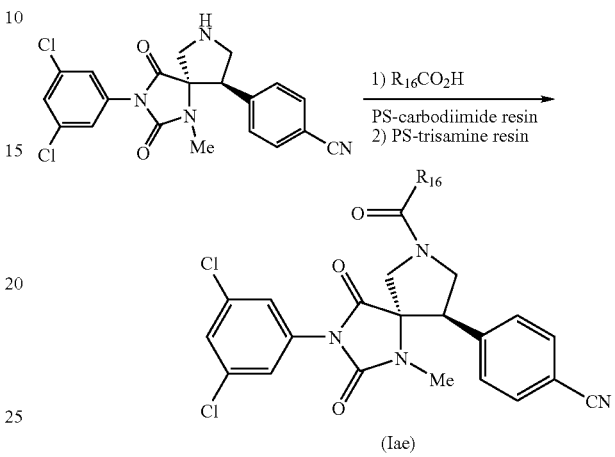

To a suspension of PS-carbodiimide (Argonaut, 0.96 mmol/g, 74 mg, 0.071 mmol) in 0.33 ml of hydroxyazabenzotriazole solution (150 mM DCM {25% DMF}, 0.05 mmol), were added 0.5 ml of the acid solutions (66 mM DCM {20% DMF}, 0.033 mmol) and 0.25 ml of a solution of Example 15 (120 mM DCM {20% DMF}, 0.03 mmol). After 24 h at RT, the mixtures were treated with PS-trisamine (Argonaut, 3.65 mmol/g, 65 mg, 0.24 mmol) overnight. After evaporation to dryness of the filtered off solutions, compounds having the formula (Iae), wherein $R_{16}$ has the values listed in Table 3, were obtained by SCX cartridge purification. For the N-Boc and/or $CO_2tBu$ protected acids, the compounds were first treated with DCM/TFA (1:1) solution for 2 h at RT.

TABLE 3

| Ex. | $R_{16}$ | Quantity (mg) | Purity (%) | Retention time | MS (M + 1) |
|---|---|---|---|---|---|
| 25 | 3-aminophenyl | 14.3 | 95 | 1.83 | 534 |
| 26 | 4-aminophenyl | 15.7 | 95 | 1.88 | 534 |
| 27 | morpholinyl | 14.8 | 95 | 1.73 | 528 |

TABLE 3-continued

| Ex. | R16 | Quantity (mg) | Purity (%) | Retention time | MS (M + 1) |
|---|---|---|---|---|---|
| 28 | 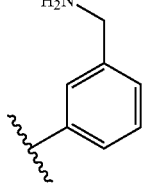 | 15.6 | 96 | 1.76 | 548 |
| 29 | 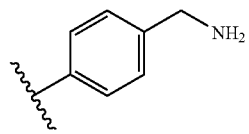 | 15 | 95 | 1.75 | 548 |
| 30 | 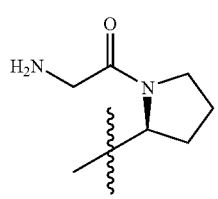 | 16 | 90 | 1.75 | 569 |
| 31 | 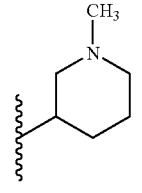 | 15.5 | 97 | 1.76 | 540 |
| 32 | 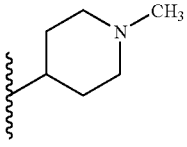 | 14.4 | 97 | 1.73 | 540 |
| 33 | 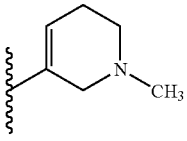 | 9.7 | 81 | 1.75 | 538 |
| 34 | 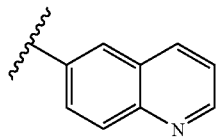 | 14.1 | 95 | 1.87 | 570 |
| 35 | 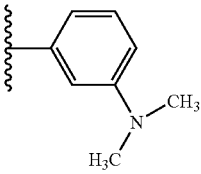 | 21 | 90 | 1.97 | 562 |
| 36 | 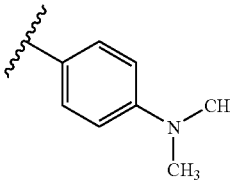 | 19.4 | 94 | 2.11 | 562 |

Example 37

5-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid

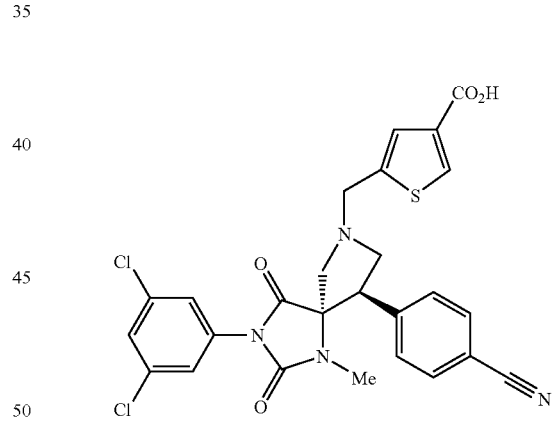

5-Formyl-3-thiophenecarboxylic acid (45 mg, 0.29 mmol) was added to a suspension of sodium sulfate (100 mg) and Example 15 (100 mg, 0.24 mmol) in 1,2-DCE (4 ml). After 20 h at room temperature, sodium triacetoxyborohydride (75 mg, 0.34 mmol) was added, and the reaction mixture was stirred at room temperature for 24 h. Water was then added, and the reaction mixture was acidified by bubbling $SO_2$ through it. The organic layer was separated and the aqueous layer extracted twice with DCM. The combined organic layers were washed with water, dried over sodium sulfate, and concentrated. The obtained solid was crystallized in MeOH to yield the desired compound as white crystals (120 mg). mp=188° C.

Example 37a

5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid

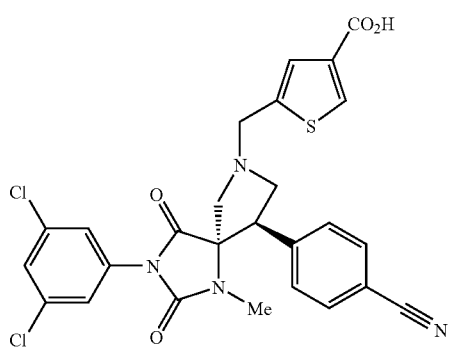

To a solution of 4-[(5S,9R)-3-(3,5-Dichlorophenyl)-1-methyl-2,4-dioxo-1,3,7-triazaspiro[4.4]non-9-yl]-benzonitrile (0.1 g, 0.24 mmol) (Example 15a) in 1,2-DCE (4 mL) were sequentially added 5-Formyl-3-thiophenecarboxylic acid (0.045 g, 0.29 mmol) and sodium sulfate (150 mgs) under a nitrogen atmosphere at room temperature. The contents were stirred at room temperature for twenty hours and sodium triacetoxyborohydride (0.075 g, 0.336 mmol) was added. The reaction was allowed to continue at room temperature for six hours and quenched by the addition of water (15 m]L). DCM (15 mL) was added, and sulfurdioxide gas was bubbled through the reaction mixture for ten minutes and the contents transferred into a separating funnel. The organic layer was separated, washed with brine (2×20 µL), dried over sodium sulfate, concentrated under reduced pressure and purified by silica gel column chromatography using DCM and MeOH to yield 0.1 g of the titled compound. Retention time: 3.09 min. YMC S5 Combiscreen 4.6×50 mm (4 minute gradient). Solvent A=10% MeOH, 90% water and 0.2% phosphoric acid. Solvent B=90% MeOH, 10% water and 0.2% phosphoric acid.

Example 37b

5-[(5R,9S)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid

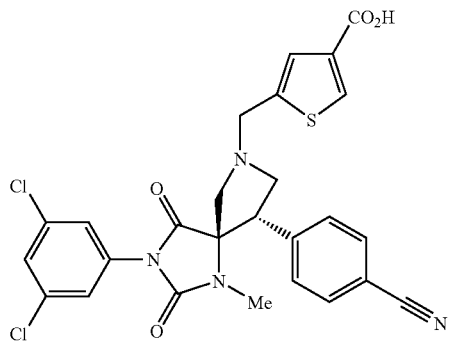

Example 37b was made in a similar fashion to what is described for Example 37a, starting from 4-[(5R,9S)-3-(3,5-Dichlorophenyl)-1-methyl-2,4-dioxo-1,3,7-triazaspiro[4.4]non-9-yl]-benzonitrile (0.1 g, 0.24 mmol) (Example 15b). Yield=0.091 g. Retention time: 3.68 min. YMC S5 ODS 4.6×50 mm (4 minute gradient). Solvent A=10% MeOH, 90% water and 0.2% phosphoric acid. Solvent B=90% MeOH, 10% water and 0.2% phosphoric acid.

Examples 38–48

(Iac)

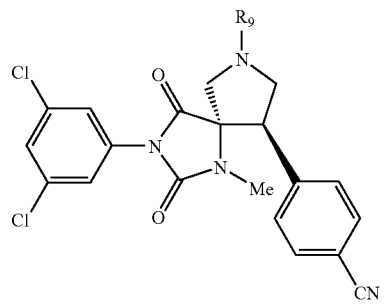

Compounds having the formula (Iac) were prepared, wherein $R_9$ has the values listed in Table 4A, using the same procedure as for Example 37, starting from Example 15 and the appropriate aldehydes or ketones.

TABLE 4A

| Ex. # | $R_9$ | Compound Name | Data |
|---|---|---|---|
| 38 | ![structure: HO-C(=O)-thiophene-CH3 with CH2 linker] | 2-[(5S*,9R*)-9-(4-Cyanophenyl)-3-(3,5-dichlorophenyl)-1-methyl-2,4-dioxo-1,3,7-triazaspiro[4.4]non-7-ylmethyl]-5-methyl-thiophene-3-carboxylic acid | White solid. mp = 150° C. |

TABLE 4A-continued

| Ex. # | R9 | Compound Name | Data |
|---|---|---|---|
| 39 | (thiophene with COOH) | 2-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid | White solid. mp = 160° C. |
| 40 | (morpholinyl-benzyl) | 4-[(5S*,9R*)-3-(3,5-Dichlorophenyl)-1-methyl-7-(2-morpholin-4-yl-benzyl)-2,4-dioxo-1,3,7-triazaspiro[4.4]non-9-yl]-benzonitrile | White solid. mp = 207° C. |
| 41 | (6-methylpyridin-2-ylmethyl) | 4-[(5S*,9R*)-3-(3,5-Dichlorophenyl)-1-methyl-7-(6-methyl-pyridin-2-ylmethyl)-2,4-dioxo-1,3,7-triazaspiro[4.4]non-9-yl]-benzonitrile | Beige solid. mp = 80–84° C. |
| 42 | (thiophene with COOH) | 5-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-2-carboxylic acid | Off-white solid. mp = 270° C. |
| 43 | (phenoxyacetic acid) | {4-[(5S*,9R*)-9-(4-Cyanophenyl)-3-(3,5-dichlorophenyl)-1-methyl-2,4-dioxo-1,3,7-triazaspiro[4.4]non-7-ylmethyl]-phenoxy}-acetic acid | Off-white solid. mp = 246° C. |
| 44 | (furan with COOH) | 5-[(5S*,9R*)-9-(4-Cyanophenyl)-3-(3,5-dichlorophenyl)-1-methyl-2,4-dioxo-1,3,7-triazaspiro[4.4]non-7-ylmethyl]-furan-2-carboxylic acid | Off-white solid. mp = 179–182° C. |
| 45 | (thiophen-3-ylmethyl) | 4-[(5S*,9R*)-3-(3,5-Dichlorophenyl)-1-methyl-2,4-dioxo-7-thiophen-3-ylmethyl-1,3,7-triazaspiro[4.4]non-9-yl]-benzonitrile | Beige solid. mp = 206° C. |
| 46 | (pyrrole with COOH) | 5-[(5S*,9R*)-9-(4-Cyanophenyl)-3-(3,5-dichlorophenyl)-1-methyl-2,4-dioxo-1,3,7-triazaspiro[4.4]non-7-ylmethyl]-1H-pyrrole-2-carboxylic acid | Off-white solid. mp = 166° C. |
| 47 | (pyrrole with COOH) | 4-[(5S*,9R*)-9-(4-Cyanophenyl)-3-(3,5-dichlorophenyl)-1-methyl-2,4-dioxo-1,3,7-triazaspiro[4.4]non-7-ylmethyl]-1H-pyrrole-2-carboxylic acid | White solid. mp = 180° C. |

TABLE 4A-continued

| Ex. # | R9 | Compound Name | Data |
|---|---|---|---|
| 48 | 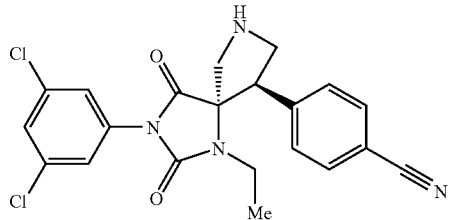 | 4-[(5S*,9R*)-7-Cyclobutyl-3-(3,5-dichlorophenyl)-1-methyl-2,4-dioxo-1,3,7-triazaspiro[4.4]non-9-yl]-benzonitrile | White solid. mp = 194° C. |

Example 49

4-[(5S*,9R*)-7-Benzyl-3-(3,5-dichlorophenyl)-1-ethyl-2,4-dioxo-1,3,7-triazaspiro[4.4]non-9-yl]-benzonitrile Using the same procedure as in Example 14, by reaction of Example 12 (100 mg, 0.2 mmol) with ethyl iodide (25 μl, 0.31 mmol), the above-titled compound was obtained (70 mg) as a white solid (mp=216° C. after crystallization from isopropyl ether). $^1$H NMR (CDCl$_3$): 7.61 (2H, d, J=8.3 Hz), 7.25–7.4 (8H, m), 6.67 (2H, d, J=1.5 Hz), 3.5–4 (5H, m), 3.25–3.35 (2H, m), 2.95–3.2 (2H, m), 1.48 (3H, t, J=7.2 Hz).

Example 50

4-[(5S*,9R*)-3-(3,5-Dichlorophenyl)-1-ethyl-2,4-dioxo-1,3,7-triazaspiro[4.4]non-9-yl]-benzonitrile

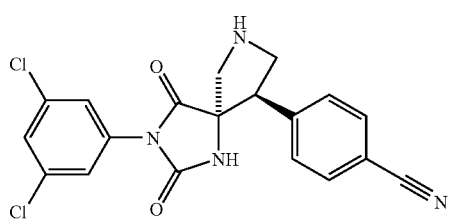

Using the procedure described in Example 15, Example 49 (3.5 g, 6.74 mmol) was reacted with 1-chloroethyl chloroformate (7.3 ml, 66.9 mmol) to yield the above-titled compound (1.8 g) as an amorphous white solid. $^1$H NMR (CDCl$_3$): 7.63 (2H, d, J=8.3 Hz), 7.25–7.35 (3H, m), 6.73 (2H, d, J=1.5 Hz), 3.35–3.85 (7H, m), 1.17 (1H, br s), 1.45 (3H, t, J=7.1 Hz).

Example 51

4-[(5S*,9R*)-3-(3,5-Dichlorophenyl)-2,4-dioxo-1,3,7-triazaspiro[4.4]non-9-yl]-benzonitrile

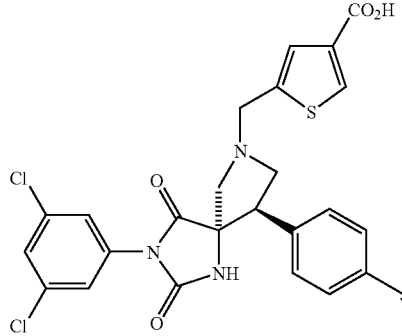

Using the procedure described in Example 15, Example 12 (5 g, 10.17 mmol) was reacted with 1-chloroethyl chloroformate (11.1 ml, 101.7 mmol) to yield the above-titled compound (2 g) as white crystals, mp=198° C. $^1$H NMR (DMSO-d$_6$): 9.08 (1H, br s), 7.84 (2H, d, J=8.2 Hz), 7.61 (1H, m), 7.45 (2H, d, J=8.2 Hz), 6.79 (2H, d, J=1.9 Hz), 3.1–3.85 (5H, m).

Example 52

5-[(5S*,9R*)-9-(4-Cyanophenyl)-3-(3,5-dichlorophenyl)-1-ethyl-2,4-dioxo-1,3,7-triazaspiro[4.4]non-7-ylmethyl]-thiophene-3-carboxylic acid

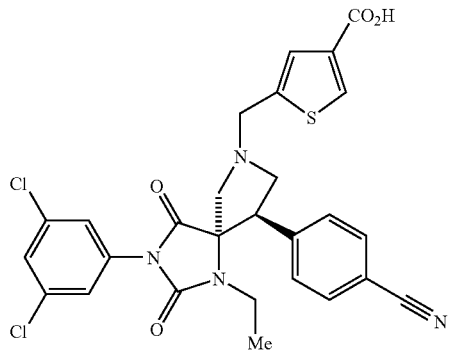

Using the procedure described for Example 37 by reaction of 5-Formyl-3-thiophenecarboxylic acid (40 mg, 0.26 mmol) with Example 50 (100 mg, 0.23 mmol), the above-titled compound was obtained as a white solid (93 mg) after crystallization from MeOH. mp=182° C.

Example 53

5-[(5S*,9R*)-9-(4-Cyanophenyl)-3-(3,5-dichlorophenyl)-2,4-dioxo-1,3,7-triazaspiro[4.4]non-7-ylmethyl]-thiophene-3-carboxylic acid Using the procedure described for Example 37 by reaction of 5-Formyl-3-thiophenecarboxylic acid (43 mg, 0.27 mmol) with Example 51 (100 mg, 0.25 mmol), the above-titled compound was obtained as a white solid (92 mg), mp=260° C.

Example 54

3-[(5S*,9R*)-9-(4-Cyanophenyl)-3-(3,5-dichlorophenyl)-1-ethyl-2,4-dioxo-1,3,7-triazaspiro[4.4]nonane-7-sulfonyl]-benzoic acid

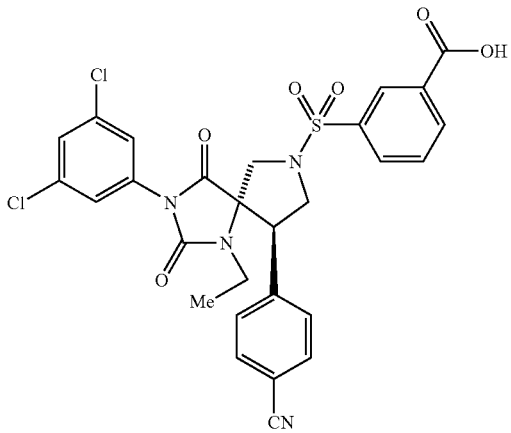

To a mixture of Example 50 (100 mg, 0.23 mmol) and 3-(chlorosulfonyl) benzoic acid (57 mg, 0.26 mmol) in THF (5 ml) was added DIEA (45 μl, 0.26 mmol) at room temperature. The reaction mixture was stirred at room temperature for 24 hours then concentrated under vacuum. The residue was partitioned between EtOAc and water. The pH was adjusted to pH=2. The aqueous layer was extracted twice with EtOAc. The combined organic layers were washed with brine, dried over $Na_2SO_4$ and concentrated. The obtained solid was chromatofraphed over silica gel using DCM/MeOH (80/20) to yield the above-titled compound (63 mg), mp=145° C. $^1$H NMR (CDCl$_3$): 8.63 (1H, s), 8.41 (1H, d, J=7.5 Hz), 8.17 (1H, d, J=7.4 Hz), 7.77 (1H, t, J=7.7 Hz), 7.62 (2H, d, J=7.7 Hz), 7.18–7.26 (3H, m), 6.60 (2H, s), 3.4–4.2 (7H, m), 1.45 (3H, t, J=6.8 Hz).

Example 55

3-[(5S*,9R*)-9-(4-Cyanophenyl)-3-(3,5-dichlorophenyl)-2,4-dioxo-1,3,7-triazaspiro[4.4]nonane-7-sulfonyl]-benzoic acid

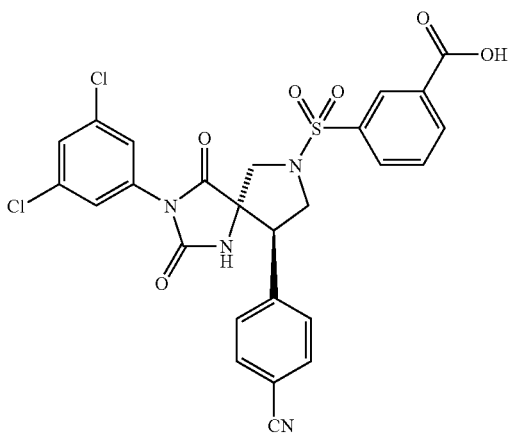

Using the procedure of Example 54, Example 51 (100 mg, 0.25 mmol) was reacted with 3-(chlorosulfonyl) benzoic acid (61 mg, 0.27 mmol) in THF (5 ml) in the presence of DIEA (48 μl, 0.27 mmol) at room temperature to yield the above-titled compound (84 mg), mp=150° C. $^1$H NMR (DMSO-d$_6$): 9.14 (1H, br s), 8.35 (1H, s), 8.29 (1H, d, J=7.7 Hz), 8.18 (1H, d, J=7.7 Hz), 7.83 (3H, m), 7.61 (1H, s), 7.38 (2H, d, J=8.1 Hz), 6.69 (2H, d, J=1.5 Hz), 3.65–4.05 (4H, m), 3.5–3.6 (1H, m).

Example 56

4-[(5S*,9R*)-7-Benzyl-9-(4-cyanophenyl)-3-(3,5-dichlorophenyl)-2,4-dioxo-1,3,7-triazaspiro[4.4]non-1-yl]-butyric acid ethyl ester hydrochloride

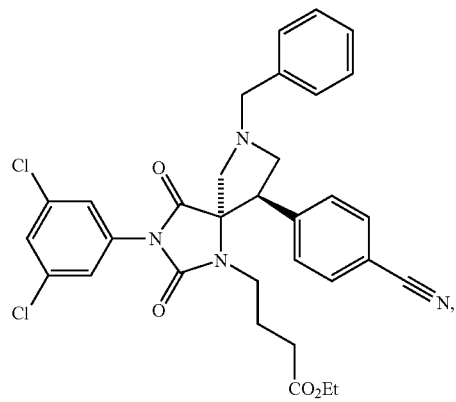

Using the procedure described for Example 14, Example 12 (100 mg, 0.2 mmol) was deprotonated with NaH (60% in oil, 12 mg, 0.3 mmol) in DMF (1 ml) and reacted with ethyl 4-bromobutyrate (44 μl, 0.3 mmol) to yield the above-titled compound which was converted into its hydrochloride by precipitation in Et$_2$O/HCl gas (86 mg). LC Mass: retention time=2.27 min, $M_{obs}$=604 (M−1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

Examples 57–58

Using the procedure described for Example 56, the following two Examples were prepared by reaction of Example 12 (100 mg) with ethyl 5-bromo-valerate and ethyl 6-bromocaproate, respectively.

Example 57

5-[(5S*,9R*)-7-Benzyl-9-(4-cyanophenyl)-3-(3,5-dichlorophenyl)-2,4-dioxo-1,3,7-triazaspiro[4.4]non-1-yl]-pentanoic acid ethyl ester hydrochloride

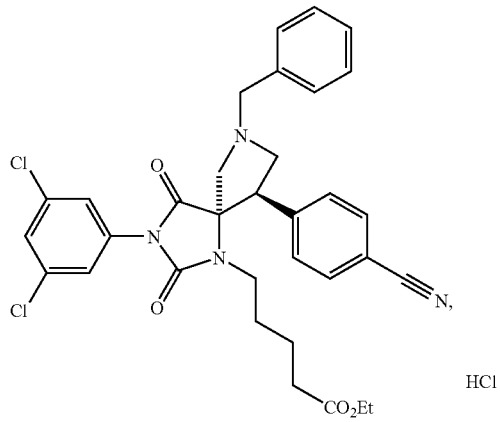

Yield: 55 mg. LC Mass: retention time=2.40 min, $M_{obs}$=618 (M−1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O$/TFA (80/20/0.05)).

Example 58

6-[(5S*,9R*)-7-Benzyl-9-(4-cyanophenyl)-3-(3,5-dichlorophenyl)-2,4-dioxo-1,3,7-triazaspiro[4.4]non-1-yl]-hexanoic acid ethyl ester hydrochloride

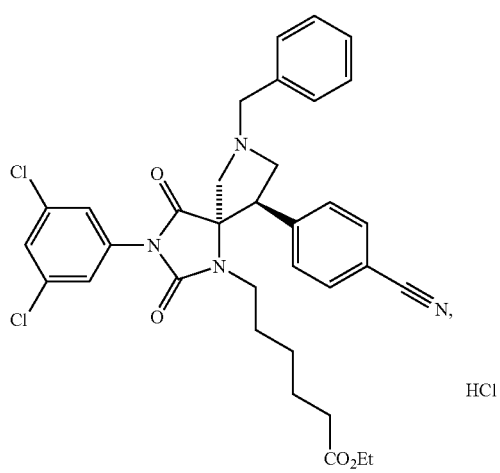

Yield: 54 mg. LC Mass: retention time=2.29 min, $M_{obs}$=632 (M−1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O$/TFA (80/20/0.05)).

Examples 59–61

ω(5S*,9R*)-7-Benzyl-9-(4-cyanophenyl)-3-(3,5-dichlorophenyl)-2,4-dioxo-1,3,7-triazaspiro[4.4]non-1-yl]-alkanoic acids

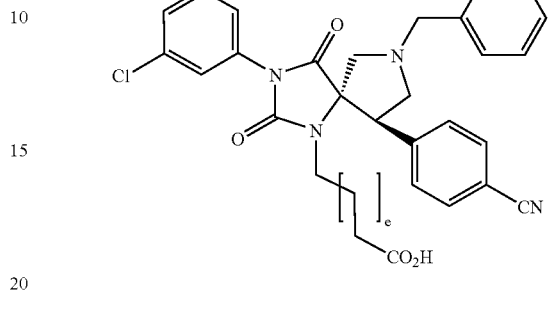

(Iaf)

To prepare Example 59 [the compound of formula (Iaf) wherein e is 1], LiOH (1N, 600 μl) was added to a suspension of Example 56 (60.3 mg, 0.1 mmol) in THF (2.5 ml). The solution was heated at 50° C. for 3 h. After concentration in vacuo, the resulting product was taken into water which was acidified by bubbling gaseous $SO_2$. Example 59 precipitated out of the solution, was collected by filtration, and dried. Yield: 17 mg, mp=148° C. Example 60 (e=2), and Example 61 (e=3), were prepared using the same method, starting from Examples 57 and 58, respectively. For Example 60: (35.4 mg). Yield: 22 mg, white crystals, mp=250° C.; for Example 61: (32.5 mg). Yield: 17.4 mg. $^1H$ NMR (CDCl$_3$): 7.61 (2H, d, J=8 Hz), 7.25–7.40 (8H, m), 6.64 (2H, s), 3.8–4.0 (3H, m), 3.5–3.8 (2H, m), 3.3–3.5 (2H, m), 3–3.3 (2H, m), 2.32.45 (2H, m), 1.7–1.9 (4H, m), 1.45–1.55 (2H, m).

Example 62

[(5S*,9R*)-9-(4-Cyanophenyl)-3-(3,5-dichlorophenyl)-1-methyl-2,4-dioxo-1,3,7-triazaspiro[4.4]non-7-yl]-acetic acid ethyl ester

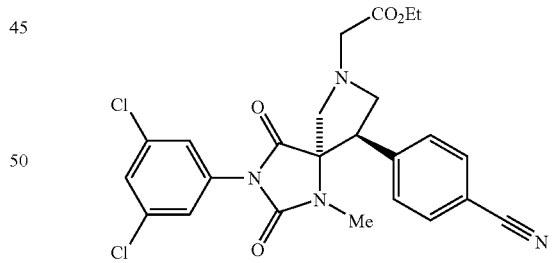

A mixture of Example 15 (100 mg, 0.24 mmol), ethyl bromo acetate (29 μl, 0.26 mmol) and $K_2CO_3$ (36.6 mg, 0.26 mmol) in toluene (2 ml) was heated to 100° C. for 5 h. After cooling to room temperature, the precipitate (unreacted starting material) was removed by filtration. The filtrate was concentrated and purified by chromatography over silica gel (eluent: DCM then acetone) to yield the above-titled compound as an oil (47.2 mg). $^1H$ NMR (CDCl$_3$): 7.63 (2H, d, J=8.3 Hz), 7.25–7.30 (3H, m), 6.68 (2H, d, J=1.5 Hz), 4.23 (2H, q, J=7.1 Hz), 3.89 (1H, dd, $J_1$=11.7 Hz, $J_2$=6.3 Hz), 3.55–3.65 (2H, m), 3.3–3.5 (3H, m), 3.26 (3H, s), 3.05 (1H, d, J=10.8 Hz), 1.31 (3H, t, J=7.1 Hz).

Example 63

[(5S*,9R*)-9-(4-Cyanophenyl)-3-(3,5-dichlorophenyl)-1-methyl-2,4-dioxo-1,3,7-triazaspiro[4.4]non-7-yl]-acetic acid tert-butyl ester

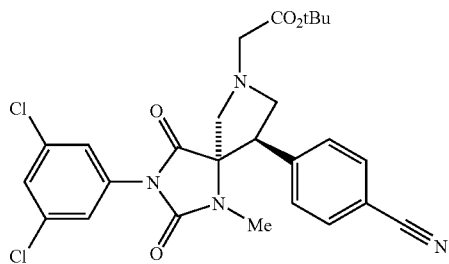

A mixture of Example 15 (2 g, 4.81 mmol), tert-butyl bromo acetate (2.4 ml, 16.3 mmol) and K₂CO₃ (2.4 g, 17.4 mmol) in dioxane (40 ml) was refluxed for 24 h. After cooling to room temperature, the solution was concentrated and partitioned between DCM/water. The aqueous layer was extracted twice with DCM. The combined organic layers were washed with brine, dried over Na₂SO₄, and concentrated to an oil which was purified by chromatography over silica gel (eluent: DCM/acetone 95/5) to yield the above-titled compound as an amorphous solid (1.56 g). $^1$H NMR (CDCl₃): 7.62 (2H, d, J=8.3 Hz), 7.25–7.30 (3H, m), 6.67 (2H, d, J=1.5 Hz), 3.80–3.95 (1H, dd), 3.55–3.65 (2H, m), 3.3–3.5 (3H, m), 3.26 (3H, s), 3.02 (1H, d, J=10.9 Hz), 1.50 (9H, s).

Example 64

[(5S*,9R*)-9-(4-Cyanophenyl)-3-(3,5-dichlorophenyl)-1-methyl-2,4-dioxo-1,3,7-triazaspiro[4.4]non-7-yl]-acetic acid

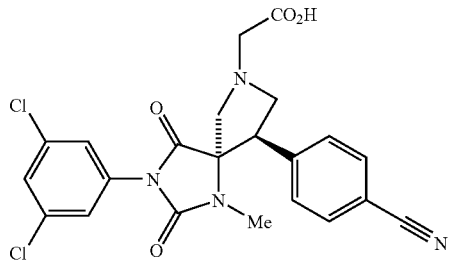

Trifluoroacetic acid (4.8 ml, 59 mmol) was added to a solution of Example 63 (1.56 g, 2.95 mmol) in DCM (40 ml). The solution was refluxed for 3 h. It was then concentrated in vacuo and partitioned between EtOAc/aqueous NH₄OH. The aqueous layer was acidified to pH=2 with SO₂. The white precipitate was separated by filtration. The aqueous layer was extracted with DCM and concentrated to give white crystals which where combined with the precipitated solid to give, after drying, the above-titled compound (1.04 g), mp=220° C.

Example 65

(5S*,9R*)-7-Benzyl-9-(4-bromophenyl)-3-(3,5-dichlorophenyl)-1-methyl-1,3,7-triazaspiro[4.4]nonane-2,4-dione

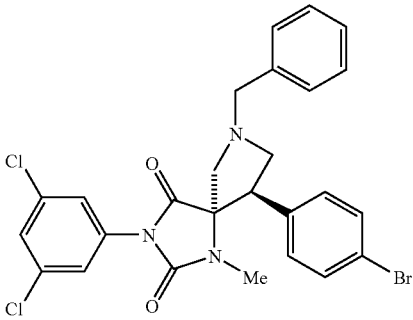

Using the procedure described for Example 14, Example 13 (5.45 g, 10 mmol) was reacted with methyl iodide (0.93 ml, 14.9 mmol) to yield the above-titled compound as a white solid (4.15 g), mp=204° C.

Example 66

(5S*,9R*)-7-Benzyl-3-(3,5-dichlorophenyl)-1-methyl-9-(4-pyrimidin-5-yl-phenyl)-1,3,7-triazaspiro[4.4]nonane-2,4-dione

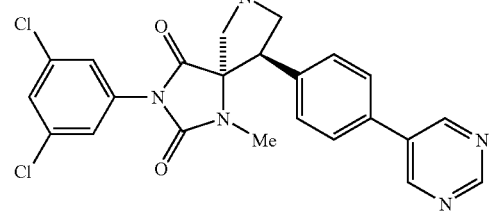

A mixture of Example 65 (2 g, 3.58 mmol), 5-trimethylstannyl-pyrimidine (1.3 g, 5.35 mmol, prepared according to patent WO 95/06636) and tetrakis(triphenylphosphine)palladium(0) (620 mg, 0.54 mmol) in toluene (50 ml) was refluxed for 10 h under a nitrogen atmosphere. After cooling to room temperature, the insoluble material was filtered off and washed twice with toluene. The toluene layers were concentrated in vacuo. The resulting orange oil (3.1 g) was chromatographed over silica gel (eluent: EtOAc) to yield the above-titled compound as a white solid after crystallization from MeOH (430 mg), mp=228° C.

Example 67

(1S*,9R*)-3-(3,5-Dichlorophenyl)-1-methyl-9-(4-pyrimidin-5-yl-phenyl)-1,3,7-triazaspiro[4.4]nonane-2,4-dione

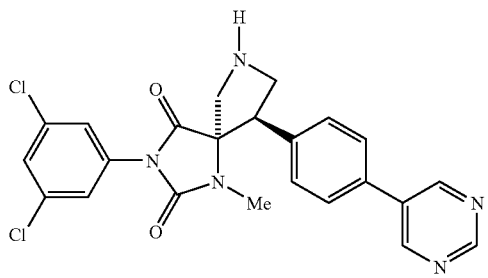

Using the procedure described for Example 15, Example 66 (358 mg, 0.64 mmol) was reacted with 1-chloroethyl chloroformate (0.28 ml, 2.6 mmol) in DCM (3 ml) to yield the above-titled compound as an amorphous soild (88 mg). $^1$H NMR (CDCl$_3$): 9.22 (1H, s), 8.94 (2H, s), 7.58 (2H, d, J=8.2 Hz), 7.35 (2H, d, J=8.2 Hz), 7.21 (1H, m), 6.66 (2H, d, J=1.6 Hz), 3.3–3.9 (5H, m), 3.23 (3H, s), 2.63 (1H, br s).

Example 68

5-[(5S*,9R*)-3-(3,5-Dichlorophenyl)-1-methyl-2,4-dioxo-9-(4-pyrimidin-5-yl-phenyl)-1,3,7-triazaspiro[4.4]non-7-ylmethyl]-thiophene-3-carboxylic acid

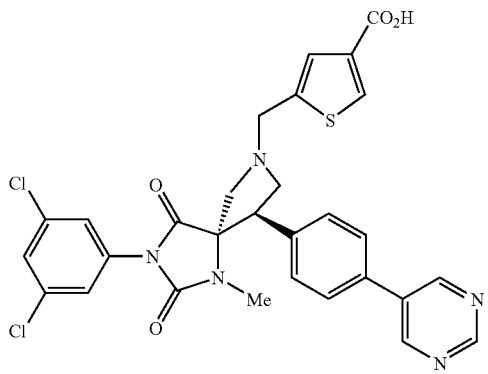

Using the procedure described for Example 37, Example 67 (37.3 mg, 0.08 mmol) was reacted with 5-formyl-3-thiophenecarboxylic acid (15 mg, 0.096 mmol) in DCE (3 ml) to yield the above-titled compound as an amorphous soild (43 mg). $^1$H NMR (CDCl$_3$): 9.23 (1H, s), 8.96 (2H, s), 8.16 (1H, s), 7.45–7.65 (3H, m), 7.29 (2H, d, J=8.1 Hz), 7.20 (1H, m), 6.65 (2H, d, J=1.4 Hz), 3.9–4.2 (3H, m), 3.2–3.5 (3H, m), 3.23 (3H, s), 3.10 (1H, d, J=11.1 Hz).

Example 69

(5S*,9R*)-3-(3,5-Dichlorophenyl)-1-methyl-7-(1-methylethyl)-9-(4-pyrimidin-5-yl-phenyl)-1,3,7-triazaspiro[4.4]nonane-2,4-dione

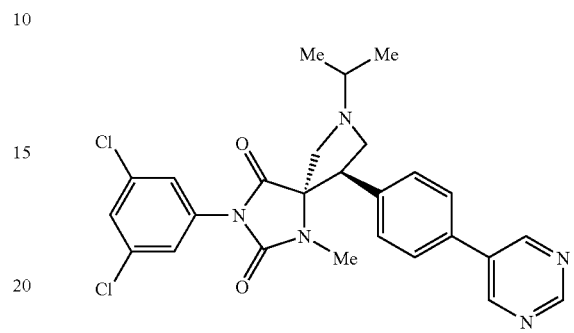

A mixture of Example 67 (49.7 mg, 0.11 mmol), 2-iodo propane (26 μl, 0.26 mmol) and K$_2$CO$_3$ (36 mg, 0.26 mmol) was heated at 80° C. for 25 h in acetonitrile (2 ml). After cooling to room temperature, the insoluble salts were removed and the filtrate concentrated to dryness. The residue was partitioned between DCM/water. The organic layer was concentrated in vacuo and chromatographed over silica gel (eluent: DCM/MeOH 95/5) to yield the above-titled compound as an amorphous white solid (38.1 mg). $^1$H NMR (CDCl$_3$): 9.21 (1H, s), 8.92 (2H, s), 7.56 (2H, d, J=8.0 Hz), 7.33 (2H, d, J=8.0 Hz), 7.20 (1H, m), 6.61 (2H, d, J=1.5 Hz), 3.90 (1H, dd, J$_1$=12 Hz, J$_2$=6 Hz), 3.4–3.5 (2H, m), 3.2–3.4 (1H, m), 3.28 (3H, s), 3.09 (1H, d, J=11 Hz), 2.79 (1H, m), 1.23 (6H, m).

Examples 70–74

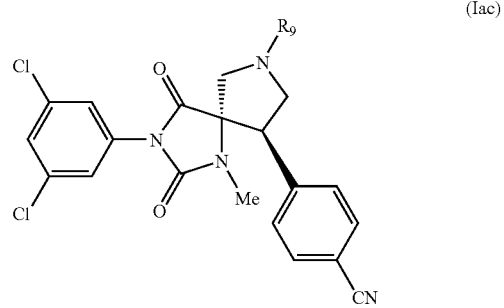

(Iac)

Compounds having the formula (Iac) were prepared, wherein R$_9$ has the values listed in Table 4B, using the same procedure as for Example 69, starting from Example 15 and the appropriate iodo compound.

TABLE 4B

| Ex. # | R9 | Compound Name | Data |
|---|---|---|---|
| 70 | H3C−CH(−)−CH3 (isopropyl) | 4-[(5S*,9R*)-3-(3,5-Dichlorophenyl)-1-methyl-7-(1-methylethyl)-2,4-dioxo-1,3,7-triazaspiro[4.4]non-9-yl]-benzonitrile | White solid (180 mg), mp = 208° C. |
| 71 | cyclopentyl | 4-[(5S*,9R*)-7-Cyclopentyl-3-(3,5-Dichlorophenyl)-1-methyl-2,4-dioxo-1,3,7-triazaspiro[4.4]non-9-yl]-benzonitrile | White solid (132 mg), mp = 178° C. |
| 72 | −CH2CH(CH3)2 (isobutyl) | 4-[(5S*,9R*)-3-(3,5-Dichlorophenyl)-1-methyl-7-(2-methylpropyl)-2,4-dioxo-1,3,7-triazaspiro[4.4]non-9-yl]-benzonitrile | White solid recrystallized from MeOH (105 mg), mp = 170° C. |
| 73 | −(CH2)3C(O)OCH3 | 4-[(5S*,9R*)-9-(4-Cyanophenyl)-3-(3,5-dichlorophenyl)-1-methyl-2,4-dioxo-1,3,7-triazaspiro[4.4]non-7-yl]-butyric acid methyl ester | Yellow oil (199 mg). |
| 74 | −(CH2)4C(O)OCH3 | 5-[(5S*,9R*)-9-(4-Cyanophenyl)-3-(3,5-dichlorophenyl)-1-methyl-2,4-dioxo-1,3,7-triazaspiro[4.4]non-7-yl]-pentanoic acid methyl ester | Yellow oil (192 mg). |

Example 75

4-[(5S*,9R*)-9-(4-Cyanophenyl)-3-(3,5-dichlorophenyl)-1-methyl-2,4-dioxo-1,3,7-triazaspiro[4.4]non-7-yl]-butyric acid

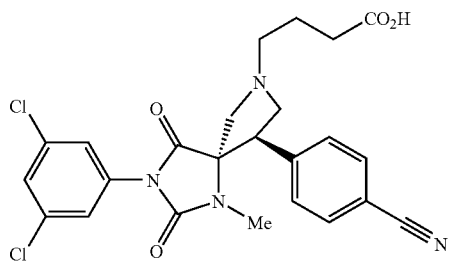

NaOH (2 ml, 1N) was added to a solution of Example 73 (199 mg, 0.48 mmol) in THF (2 ml). After 3 h at room temperature the solution was acidified with SO2 and concentrated in vacuo. The resulting solid was partitioned between water and EtOAc. The organic layer was dried over Na2SO4 and concentrated to yield the above-titled compound which was crystallized from MeOH (23 mg), mp=228° C.

Example 76

5-[(5S*,9R*)-9-(4-Cyanophenyl)-3-(3,5-dichlorophenyl)-1-methyl-2,4-dioxo-1,3,7-triazaspiro[4.4]non-7-yl]-pentanoic acid

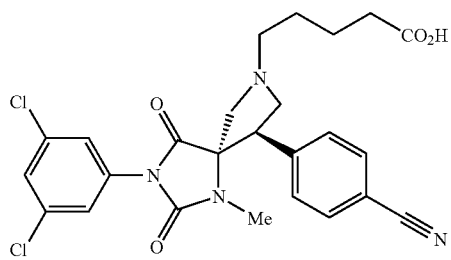

Using the same procedure as for Example 75, Example 74 (190 mg, 0.36 mmol) was converted into the above-titled compound (152 mg). White solid, mp=240° C.

Example 77

[(5S*,9R*)-9-(4-Cyanophenyl)-3-(3,5-dichlorophenyl)-1-methyl-2,4-dioxo-1,3,7-triazaspiro[4.4]non-7-yl]-acetamide

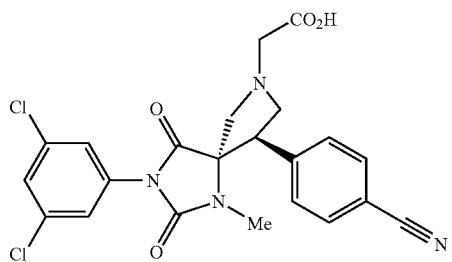

Isobutyl chloroformate (27 µl, 0.21 mmol) was added to a cooled (5° C.) suspension of Example 64 (90 mg, 0.19 mmol) and N-methyl morpholine (23 µl, 0.2 mmol) in DCM (4 ml). After 1 h, ammonia (420 µl, 0.5 M in dioxane, 0.21 mmol) was added. After 1 h at 5° C. and 3 h at RT, water (2 ml) was added. The organic layer was separated and the aqueous layer extracted with DCM. The combined organic layers were concentrated in vacuo and the resulting material was purified by chromatography over silica gel (eluent: DCM/MeOH 95/5) to yield the above-titled compound as a solid (49.6 mg). $^1$H NMR (CDCl$_3$): 7.64 (2H, d, J=8.2 Hz), 7.25–7.30 (3H, m), 6.84 (1H, br s), 6.65 (2H, d, J=1.5 Hz), 6.18 (1H, br s), 3.87 (1H, t), 3.4–3.5 (5H, m), 3.24 (3H, s), 3.15 (1H, d, J=10.9 Hz).

Examples 78–79

Using the experimental procedure described in Example 77, the following Examples were prepared.

Example 78

[(5S*,9R*)-9-(4-Cyanophenyl)-3-(3,5-dichlorophenyl)-1-methyl-2,4-dioxo-1,3,7-triazaspiro[4.4]non-7-yl]-N-methyl-acetamide

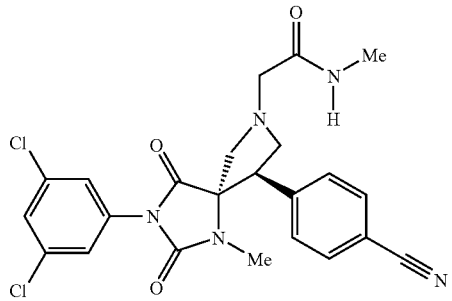

Using Example 64 (90 mg, 0.19 mmol) and methylamine (105 µl, 2 M in THF, 0.21 mmol), the above-titled compound was obtained as a solid (47.1 mg). $^1$H NMR (CDCl$_3$): 7.64 (2H, d, J=8.1 Hz), 7.27–7.31 (3H, m), 6.95 (1H, br s), 6.65 (2H, d, J=1.3 Hz), 3.87 (1H, t), 3.35–3.5 (5H, m), 3.25 (3H, s), 3.16 (1H, d, J=10.9 Hz), 2.89 (3H, d, J=4.9 Hz).

Example 79

[(5S*,9R*)-9-(4-Cyanophenyl)-3-(3,5-dichlorophenyl)-1-methyl-2,4-dioxo-1,3,7-triazaspiro[4.4]non-7-yl]-N,N-dimethyl-acetamide

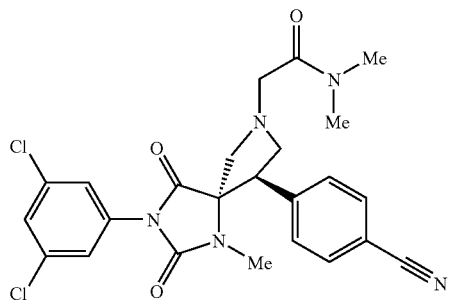

Using Example 64 (90 mg, 0.19 mmol) and dimethylamine (105 µl, 2 M in THF, 0.21 mmol), the above-titled compound was obtained as a solid (78.8 mg). $^1$H NMR (CDCl$_3$): 7.62 (2H, d, J=8 Hz), 7.15–7.3 (3H, m), 6.68 (2H, d, J=1.8 Hz), 3.92 (1H, dd, J$_1$=11.4 Hz, J$_2$=6.2 Hz), 3.6–3.75 (2H, m), 3.35–3.5 (3H, m), 3.26 (3H, s), 3.05 (3H, s), 2.99 (3H, s), 2.95–3.0 (1H, m).

Example 80

N-{5-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-3-carbonyl}-methanesulfonamide

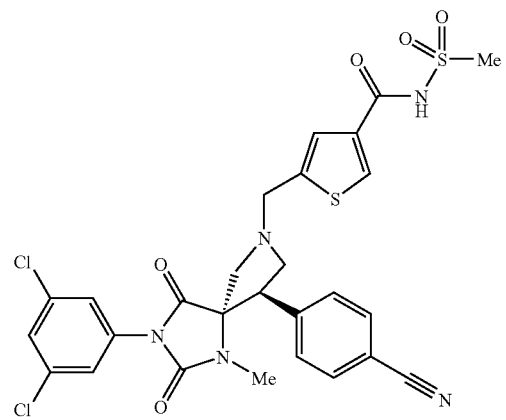

EDCI (84 mg, 0.44 mmol) was added to a solution of Example 37 (100 mg, 0.18 mmol), methanesulfonamide (38 mg, 0.38 mmol), triethylamine (62 µl, 0.43 mmol) and a trace of DMAP in DCM (5 ml) at room temperature. After 48 h, water was added and the mixture was acidified by bubbling SO$_2$. The organic layer was separated and the aqueous layer extracted twice with DCM. The combined organic layers were washed with brine and concentrated in vacuo. The resulting product was chromatographed over silica gel to yield the above-titled compound (38.9 mg) as an amorphous solid along with 55.6 mg of unreacted starting material. $^1$H NMR (CDCl$_3$) δ 8.04 (1H, s), 7.62 (2H, d, J=8 Hz), 7.40 (1H, s), 7.25–7.3 (3H, m), 6.65 (2H, d, J=1.5 Hz), 3.8–4.1 (3H, m), 3.86 (3H, s), 3.3–3.4 (2H, m), 3.3.25 (3H, s), 3.15–3.3 (1H, m), 3.01 (1H, d, J=11 Hz).

Example 81

N-{4-[(5S*,9R*)-9-(4-Cyanophenyl)-3-(3,5-dichlorophenyl)-1-methyl-2,4-dioxo-1,3,7-triazaspiro[4.4]non-7-ylmethyl]-benzoyl}-methanesulfonamide

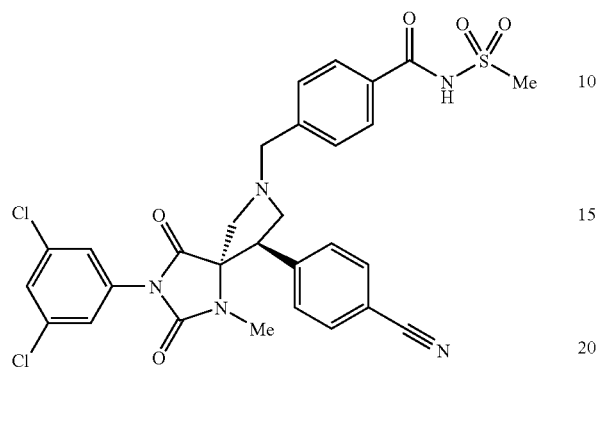

Using the same procedure as in Example 80 by reaction of Example 185 (200 mg, 0.36 mmol) with methanesulfonamide (38.1 mg, 0.4 mmol), the above-titled compound was obtained (64 mg). ¹H NMR (CDCl₃): 7.86 (2H, d, J=8.1 Hz), 7.63 (2H, d, J=8 Hz), 7.55 (2H, d, J=8 Hz), 7.25–7.3 (3H, m), 6.65 (2H, d, J=1.3 Hz), 3.85–4.05 (3H, m), 3.2–3.45 (3H, m), 3.44 (3H, s), 3.24 (3H, s), 3.05 (1H, J=11.1 Hz).

Example 82

4-[(5S*,9R*)-3-(3,5-Dichlorophenyl)-1-methyl-2,4-dioxo-7-pyrimidin-2-yl-1,3,7-triazaspiro[4.4]non-9-yl]-benzonitrile

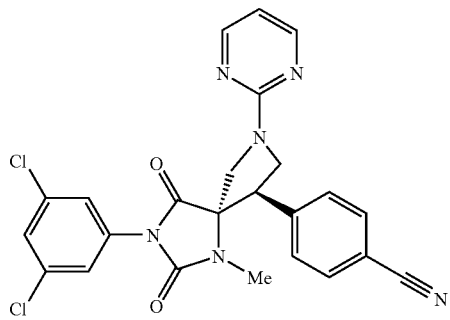

A mixture of Example 15 (100 mg, 0.24 mmol), K₂CO₃ (37 mg, 0.27 mmol) and 2-bromo-pyrimidine (42 mg, 0.27 mmol) was heated at 100° C. in DMF (1 ml) for 20 h. After cooling to room temperature, the insoluble salts were removed and the filtrate was partitioned between water and EtOAc. The aqueous layer was extracted twice with EtOAc. The combined organic layers were washed with brine, concentrated in vacuo and purified using chromatography on silica gel (eluent: DCM/acetone 95/5) to yield the above-titled compound (36.1 mg). White crystals from MeOH, mp=234° C.

Example 83

4-[(5S*,9R*)-7-(6-Chloropyridazin-3-yl)-3-(3,5-dichlorophenyl)-1-methyl-2,4-dioxo-1,3,7-triazaspiro[4.4]non-9-yl]-benzonitrile

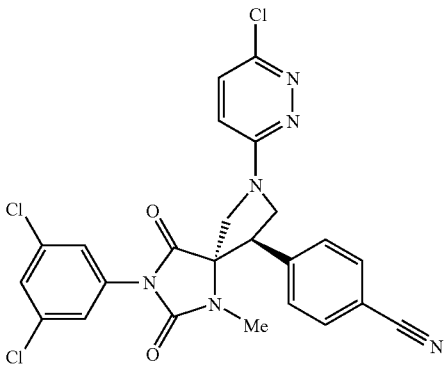

Using the same experimental procedure as in Example 82, Example 15 (100 mg, 0.24 mmol) was reacted with 3,6-dichloropyridazine (39 mg, 0.26 mmol) to yield the above-titled compound (27.1 mg), mp=125° C.

Example 84

4-[(5S*,9R*)-3-(3,5-dichlorophenyl)-1-methyl-2,4-dioxo-7-pyridin-2-yl-1,3,7-triazaspiro[4.4]non-9-yl]-benzonitrile

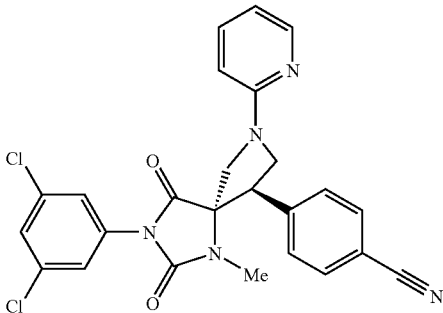

Using the same experimental procedure as in Example 82, Example 15 (100 mg, 0.24 mmol) was reacted with 2-bromopyridine (25 µl, 0.26 mmol) to yield the above-titled compound (30 mg). ¹H NMR (CDCl₃): 8.22 (1H, m), 7.7 (2H, m), 7.55 (1H, m), 7.39 (2H, m), 7.1 (1H, m), 6.79 (2H, d), 6.70 (1H, m), 6.5 (1H, d), 3.95–4.3 (5H, m), 3.24 (3H, s).

Example 85

4-[(5S*,9R*)-1-Acetyl-3-(3,5-dichlorophenyl)-2,4-dioxo-1,3,7-triazaspiro[4.4]non-9-yl]-benzonitrile

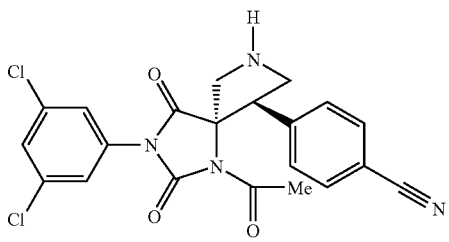

Using the same experimental procedure as in Example 15, Example 11 (533 mg, 1 mmol) was reacted with 1-chloroethyl chloroformate to yield the above-titled compound (76 mg), mp=125° C. $^1$H NMR (CDCl$_3$): 7.66 (2H, d, J=8.3 Hz), 7.25–7.35 (3H, m), 6.52 (2H, d, J=1.5 Hz), 4.10 (1H, dd, J$_1$=11.3 Hz, J$_2$=7.1 Hz), 3.74 (1H, d, J=13.1 Hz), 3.45–3.60 (3H, m), 2.78 (1H, br s), 2.73 (3H, s).

Example 86

4-[(5S*,9R*)-9-(4-Cyanophenyl)-3-(3,5-dichlorophenyl)-1-methyl-2,4-dioxo-1,3,7-triazaspiro[4.4]non-7-yl]-4-oxo-butyric acid

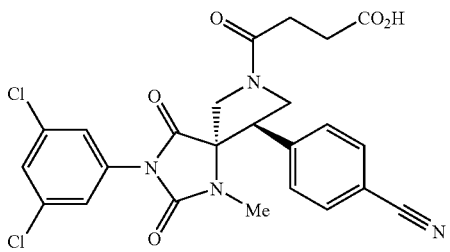

A solution of Example 15 (100 mg, 0.24 mmol) and succinic anhydride (24.1 mg, 0.24 mmol) in DCM (2 ml) was stirred at room temperature for 24 h. After concentration to dryness the above-titled compound was obtained as an amorphous solid (128 mg). LC Mass: retention time=1.87 min, M$_{obs}$=514 (M−1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

Example 87

5-[(5S*,9R*)-9-(4-Cyanophenyl)-3-(3,5-dichlorophenyl)-1-methyl-2,4-dioxo-1,3,7-triazaspiro[4.4]non-7-yl]-5-oxo-pentanoic acid

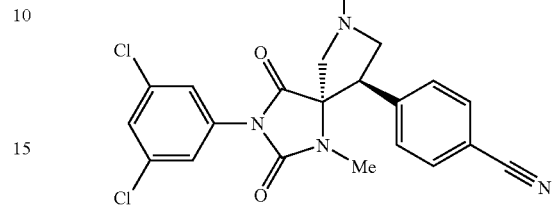

Using the same experimental conditions as in Example 86, Example 15 (100 mg, 0.24 mmol) was reacted with glutaric anhydride (41.5 mg, 0.36 mmol) to yield the above-titled compound as an amorphous solid (132 mg). LC Mass: retention time=1.89 min, M$_{obs}$=528 (M−1) (LCMS conditions: LC Micromass platform (APCI+, DAD (210400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

Example 88

4-[(5S*,9R*)-7-Cyclopropyl-3-(3,5-dichlorophenyl)-1-methyl-2,4-dioxo-1,3,7-triazaspiro[4.4]non-9-yl]-benzonitrile

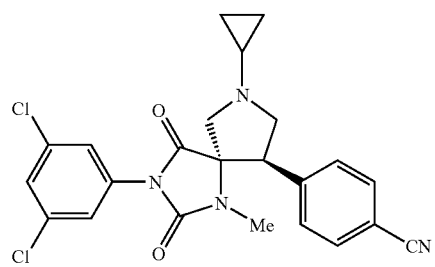

Sodium cyanoborohydride (202 mg, 3.25 mmol) was added to a methanolic solution (10 ml) of 1-ethoxy-1-trimethylsilyloxy-cyclopropane (871 μl, 4.33 mmol), Example 15 (300 mg, 0.72 mmol) and acetic acid (413 μl, 7.2 mmol). The solution was refluxed for 2.5 h, concentrated in vacuo and partitioned between DCM and brine. The aqueous layer was extracted twice with DCM. The combined organic layers were dried over Na$_2$SO$_4$ and concentrated. The resulting product was crystallized from MeOH to yield the above-titled compound as a white solid (107 mg), mp=216° C.

Example 89

4-[(5S*,9R*)-3-(3,5-Dichlorophenyl)-1,7-dimethyl-2,4-dioxo-1,3,7-triazaspiro[4.4]non-9-yl]-benzonitrile

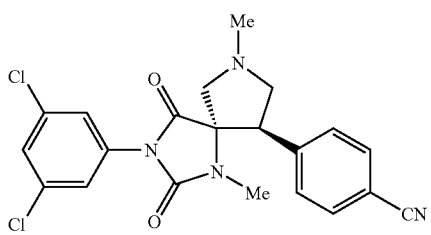

Formaldehyde (80 μl, 37% in water, 1.1 mmol) was added to a solution of Example 15 (300 mg, 0.72 mmol) in formic acid (1 ml). After 4 h at 90° C., the solution was cooled to 0° C., basified with NaOH 2N, and extracted with EtOAc. After concentration, the compound was purified by crystallization of its TFA salt in ether. After basification, the above-titled compound was obtained as a white solid (123 mg). $^1$H NMR (CDCl$_3$): 7.63 (2H, d, J=8.0 Hz), 7.25–7.35 (3H, m), 6.67 (2H, m), 3.83 (1H, dd, J$_1$=11.7 Hz, J$_2$=6.0 Hz), 3.2–3.4 (2H, m), 3.24 (3H, s), 3.09 (1H, m), 2.94 (1H, d, J=10.9 Hz), 2.52 (3H, s).

Examples 90–101

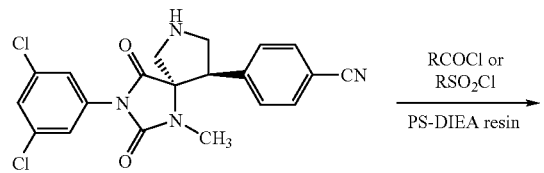

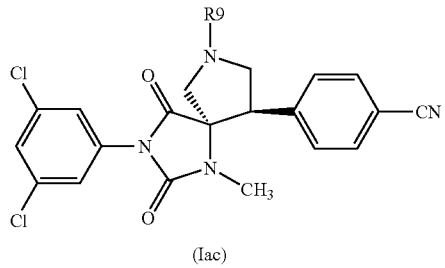

(Iac)

R9 = COR or SO$_2$R

Using the same procedure as described for Examples 16–21 (Method A) or Examples 22–24 (Method B), the compounds having the above formula (Iac), listed in Table 5, were obtained after filtration and evaporation to dryness. Some compounds were further purified by reverse phase HPLC (gradient from CH$_3$CN/H$_2$O/TFA: 5/95/0.05 to CH$_3$CN/H$_2$O/TFA: 80/20/0.05). Examples 99 and 100 were obtained after hydrolysis of their corresponding esters following the general Method C (0.06 mmol in 3 ml THF, with a 2N solution of LiOH (240 μl, 0.48 mmol)). These compounds were then purified by reverse phase HPLC (gradient from CH$_3$CN/H$_2$O/TFA: 5/95/0.05 to CH$_3$CN/H$_2$O/TFA: 80/20/0.05). For each compound LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

TABLE 5

| Ex. | Structure | Method | Quantity (mg) | Retention time | Analysis |
|---|---|---|---|---|---|
| 90 | 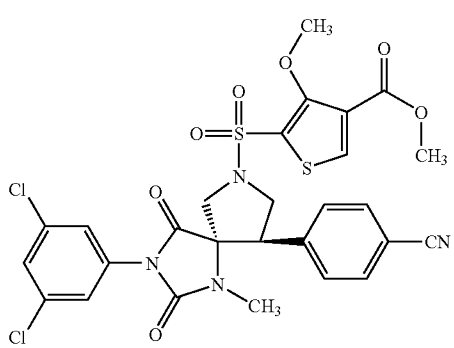 | A | 23.9 | 2.31 | 649(M + 1) |

TABLE 5-continued

| Ex. | Structure | Method | Quantity (mg) | Retention time | Analysis |
|---|---|---|---|---|---|
| 91 | 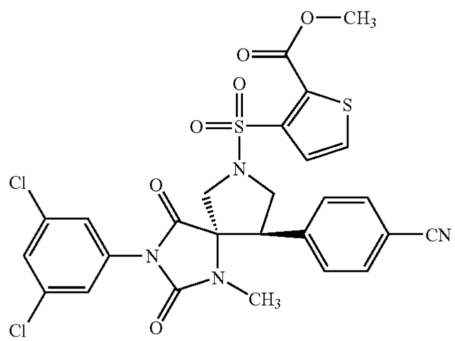 | A | 20.3 | 2.28 | 619(M + 1) |
| 92 | 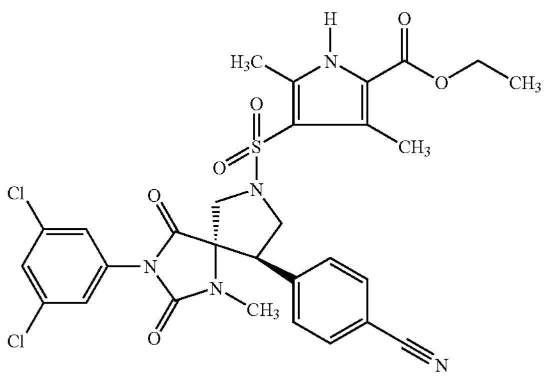 | A | 4.2 | 2.4 | 6.44(M + 1) |
| 93 | 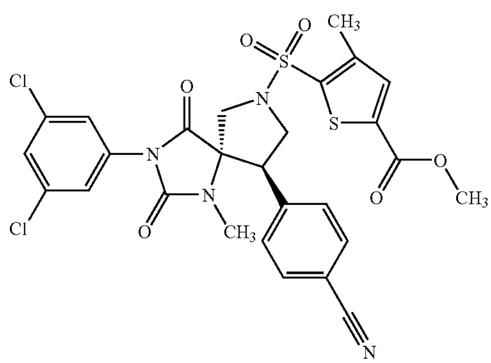 | A | 4.7 | 2.48 | 1H NMR(CDCl3): 7.69–7.58 (3H, m), 7.29–7.19(3H, m), 6.62(2H, s), 4.17–3.69(8H, m), 3.20(3H, s), 2.58(3H, s) |
| 94 | 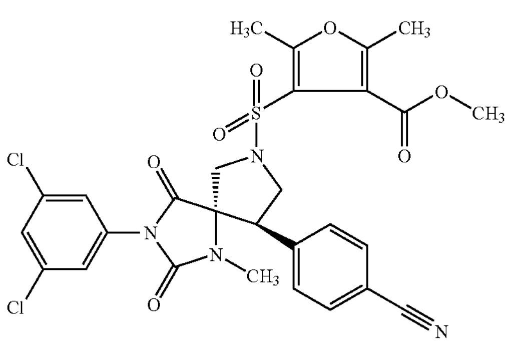 | A | 4.7 | 2.47 | 631(M + 1) |

TABLE 5-continued
| Ex. | Structure | Method | Quantity (mg) | Retention time | Analysis |
|-----|-----------|--------|---------------|----------------|----------|
| 95 | 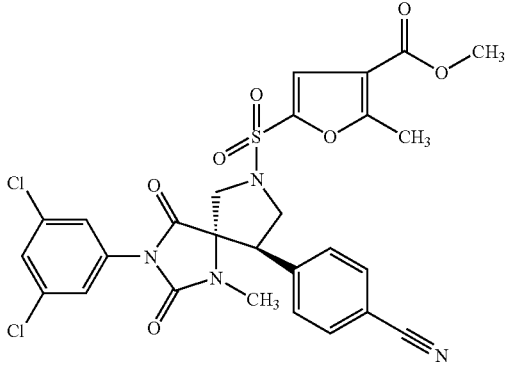 | A | 3.2 | 2.43 | 1H NMR(CDCl3): 7.67(2H, d), 7.41(1H, s), 7.29–7.18(3H, m), 6.69(2H, s), 4.11–3.9(7H, m), 3.19(3H, s), 2.65(3H, s) |
| 96 | 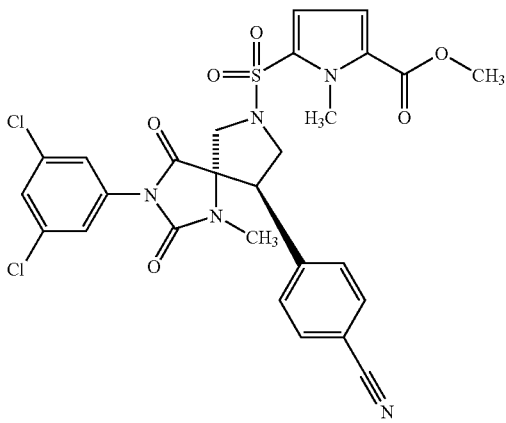 | A | 3.8 | 2.34 | 616(M + 1) |
| 97 | 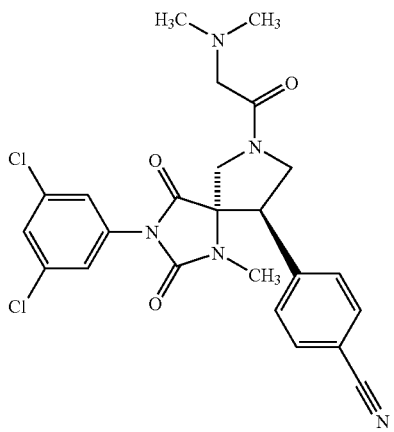 | A | 3.8 | 1.71 | 500(M + 1) |

TABLE 5-continued

| Ex. | Structure | Method | Quantity (mg) | Retention time | Analysis |
|---|---|---|---|---|---|
| 98 | 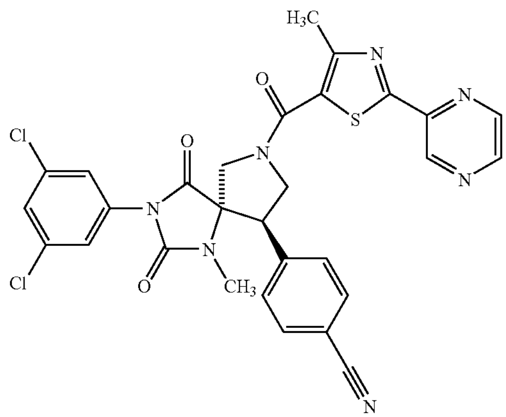 | A | 5.2 | 2.11 | 618(M + 1) |
| 99 | 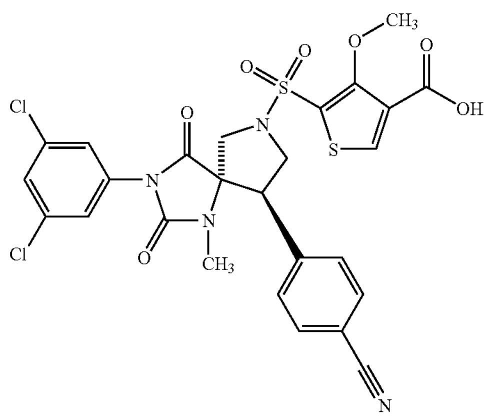 | A & C | 2.4 | 2.11 | 650(M + 1) |
| 100 | 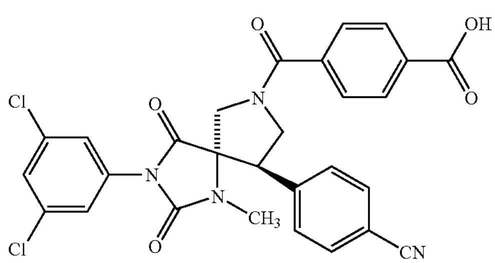 | A & C | 5.9 | 1.45* | 562(M − 1)* |
| 101 | 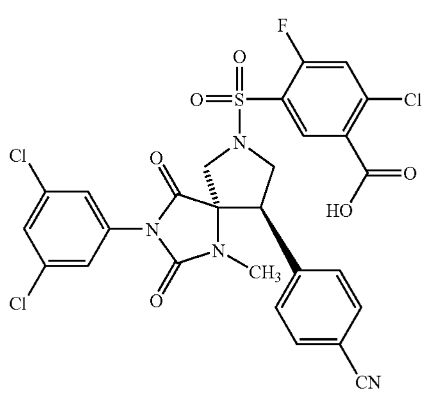 | B | 3 | 2.33* | 651(M − 1)* |

*(APCI -) as in Example 152

Example 102

4-[(5S*, 9R*)-3-(3,5-Dichloro-phenyl)-1-methyl-2,4-dioxo-7-(quinoxaline-6-carbonyl)-1,3,7-triaza-spiro[4.4]non-9-yl]-benzonitrile

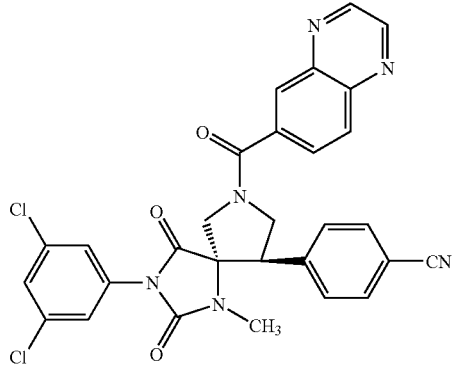

To a solution of quinoxaline-6-carboxylic acid (56.2 mg, 0.318 mmol) in 7 ml DMF were added EDCI (62 mg, 0.32 mmol), TEA (53.9 µl, 0.38 mmol) and HOBt (49.3 mg, 0.36 mmol). After 30 min, a solution of Example 15 (103.4 mg, 0.249 mmol) in 1 ml DMF was added. The reaction mixture was then stirred overnight at RT before evaporation to dryness. The residue was partitioned between DCM (50 ml) and 1N solution of HCl (20 ml). The DCM layer was washed with 10% solution of sodium carbonate (2×20 ml), dried over sodium sulfate, concentrated and purified by reverse phase HPLC (gradient from CH$_3$CN/H$_2$O/TFA: 5/95/0.05 to CH$_3$CN/H$_2$O/TFA: 80/20/0.05) to yield the titled compound (35 mg). Retention time: 2.16 min., 571 (M+1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

Examples 103–134

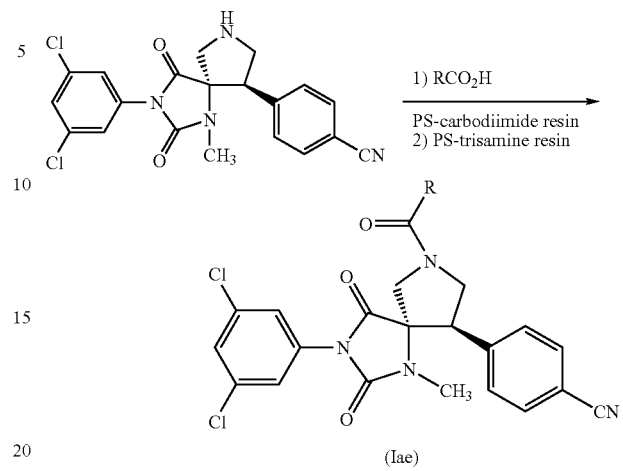

Using the same procedure as described for Examples 25–36 (Method D), the compounds having the above formula (Iae), listed in Table 6, were obtained after filtration and evaporation to dryness. For the N-Boc and/or CO$_2$tBu protected R, the compounds were treated with DCM/TFA (1:1) solution for 2 h at RT, and the resulting basic or acidic compounds were further purified by SCX or SAX cartridge, respectively (Method L).

Some compounds were further purified by reverse phase HPLC (gradient from CH$_3$CN/H$_2$O/TFA: 5/95/0.05 to CH$_3$CN/H$_2$O/TFA: 80/20/0.05). For each compound, the LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

TABLE 6

| Ex. | Structure | Method | Quantity (mg) | Retention time | Analysis |
|---|---|---|---|---|---|
| 103 | 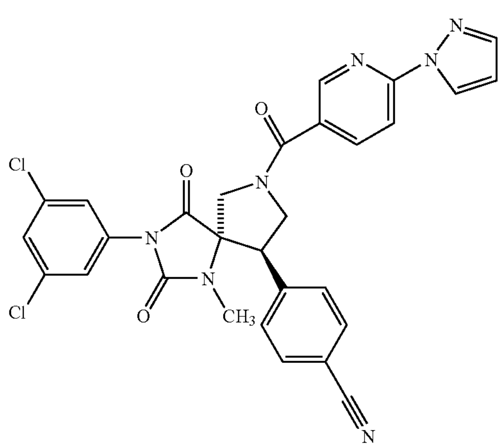 | D | 14.9 | 10.802* | 586(M + 1)* |

TABLE 6-continued
| Ex. | Structure | Method | Quantity (mg) | Retention time | Analysis |
|---|---|---|---|---|---|
| 104 | 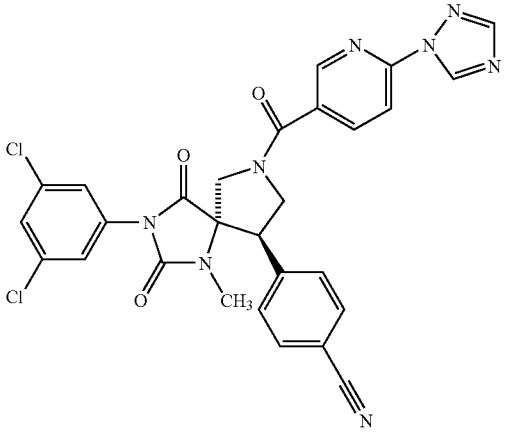 | D | 9.6 | 9.768* | 588(M + 1)* |
| 105 | 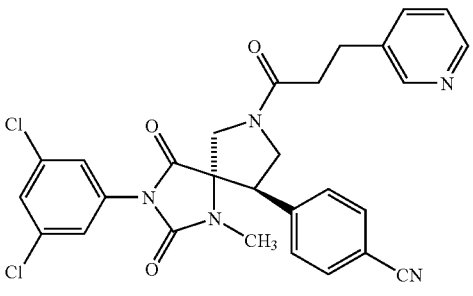 | D | 16.1 | 1.77 | 548(M + 1); 1H NMR (CDCl3): 8.6–8.4(2H, m), 7.75–7.55(3H, m), 7.4–7.15 (4H, m), 6.85–6.7(2H, m), 4.45–4.15(1H, m), 4.15–3.65 (4H, m), 3.2(3H, s), 3.15–3.0 (2H, m), 2.8–2.55(2H, m) |
| 106 | 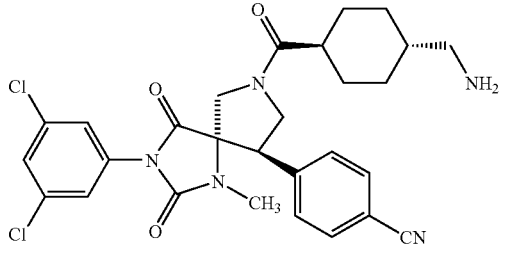 | D & L | 15.1 | 1.76 | 554(M + 1) |
| 107 | 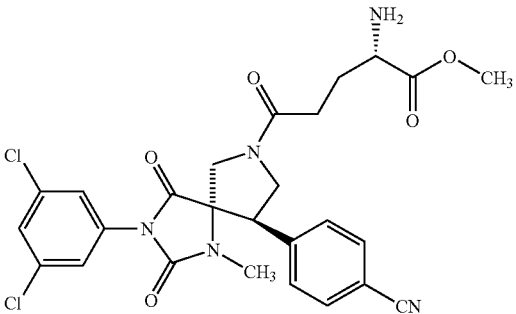 | D & L | 14.6 | 1.74 | 558(M + 1) |

TABLE 6-continued

| Ex. | Structure | Method | Quantity (mg) | Retention time | Analysis |
|---|---|---|---|---|---|
| 108 | 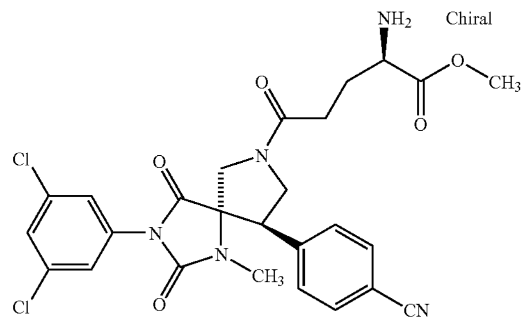 | D & L | 15.4 | 1.74 | 558(M + 1) |
| 109 | 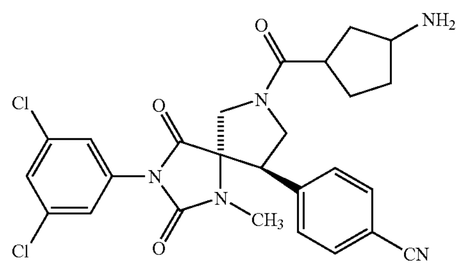 | D & L | 15 | 1.76 | 526 |
| 110 | 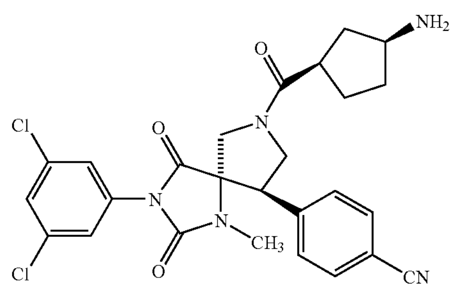 | D & L | 14.7 | 1.76 | 526(M + 1) |
| 111 | 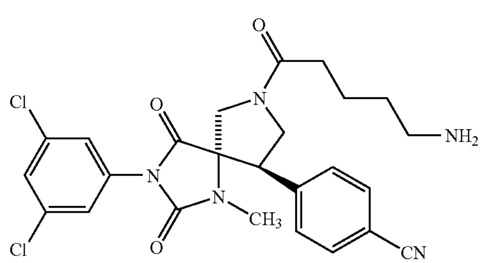 | D & L | 13.4 | 1.72 | 514(M + 1) |
| 112 | 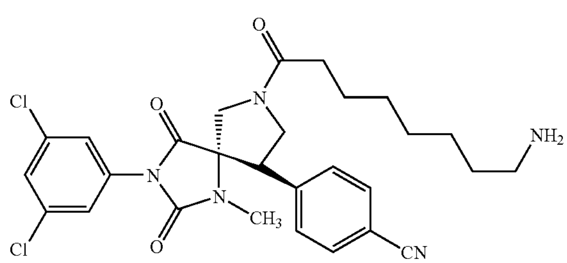 | D & L | 15 | 1.8 | 556(M + 1) |

TABLE 6-continued

| Ex. | Structure | Method | Quantity (mg) | Retention time | Analysis |
|---|---|---|---|---|---|
| 113 | 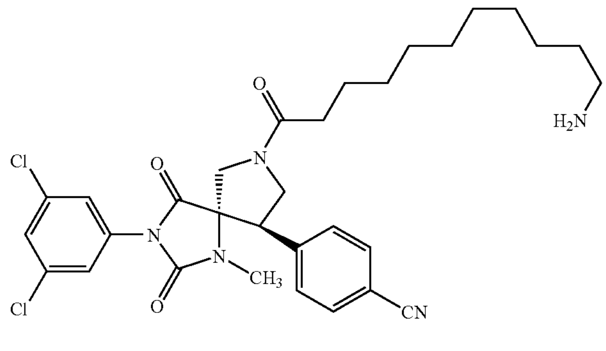 | D & L | 17 | 1.93 | 598(M + 1) |
| 114 | 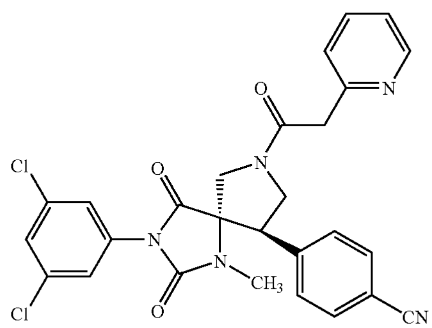 | D | 13.2 | 1.75 | 534(M + 1) |
| 115 | 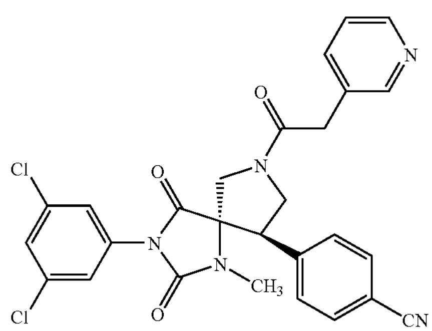 | D | 14.5 | 1.73 | 534(M + 1) |
| 116 | 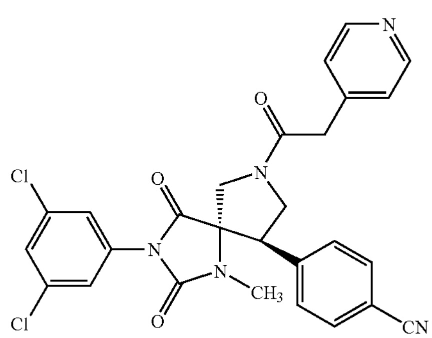 | D | 11.7 | 1.74 | 534(M + 1) |

TABLE 6-continued

| Ex. | Structure | Method | Quantity (mg) | Retention time | Analysis |
|---|---|---|---|---|---|
| 117 | 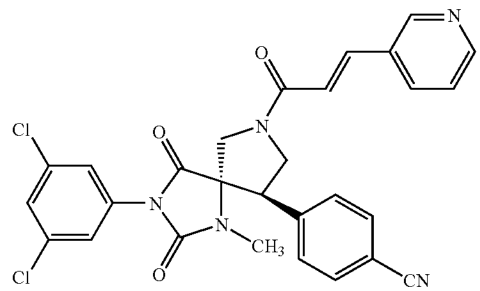 | D | 11.7 | 1.81 | 546(M + 1) |
| 118 | 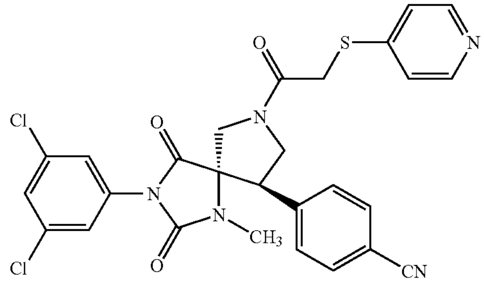 | D | 5.2 | 1.79 | 566(M + 1) |
| 119 | 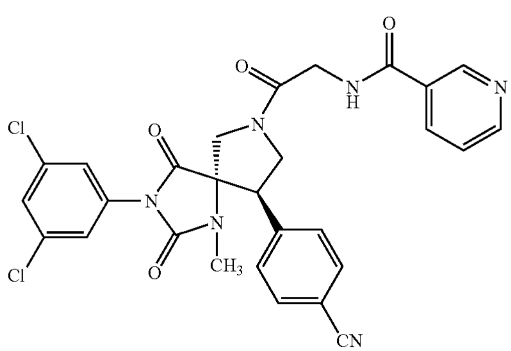 | D | 11.6 | 1.77 | 577(M + 1) |
| 120 | 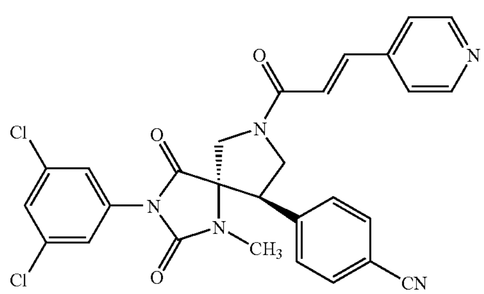 | D | 12.7 | 1.79 | 546(M + 1) |
| 121 | 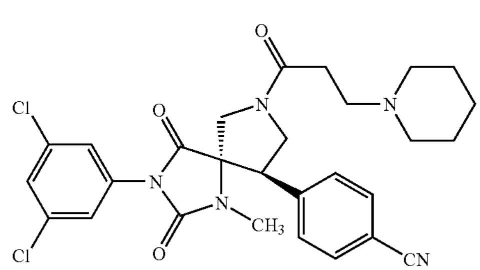 | D | 16.9 | 1.79 | 554(M + 1) |

TABLE 6-continued
| Ex. | Structure | Method | Quantity (mg) | Retention time | Analysis |
|---|---|---|---|---|---|
| 122 | 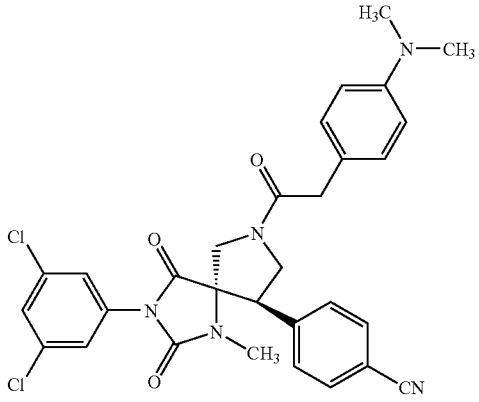 | D | 21.4 | 1.82 | 576(M + 1) |
| 123 | 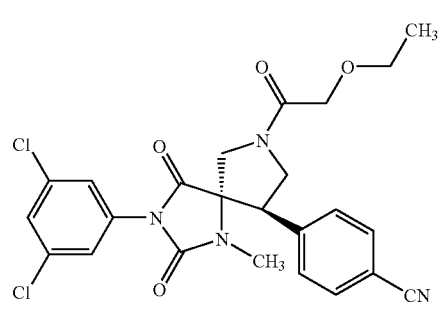 | D | 15.5 | 1.99 | 501(M + 1) |
| 124 | 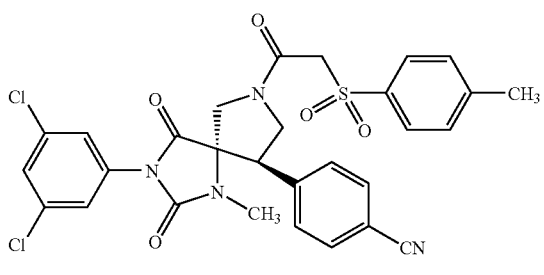 | D | 12 | 2.17 | 611(M + 1) |
| 125 | 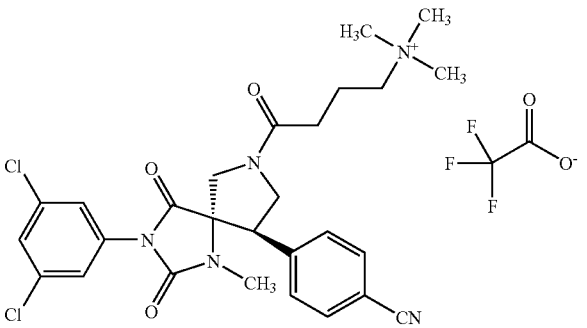 | D | 4.6 | 1.75 | 542(M + 1) |

TABLE 6-continued

| Ex. | Structure | Method | Quantity (mg) | Retention time | Analysis |
|---|---|---|---|---|---|
| 126 | 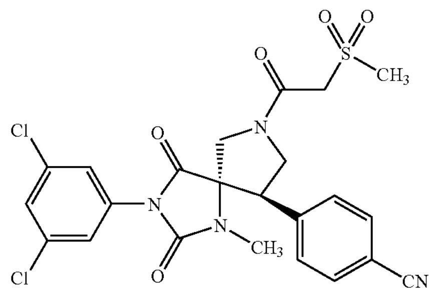 | D | 10.8 | 1.93 | ¹H NMR(CDCl3): 7.69(2H, d), 7.39–7.24(3H, m), 6.78 (2H, d), 4.6–3.78(7H, m), 3.27–3.15(6H, m) |
| 127 | 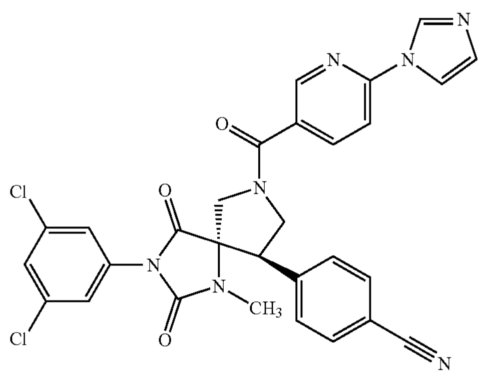 | D | 12.7 | 1.87 | 586(M + 1) |
| 128 | 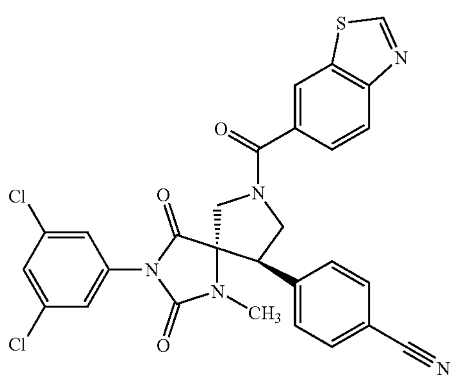 | D | 10.3 | 2.06 | 578(M + 1) |
| 129 | 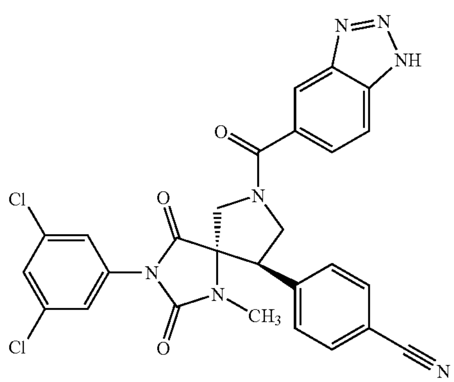 | D | 9.5 | 1.92 | 560(M + 1) |

TABLE 6-continued

| Ex. | Structure | Method | Quantity (mg) | Retention time | Analysis |
|---|---|---|---|---|---|
| 130 | 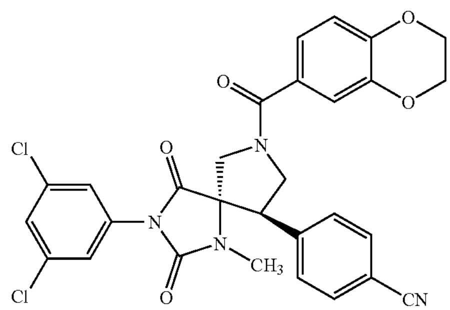 | D | 17.1 | 2.13 | 577(M + 1) |
| 131 | 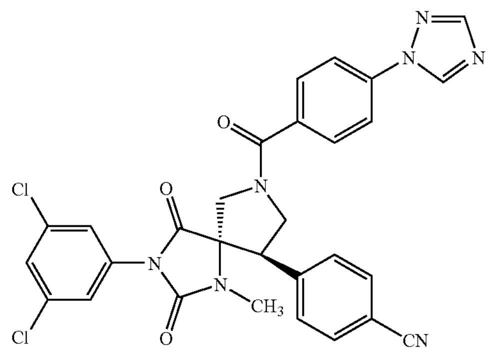 | D | 10.7 | 2 | 586(M + 1) |
| 132 | 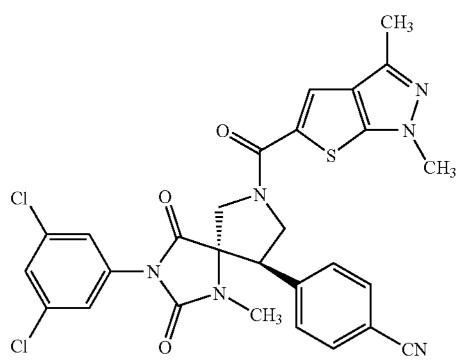 | D | 19.6 | 2.13 | 593(M + 1) |
| 133 | 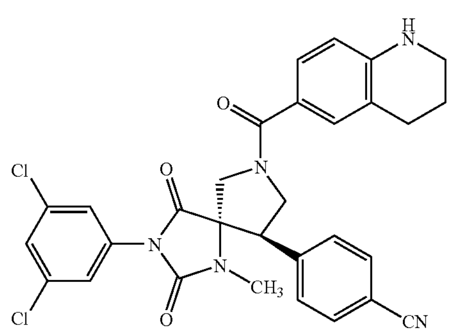 | D | 16.2 | 2.03 | 574(M + 1) |

TABLE 6-continued

| Ex. | Structure | Method | Quantity (mg) | Retention time | Analysis |
|---|---|---|---|---|---|
| 134 | 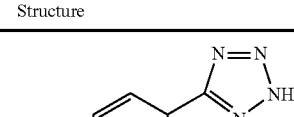 | D' | 4 | 2.1 | 587(M + 1) |

*(APCI -) as in Example 152
D': Method D without PS-Trisamine treatment

Examples 135–140

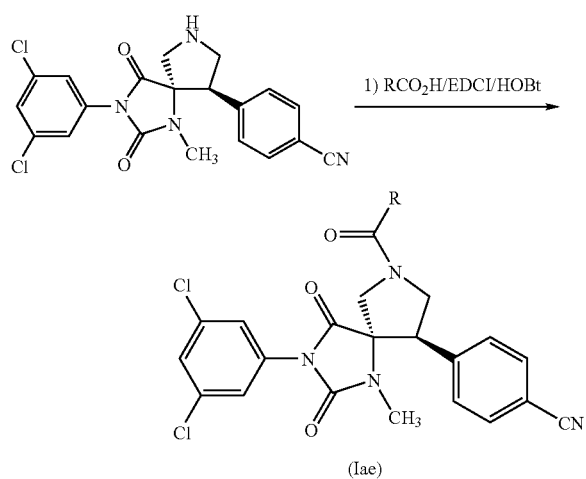

(Iae)

To di-carboxylic acid reagents (0.24 mmol) were added 1 ml of a mixture of EDCI (95.9 mg, 0.5 mmol) and TEA (84 µl, 0.6 mmol) in DMF (7 ml) and 0.1 ml of HOBt solution (78 mg, 0.57 mmol in 0.7 ml DMF). After 15 min., 0.3 ml of Example 15 solution (174.5 mg, 0.42 mmol, in 2.1 ml DMF), was added. The reaction mixtures were then stirred overnight at RT before evaporation to dryness (Method E). The residues were purified by reverse phase HPLC (gradient from $CH_3CN/H_2O/TFA$: 5/95/0.05 to $CH_3CN/H_2O/TFA$: 80/20/0.05), to provide compounds having the above formula (Iae), listed in Table 7. LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 7

| Ex. | Structure | Method | Quantity (mg) | Retention time | Analysis |
|---|---|---|---|---|---|
| 135 | 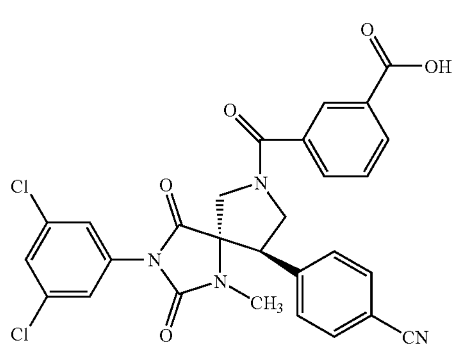 | E | 8.1 | 1.489 | 562(M−1)* |

TABLE 7-continued

| Ex. | Structure | Method | Quantity (mg) | Retention time | Analysis |
|-----|-----------|--------|---------------|----------------|----------|
| 136 | 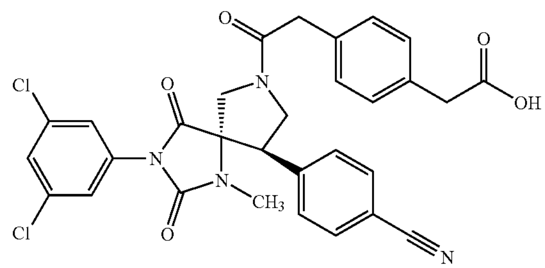 | E | 13.8 | 2.06 | 591(M+1) |
| 137 | 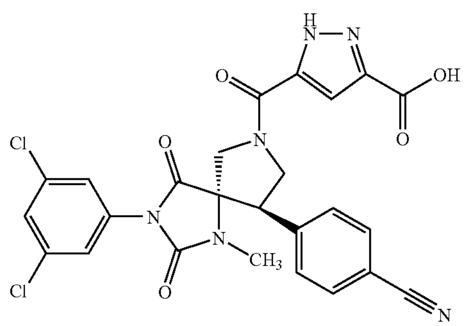 | E | 20.1 | 1.89 | 553(M+1) |
| 138 | 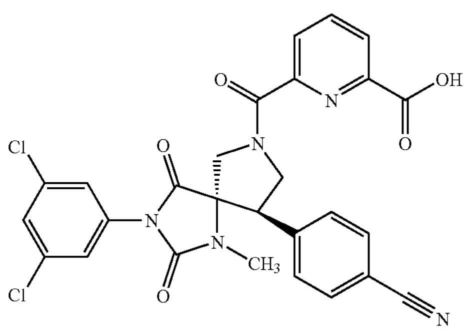 | E | 13.5 | 1.95 | 564(M+1) |
| 139 | 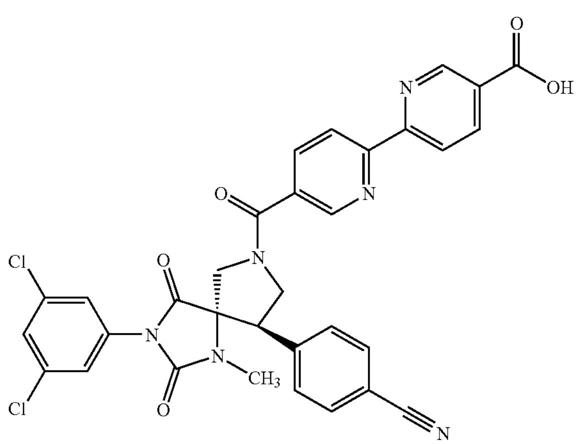 | E | 8.4 | 2.03 | 641(M+1) |

TABLE 7-continued

| Ex. | Structure | Method | Quantity (mg) | Retention time | Analysis |
|---|---|---|---|---|---|
| 140 | (structure shown) | E | 10 | 2.15 | 553(M+1) |

*(APCI −) as in Example 152

Examples 141–151

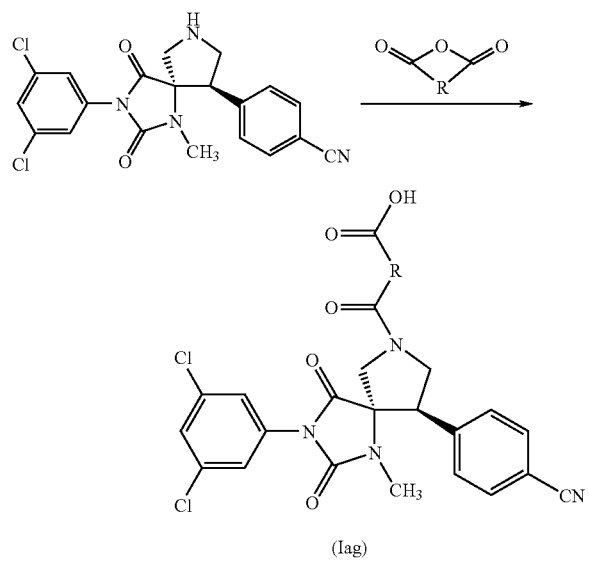

To solutions of anhydride carboxylic acid reagents (0.072 mmol) in 1.5 ml THF, was added 0.5 ml of a solution of Example 15 (448.5 mg, 1.08 mmol, in 9 ml THF). The reaction mixtures were stirred overnight at RT before evaporation to dryness (Method F). The compounds were then purified by SAX cartridge and some further purified by reverse phase HPLC (gradient from $CH_3CN/H_2O/TFA$: 5/95/0.05 to $CH_3CN/H_2O/TFA$: 80/20/0.05), to provide compounds having the above formula (Iag), listed in Table 8. LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 8

| Ex. | Structure | Method | Quantity (mg) | Retention time | Analysis |
|---|---|---|---|---|---|
| 141 | (structure shown) | F | 4.9 | 2.01 | 579(M+1) |

TABLE 8-continued

| Ex. | Structure | Method | Quantity (mg) | Retention time | Analysis |
|---|---|---|---|---|---|
| 142 | 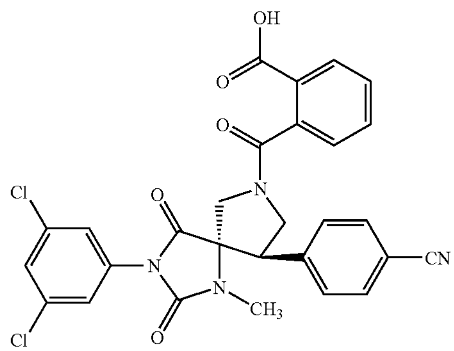 | F | 3.1 | 2.01 | 563(M+1) |
| 143 | 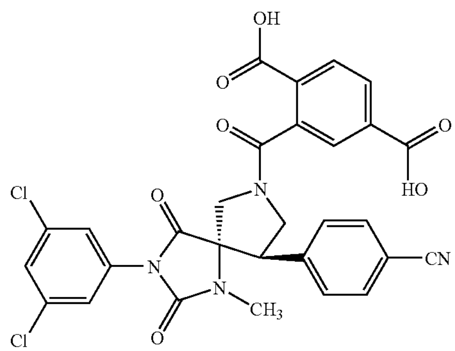 | F | 0.6 | 1.85 | 607(M+1) |
| 144 | 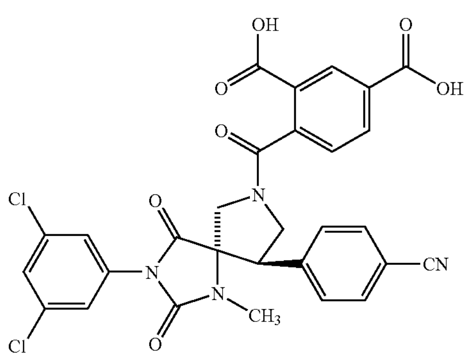 | F | 1 | 1.89 | 607(M+1) |
| 145 | 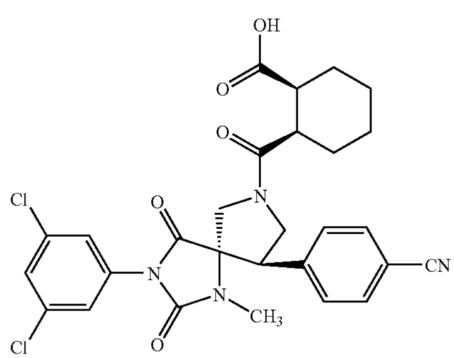 | F | 1.2 | 2.1 | 569(M+1) |

TABLE 8-continued

| Ex. | Structure | Method | Quantity (mg) | Retention time | Analysis |
|---|---|---|---|---|---|
| 146 | 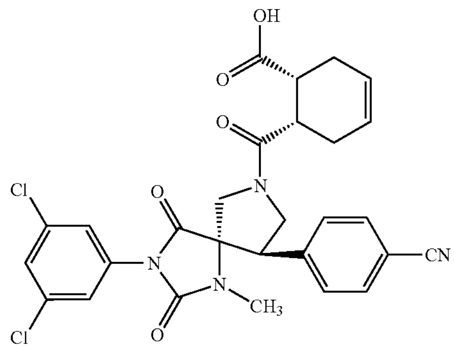 | F | 2 | 2.04 | 567(M+1) |
| 147 | 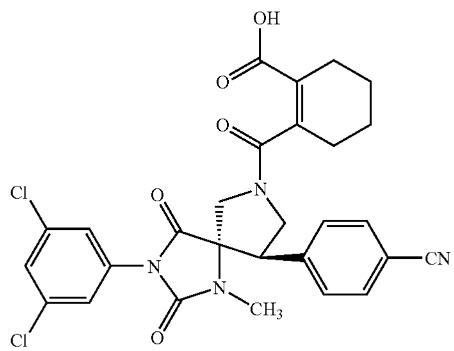 | F | 2.8 | 2.03 | 567(M+1) |
| 148 | 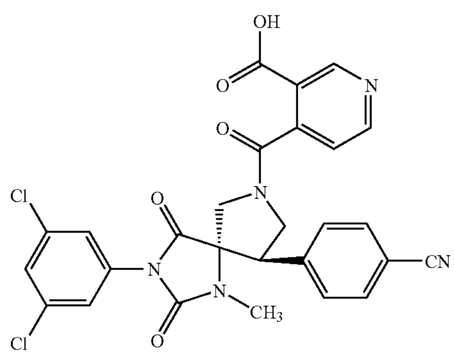 | F | 8.2 | 1.84 | 564(M+1) |
| 149 | 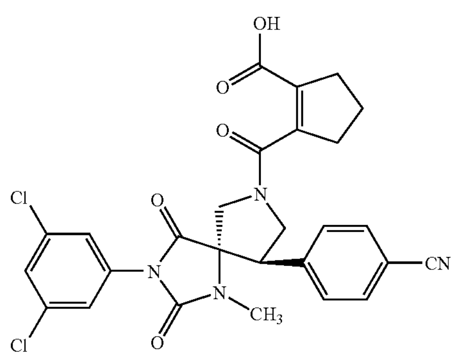 | F | 7.6 | 1.98 | 553(M+1) |

TABLE 8-continued

| Ex. | Structure | Method | Quantity (mg) | Retention time | Analysis |
|---|---|---|---|---|---|
| 150 | 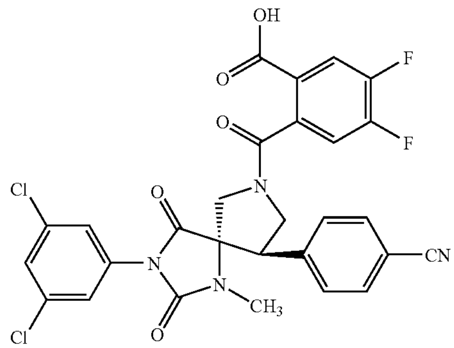 | F | 8.7 | 2.09 | 581(M−18) |
| 151 | 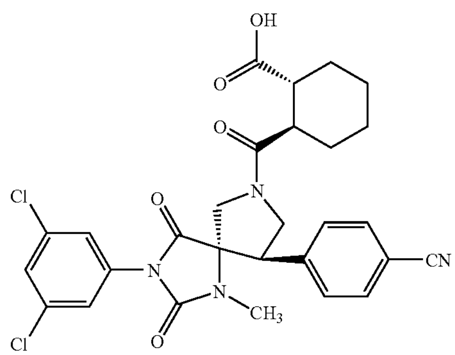 | F | 4.5 | 2.06 | 551(M−18) |

Example 152

4-[(5S*, 9R*)-7-(2-Benzylamino-acetyl)-3-(3,5-dichloro-phenyl)-1-methyl-2,4-dioxo-1,3,7-triaza-spiro[4.4]non-9-yl]-benzonitrile

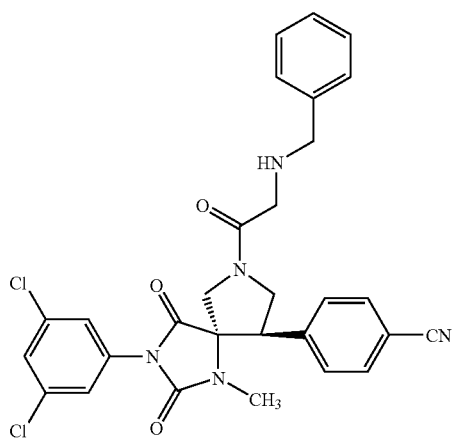

To a solution of Example 15 (41.5 mg, 0.1 mmol) in 1 ml THF, were added TEA (0.0194 ml, 0.14 mmol) and chloroacetyl chloride (0.0095 ml, 0.12 mmol). After 15 min. at RT, the reaction mixture was evaporated to dryness to yield 47.8 mg of crude intermediate. To this intermediate (37.7 mg, 0.077 mmol) in 1 ml THF, were added PS-DIEA (Argonaut, 21 mg, 0.06 mmol), benzylamine (4.9 μl, 0.045 mmol) and PS-DMAP (Argonaut, 20 mg, 0.06 mmol). The reaction mixture was stirred for 24 h at RT before evaporation to dryness. The residue was purified by reverse phase HPLC (gradient from $CH_3CN/H_2O/TFA$: 5/95/0.05 to $CH_3CN/H_2O/TFA$: 80/20/0.05) to yield the titled compound (4.2 mg). Retention time: 10.65 min., 563 (M+1); (LCMS conditions: HP 1100 MSD platform (APCI-, DAD (210–400 nm)), Column: TSK gel Super ODS 4.6 mm ID×10 cm, Flow rate: 1 mL/min, Gradient: from 5% to 95% eluent B in 15 min., with a plateau with 95% eluent B during 5 min. Eluent A: $H_2O$ (0.1% ammonium formate), Eluent B: $CH_3CN$). $^1H$ NMR ($CDCl_3$): 7.75–7.6 (2H, d), 7.6–7.15 (8H, m), 7.75 (2H, d), 4.25 (2H, s), 4.2–3.6 (7H,m), 3.3–3.05 (3H, m).

Examples 153–162

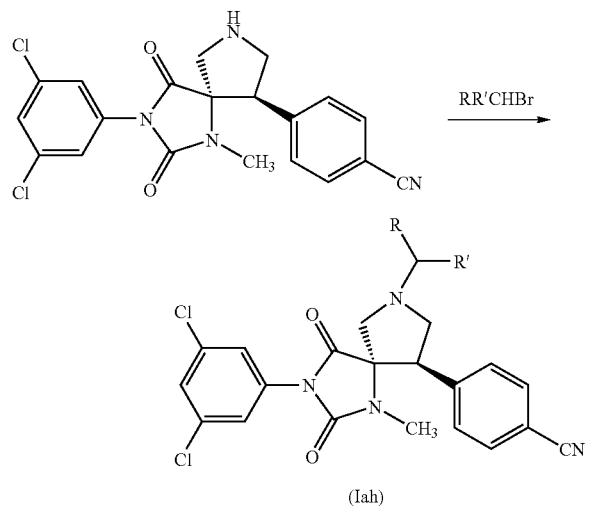

(Iah)

Compounds having the above formula (Iah), listed in Table 9, were obtained by adding Example 15 (10.9 mg, 0.045 mmol) and TEA (6.74 μl, 0.048 mmol) to solutions of appropriate alkyl, aryl or heteroaryl bromide reagents (RR'CHBr) (0.03 mmol) in 1 ml dioxane. The reaction mixtures were stirred overnight at RT before evaporation to dryness (Method G). The compounds were purified by SCX cartridge and PS-Isocyanate (Argonaut, 0.06 mmol) when desired; some compounds were also purified by reverse phase HPLC (gradient from $CH_3CN/H_2O/TFA$: 5/95/0.05 to $CH_3CN/H_2O/TFA$: 80/20/0.05). Examples 162–164 were obtained after hydrolysis of their corresponding esters following the general Method C as in Examples 90–101. These compounds were then purified by reverse phase HPLC (gradient from $CH_3CN/H_2O/TFA$: 5/95/0.05 to $CH_3CN/H_2O/TFA$: 80/20/0.05).

LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 9

| Ex. | Structure | Method | Quantity (mg) | Retention time | Analysis |
|---|---|---|---|---|---|
| 153 | 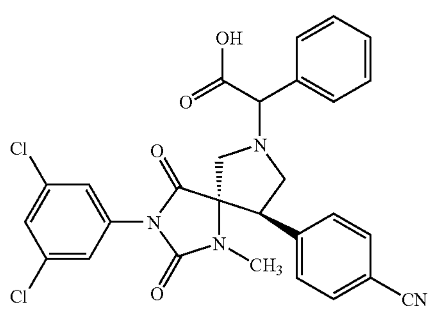 | G | 3.2 | 1.98 | 549(M+1) |
| 154 | 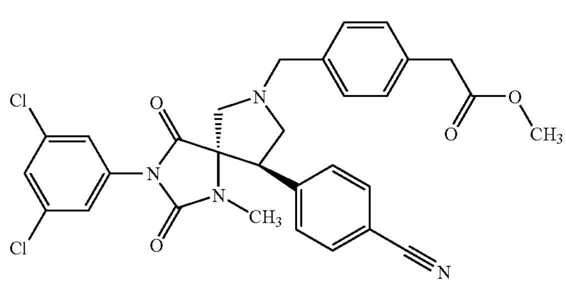 | G | 4.4 | 1.96 | 1H NMR(CDCl3): 7.62(4H, d), 7.41–7.1 (5H, m), 6.62(2H, s), 4.62–4.31(3H, m), 4.10–3.75(3H, m), 3.62–3.58(5H, m), 3.51–3.38(1H, m), 3.34(3H, s) |
| 155 | 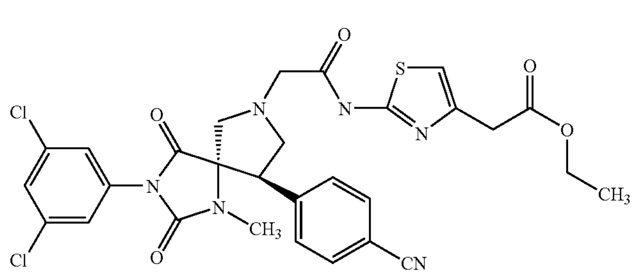 | G | 12.9 | 2.03 | 641(M+1) |

TABLE 9-continued

| Ex. | Structure | Method | Quantity (mg) | Retention time | Analysis |
|---|---|---|---|---|---|
| 156 | 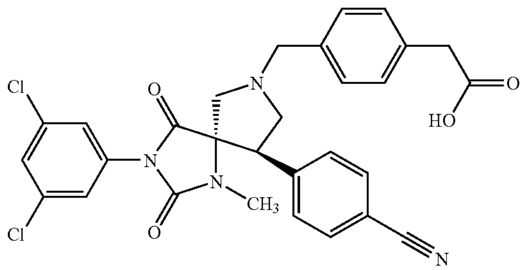 | G | 3.3 | 1.82 | 563 |
| 157 | 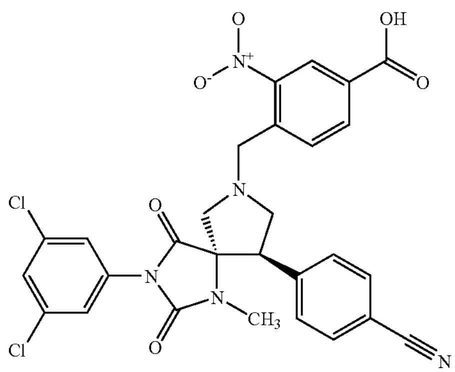 | G | 9.9 | 2.11 | 594(M+1) |
| 158 | 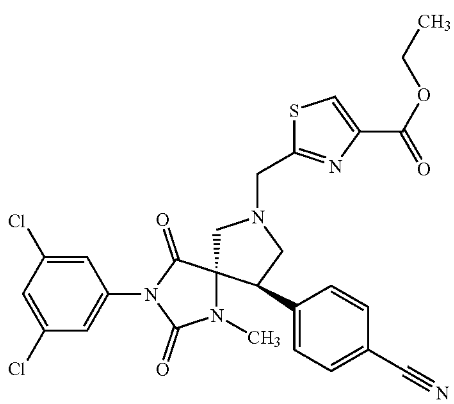 | G | 7.3 | 2.14 | 584(M+1) |
| 159 | 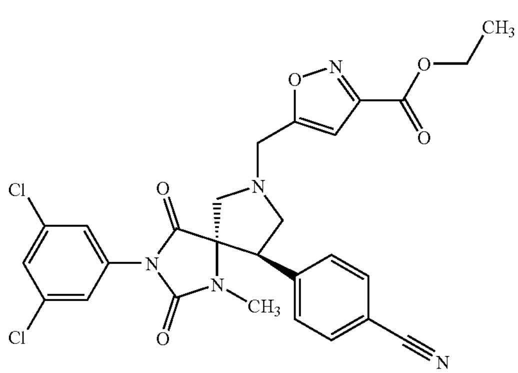 | G | 11.7 | — | 1H NMR(CDCl3): 7.6(2H, d), 7.3(2H, d), 7.2(1H, s), 6.8(1H, s), 6.7(2H, s), 6.2(1H, s), 4.45(2H, q), 4.2(2H, s), 3.93–4.03(1H, m), 3.5–3.7(3H, m), 3.3(1H, d), 3.2(3H, s), 1.4(3H, t) |

TABLE 9-continued
| Ex. | Structure | Method | Quantity (mg) | Retention time | Analysis |
|---|---|---|---|---|---|
| 160 | 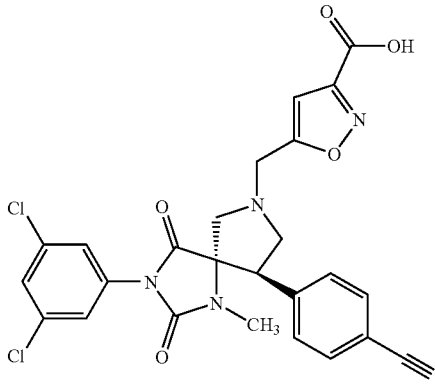 | G & C | 8.5 | 1.71 | 543(M+1) |
| 161 | 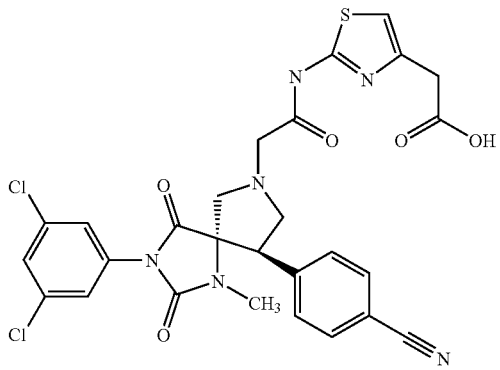 | G & C | 1.6 | 1.86 | 613(M+1) |
| 162 | 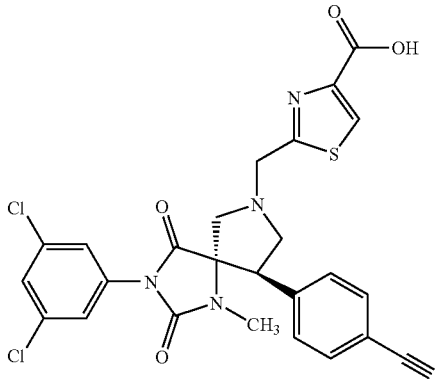 | G & C | 6 | 1.83 | 556(M+1) |
Examples 163–181
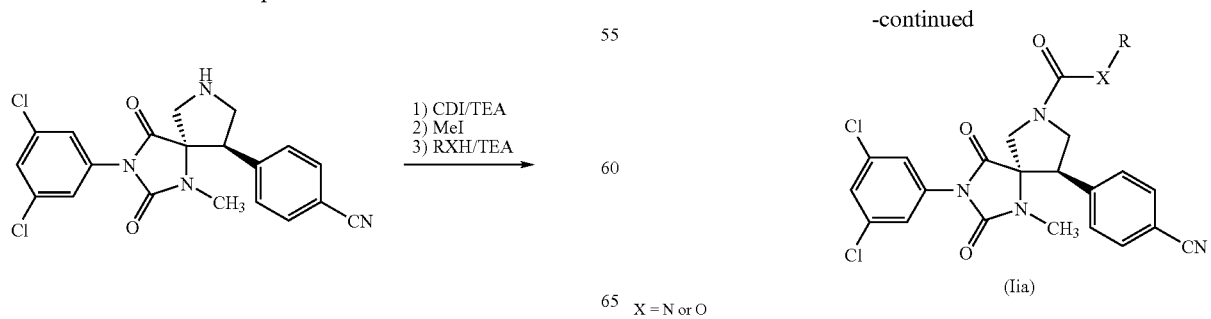
X = N or O
(Iia)

To a solution of Example 15 (873.1 mg, 2.1 mmol) and TEA (408 μl, 2.94 mmol) in 5 ml THF was added dropwise a solution of 1,1'-carbonyldiimidazole (479.3 mg, 2.94 mmol, in 6 ml THF). The reaction mixture was stirred at RT for 24 h before evaporation to dryness. The residue was partitioned between DCM (50 ml) and brine (20 ml). The DCM layer was dried over sodium sulfate and concentrated. This residue was stirred at 60° C. overnight with methyl iodide (523 μl, 8.4 mmol) in 20 ml ACN, and the reaction mixture was evaporated to dryness, furnishing the crude reactive intermediate.

To solutions of appropriately-substituted amine or alcohol reagents (RXH) (0.072 mmol) in 1.8 ml (DCM/DMF: 8/2), was added 0.5 ml of a solution of the reactive intermediate (1.62 mmol), with TEA (0.5 ml, 3.56 mmol), in 13 ml DCM. The reaction mixtures were stirred overnight at RT before evaporation to dryness (Method H). The compounds were purified by reverse phase HPLC (gradient from CH₃CN/H₂O/TFA: 5/95/0.05 to CH₃CN/H₂O/TFA: 80/20/0.05), to provide compounds having the above formula (Iai), listed in Table 10. Examples 174–179 were obtained after hydrolysis of their corresponding esters following the general Method C as in Examples 90–101. These compounds were then purified by reverse phase HPLC (gradient from CH₃CN/H₂O/TFA: 5/95/0.05 to CH₃CN/H₂O/TFA: 80/20/0.05). LC Mass results are reported (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H₂O (0.05% TFA), Eluent B: CH₃CN/H₂O/TFA (80/20/0.05)).

TABLE 10

| Ex. | Structure | Method | Quantity (mg) | Retention time | Analysis |
|-----|-----------|--------|---------------|----------------|----------|
| 163 | 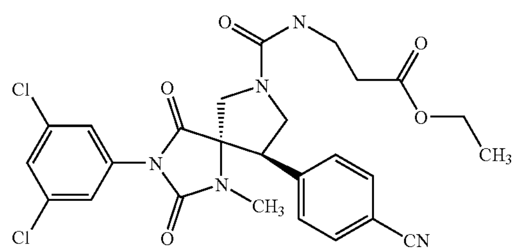 | H | 2.2 | 2.01 | 558(M+1) |
| 164 | 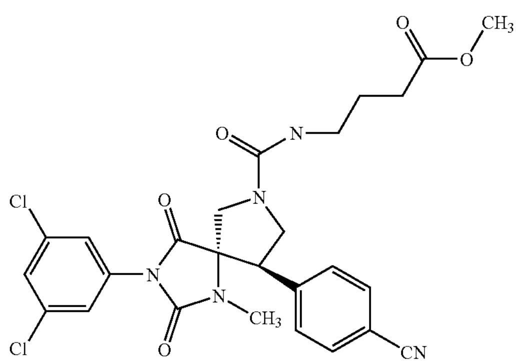 | H | 2.5 | 1.95 | 558(M+1) |
| 165 | 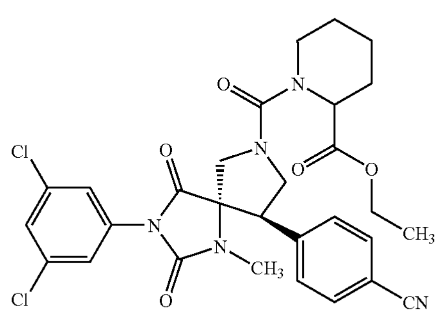 | H | 4.5 | 2.22 | 598(M+1) |

TABLE 10-continued

| Ex. | Structure | Method | Quantity (mg) | Retention time | Analysis |
|---|---|---|---|---|---|
| 166 | 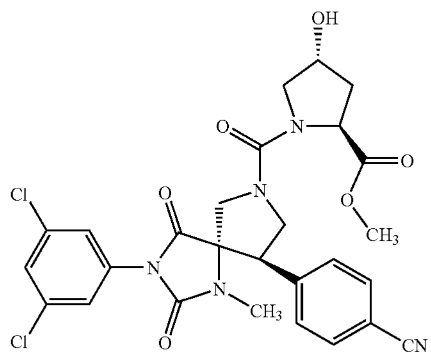 | H | 1.7 | 1.89 | 586(M+1) |
| 167 | 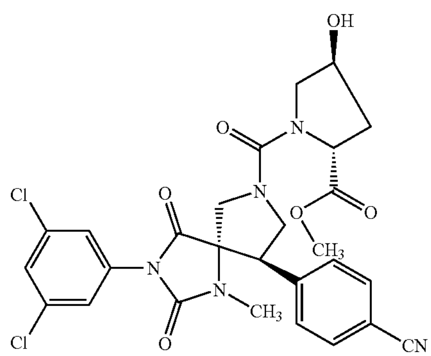 | H | 2.7 | 1.86 | 586(M+1) |
| 168 | 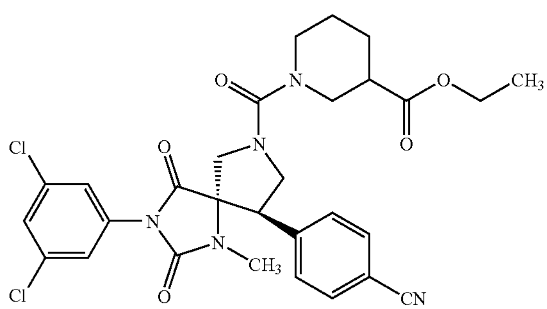 | H | 2.9 | 2.19 | 598(M+1) |
| 169 | 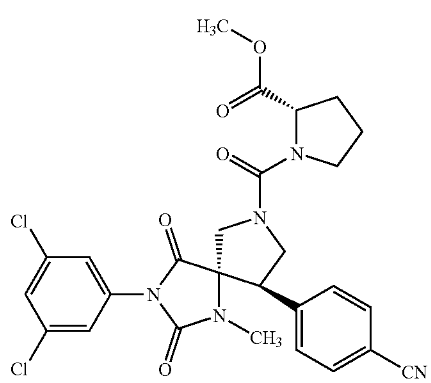 | H | 3.7 | 2.07 | 570(M+1) |

TABLE 10-continued
| Ex. | Structure | Method | Quantity (mg) | Retention time | Analysis |
|---|---|---|---|---|---|
| 170 | 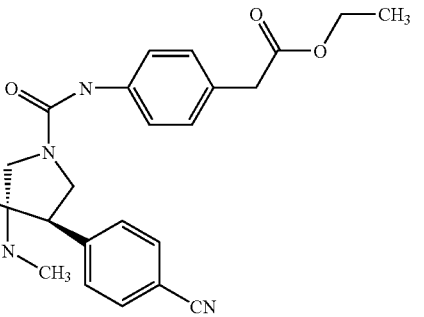 | H | 1.7 | 2.18 | 622(M+1) |
| 171 | 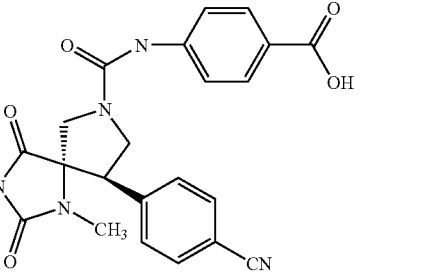 | H | 4 | 1.87 | 534(M−44) |
| 172 | 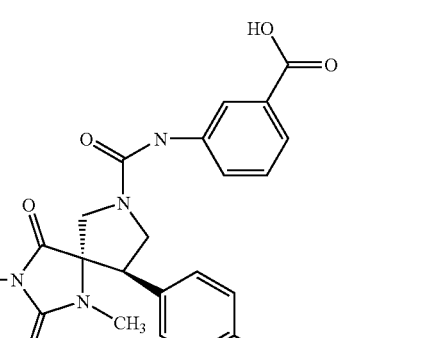 | H | 7.2 | 1.89 | 1H NMR(CDCl3): 7.71(2H, d), 7.57–7.25(4H, m), 7.14(2H, d), 7.00(1H, d), 6.75(2H, d), 4.6–3.88(5H, m), 3.24(3H, s) |
| 173 | 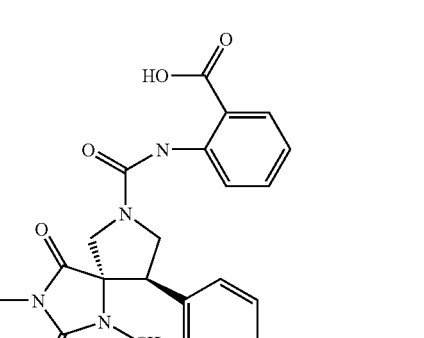 | H | 6.9 | 2.05 | 534(M−44) |

TABLE 10-continued

| Ex. | Structure | Method | Quantity (mg) | Retention time | Analysis |
|---|---|---|---|---|---|
| 174 | 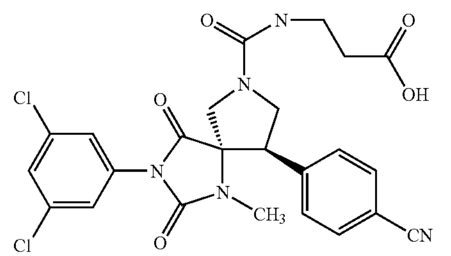 | H & C | 8.2 | 1.83 | 530(M+1) |
| 175 | 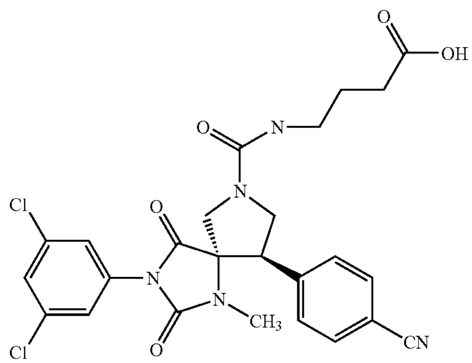 | H & C | 4.8 | 1.85 | 544(M+1) |
| 176 | 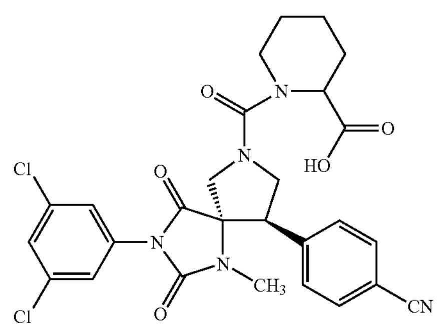 | H & C | 1.1 | 2.04 | 570(M+1) |
| 177 | 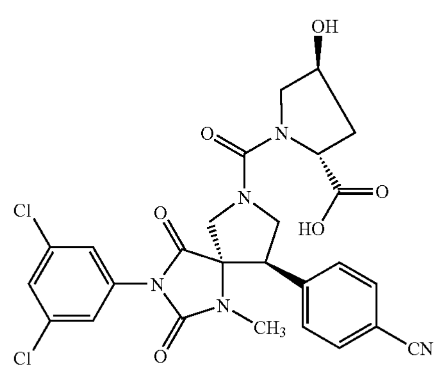 | H & C | 3.2 | 1.81 | 572(M+1) |

TABLE 10-continued

| Ex. | Structure | Method | Quantity (mg) | Retention time | Analysis |
|---|---|---|---|---|---|
| 178 | 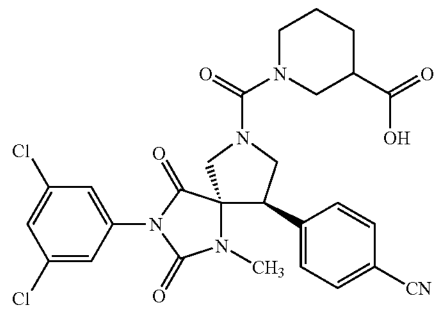 | H & C | 3.8 | 1.98 | 570(M+1) |
| 179 | 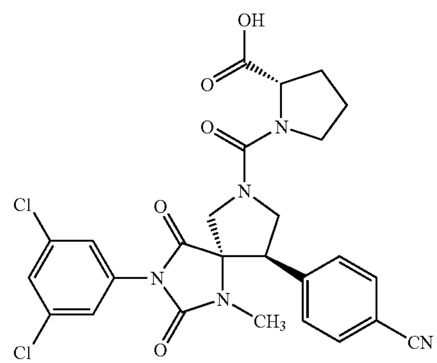 | H & C | 2.4 | 1.94 | 556(M+1) |
| 180 | 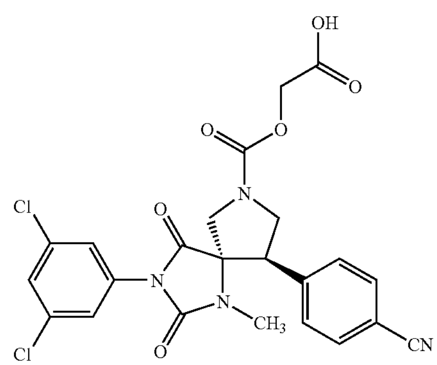 | H | 3.8 | 1.95 | $^1$H NMR(CDCl3): 7.7(2H, d), 7.5–7.3(3H, m), 6.8(2H, d), 4.8(1H, d), 4.57(1H, d), 4.1–3.89(5H, m), 3.24(3H, s) |
| 181 | 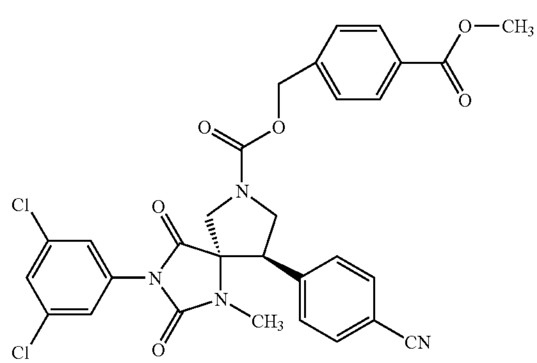 | H | 2.5 | 2.28 | $^1$H NMR(CDCl3): 8.05(2H, d), 7.7(2H, d), 7.45(2H, d), 7.4–7.2(3H, m), 6.8(2H, d), 5.3(2H, d), 4.5 4.2(1H, m), 4.2–3.75(8H, m), 3.2(3H, s) |

Example 182

{[(5S*, 9R*)-9-(4-Cyano-phenyl)-3-(3,5-dichloro-phenyl)-1-methyl-2,4-dioxo-1,3,7-triaza-spiro[4.4]nonane-7-carbonyl]-amino}-acetic acid ethyl ester

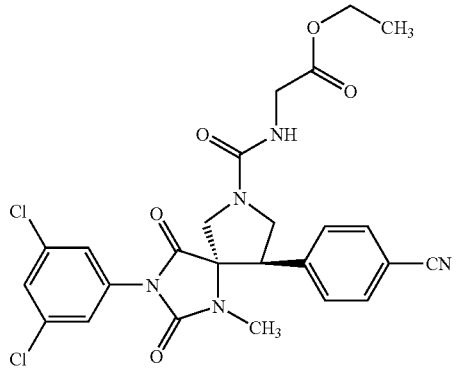

To a solution of Example 15 (24.9 mg, 0.06 mmol) in 1 ml THF/DMF (9/1), was added ethyl isocyanatoacetate (11.6 mg, 0.089 mmol), and the reaction mixture was stirred overnight at RT. The titled compound was obtained (33.3 mg) after treatment with PS-Trisamine (Argonaut, 73 mg, 0.267 mmol) and PS-Isocyanate (Argonaut, 85 mg, 0.122 mmol). Retention time: 1.99 min., 544 (M+1); (LCMS conditions: LC Micromass platform (APCI+, DAD (210–400 nm)), Column: TSK gel Super ODS 4.6 mm IDx5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

Examples 183–216

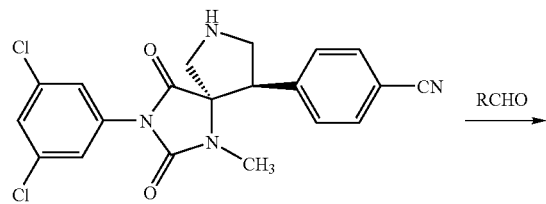

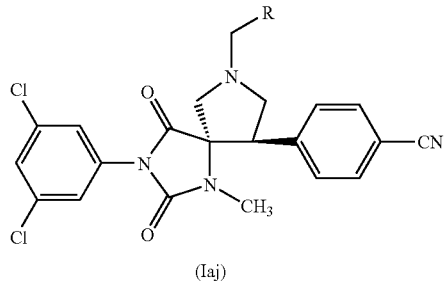

(Iaj)

Compounds having the above formula (Iaj), listed in Table 11, were obtained either by Method I or Method J, below, after SCX cartridge purification. Some compounds were further purified by reverse phase HPLC (gradient from CH$_3$CN/H$_2$O/TFA: 5/95/0.05 to CH$_3$CN/H$_2$O/TFA: 80/20/0.05). Example 207 was obtained after hydrolysis of its corresponding ethyl ester following the general Method C as in Examples 90–101, and purified by reverse phase HPLC (gradient from CH$_3$CN/H$_2$O/TFA: 5/95/0.05 to CH$_3$CN/H$_2$O/TFA: 80/20/0.05).

Method I: To solutions of aldehyde reagents (0.12 mmol) in 1.2 ml 1,2-DCE, were added sodium sulfate (12.8 mg) and 0.5 ml of Example 15 solution (0.797 mg, 1.92 mmol, in 16 ml 1,2-DCE). The reaction mixtures were then stirred 24 h at RT before addition of sodium triacetoxyborohydride (20 mg, 0.084 mmol). The reactions were allowed to continue at RT for 24 h.

Method J: To solutions of aldehyde reagents (0.135 mmol) and triacetoxyborohydride (19 mg, 0.09 mmol) in 1.5 ml of 1,2-DCE, were added 0.4 ml of a mixture trimethyl orthoformate/acetic acid: (10.5 ml/0.225 ml) and 0.5 ml of Example 15 solution (0.486 mg, 1.17 mmol, in 75 ml 1,2-DCE). The reaction mixtures were then stirred 24 h at RT, before treatment by PS-TsNHNH$_2$ (Argonaut, 159 mg, 0.405 mmol).

For each compound, LC Mass results are reported in Table 11 (LCMS conditions: LC Micromass platform (APCI+, DAD (210–400 nm)), Column: TSK gel Super ODS 4.6 mm IDx5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

TABLE 11

| Ex. | Structure | Method | Quantity (mg) | Retention time | Analysis |
|---|---|---|---|---|---|
| 183 | 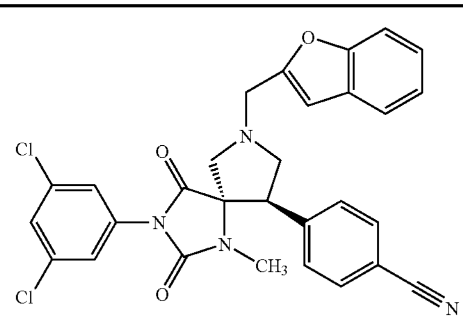 | I | 12.7 | 2.24 | 545(M+1) |

TABLE 11-continued

| Ex. | Structure | Method | Quantity (mg) | Retention time | Analysis |
|---|---|---|---|---|---|
| 184 | 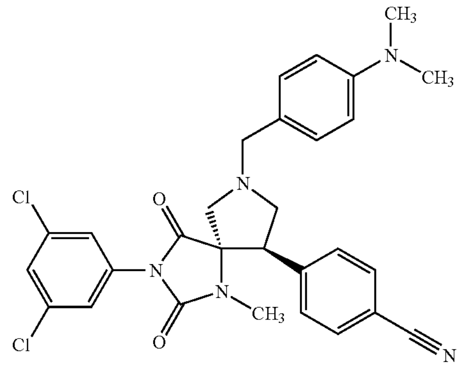 | J | 6.6 | 1.87 | 548(M+1);<br>1H NMR(CDCl3):<br>7.6(2H, d), 7.4–7.15(5H, m), 6.85–6.6(4H, m),<br>3.9–3.55(3H, m),<br>3.45–2.85(13H, m) |
| 185 | 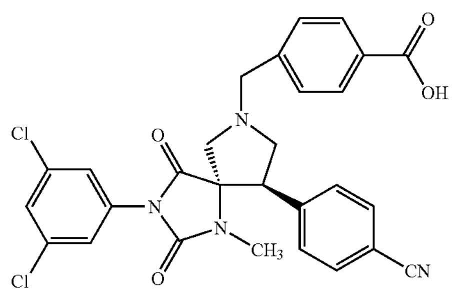 | J | 4 | 1.85 | 549(M+1) |
| 186 | 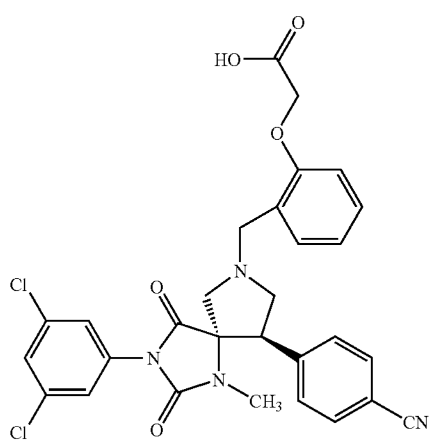 | J | 4.5 | 1.91 | 579(M+1) |
| 187 | 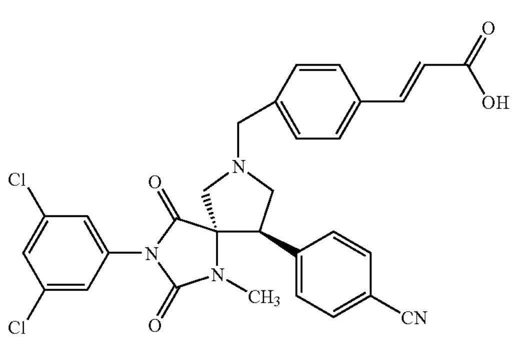 | J | 4.5 | 1.88 | 575(M+1) |

TABLE 11-continued

| Ex. | Structure | Method | Quantity (mg) | Retention time | Analysis |
|-----|-----------|--------|---------------|----------------|----------|
| 188 | 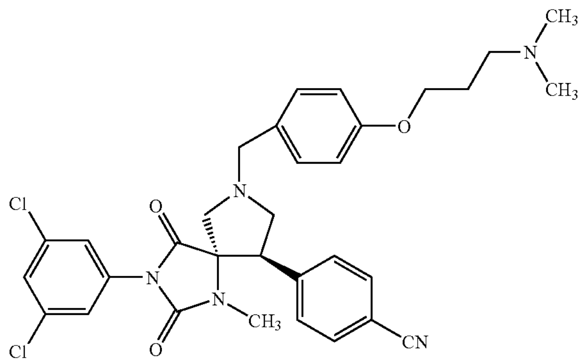 | J | 2.8 | 1.72 | 606(M+1) |
| 189 | 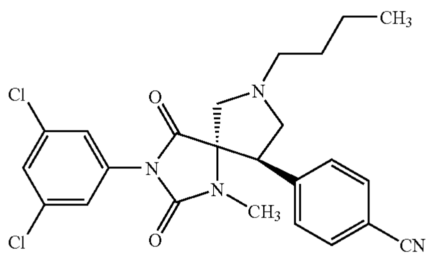 | J | 3.6 | 1.89 | 471(M+1) |
| 190 | 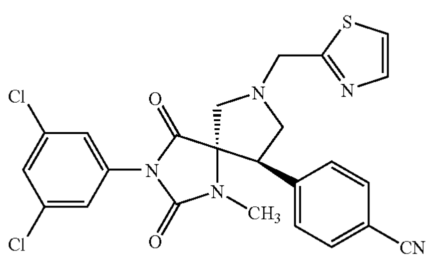 | J | 3.2 | 2.32 | 512(M+1) |
| 191 | 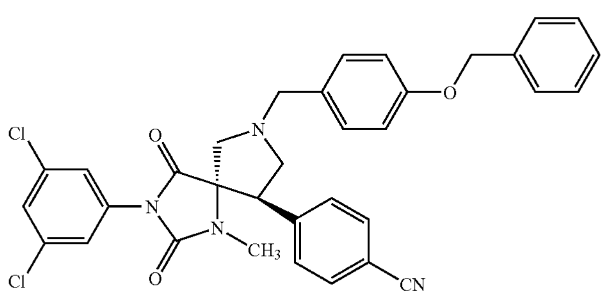 | J | 3.2 | 2.16 | 611(M+1) |
| 192 | 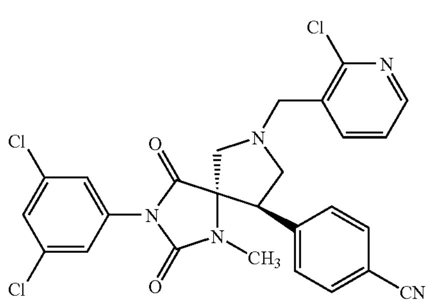 | J | 3 | 1.99 | 580(M+41); 540(M+1) |

TABLE 11-continued

| Ex. | Structure | Method | Quantity (mg) | Retention time | Analysis |
|---|---|---|---|---|---|
| 193 | 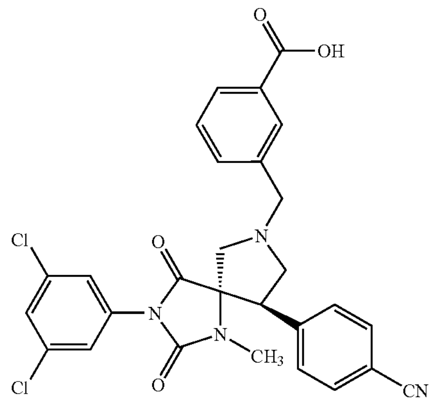 | J | 2.5 | 1.84 | 549(M+1); 590(M+41) |
| 194 | 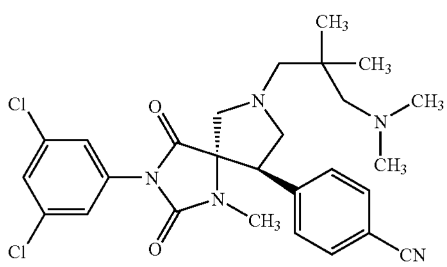 | J | 6.4 | 1.69 | 568(M+41) |
| 195 | 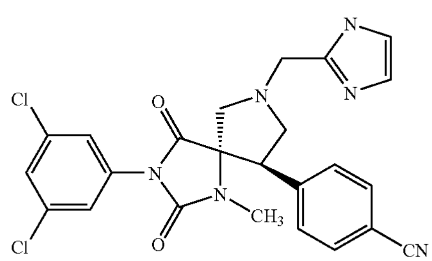 | J | 9.5 | 1.75 | 495(M+1) |
| 196 | 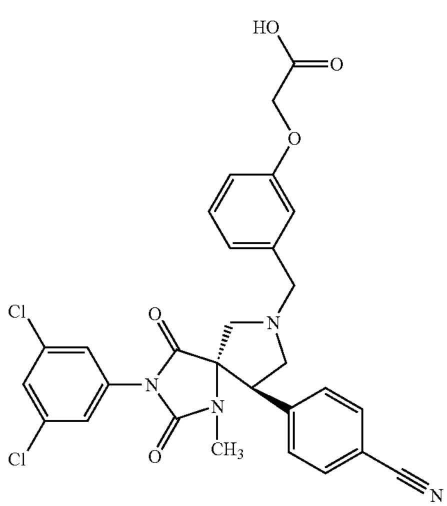 | J | 1.3 | 1.82 | 579(M+1) |

TABLE 11-continued
| Ex. | Structure | Method | Quantity (mg) | Retention time | Analysis |
|---|---|---|---|---|---|
| 197 | 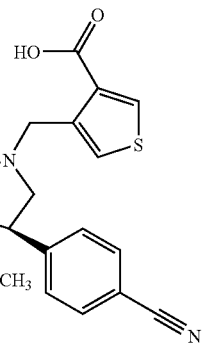 | J | 13.6 | 1.84 | 555(M+1) |
| 198 | 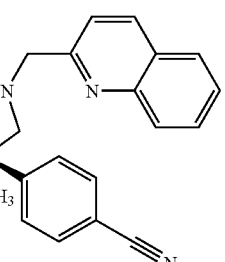 | J | 7.4 | 1.97 | 556(M+1) |
| 199 | 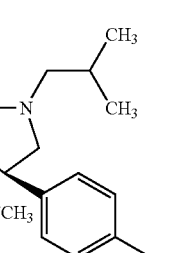 | J | 1.9 | 1.83 | 471(M+1) |
| 200 | 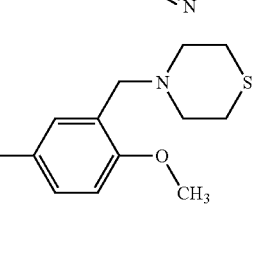 | J | 3.3 | 10.734* | 650(M−1)* |
| 201 | 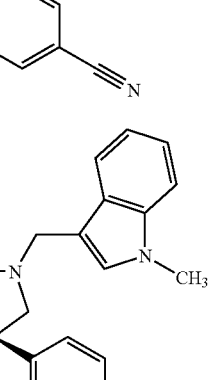 | J | 14.6 | 2.02 | 560(M+1) |

TABLE 11-continued
| Ex. | Structure | Method | Quantity (mg) | Retention time | Analysis |
|---|---|---|---|---|---|
| 202 | 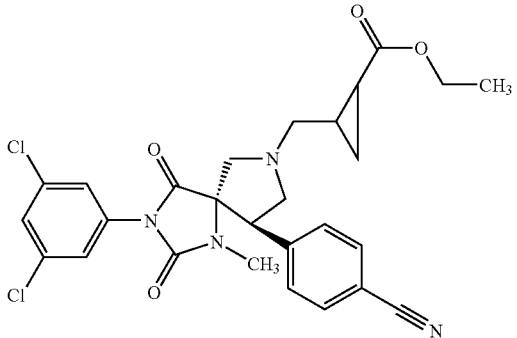 | J | 16.8 | 1.92 | 541(M+1) |
| 203 | 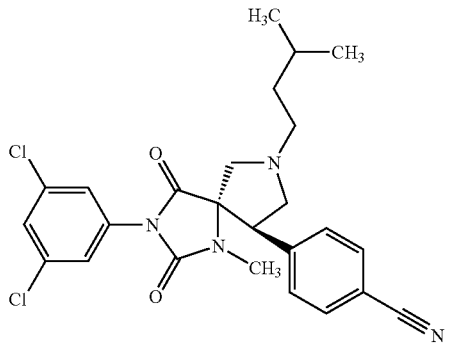 | J | 20.1 | 1.92 | 485(M+1) |
| 204 | 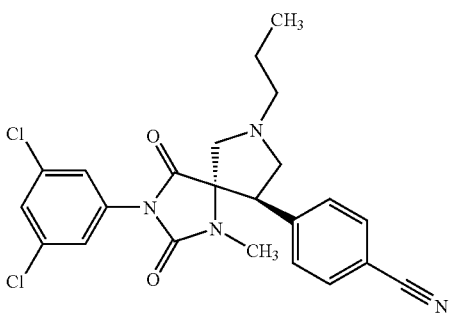 | J | 18.3 | 1.79 | 457(M+1) |
| 205 | 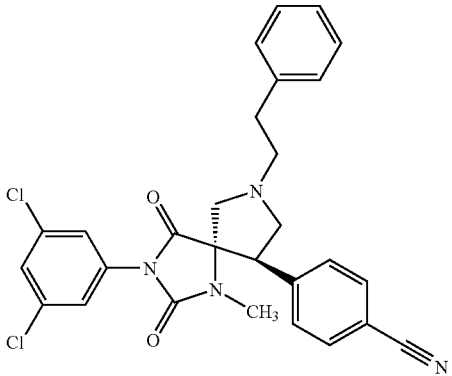 | J | 9.6 | 2.02 | 519(M+1) |

TABLE 11-continued

| Ex. | Structure | Method | Quantity (mg) | Retention time | Analysis |
|---|---|---|---|---|---|
| 206 | 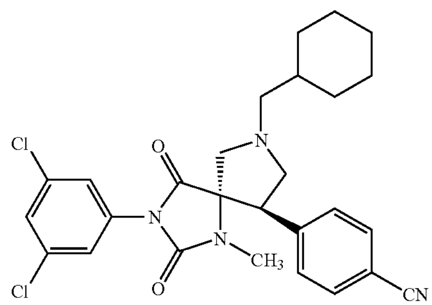 | J | 3.7 | 1.75 | 513(M+1) |
| 207 | 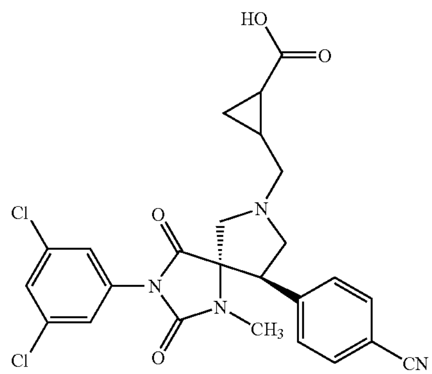 | J & C | 12.5 | 1.75 | 513(M+1) |
| 208 | 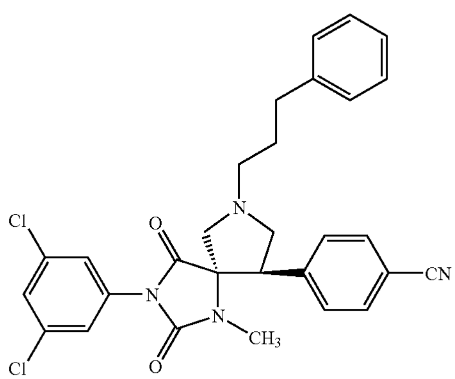 | J | 12.6 | 2.17 | 533(M+1) |
| 209 | 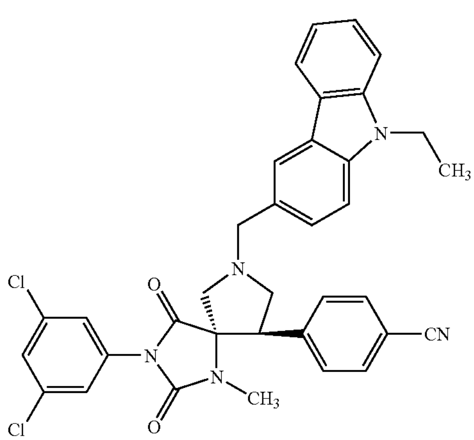 | J | 7.4 | 2.34 | 622(M+1) |

TABLE 11-continued

| Ex. | Structure | Method | Quantity (mg) | Retention time | Analysis |
|---|---|---|---|---|---|
| 210 | 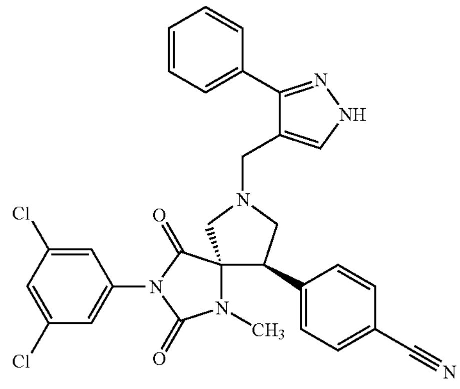 | J | 7.8 | 1.9 | 571(M+1) |
| 211 | 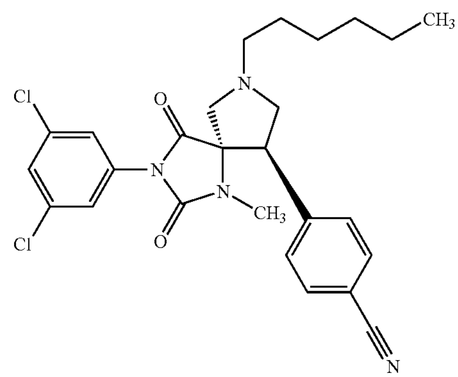 | J | 5.8 | 2.09 | 499(M+1) |
| 212 | 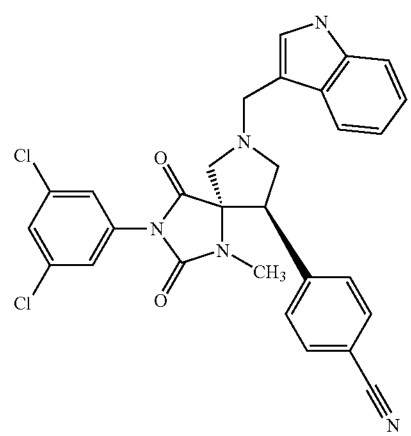 | J | 7 | 2.11 | 544(M+1) |
| 213 | 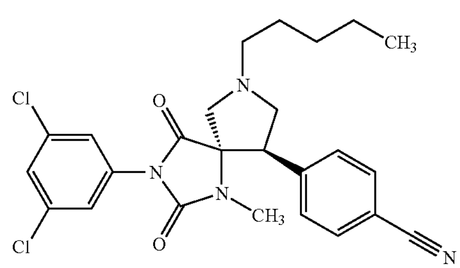 | J | 6.5 | 2.12 | 485(M+1) |

TABLE 11-continued
| Ex. | Structure | Method | Quantity (mg) | Retention time | Analysis |
|---|---|---|---|---|---|
| 214 | 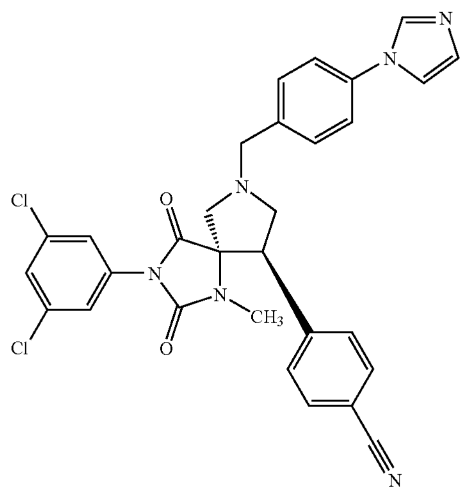 | J | 4 | 1.69 | 571(M+1) |
| 215 | 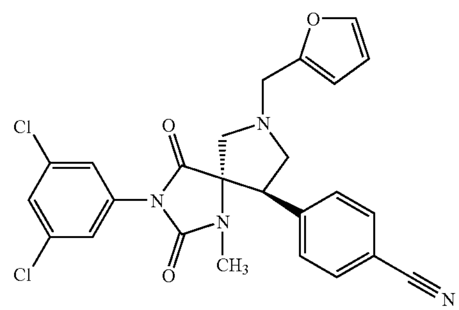 | J | 9 | 2.01 | 495(M+1) |
| 216 | 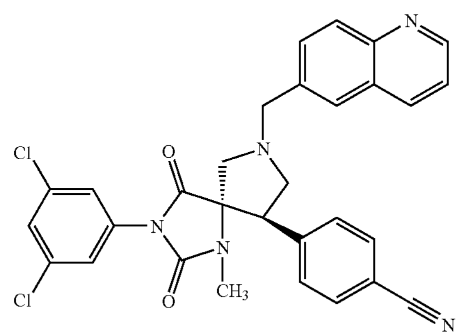 | J | 20 | 1.85 | 556(M+1) |
*(APCI −) as in Example 152
Examples 217–250
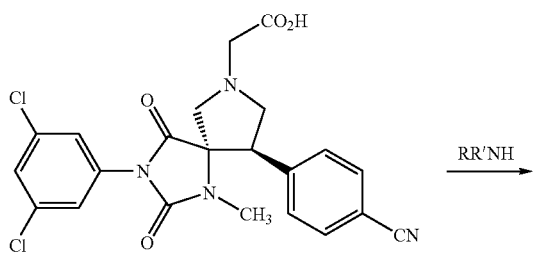
Example 64

-continued

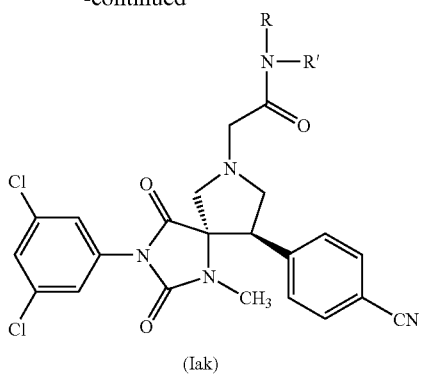

(Iak)

To a suspension of PS-carbodiimide (Argonaut, 0.96 mmol/g, 74 mg, 0.071 mmol) in 0.33 ml of hydroxyazabenzotriazole solution (153 mM DCM {25% DMF}, 0.05 mmol), were added 0.5 ml of a solution of Example 64 (60 mM DCM {20% DMF}, 0.03 mmol) and 0.5 ml of solution having the desired amine reagent RR'NH (54 mM DCM {20% DMF}, 0.027 mmol). After 24 h at RT, the mixtures were treated with PS-trisamine (Argonaut, 3.65 mmol/g, 65 mg, 0.24 mmol) overnight. After evaporation to dryness of the filtered solutions, compounds having the formula (Iak), listed in Table 12, were obtained. For N-Boc and/or CO$_2$tBu protected acids (Examples 245–250), the compounds were treated with DCM/TFA (1:1) solution for 2 h at RT, following respectively by SCX or SAX cartridge purification (Method L). Examples 242–244 were obtained after hydrolysis of their corresponding esters following the general Method C as in Examples 90–101. These compounds were then purified by SAX cartridge. Some compounds were obtained after purification by reverse phase HPLC (gradient from CH$_3$CN/H$_2$O/TFA: 5/95/0.05 to CH$_3$CN/H$_2$O/TFA: 80/20/0.05).

For each compound, LC Mass results are reported in Table 12 (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: H$_2$O (0.05% TFA), Eluent B: CH$_3$CN/H$_2$O/TFA (80/20/0.05)).

TABLE 12

| Ex. | Structure | Method | Quantity (mg) | Retention time | Analysis |
|---|---|---|---|---|---|
| 217 | 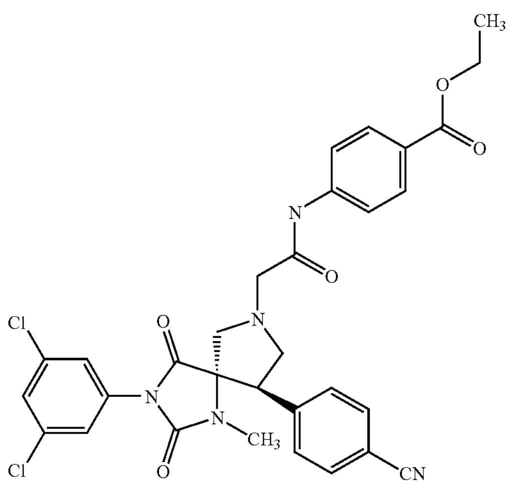 | K | 2 | 2.25 | 620(M+1) |
| 218 | 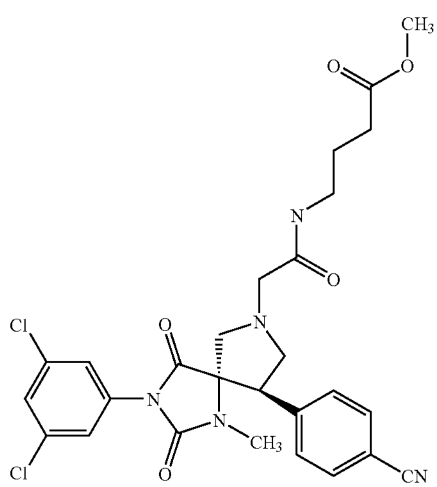 | K | 1.6 | 1.97 | 572(M+1) |

TABLE 12-continued

| Ex. | Structure | Method | Quantity (mg) | Retention time | Analysis |
|---|---|---|---|---|---|
| 219 | 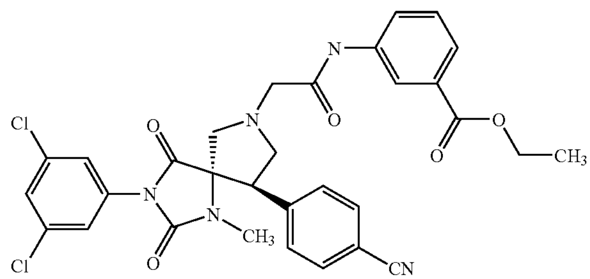 | K | 1.9 | 2.26 | 620(M+1) |
| 220 | 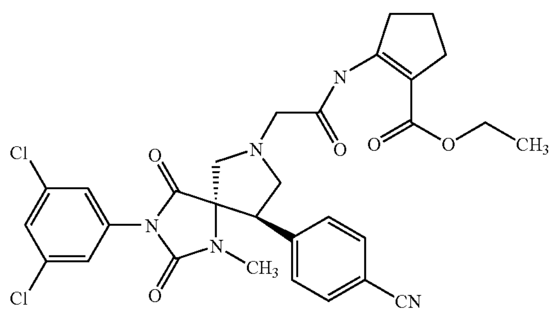 | K | 1.3 | 2.59 | 610(M+1) |
| 221 | 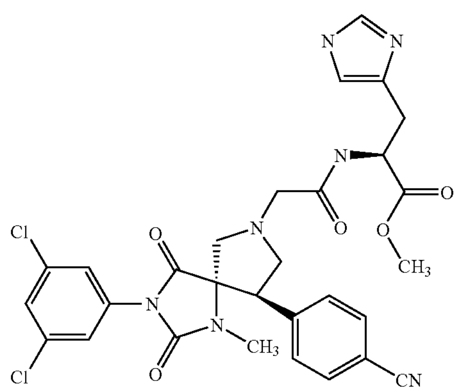 | K | 2.1 | 1.83 | 624(M+1) |
| 222 | 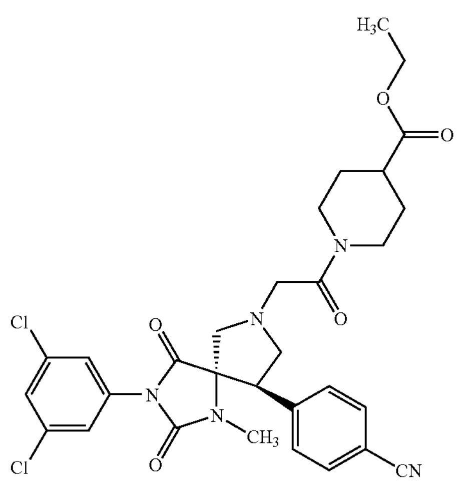 | K | 1.9 | 2.05 | 612(M+1) |

TABLE 12-continued

| Ex. | Structure | Method | Quantity (mg) | Retention time | Analysis |
|---|---|---|---|---|---|
| 223 | 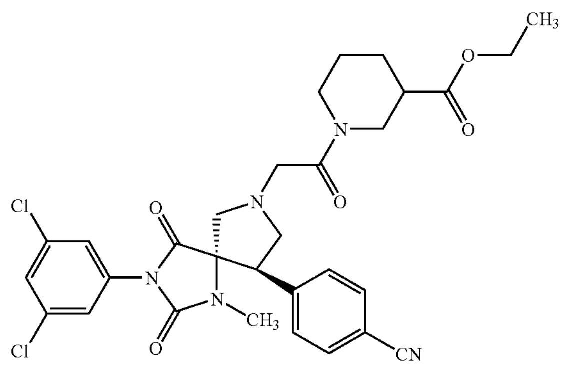 | K | 1.9 | 2.07 | 612(M+1) |
| 224 | 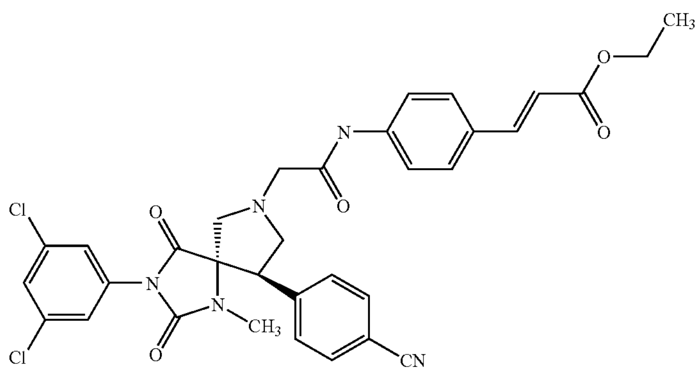 | K | 1.7 | 2.27 | 646(M+1) |
| 225 | 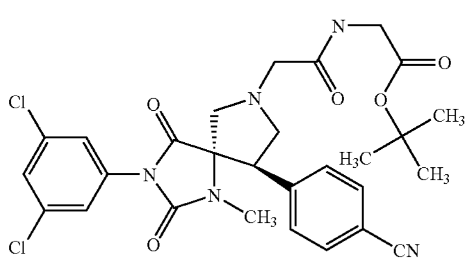 | K | 1.2 | 2.14 | 586(M+1) |
| 226 | 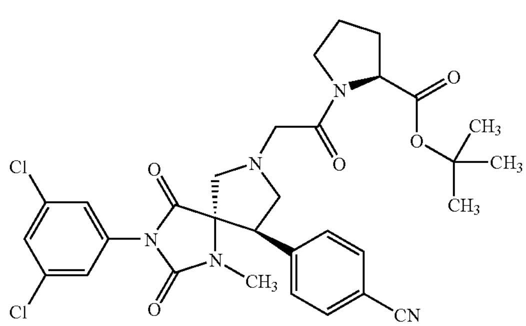 | K | 1.7 | 2.16 | 626(M+1) |

TABLE 12-continued

| Ex. | Structure | Method | Quantity (mg) | Retention time | Analysis |
|---|---|---|---|---|---|
| 227 | 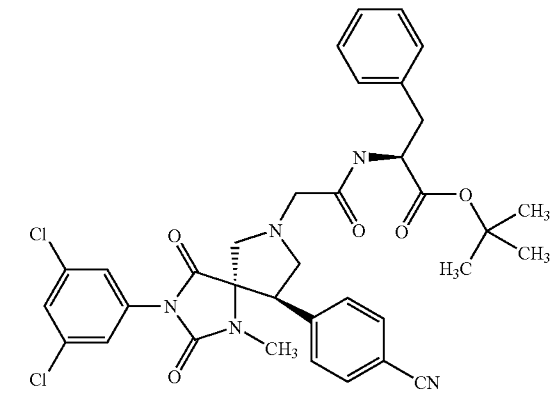 | K | 1.9 | 2.4 | 676(M+1) |
| 228 | 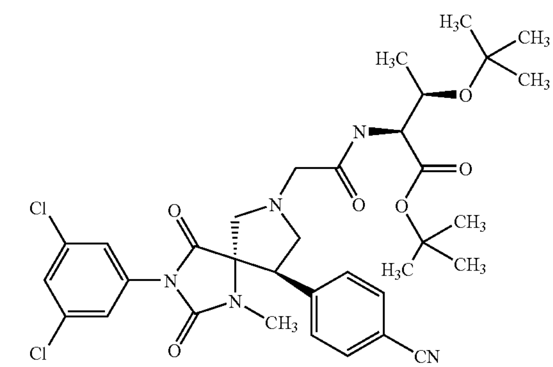 | K | 1.7 | 2.47 | 686(M+1) |
| 229 | 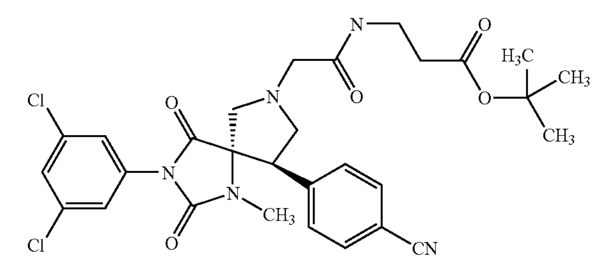 | K | 1.8 | 2.15 | 600(M+1) |
| 230 | 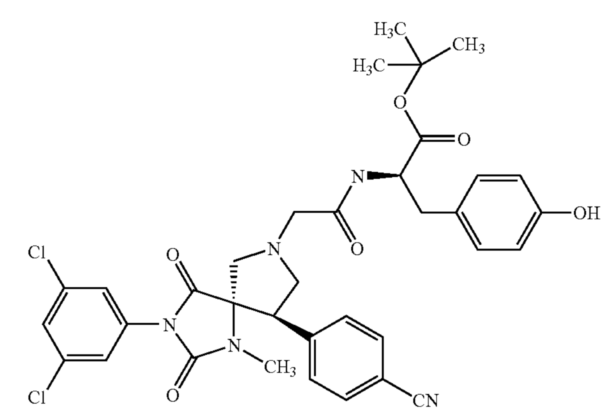 | K | 1.6 | 2.23 | 692(M+1) |

TABLE 12-continued
| Ex. | Structure | Method | Quantity (mg) | Retention time | Analysis |
|---|---|---|---|---|---|
| 231 | 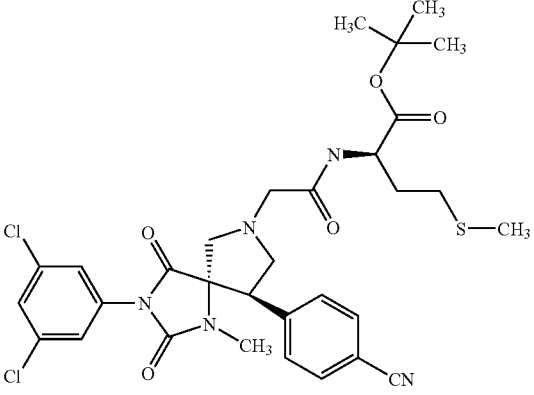 | K | 1.7 | 2.29 | 660(M+1) |
| 232 | 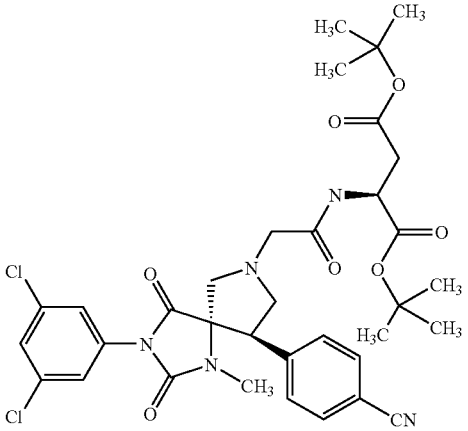 | K | 1.5 | 2.46 | 700(M+1) |
| 233 | 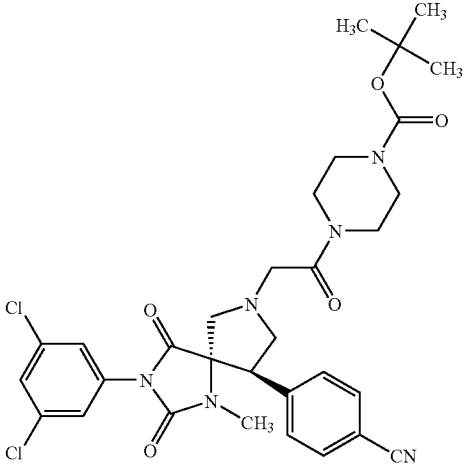 | K | 1.7 | 2.13 | 641(M+1) |

TABLE 12-continued

| Ex. | Structure | Method | Quantity (mg) | Retention time | Analysis |
|---|---|---|---|---|---|
| 234 | 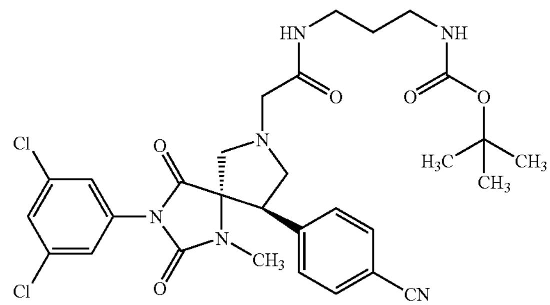 | K | 1.8 | 2.11 | 629(M+1) |
| 235 | 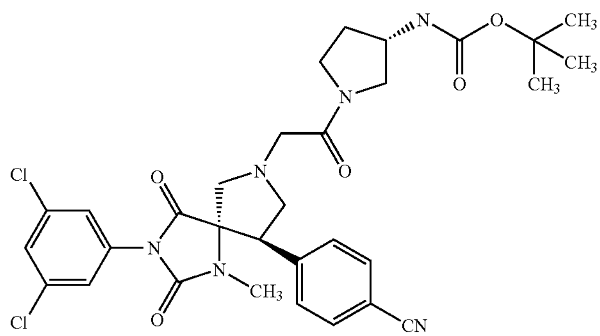 | K | 1.9 | 2.09 | 641(M+1) |
| 236 | 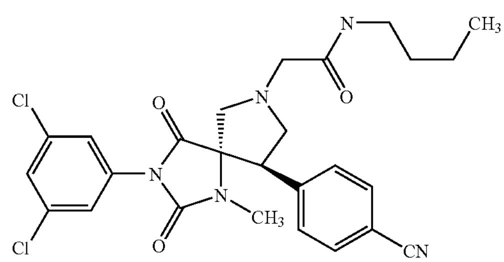 | K | 5.5 | 2.08 | 528(M+1) |
| 237 | 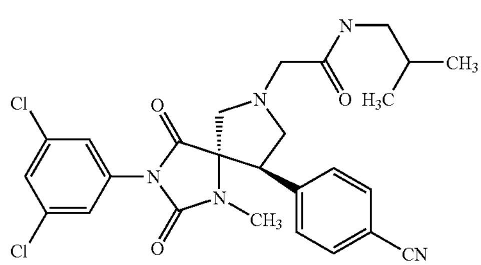 | K | 7 | 1.77 | 528(M+1) |
| 238 | 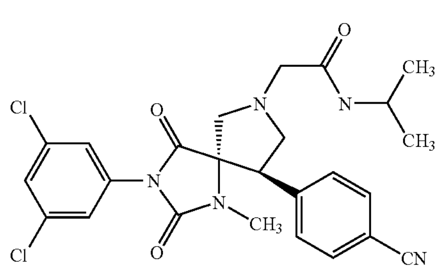 | K | 12.2 | 1.97 | 514(M+1) |

TABLE 12-continued

| Ex. | Structure | Method | Quantity (mg) | Retention time | Analysis |
|---|---|---|---|---|---|
| 239 | 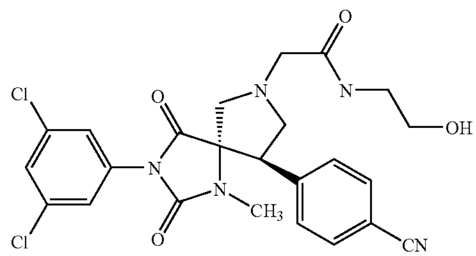 | K | 16.7 | 1.8 | 516(M+1) |
| 240 | 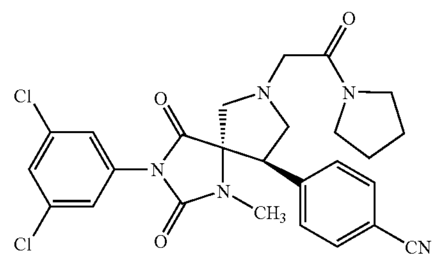 | K | 14.8 | 1.94 | 526(M+1) |
| 241 | 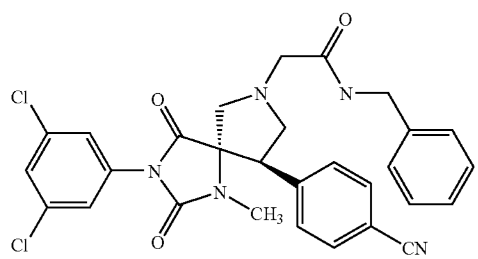 | K' (SCX) | 13.6 | 2.12 | 562(M+1) |
| 242 | 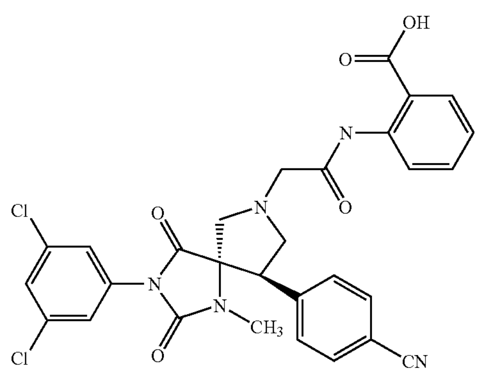 | K & C | 1.1 | 2.13 | 592(M+1) |
| 243 | 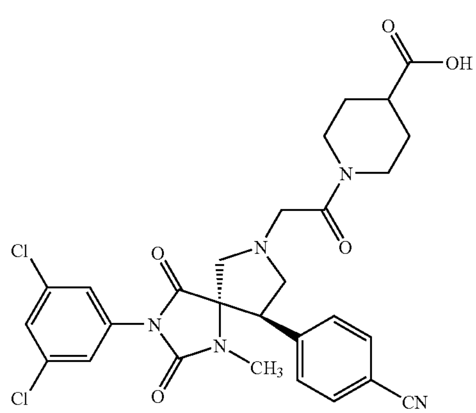 | K & C | 1.3 | 1.8 | 584(M+1) |

TABLE 12-continued

| Ex. | Structure | Method | Quantity (mg) | Retention time | Analysis |
|---|---|---|---|---|---|
| 244 | 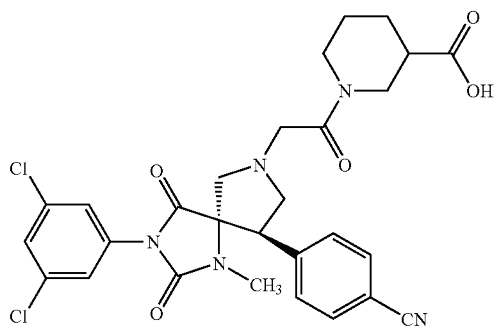 | K & C | 1.5 | 1.81 | 584(M+1) |
| 245 | 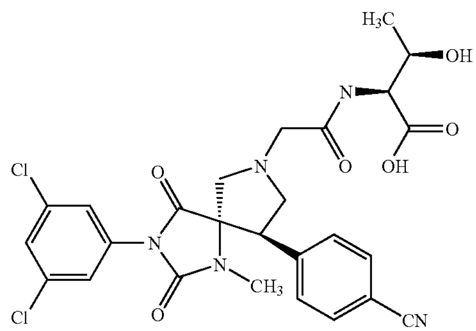 | K & L | 1.5 | 1.71 | 574(M+1) |
| 246 | 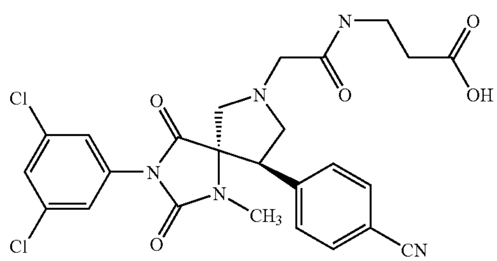 | K & L | 4.7 | 1.71 | 544(M+1) |
| 247 | 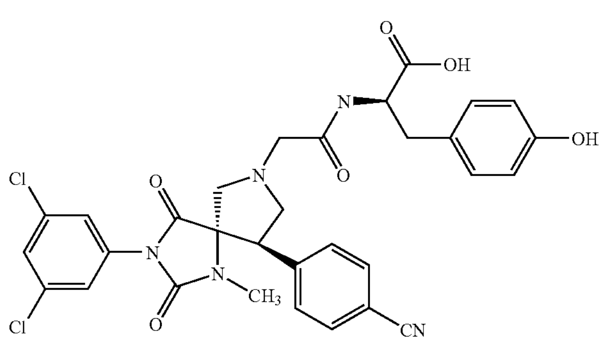 | K & L | 4.5 | 1.81 | 636(M+1) |

TABLE 12-continued

| Ex. | Structure | Method | Quantity (mg) | Retention time | Analysis |
|---|---|---|---|---|---|
| 248 | 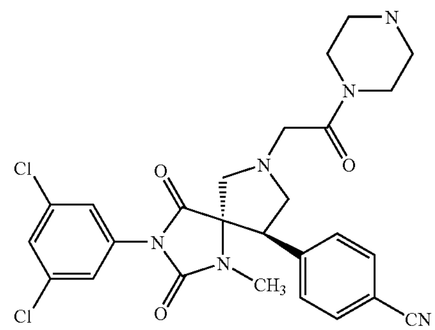 | K & L | 16.7 | 1.57 | 541(M+1) |
| 249 | 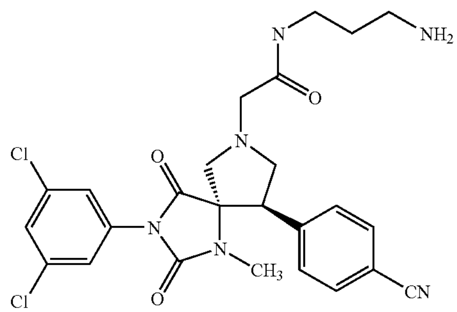 | K & L | 17.7 | 1.59 | 529(M+1) |
| 250 | 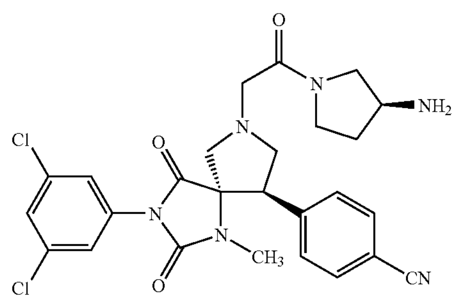 | K & L | 17.5 | 1.57 | 541(M+1) |

Examples 251–268

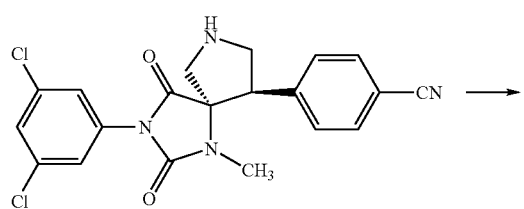

→

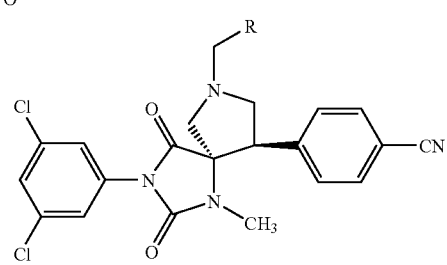

(Iaj)

Compounds having the formula (Iaj), listed in Table 13, were obtained using Method G or I, as described for Examples 153–162 and 183–216, after SCX cartridge purification. Some compounds were further purified by reverse phase HPLC (gradient from $CH_3CN/H_2O/TFA$: 5/95/0.05 to $CH_3CN/H_2O/TFA$: 80/20/0.05). Example 268 was obtained after hydrolysis of its corresponding ethyl ester (example 267) following the general Method C as in Examples 90–101. For each compound, LC Mass results are reported in Table 13 (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 13
| Ex. | Structure | Method | Quantity (mg) | Retention Time | Analysis |
|---|---|---|---|---|---|
| 251 | 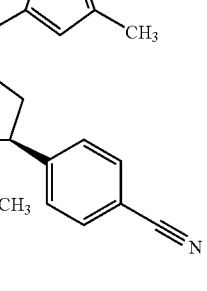 | I | 4.5 | 1.9 | 523(M+1) |
| 252 | 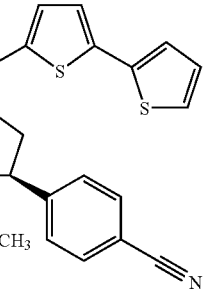 | I | 9.6 | 2.04 | 593(M+1) |
| 253 | 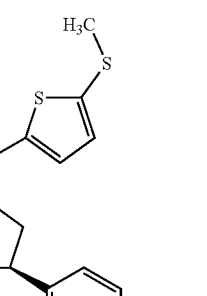 | I | 7.6 | 1.97 | 557(M+1) |
| 254 | 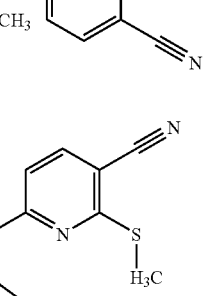 | I | 8.5 | 1.92 | 577(M+1) |

TABLE 13-continued

| Ex. | Structure | Method | Quantity (mg) | Retention Time | Analysis |
|---|---|---|---|---|---|
| 255 | 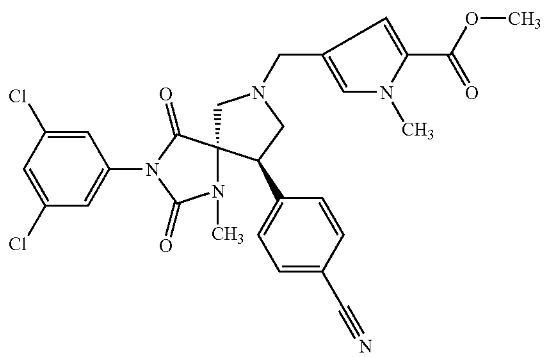 | I | 10.3 | 1.82 | 566(M+1) |
| 256 | 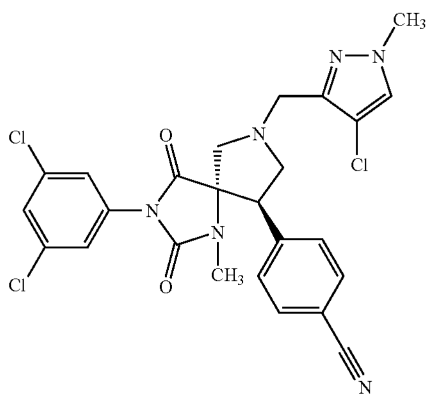 | I | 11.2 | 1.81 | 543(M+1) |
| 257 | 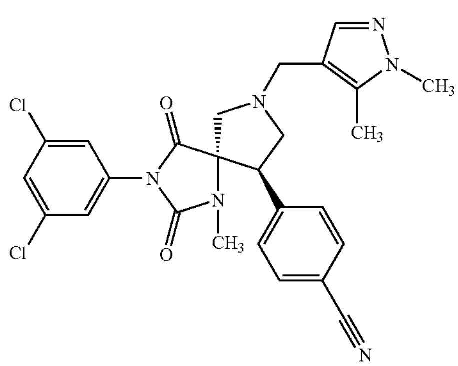 | I | 18.1 | 1.72 | 523(M+1) |
| 258 | 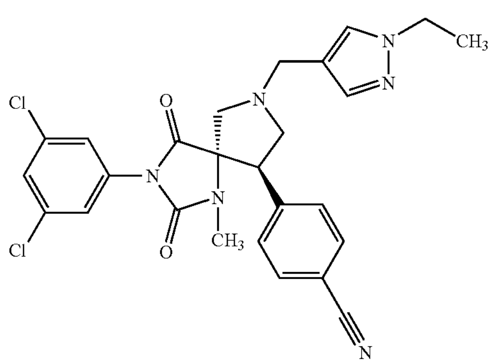 | I | 9.3 | 1.74 | 523(M+1) |

TABLE 13-continued

| Ex. | Structure | Method | Quantity (mg) | Retention Time | Analysis |
|---|---|---|---|---|---|
| 259 | 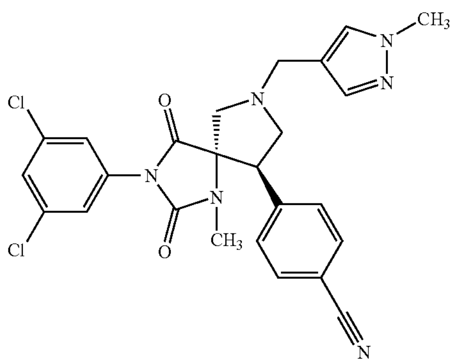 | I | 16.5 | 1.7 | 509(M+1) |
| 260 | 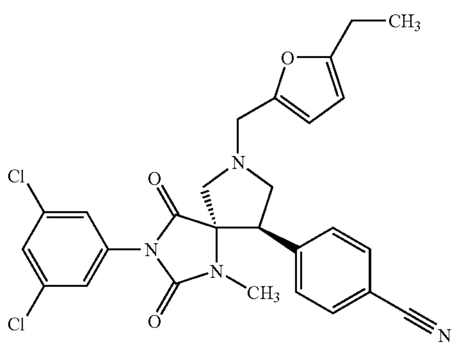 | I | 11.5 | 1.9 | 523(M+1) |
| 261 | 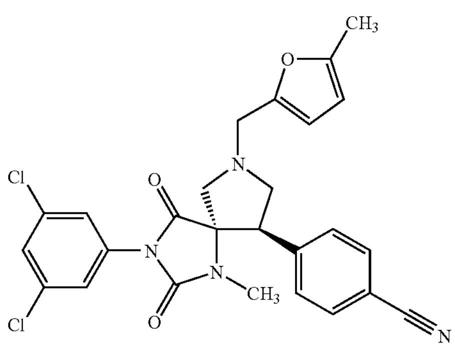 | I | 14.8 | 1.85 | 509(M+1) |
| 262 | 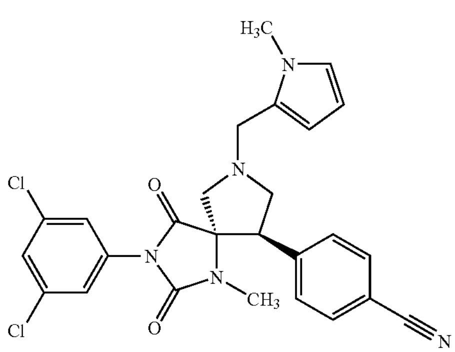 | I | 8 | 1.82 | 508(M+1) |

TABLE 13-continued
| Ex. | Structure | Method | Quantity (mg) | Retention Time | Analysis |
|---|---|---|---|---|---|
| 263 | 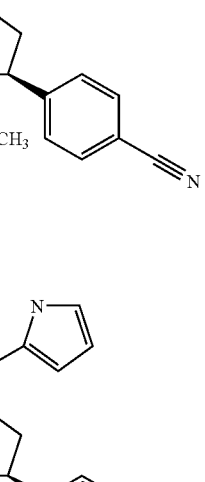 | I | 6.1 | 1.89 | 525(M+1) |
| 264 | 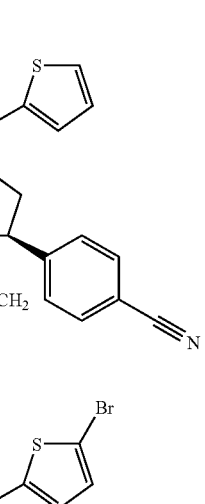 | I | 12.8 | 1.77 | 494(M+1) |
| 265 | 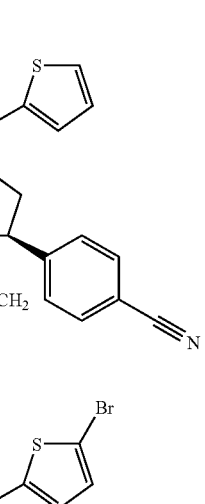 | I | 3.9 | 1.85 | 511(M+1) |
| 266 | 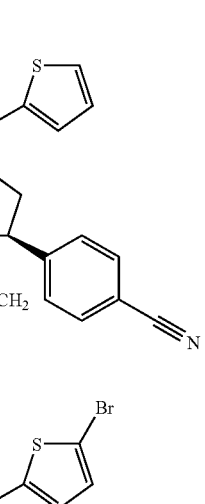 | I | 7.6 | 2 | 591(M+1) |

TABLE 13-continued

| Ex. | Structure | Method | Quantity (mg) | Retention Time | Analysis |
|---|---|---|---|---|---|
| 267 | 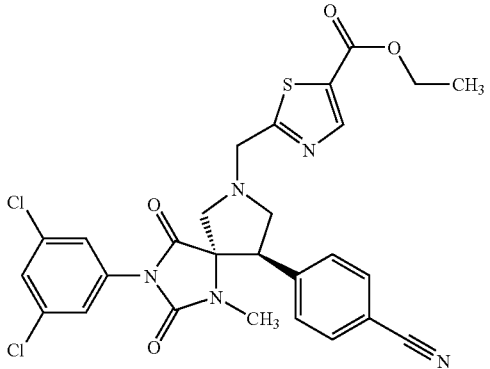 | G | 2.5 | 1.97 | 584(M+1) |
| 268 | 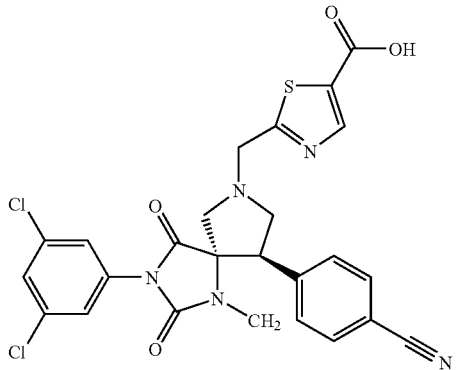 | G + C | 2 | 1.76 | 557(M+1) |

Examples 269–278

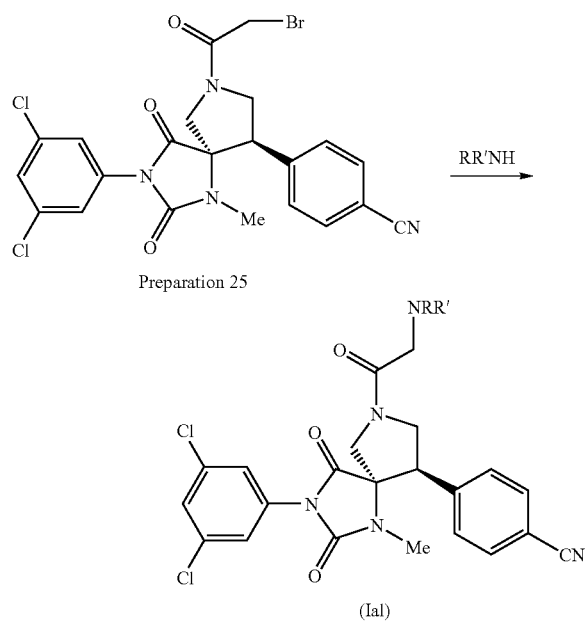

Compounds having the above formula (Ial), listed in Table 14, were obtained by adding 0.1 ml of TEA solution (720 mM in THF, 0.072 mmol), 0.1 ml of DMAP solution (60 mM in THF, 0.006 mmol) and 1 ml of Preparation 25 solution (60 mM in THF, 0.06 mmol), to a solution of an appropriately-substituted amine RR'NH (0.5 ml, 18 mM in THF, 0.09 mmol). The reaction mixtures were stirred at RT overnight and concentrated to dryness (Method M). The residues were purified by reverse phase HPLC (gradient from $CH_3CN/H_2O/TFA$: 5/95/0.05 to $CH_3CN/H_2O/TFA$: 80/20/0.05). N-Boc and/or $CO_2tBu$ protected compounds were treated with DCM/TFA (1:1) solution for 2 h at RT, followed respectively by SCX or SAX cartridge purification for the resulting basic or acidic compounds (Method L). LC Mass results are reported (APCI+, DAD (210–400 nm)), Column: TSK gel Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

TABLE 14

| Ex. | Structure | Method | Quantity (mg) | Retention time | Analysis |
|---|---|---|---|---|---|
| 269 | 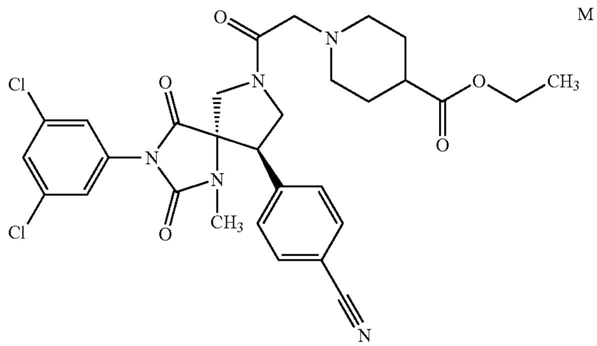 | M | 5.3 | 1.86 | 572(M+1) |
| 270 | 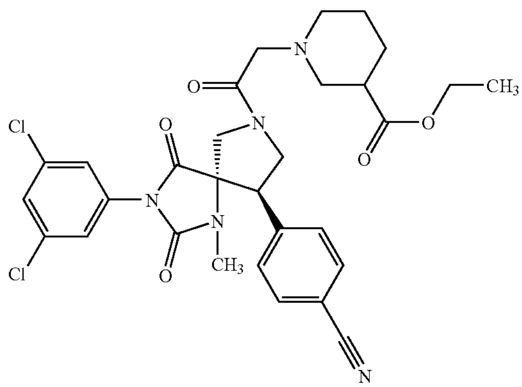 | M | 3.5 | 1.86 | 612(M+1) |
| 271 | 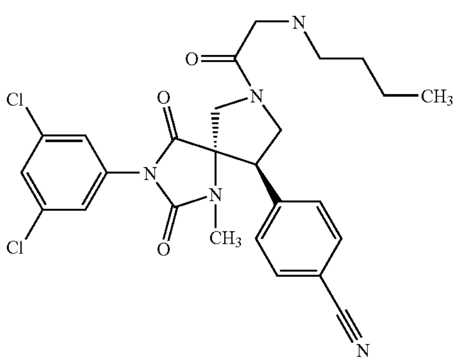 | M | 7.8 | 1.89 | 612(M+1) |
| 272 | 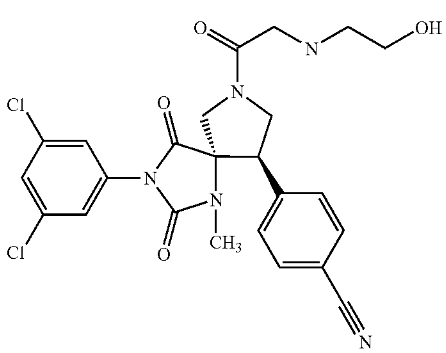 | M | 9.1 | 1.86 | 528(M+1) |

TABLE 14-continued

| Ex. | Structure | Method | Quantity (mg) | Retention time | Analysis |
|---|---|---|---|---|---|
| 273 | 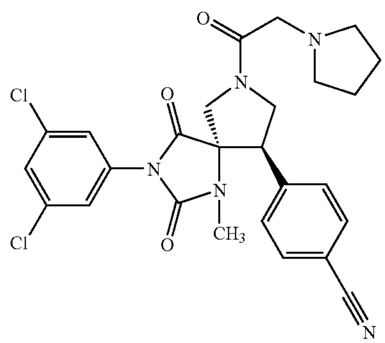 | M | 11.2 | 1.7 | 516(M+1) |
| 274 | 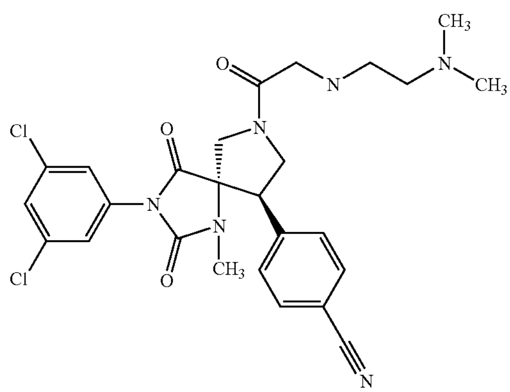 | M | 8.8 | 1.78 | 526(M+1) |
| 275 | 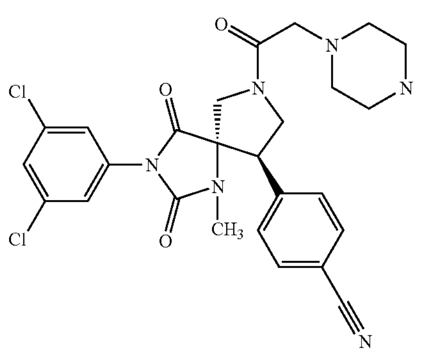 | M + L | 13.2 | 1.64 | 541(M+1) |
| 276 | 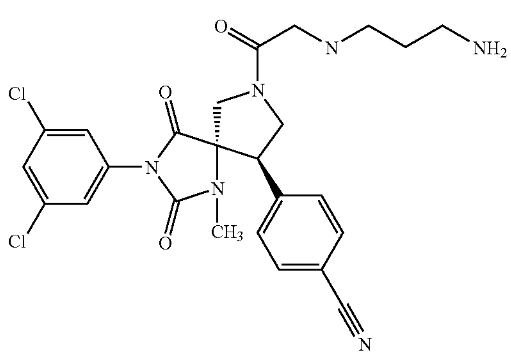 | M + L | 6.8 | 1.59 | 529(M+1) |

TABLE 14-continued

| Ex. | Structure | Method | Quantity (mg) | Retention time | Analysis |
|---|---|---|---|---|---|
| 277 | 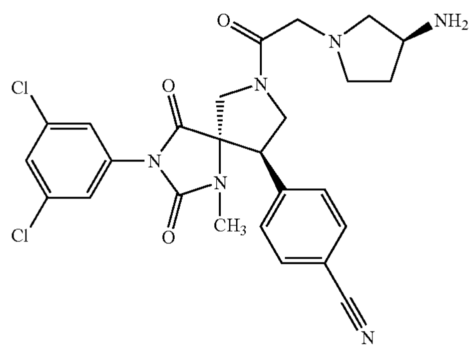 | M + L | 10.7 | 1.58 | 541(M+1) |
| 278 | 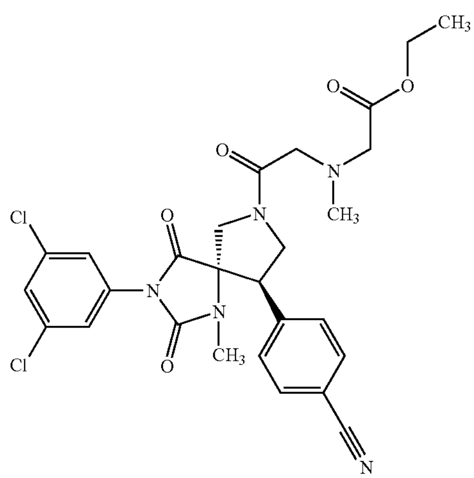 | M | 3.7 | 1.86 | 572(M+1) |

Example 279

4-[(5S*,9R*)-7-Benzyl-3-(2,6-dichloro-pyridin-4-yl)-1-methyl-2,4-dioxo-1,3,7-triazaspiro[4.4]non-9-yl]-benzonitrile

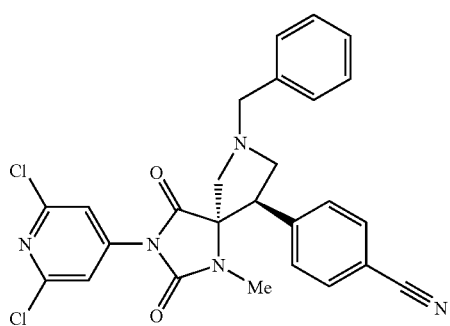

Using the experimental procedure described for Example 11, Preparation 20 (5.6 g, 15 mmol) was converted into the above-titled compound as a white solid (7.5 g), mp=174–176° C. $^1$H NMR (CDCl$_3$): 7.60 (2H, d, J=8 Hz), 7.25–7.35 (7H, m), 7.11 (2H, m), 3.65–4.0 (4H, m), 3.0–3.4 (2H, m), 3.23 (3H, s), 2.97 (1H, d, J=10.9 Hz).

Example 280

4-[(5S*,9R*)-9-(4-Cyanophenyl)-3-(3,5-dichlorophenyl)-1-methyl-2,4-dioxo-1,3,7-triazaspiro[4.4]non-7-yl]-benzoic acid

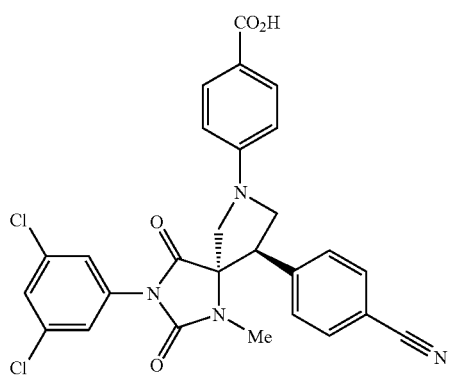

Trifluoroacetic acid (122 μl, 1.6 mmol) was added to a cooled (5° C.) solution of Preparation 27 (97 mg, 0.16 mmol) in DCM (3 ml). After 24 h at RT, water was added and the pH was brought to 10 with NH$_4$OH. SO$_2$ was then

Example 281

4-[(5S*,9R*)-3-(3,5-Dichlorophenyl)-1-methyl-2,4-dioxo-7-(2-H-tetrazol-5-yl-acetyl)-1,3,7-triazaspiro[4.4]non-9-yl]-benzonitrile

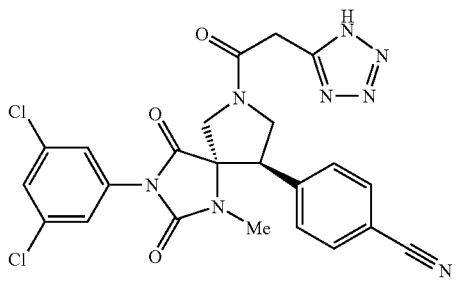

Using the same procedure as in Example 102, the above titled compound was obtained (33.3 mg) after purification by reverse phase HPLC (gradient from $CH_3CN/H_2O/TFA$: 5/95/0.05 to $CH_3CN/H_2O/TFA$: 80/20/0.05) from Example 15 (41.3 mg, 0.1 mmol) and tetrazole-5-acetic acid (22 mg, 0.17 mmol). $^1H$ NMR ($CDCl_3$): 7.65–7.5 (2H, m), 7.35–7.1 (3H, m), 6.67 (2H, d), 4.5–3.7 (7H, m), 3.1 (3H, d).

Example 282

4-{(5S*,9R*)-3-(3,5-Dichlorophenyl)-1-methyl-2,4-dioxo-7-[2-(1H-tetrazol-5-yl)-ethyl]-1,3,7-triazaspiro[4.4]non-9-yl}-benzonitrile

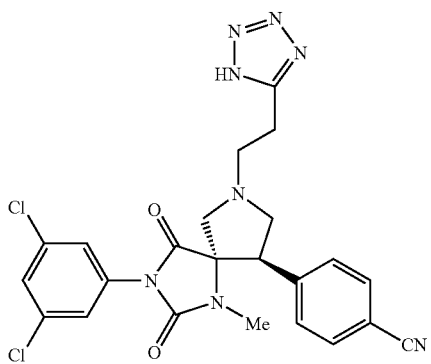

To Example 15 (24.9 mg, 0.06 mmol) in 1 ml $CH_3CN$, were added sodium iodide (8.4 mg, 0.084 mmol), potassium carbonate (5.5 mg, 0.06 mmol) and 5-(2-chloroethyl)-1H-tetrazole (5.3 mg, 0.04 mmol). The reaction mixture was stirred at 70° C. overnight. The above titled compound was obtained (1.3 mg) after SCX cartridge purification and PS-isocyanate treatment (Argonaut, 83 mg). Retention time: 1.36 min., $M_{obs}$=511 (M+1) (LCMS conditions: LC Micromass platform (APCI+, DAD (210–400 nm)), Column: TSK gel. Super ODS 4.6 mm ID×5 cm, Flow rate: 2.75 mL/min, Gradient: from 100% eluent A to 100% eluent B in 2 min., with a plateau with 100% eluent B during 1 min. Eluent A: $H_2O$ (0.05% TFA), Eluent B: $CH_3CN/H_2O/TFA$ (80/20/0.05)).

Example 283

4-{(5S*,9R*)-3-(3,5-Dichlorophenyl)-1-methyl-2,4-dioxo-7-[2-(1H-tetrazol-5-yl)-benzyl]-1,3,7-triazaspiro[4.4]non-9-yl}-benzonitrile

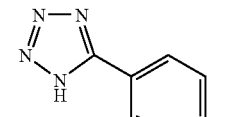
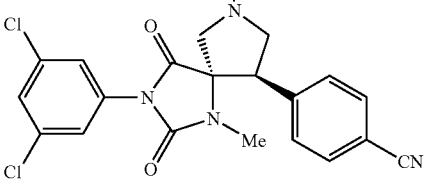

A mixture of Example 15 (33 mg, 0.08 mmol), Preparation 29 (57.8 mg, 0.12 mmol), TEA (16.7 µl, 0.12 mmol) and PS-DMAP (Argonaut, 5 mg) was stirred at RT overnight. The above titled compound was obtained (4.1 mg) after purification by reverse phase HPLC (gradient from $CH_3CN/H_2O/TFA$: 5/95/0.05 to $CH_3CN/H_2O/TFA$: 80/20/0.05). Retention time: 1.49 min., 573 (M+1) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B).

Example 284

6-[(5S*,9R*)-9-(4-Cyanophenyl)-3-(3,5-dichlorophenyl)-1-methyl-2,4-dioxo-1,3,7-triazaspiro[4.4]non-7-ylmethyl]-nicotinic acid methyl ester

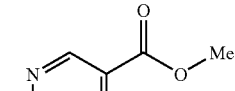
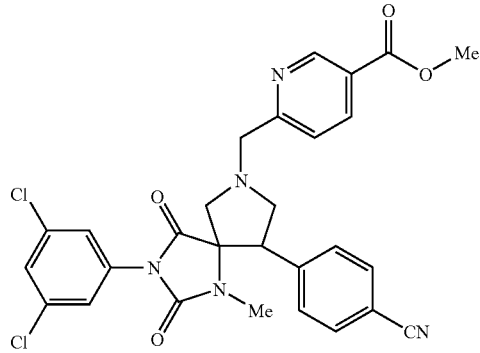

The above titled compound was obtained using the procedure described for Example 283 from Example 15 and Preparation 31. Retention time: 1.47 min., $M_{obs}$=564/566 (M and M+2) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B).

Example 285

6-[(S*,9R*)-9-(4-Cyanophenyl)-3-(3,5-dichlorophenyl)-1-methyl-2,4-dioxo-1,3,7-triazaspiro[4.4]non-7-ylmethyl]-nicotinic acid

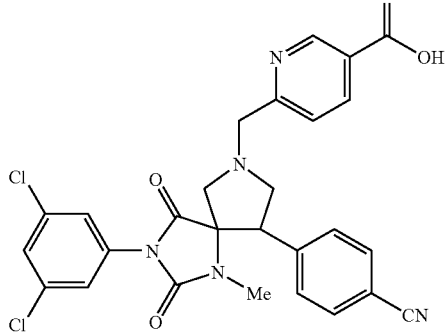

The above titled compound was obtained from Example 284 using the procedure described for Example 59. Retention time: 1.38 min., $M_{obs}$=550/552 (M and M+2) (LCMS conditions: LC Micromass platform (APCI+, DAD (210–400 nm)), Column: TSK gel Super ODS 4.6 mm ID×5 cm, Flow rate: 2.75 mL/min, Gradient: from 100% eluent A to 100% eluent B).

Example 286

4-[(S*,9R*)-3-(2,6-Dichloro-pyridin-4-yl)-1-methyl-2,4-dioxo-1,3,7-triazaspiro[4.4]non-9-yl]-benzonitrile

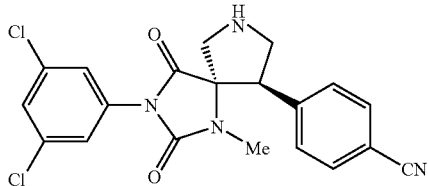

The above titled compound was obtained from Example 279 using the procedure described for Example 15. White solid, mp=202° C.

Example 287

4-{(5S*,9R*)-3-(3,5-Dichlorophenyl)-1-methyl-2,4-dioxo-7-[4-(1H-tetrazol-5yl)-thiophen-2-ylmethyl]-1,3,7-triazaspiro[4.4]non-9-yl}-benzonitrile

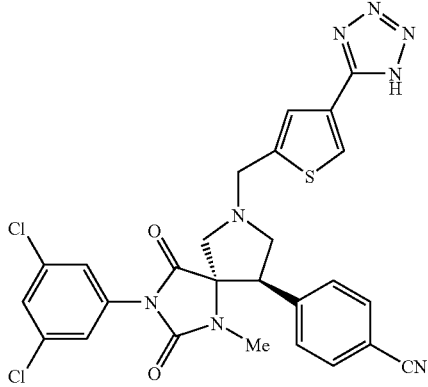

Example 287 was prepared from Example 15 and Preparation 32 by the reductive amination procedure described for Example 37. Retention time: 8.40 min., $M_{obs}$=580 (M+1); (LCMS conditions: HP 1100 MSD platform (APCI+, DAD (210400 nm)), Column: TSK gel Super ODS 4.6 mm ID×10 cm, Flow rate: 1 mL/min, Gradient: from 5% to 95% eluent B in 15 min., with a plateau with 95% eluent B during 5 min. Eluent A: H₂O (0.1% ammonium formate), Eluent B: CH₃CN).

Example 288

5-[(5S*,9R*)-9-(4-Cyanophenyl)-3-(2,6-Dichloropyridin-4-yl)-1-methyl-2,4-dioxo-1,3,7-triazaspiro[4.4]non-7-ylmethyl]-thiophene-3-carboxylic acid

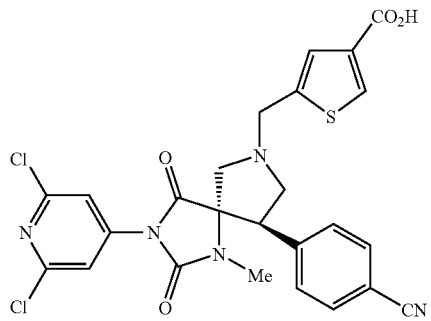

Example 288 was prepared as described for Example 287, using the appropriate aldehyde. White solid, mp=230–232° C.

Example 289

5-[(S*,9R*)-9-(4-Cyanophenyl)-3-(2,6-Dichloropyridin-4-yl)-1-methyl-2,4-dioxo-1,3,7-triazaspiro[4.4]non-7-ylmethyl]-thiophene-2-carboxylic acid

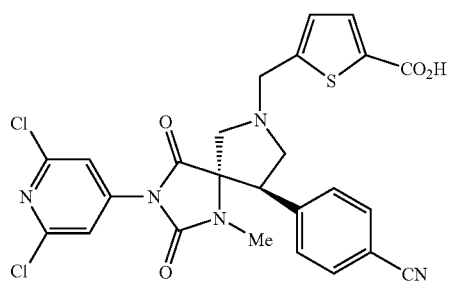

Example 289 was prepared as described for Example 287, using the appropriate aldehyde. Off-white solid, mp=252° C.

Example 290

5-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid methyl ester

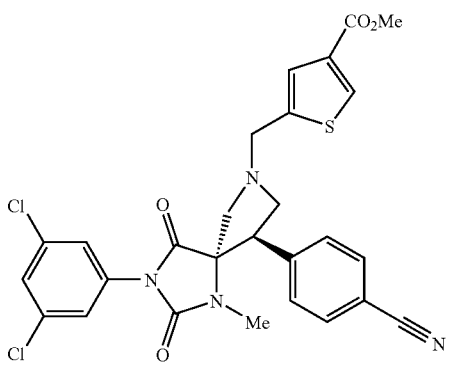

To a solution of 5-[(5S*,9R*)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (example 37) (0.150 g, 0.27 mmol) in DCM/MeOH (5:1 mL) was added trimethylsilyldiazomethane (2.0 M solution in hexane, 0.33 mL, 0.67 mmol) over a period of three minutes at RT. The reaction mixture was stirred at RT for twenty minutes, quenched by the slow addition of acetic acid (approximately ten drops) and partitioned between DCM (20 mL) and saturated aqueous sodium bicarbonate (15 mL). The DCM layer was washed with brine (20 mL), dried over sodium sulfate and concentrated to yield a thick oil. LC retention time=3.34 min. Column used: YMC S5 combiscreen ODS 4.6×50 mm (4 min. gradient); Solvent A=10% MeOH, 90% $H_2O$ and 0.2% $H_3PO_4$; solvent B=90% MeOH, 10% $H_2O$, 0.2% $H_3PO_4$.

We claim:

1. A compound according to formula (I),

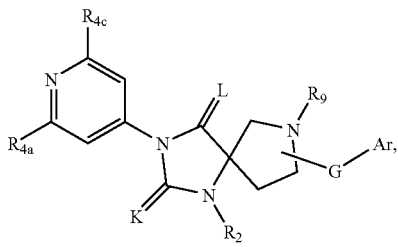

its enantiomers, diastereomers, or a pharmaceutically-acceptable salt, hydrate, solvate, or prodrug thereof, in which:

L and K, taken independently, are O or S;

Z is N;

Ar is aryl or heteroaryl;

G is selected from a bond, —O—, —N—, —S—, $C_{1-4}$alkylene, $C_{1-4}$substituted alkylene, bivalent alkoxy, alkylthio, aminoalkyl, sulfonyl, sulfonamidyl, acyl, and alkoxycarbonyl;

$R_2$ is selected from hydrogen, alkyl, substituted alkyl, $OR_{12}$, $NR_{12}R_{13}$, $C(=O)R_{12}$, $CO_2R_{12}$, $C(=O)NR_{12}R_{13}$, $NR_{12}C(=O)R_{13}$, $NR_{12}C(=O)OR_{13}$, $S(O)_pR_{13a}$, $NR_{12}SO_2R_{13a}$, $SO_2NR_{12}R_{13}$ cycloalkyl, heterocyclo, aryl, and heteroaryl;

$R_{4a}$, and $R_{4c}$ are independently selected from hydrogen, halogen, alkyl, substituted alkyl, alkenyl, substituted alkenyl, nitro, cyano, $SR_{14}$, $OR_{14}$, $NR_{14}R_{15}$, $NR_{14}C(=O)R_{15}$, $CO_2R_{14}$, $C(=O)R_{14}$, —C(=O)$NR_{14}R_{15}$, aryl, heterocyclo, cycloalkyl, and heteroaryl;

$R_3$ is independently selected from hydrogen, alkyl, substituted alkyl, hydroxy, alkoxy, alkenyl, substituted alkenyl, aminoalkyl, alkylthio, C(=O)H, acyl, amide, alkoxycarbonyl, sulfonyl, sulfonamidyl, cycloalkyl, heterocyclo, aryl, and heteroaryl;

$R_9$ is —$A_1$—Q—$A_2$—$R_{16}$;

$A_1$ is a bond, $C_{1-2}$alkylene, or $C_{2-3}$alkenylene;

Q is a bond, —C(=O)—, —C(=O)$NR_{17}$—, —C(=S)$NR_{17}$—, —$SO_2$—, —$SO_2NR_{17}$—, —$CO_2$—, or —$NR_{17}CO_2$—;

$A_2$ is a bond, $C_{1-3}$alkylene, $C_{2-3}$alkenylene, —$C_{1-4}$alkylene-$NR_{17}$—, —$C_{1-4}$alkylene-$NR_{17}$C(=O)—, —$C_{1-4}$alkylene-S—, —$C_{1-4}$alkylene-$SO_2$—, —$C_{1-4}$alkylene-O—, wherein said $A_2$ alkylene groups are branched or straight chain and optionally substituted with a group selected from —$CO_2H$, —$CO_2(C_{1-4}$alkyl), —$S(C_{1-4}$alkyl), $NH_2$, —$NH(C_{1-4}$alkyl), or —$N(C_{1-4}$alkyl)$_2$;

$R_{12}$, $R_{13}$, $R_{14}$ and $R_{15}$ (i) are selected independently of each other from hydrogen, alkyl, substituted alkyl, cycloalkyl, aryl, heteroaryl, and heterocyclo; or (ii) $R_{12}$ is taken together with $R_{13}$, and/or $R_{14}$ is taken together with $R_{15}$ to form a heteroaryl or heterocyclo ring;

$R_{13a}$ is selected from alkyl, substituted alkyl, cycloalkyl, aryl, heteroaryl, and heterocyclo;

$R_{16}$ is selected from alkyl, substituted alkyl, alkenyl, substituted alkenyl, aryl, heteroaryl, cycloalkyl, and heterocyclo; and $R_{17}$ is hydrogen or alkyl; and p is 1 or 2.

2. A compound according to claim 1, or a pharmaceutically-acceptable salt, hydrate, prodrug, or enantiomer thereof, wherein:

G is a bond;

Ar is an aryl or heteroaryl substituted with one to three $R_1$;

$R_1$ is selected from alkyl, substituted alkyl, halogen, cyano, nitro, $OR_{10}$, $NR_{10}R_{11}$, $C(=O)R_{10}$, $CO_2R_{10}$, $C(=O)NR_{10}R_{11}$, $NR_{10}C(=O)R_{11}$, $NR_{10}C(=O)OR_{11}$, $SR_{10}$, $S(O)_oR_{10a}$, $NR_{10}SO_2R_{10a}$, NHCH(alkyl)$CO_2R_{10}$, $SO_2NR_{10}R_{11}$, cycloalkyl, heterocyclo, aryl, and heteroaryl;

$R_{10}$ and $R_{11}$ (i) are selected independently of each other from hydrogen, alkyl, substituted alkyl, cycloalkyl, aryl, heteroaryl, and heterocyclo; or (ii) $R_{10}$ is taken together with $R_{11}$ to form a heteroaryl or heterocyclo;

$R_{10a}$ is alkyl, substituted alkyl, cycloalkyl, aryl, heteroaryl, or heterocyclo; and o is 1 or 2.

3. A compound according to claim 1, or a pharmaceutically-acceptable salt, hydrate, prodrug, or enantiomer thereof, in which:

$R_{16}$ is selected from cycloalkyl, heterocyclo, aryl or heteroaryl optionally substituted with one to three $R_{18}$;

$R_{18}$ is selected from $C_{1-6}$alkyl, substituted $C_{1-6}$alkyl, halogen, cyano, nitro, $OR_{20}$, $NR_{20}R_{21}$, $C(=O)R_{20}$, $CO_2R_{20}$, $C(=O)NR_{20}R_{21}$, $C(=O)NR_{20}SO_2R_{20a}$, $NR_{20}C(=O)R_{21}$, $NR_{20}C(=O)OR_{21}$, $SR_{20}$, $S(O)_uR_{20a}$, $NR_{20}SO_2R_{20a}$, NHCH(alkyl)$CO_2R_{20}$, $SO_2NR_{20}R_{21}$, $C_{3-7}$cycloalkyl, phenyl, four to seven membered heterocyclo, or five or six membered heteroaryl, said $C_{3-7}$cycloalkyl, phenyl, four to seven membered heterocyclo, or five or six membered heteroaryl groups in turn being optionally substituted with one to two $R_{22}$;

$R_{20}$ and $R_{21}$ are selected from hydrogen, alkyl, alkenyl, $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl; wherein each of $R_{20}$ and $R_{21}$ in turn is optionally substituted with one to two $R_{22}$;

$R_{20a}$ is selected from hydrogen, alkyl, alkenyl, $CO_2H$, $CO_2$(alkyl), $C_{3-7}$cycloalkyl, phenyl, benzyl, phenylethyl, napthyl, a four to seven membered heterocyclo, or a five to six membered heteroaryl; wherein each $R_{20a}$ in turn is optionally substituted with one to two $R_{22}$; and $R_{22}$ is selected from the group consisting of $(C_{1-4})$alkyl, $(C_{2-4})$alkenyl, hydroxy, cyano, $CF_3$, $O(C_{1-4}$alkyl$)$, $OCF_3$, $C(=O)H$, $C(=O)(C_{1-4}$alkyl$)$, $CO_2H$, $CO_2(C_{1-4}$ alkyl$)$, $NHCO_2(C_{1-4}$alkyl$)$, $—S(C_{1-4}$alkyl$)$, $—NH_2$, $NH(C_{1-4}$alkyl$)$, $N(C_{1-4}$alkyl$)_2$, $N(CH_3)_3^+$, $SO_2(C_{1-4}$ alkyl$)$, $C(=O)(C_{1-4}$alkylene$)NH_2$, $C(=O)(C_{1-4}$alkylene$)NH$(alkyl), and $C(=O)(C_{1-4}$alkylene$)N(C_{1-4}$alkyl$)_2$.

4. A compound according to claim 3, or a pharmaceutically-acceptable salt, hydrate, prodrug, or enantiomer thereof, in which:

$R_{1a}$ and $R_{1b}$ are independently selected from halogen, $C_{1-4}$alkyl, hydroxy, alkoxy, haloalkyl, haloalkoxy, cyano, nitro, $—CO_2H$, $—C(=O)H$, $—CO_2$alkyl, $—C(=O)$alkyl, $—C(=O)NH(CH_2)_{1-4}CO_2H$, $—C(=O)NH(CH_2)_{1-4}CO_2$(alkyl), and $S(O)_2$alkyl; or from phenyl, benzyl, phenyloxy, benzyloxy and heteroaryl in turn optionally substituted with halogen, $C_{1-4}$alkyl, hydroxy, alkoxy, haloalkyl, haloalkoxy, cyano, nitro, $—CO_2H$, $—C(=O)H$, $—CO_2$alkyl, and/or $—C(=O)$alkyl; or alternatively, two $R_{1b}$ groups join together with each other or one $R_{1b}$ joins together with $R_{1a}$ to form a fused benzo ring;

$R_{4a}$ and $R_{4c}$ are selected from halogen, alkyl, cyano, haloalkyl, haloalkoxy, nitro, aryloxy, and arylthio;

n is 0, 1, or 2; and y is 0, 1 or 2.

5. A compound according to claim 1, or a pharmaceutically-acceptable salt, hydrate, prodrug, or enantiomer thereof, having the formula:

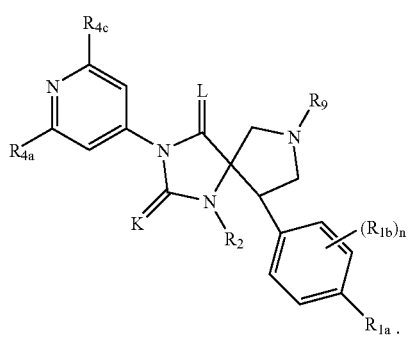

6. A compound according to claim 5, or a pharmaceutically-acceptable salt, hydrate, prodrug, or enantiomer thereof, in which $R_{1a}$ is halogen or cyano, and $R_{4a}$ and $R_{4c}$ are independently selected from halogen, alkyl, cyano, trifluoromethyl, and nitro.

7. A compound according to claim 1, having the formula (Ie),

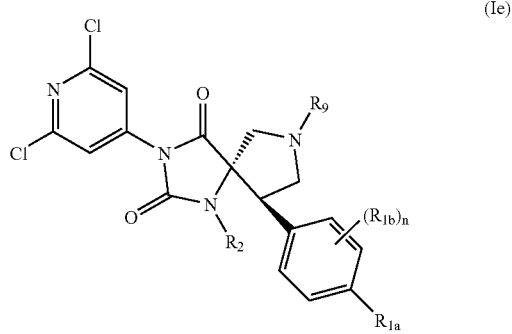

or a pharmaceutically-acceptable salt, hydrate, prodrug, or enantiomer thereof, in which:

$R_{1a}$ and $R_{1b}$ are independently selected from halogen, $C_{1-4}$alkyl, hydroxy, alkoxy, haloalkyl, haloalkoxy, cyano, nitro, $—CO_2H$, $—C(=O)H$, $—CO_2$alkyl, $—C(=O)$alkyl, $—C(=O)NH(CH_2)_{1-4}CO_2H$, $—C(=O)NH(CH_2)_{14}CO_2$(alkyl), and $S(O)_2$alkyl; or from phenyl, benzyl, phenyloxy, benzyloxy and heteroaryl in turn optionally substituted with halogen, $C_{1-4}$alkyl, hydroxy, alkoxy, haloalkyl, haloalkoxy, cyano, nitro, $—CO_2H$, $—C(=O)H$, $—CO_2$alkyl, and/or $—C(=O)$alkyl; or alternatively, two $R_{1b}$ groups join together with each other or one $R_{1b}$ joins together with $R_{1a}$ to form a fused benzo ring; and n is 0, 1 or 2.

8. A compound according to claim 7, or a pharmaceutically-acceptable salt, hydrate, prodrug, or enantiomer thereof, in which:

$R_{1a}$ is halogen, cyano, nitro, trifluoromethyl, $OCF_3$, aryl or heteroaryl;

$R_{1b}$ is halogen, $C_{1-4}$alkyl, cyano, nitro, $—CO_2H$, $—C(=O)H$, $—CO_2$alkyl, or $—C(=O)$alkyl;

$R_2$ is hydrogen, $C_{1-6}$alkyl, or $C_{1-6}$alkyl substituted with $CO_2H$ or $CO_2(C_{1-4}$alkyl$)$;

$R_9$ is selected from hydrogen, $C_{1-10}$alkyl, substituted $C_{1-10}$alkyl, $C_{2-10}$alkenyl, substituted $C_{2-10}$alkenyl, $C_{3-6}$cycloalkyl, phenyl, pyridyl, pyridazinyl, pyrimidinyl, $—(CH_2)_s$phenyl, $—(CH_2)_s$tetrazolyl, $—(CH_2)_s$pyridyl, $—(CH_2)_s$thienyl, $—(CH_2)_s$carbazolyl, $—(CH_2)_s$indolyl, $—(CH_2)_s$furyl, $—(CH_2)_s$quinolyl, $—(CH_2)_n C_{3-6}$cycloalkyl, $—(CH_2)_s$thiazolyl, $—(CH_2)_s$pyrrolyl, $—(CH_2)_s$imidazolyl, $—(CH_2)_s$isoxazolyl, $—(CH_2)_s$ benzofuryl, $—(CH_2)_s$pyrazolyl, $—C(=O)H$, $—C(=O)$(alkyl), $—C(=O)C_{1-10}$alkyl, $—C(=O)$phenyl, $—C(=O)$piperidyl, $—C(=O)$morpholinyl, $—C(=O)C_{3-6}$cycloalkyl, $—C(=O)$pyrrolidinyl, $—C(=O)$quinolyl, $—C(=O)$imidazolyl, $—C(=O)$ pyrazolyl, $—C(=O)$thiazolyl, $—C(=O)$quinoxalinyl, $—C(=O)$pyridyl, $—C(=O)$-1,2,5,6-tetrahydropyridyl, $—C(=O)$benzothiazolyl, $—C(=O)$benzotriazolyl, $—C(=O)$benzodioxanyl, $—C(=O)$benzooxadiazolyl, $—C(=O)$ 1,2,3,4-tetrahydroquinolyl, $—C(=O)$ thienopyrazolyl, $—C(=O)(CH_2)_s$tetrazolyl, $—C(=O)$ $(CH_2)_s$pyridyl, $—C(=O)(CH_2)_s$phenyl, $—C(=O)$ $(CH_2)_s$pyrrolidinyl, $—C(=O)(CH_2)_s$piperidyl, $—C(=O)CH=CH$(phenyl), $—C(=O)CH=CH$(pyridyl), $—C(=O)CH_2O$(alkyl), $—C(=O)CH_2S$(alkyl), $—C(=O)CH_2S$(pyridyl), $—C(=O)CH_2SO_2$(alkyl), $—C(=O)CH_2SO_2$(phenyl), $—C(=O)CH_2NH$(phenyl), $—C(=O)CH_2NH$(benzyl), $—C(=O)CH_2NH$ (thiazolyl), —C(=O)CH₂NHC(=O)pyridyl, —C(=O)CH₂NHC(=O)phenyl, —(CH₂)ₜSO₂(alkyl), —(CH₂)ₜSO₂(phenyl), —(CH₂)ₜSO₂(thienyl), —(CH₂)ₜSO₂(imidazolyl), —(CH₂)ₜSO₂(furyl), —(CH₂)ₜSO₂(pyrrolyl), SO₂NH(phenyl), —C(=S)NH₂, —C(=S)NH(alkyl), —C(=S)NH(phenyl), —(CH₂)C(=O)pyrrolidinyl, —(CH₂)C(=O)piperidyl, —(CH₂)C(=O)piperazinyl, —CO₂(alkyl), —CO₂(phenyl), —CO₂(benzyl), NHCO₂(alkyl), —(CH₂)ₜC(=O)NH (phenyl), —(CH₂)ₜC(=O)NH(piperidyl), —(CH₂)ₜC(=O)NH(thienyl), —(CH₂)ₜC(=O)NH(thiazolyl), —(CH₂)ₜC(=O)NH(cyclopentyl), —(CH₂)ₜC(=O)NH(cyclopentenyl), —(CH₂)ₜC(=O)NH(benzyl), —(CH₂)ₜC(=O)NH(pyrrolidinyl), —(CH₂)ₜC(=O)NH(piperazinyl), —(CH₂)ₜC(=O)NH₂, —(CH₂)ₜC(=O)NH(alkyl), —(CH₂)ₜC(=O)N(alkyl)₂, —(CH₂)ₜC(=O)N(C₁₋₄alkyl)(phenyl), —(CH₂)ₜC(=O)N(C₁₋₄alkyl)(thienyl), —(CH₂)ₜC(=O)N(C₄alkyl)(thiazolyl), —(CH₂)ₜC(=O)N(C₁₋₄alkyl)(benzyl), —(CH₂)ₜC(=O)N(C₁₋₄alkyl)CO₂(alkyl), wherein each R₉ is optionally substituted with one to two R₁₈;

R₁₈ is selected from —(CH₂)_q halogen, —(CH₂)_q nitro, —(CH₂)_q cyano, —(CH₂)_q haloalkyl, —(CH₂)_q haloalkoxy, —(CH₂)_q SR₂₄, C₃₋₇cycloalkyl, —SO₂R₂₄, —OR₂₄, —(CH₂)_q CO₂R₂₄, —(CH₂)_q NR₂₄R₂₅, —(CH₂)_q NHCO₂R₂₄, —C(=O)NH—SO₂R₂₄, —C(=O)(CH₂)_q NR₂₄R₂₅, —O(CH₂)ᵣNR₂₄R₂₅, —C(=O)R₂₄, —(CH₂)_q R₂₄ and —C₁₋₄alkyl or —C₂₋₄ alkenyl optionally substituted with CO₂R₂₄;

R₂₄ is selected from hydrogen, alkyl, phenyl, benzyl, C₃₋₇cycloalkyl, five or six membered heteroaryl, and four to seven membered heterocyclo, in turn optionally substituted with one to two C₁₋₄alkyl, halogen, hydroxy, trifluoromethyl, trifluoromethoxy, —CO₂H, CO₂C₁₋₄alkyl, C₁₋₄alkoxy, —S(C₁₋₄alkyl), amino, and/ or aminoC₁₋₄alkyl, provided that when R₂₄ is attached to a sulfonyl group as in —SO₂R₂₄, then R₂₄ is not hydrogen;

R₂₅ is selected from hydrogen and alkyl; and n is 0, 1, or 2;

p is 1 or 2;

q is 0, 1, 2, 3, or 4;

r is 1, 2, 3, or 4;

s is 0, 1, 2, 3, or 4; and t is 1, 2, 3, or 4.

9. A compound according to claim 1, or a pharmaceutically-acceptable salt, hydrate, prodrug, or enantiomer thereof, wherein R₉ is selected from:

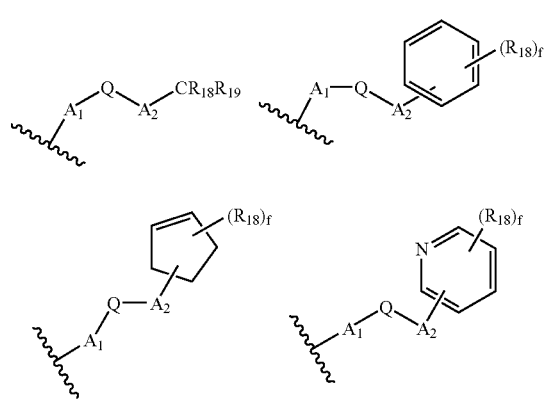

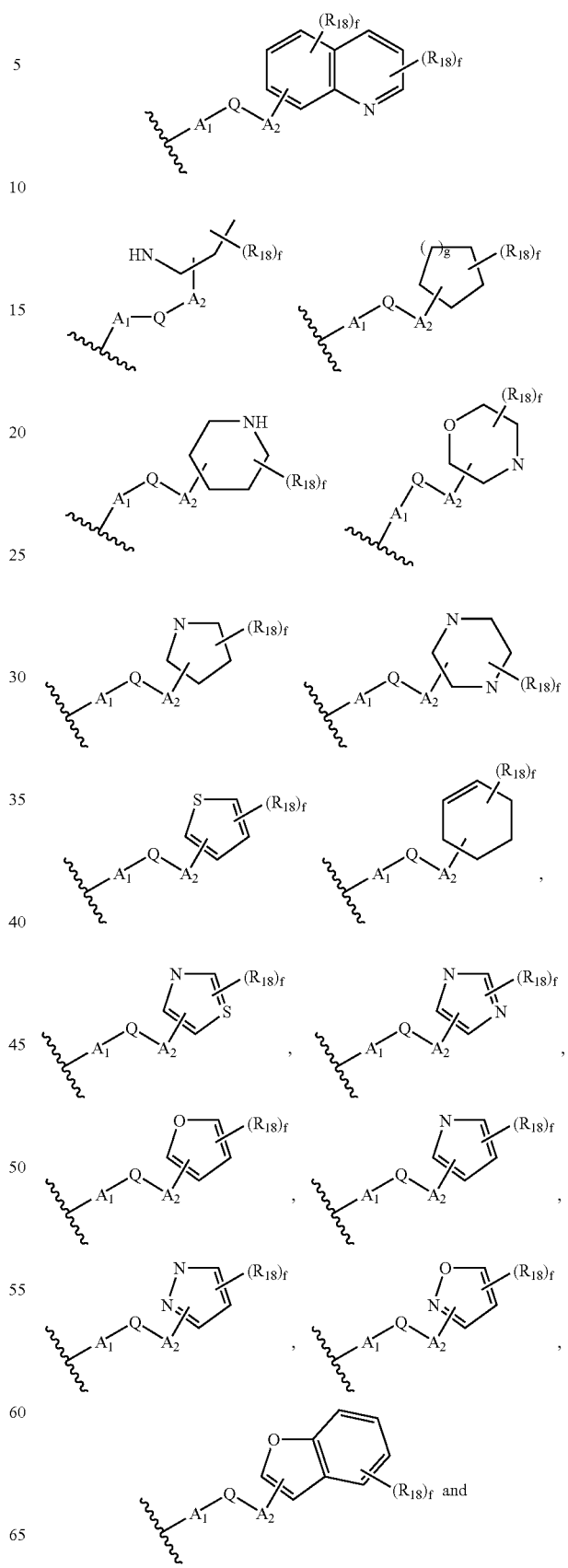

-continued

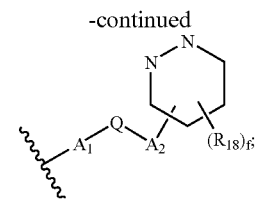

$A_1$ is a bond, $C_{1-2}$alkylene, or $C_{2-3}$alkenylene;

Q is a bond, —C(=O)—, —C(=O)NR$_{17}$—, —SO$_2$—, —CO$_2$—, or —NR$_{17}$CO$_2$—;

$A_2$ is a bond, $C_{1-3}$alkylene, $C_{2-3}$alkenylene, —C$_{1-4}$alkylene-NR$_{17}$—, —C$_{1-4}$alkylene-NR$_{17}$C(=O)—, —C$_{1-4}$ alkylene-S—, —C$_{1-4}$alkylene-SO$_2$—, or —C$_{1-4}$alkylene-O—, wherein said $A_2$ alkylene groups are branched or straight chain and optionally substituted with a group selected from —CO$_2$H, —CO$_2$(C$_{1-4}$ alkyl), —S(C$_{1-4}$alkyl), NH$_2$, —NH(C$_{1-4}$alkyl), or —N(C$_{1-4}$alkyl)$_2$;

$R_{17}$ is hydrogen or alkyl;

$R_{18}$ and $R_{19}$ are selected from hydrogen, (C$_{1-6}$) alkyl, (C$_{2-6}$) alkenyl, CO$_2$H, CO$_2$(C$_{1-6}$alkyl), C(=O)H, C(=O)(C$_{1-6}$alkyl), halogen, cyano, hydroxy, (C$_{1-4}$) alkoxy, (C$_{1-4}$)haloalkyl, (C$_{1-4}$)haloalkoxy, NH$_2$, NH(C$_{1-4}$alkyl), N(C$_{1-4}$alkyl)$_2$, N(C$_{1-4}$alkyl)$_3^+$, —C(=O)(CH$_2$)NH$_2$, —NHCO$_2$(C$_{1-4}$alkyl), —C(=O)NHSO$_2$(C$_{1-4}$alkyl), SO$_2$(C$_{1-4}$alkyl), phenyl, C$_{3-7}$cycloalkyl, five to six membered heteroaryl, and four to seven membered heterocyclo, wherein each group $R_{18}$ and $R_{19}$ in turn is optionally substituted with one to two of (C$_{1-4}$) alkyl, (C$_{2-4}$) alkenyl, CO$_2$H, CO$_2$(C$_{1-4}$alkyl), C(=O)H, C(=O)(C$_{1-4}$alkyl), halogen, cyano, hydroxy, (C$_{1-4}$)alkoxy, trifluoromethyl, trifluoromethoxy, NH$_2$, NH(C$_{1-4}$alkyl), N(C$_{1-4}$alkyl)$_2$, N(C$_{1-4}$ alkyl)$_3^+$, —C(=O)(CH$_2$)NH$_2$, —NHCO$_2$(C$_{1-4}$alkyl), and/or SO$_2$(C$_{1-4}$alkyl));

f is 0, 1, 2 or 3; and g is −1, 0, 1, or 2.

10. A compound according to claim 1, having the formula,

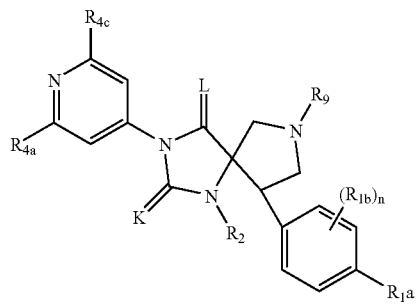

or a pharmaceutically-acceptable salt, hydrate, prodrug, or enantiomer thereof, wherein $R_9$ is selected from one of:

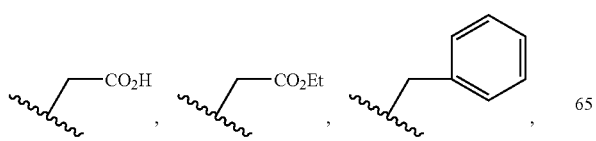

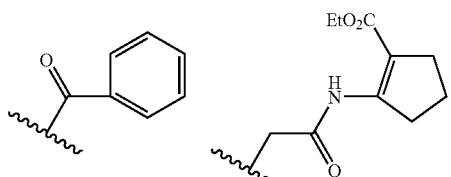

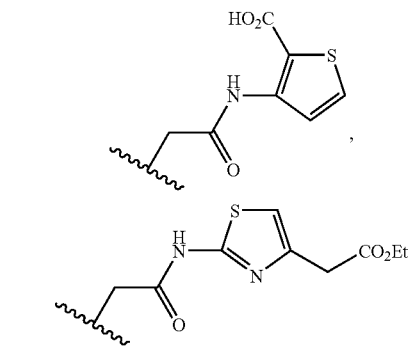

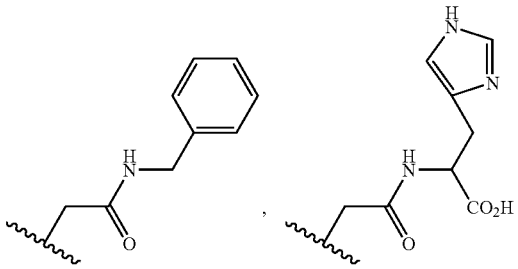

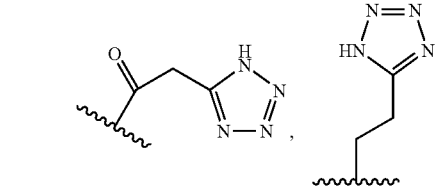

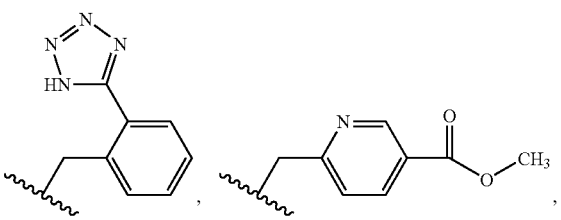

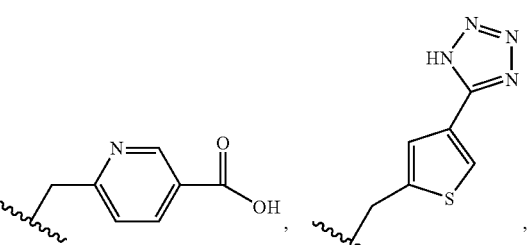

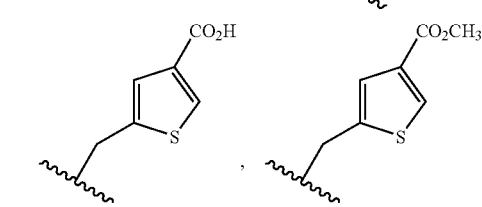

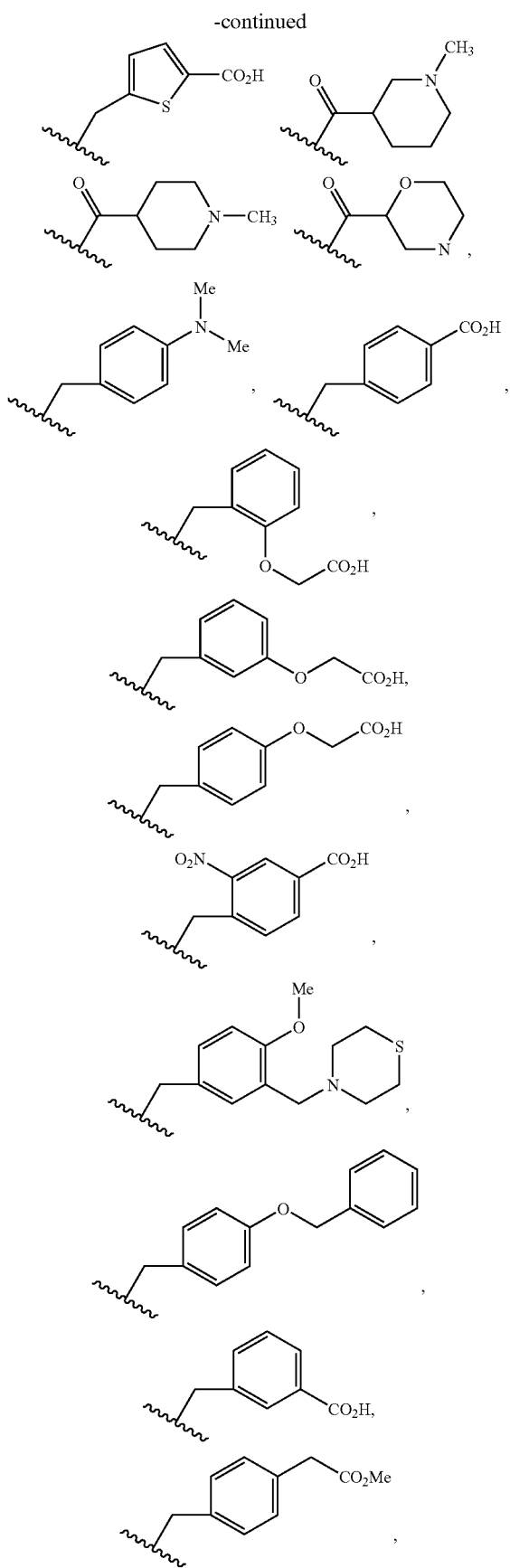
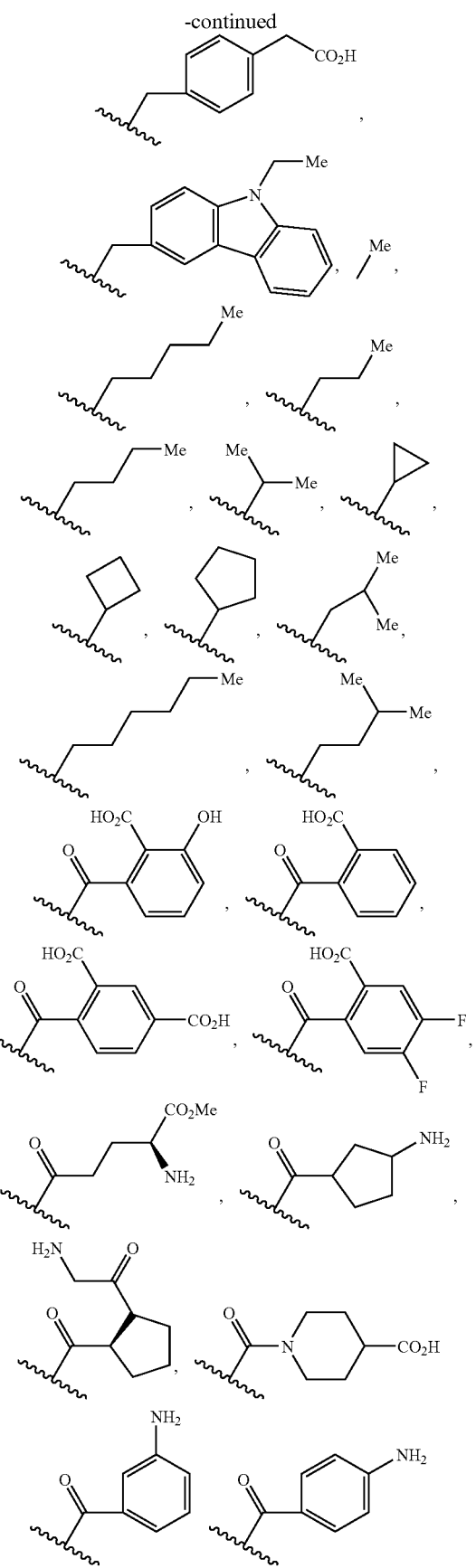

-continued
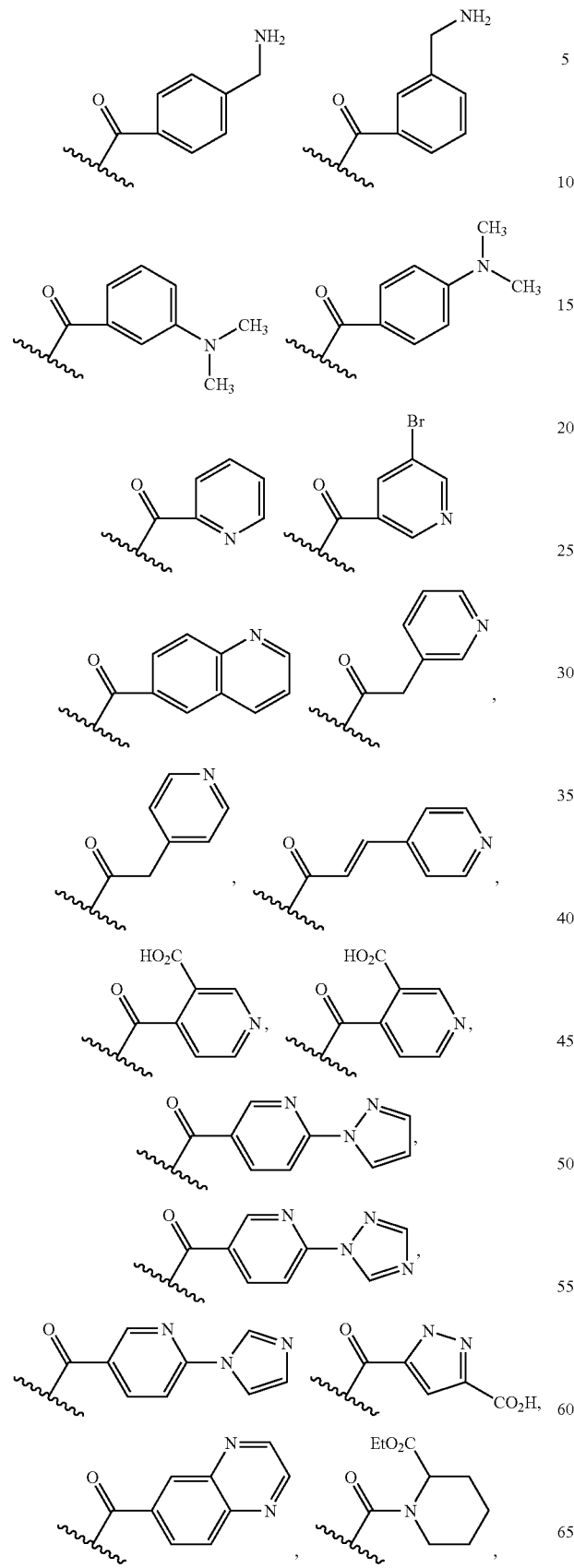
-continued
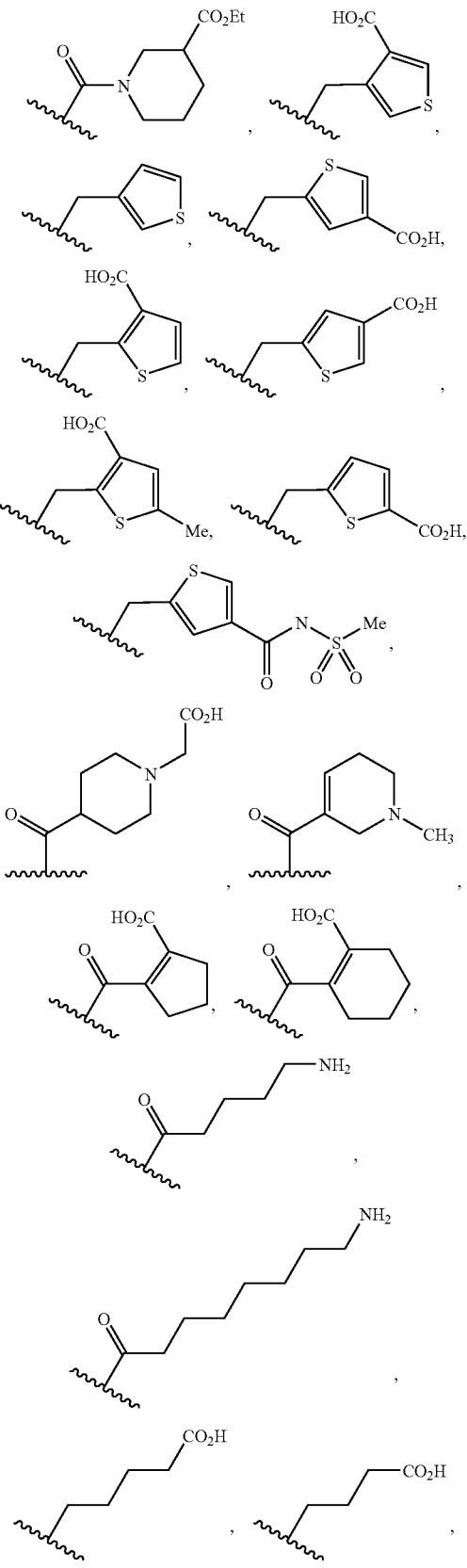

-continued
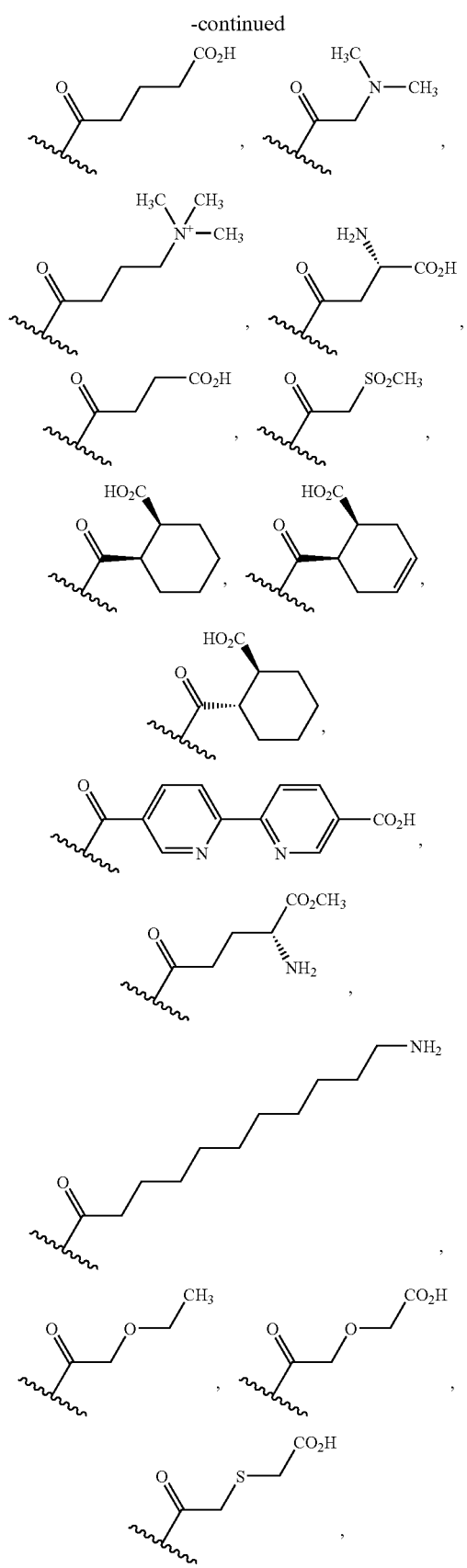
-continued
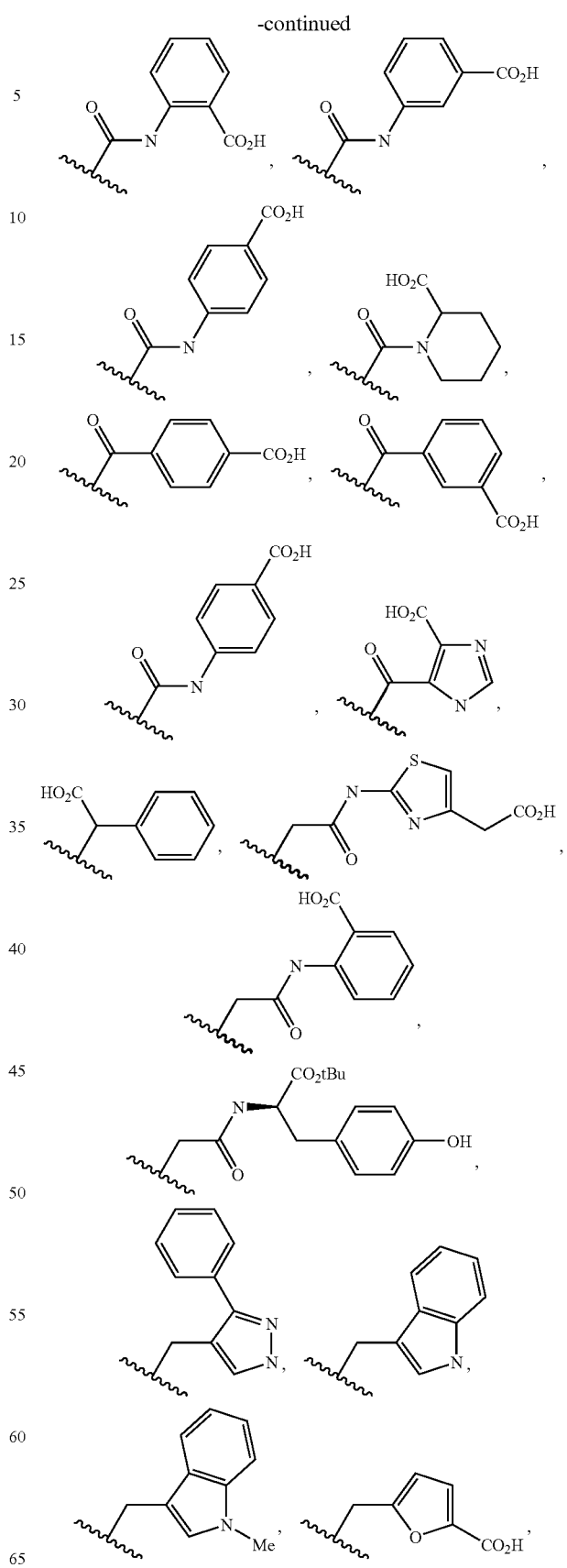

-continued
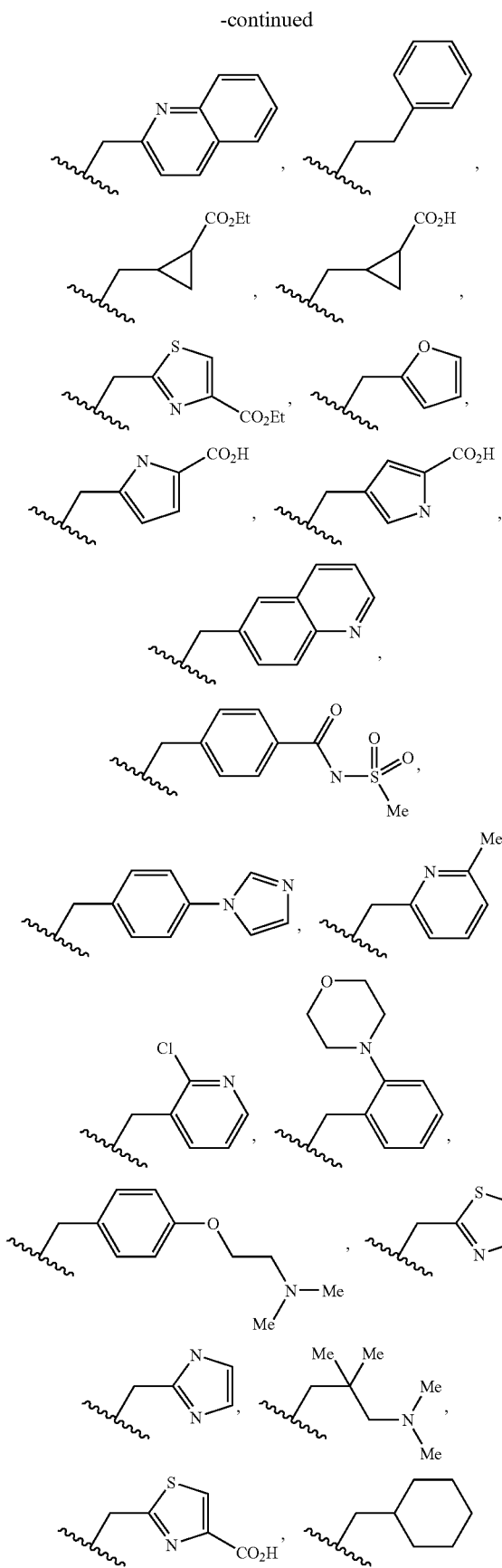
-continued
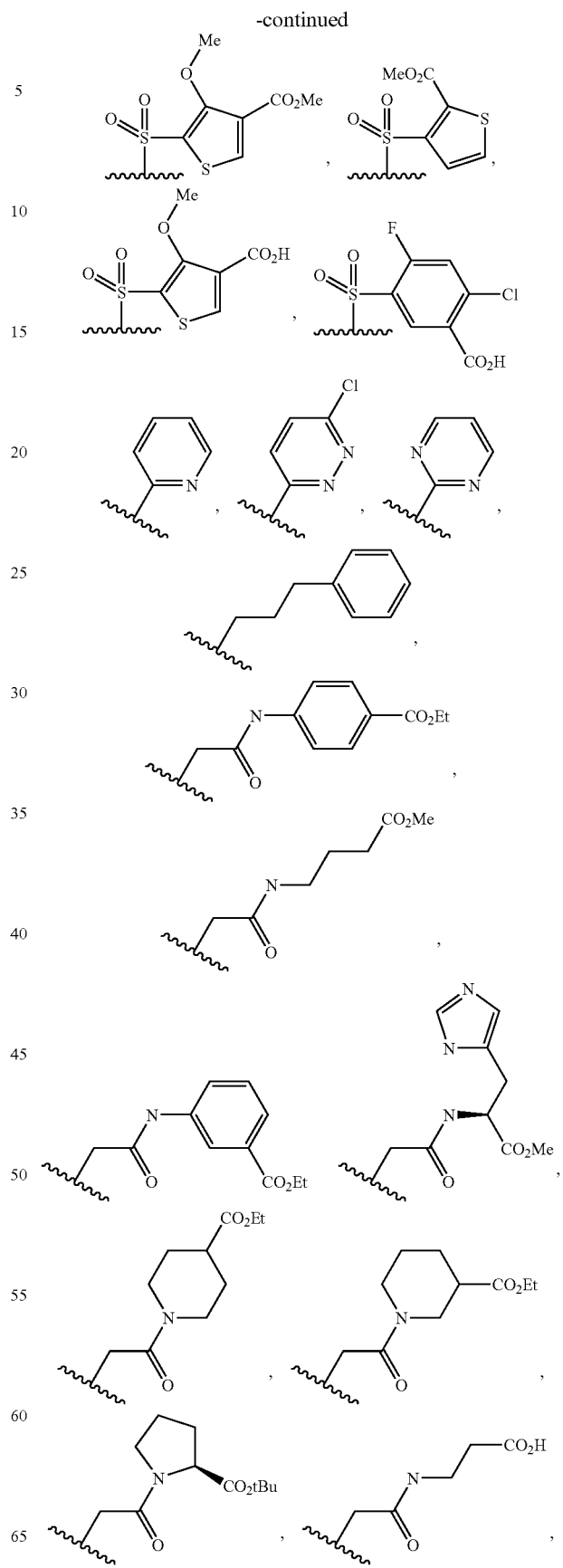

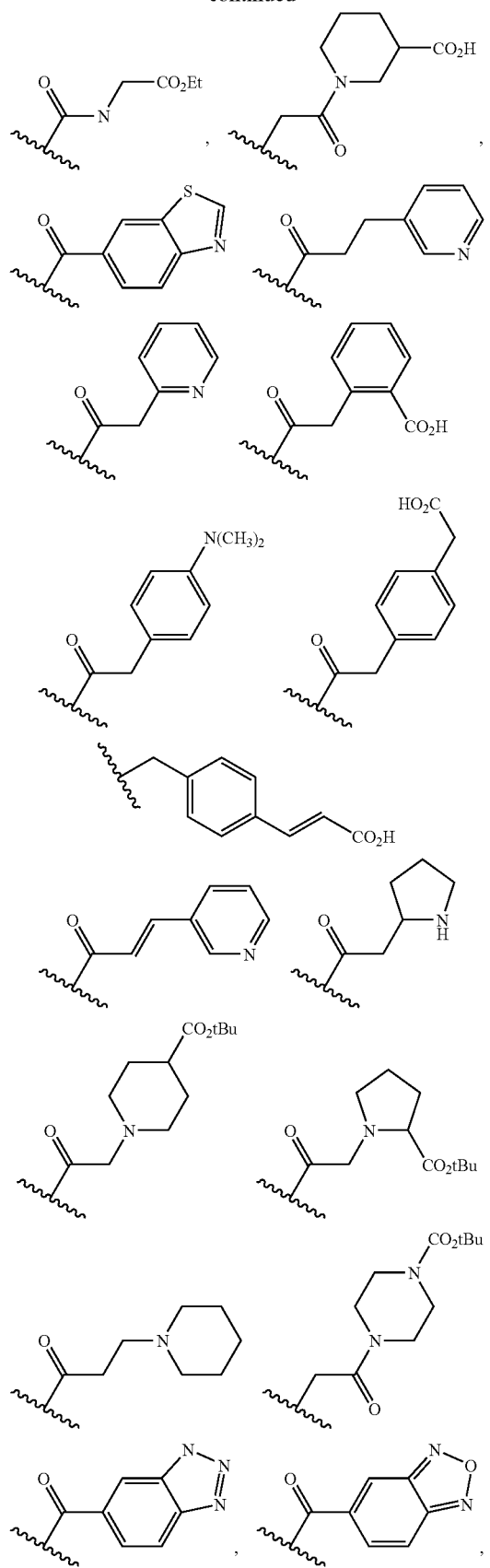
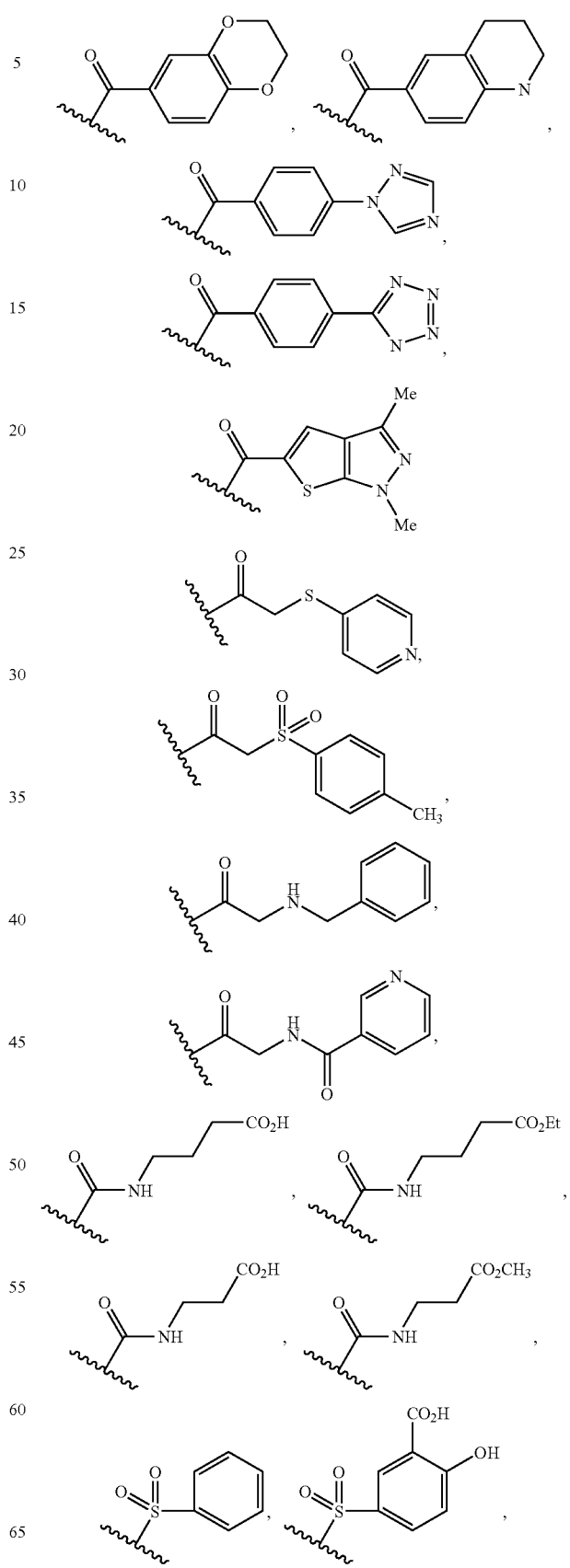

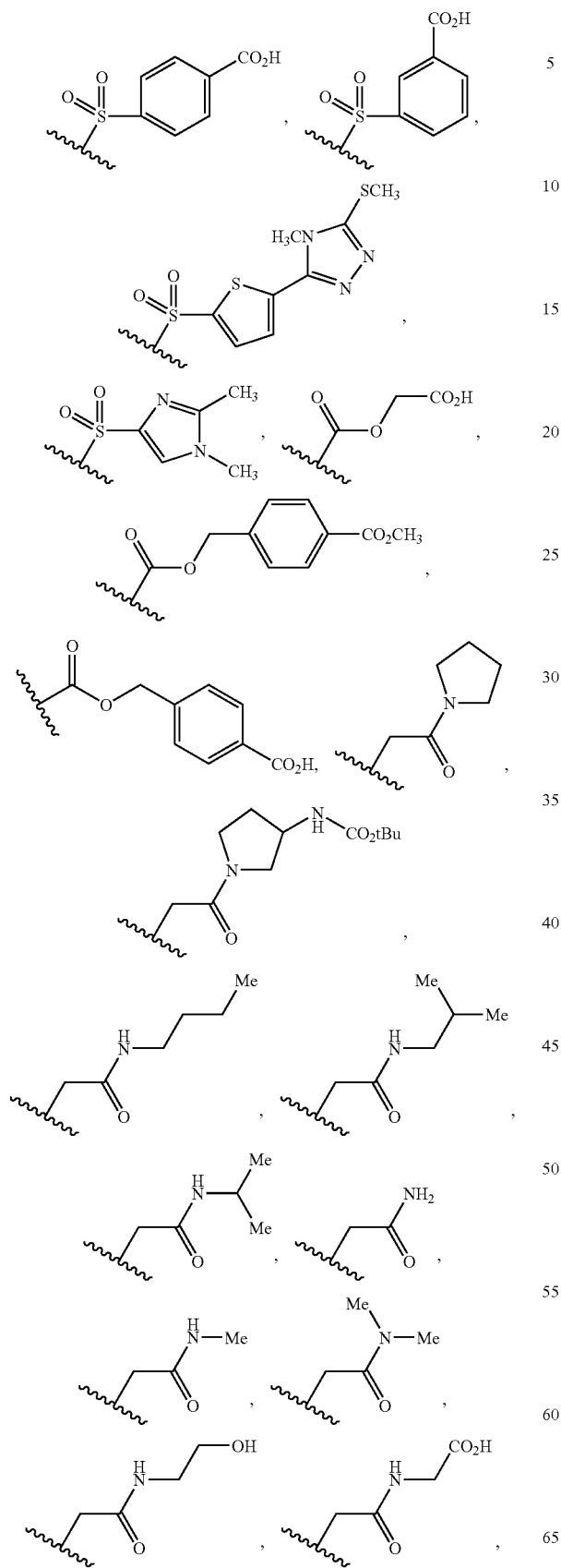
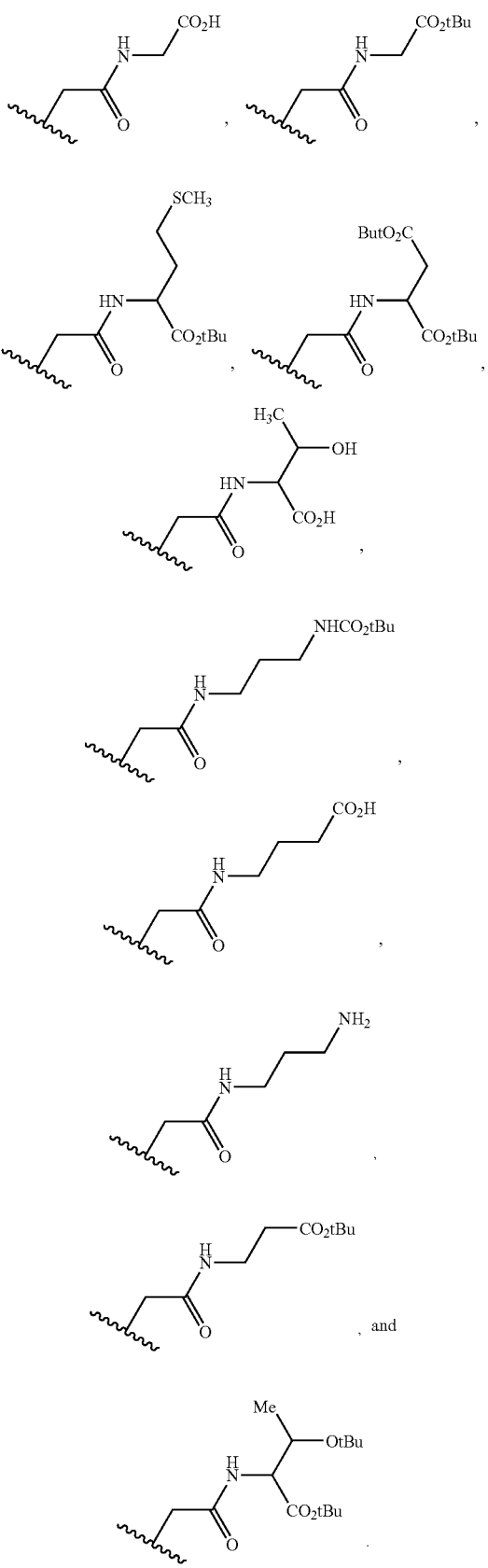

11. A compound according to claim 1, having the formula,

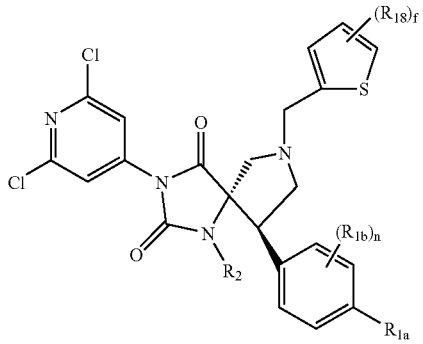

or a pharmaceutically-acceptable salt, hydrate, prodrug, or enantiomer thereof, in which:

$R_{1a}$ is halogen, cyano, nitro, trifluoromethyl, $OCF_3$, aryl or heteroaryl;

$R_{1b}$ is halogen, $C_{1-4}$alkyl, cyano, nitro, —$CO_2H$, —C(=O)H, —$CO_2$alkyl, or —C(=O)alkyl;

$R_2$ is hydrogen, $C_{1-6}$alkyl, or $C_{1-6}$alkyl substituted with $CO_2H$ or $CO_2(C_{1-4}$alkyl);

$R_{18}$ is selected from $(C_{1-4})$ alkyl, $CO_2H$, $CO_2(C_{1-4}$alkyl), C(=O)H, C(=O)($C_{1-4}$alkyl), halogen, cyano, hydroxy, $(C_{1-4})$alkoxy, $(C_{1-4})$haloalkyl, $(C_{1-4})$haloalkoxy, $NH_2$, $NH(C_{1-4}$alkyl), $N(C_{1-4}$alkyl)$_2$, $N(C_{1-4}$alkyl)$_3^+$, —C(=O)($CH_2$)$NH_2$, —$NHCO_2(C_{1-4}$alkyl), —C(=O)$NHSO_2(C_{1-4}$alkyl), $SO_2(C_{1-4}$alkyl), thienyl, tetrazolyl, triazolyl, pyrazolyl, and imidazolyl;

f is 0, 1, 2 or 3; and n is 0 or 1.

12. A compound according to claim 1, having the formula,

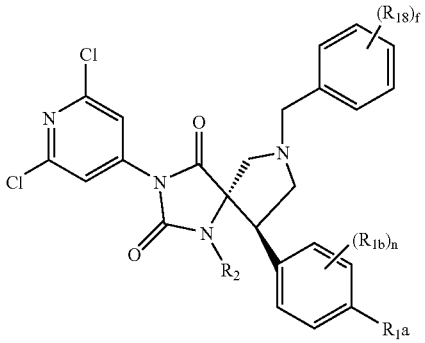

or a pharmaceutically-acceptable salt, hydrate, prodrug, or enantiomer thereof, in which:

$R_{1a}$ is halogen, cyano, nitro, trifluoromethyl, $OCF_3$, aryl or heteroaryl;

$R_{1b}$ is halogen, $C_{1-4}$alkyl, cyano, nitro, —$CO_2H$, —C(=O)H, —$CO_2$alkyl, or —C(=O)alkyl;

$R_2$ is hydrogen, $C_{1-6}$alkyl, or $C_{1-6}$alkyl substituted with $CO_2H$ or $CO_2(C_{1-4}$alkyl);

$R_{18}$ is selected from $(C_{1-4})$ alkyl, $CO_2H$, $CO_2(C_{1-4}$alkyl), C(=O)H, C(=O)($C_{1-4}$alkyl), halogen, cyano, hydroxy, $(C_4)$alkoxy, $(C_{1-4})$haloalkyl, $(C_{1-4})$haloalkoxy, $NH_2$, $NH(C_{1-4}$alkyl), $N(C_{1-4}$alkyl)$_2$, $N(C_{1-4}$alkyl)$_3^+$, —C(=O)($CH_2$)$NH_2$, —$NHCO_2(C_{1-4}$alkyl), —C(=O)$NHSO_2(C_{1-4}$alkyl), $SO_2(C_{1-4}$alkyl), thienyl, tetrazolyl, triazolyl, pyrazolyl, and imidazolyl;

f is 0, 1, 2 or 3; and n is 0 or 1.

13. A compound having the formula,

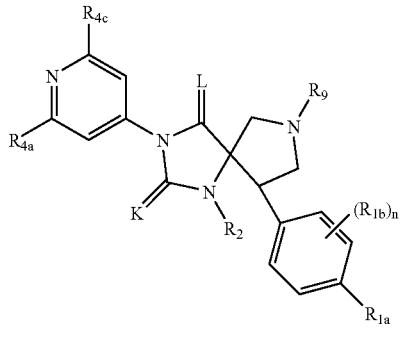

or a pharmaceutically-acceptable salt, hydrate, prodrug, or enantiomer thereof, in which:

L and K, taken independently, are O or S;

$R_{1a}$ and $R_{1b}$ are independently selected from alkyl, substituted alkyl, halogen, cyano, nitro, $OR_{10}$, $NR_{10}R_{11}$, C(=O)$R_{10}$, $CO_2R_{10}$, C(=O)$NR_{10}R_{11}$, $NR_{10}C(=O)R_{11}$, $NR_{10}C(=O)OR_{11}$, $SR_{10}$, $S(O)_oR_{10a}$, $NR_{10}SO_2R_{10a}$, $NHCH(alkyl)CO_2R_{10}$, $SO_2NR_{10}R_{11}$, cycloalkyl, heterocyclo, aryl, and heteroaryl; or alternatively, two $R_{1b}$ groups join together with each other or one $R_{1b}$ joins together with $R_{1a}$ to form a fused benzo ring;

$R_2$ is selected from hydrogen, alkyl, substituted alkyl, cycloalkyl, aryl, heterocyclo, and heteraryl;

$R_{4a}$ and $R_{4c}$ are selected from halogen, alkyl, cyano, haloalkyl, haloalkoxy, aryloxy, arylthio, and nitro;

$R_9$ is selected from hydrogen and $A_1$—Q—$A_2$—$R_{16}$;

$A_1$ is a bond, $C_{1-2}$alkylene, or $C_{2-3}$alkenylene;

Q is a bond, —C(=O)—, —C(=O)$NR_{17}$—, —$SO_2$—, —$CO_2$—, or —$NR_{17}CO_2$—;

$A_2$ is a bond, $C_{1-3}$alkylene, $C_{2-3}$alkenylene, —$C_{1-4}$alkylene-$NR_{17}$—, —$C_{1-4}$alkylene-$NR_{17}$C(=O)—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted with a group selected from —$CO_2H$, —$CO_2(C_{1-4}$alkyl), —S($C_{1-4}$alkyl), $NH_2$, —$NH(C_{1-4}$alkyl), or —$N(C_{1-4}$alkyl)$_2$;

$R_{10}$ and $R_{11}$ (i) are selected independently of each other from hydrogen, alkyl, substituted alkyl, cycloalkyl, aryl, heteroaryl, and heterocyclo; or (ii) $R_{10}$ is taken together with $R_{12}$ to form a heteroaryl or heterocyclo;

$R_{10a}$ is alkyl, substituted alkyl, cycloalkyl, aryl, heteroaryl, or heterocyclo;

$R_{16}$ is selected from alkyl, alkenyl, aryl, heteroaryl, cycloalkyl, or heterocyclo, wherein each $R_{16}$ is optionally substituted with one to three $R_{18}$;

$R_{17}$ is hydrogen or alkyl;

$R_{18}$ is selected from $C_{1-6}$alkyl, substituted $C_{1-6}$alkyl, halogen, cyano, nitro, $OR_{20}$, $NR_2OR_{21}$, C(=O)$R_{20}$, $CO_2R_{20}$, C(=O)$NR_2OR_{21}$, C(=O)$NR_{20}SO_2R_{20a}$, $NR_{20}C(=O)R_{21}$, $NR_{20}C(=O)OR_{21}$, $SR_{20}$, $S(O)_uR_{20a}$, $NR_{20}SO_2R_{20a}$, $NHCH(alkyl)CO_2R_{20}$, NH—($CH_2$)$_{1-4}$—$CO_2R_{20}$, $SO_2NR_2OR_{21}$, $C_{3-7}$cycloalkyl, phenyl, four to seven membered heterocyclo, or five or six membered heteroaryl, said $C_{3-7}$cycloalkyl, phenyl, four to seven membered heterocyclo, or five or six membered heteroaryl groups in turn being optionally substituted with one to two $R_{22}$;

$R_{20}$ and $R_{21}$ are selected from hydrogen, alkyl, alkenyl, $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl; wherein each of $R_{20}$ and $R_{21}$ in turn is optionally substituted with one to two $R_{22}$;

$R_{20a}$ is selected from alkyl, alkenyl, $CO_2H$, $CO_2$(alkyl), $C_{3-7}$cycloalkyl, phenyl, benzyl, phenylethyl, napthyl, a four to seven membered heterocylo, or a five to six membered heteroaryl; wherein each $R_{20a}$ in turn is optionally substituted with one to two $R_{22}$;

$R_{22}$ is selected from the group consisting of $(C_{1-6})$alkyl, $(C_{2-6})$alkenyl, hydroxy, cyano, $CF_3$, $O(C_{1-6}$alkyl), $OCF_3$, $C(=O)H$, $C(=O)(C_{1-6}$alkyl), $CO_2H$, $CO_2(C_{1-6}$alkyl), $NHCO_2(C_{1-6}$alkyl), $-S(C_{1-6}$alkyl), $-NH_2$, $NH(C_{1-6}$alkyl), $N(C_{1-6}$alkyl)$_2$, $N(CH_3)_3{}^+$, $SO_2(C_{1-6}$alkyl), $C(=O)(C_{1-4}$alkylene)$NH_2$, $C(=O)(C_{1-4}$alkylene)$NH$(alkyl), and $C(=O)(C_{1-4}$alkylene)$N(C_{1-4}$alkyl)$_2$;

o and u are independently 1 or 2; and n is 0, 1 or 2.

14. A compound according to claim 13, or a pharmaceutically-acceptable salt, hydrate, prodrug, or enantiomer thereof, wherein $R_{4a}$ and $R_{4c}$ are chloro.

15. A compound according to claim 13, or a pharmaceutically-acceptable salt, hydrate, prodrug, or enantiomer thereof, wherein $R_{1a}$ is cyano or halogen.

16. A compound according to claim 15, having the formula,

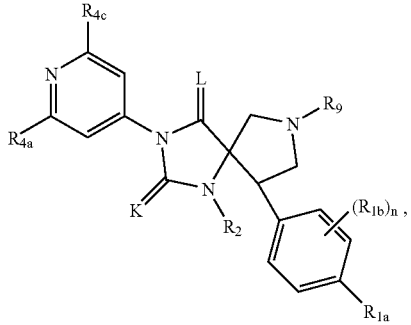

or a pharmaceutically-acceptable salt, hydrate, prodrug, or enantiomer thereof.

17. A compound according to claim 16, or a pharmaceutically-acceptable salt, hydrate, prodrug, or enantiomer thereof, in which:

$R_2$ is selected from hydrogen, $C_{1-6}$alkyl, and $C_{1-6}$alkyl substituted with amino, $NH(C_{1-4}$alkyl), $N$(alkyl)$_2$, $C(=O)H$, $C(=O)C_{1-4}$alkyl, $CO_2H$, $CO_2(C_{1-4}$alkyl), $SO_2C_{1-4}$alkyl, $SO_3H$, and/or $PO(OH)_2$;

$R_{4a}$ and $R_{4c}$ are selected from halogen, $C_{1-4}$alkyl, cyano, halo $C_{1-4}$alkyl, and halo$C_{1-4}$alkoxy;

$R_{9c}$ is $A_1-Q-A_2-R_{16}$;

$R_{16}$ is selected from (a) hydrogen and $C_{1-6}$alkyl or $C_{2-6}$alkenyl optionally substituted with one to two of OH, $O(C_{1-4}$alkyl), $-CO_2H$, $-CO_2(C_{1-4}$alkyl), $NH_2$, $-NH(C_{1-4}$alkyl), and/or $N(C_{1-4}$alkyl)$_2$, or from (b) furanyl, indolyl, carbazolyl, pyrazolyl, pyrrolyl, thienyl, pyridyl, pyrimidinyl, benzofuranyl, isoxazolyl, imidazolyl, triazolyl, tetrazolyl, phenyl, piperidyl, pyrrolidinyl, pyridazinyl, $C_{3-7}$cycloalkyl, piperazinyl, thiazolyl, morpholinyl, 1,2,5,6-tetrahydropyridyl, quinoxalinyl, benzothiazolyl, benzotriazolyl, benzodioxanyl, benzooxadiazolyl, thienopyrazolyl, tetrahydroquinolinyl, and quinolinyl, wherein each of said cyclic $R_{16}$ groups in turn is optionally substituted with up to three $R_{18}$;

$R_{17}$ is hydrogen or alkyl; and $R_{18}$ is selected from hydrogen, $(C_{1-6})$alkyl, $(C_{2-6})$alkenyl, $CO_2H$, $CO_2(C_{1-6}$alkyl), $C(=O)H$, $C(=O)(C_{1-6}$alkyl), halogen, cyano, hydroxy, $(C_{1-4})$alkoxy, $(C_{1-4})$haloalkyl, $(C_{1-4})$haloalkoxy, $NH_2$, $NH(C_{1-4}$alkyl), $N(C_{1-4}$alkyl)$_2$, $N(C_{1-4}$alkyl)$_3{}^+$, $-C(=O)(CH_2)NH_2$, $-NHCO_2(C_{1-4}$alkyl), $SO_2(C_{1-4}$alkyl), phenyl, $C_{3-7}$cycloalkyl, five to six membered heteroaryl, and four to seven membered heterocyclo, wherein each group $R_{18}$ in turn is optionally substituted with one to two of $(C_{1-4})$ alkyl, $(C_{2-4})$ alkenyl, $CO_2H$, $CO_2(C_{1-4}$alkyl), $C(=O)H$, $C(=O)(C_{1-4}$ alkyl), halogen, cyano, hydroxy, $(C_{1-4})$alkoxy, trifluoromethyl, trifluoromethoxy, $NH_2$, $NH(C_{1-4}$alkyl), $N(C_{1-4}$alkyl)$_2$, $N(C_{1-4}$alkyl)$_3{}^+$, $-C(=O)(CH_2)NH_2$, $-NHCO_2(C_{1-4}$alkyl), and/or $SO_2(C_{1-4}$alkyl).

18. A compound according to claim 17, having the formula,

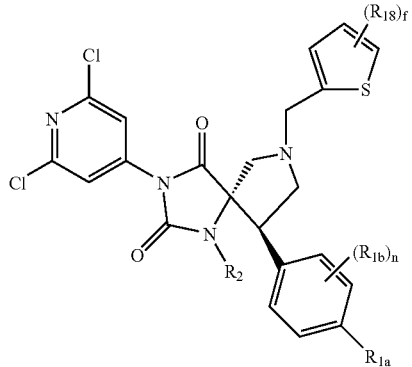

or a pharmaceutically-acceptable salt, hydrate, prodrug, or enantiomer thereof, in which:

$R_{1a}$ is cyano or halogen;

$R_{1b}$ is halogen, $C_{1-4}$alkyl, cyano, nitro, $-CO_2H$, $-C(=O)H$, $-CO_2$alkyl, or $-C(=O)$alkyl;

$R_2$ is hydrogen, $C_{1-6}$alkyl, or $C_{1-6}$alkyl substituted with $CO_2H$ or $CO_2(C_{1-4}$alkyl);

$R_{18}$ is selected from $(C_{1-4})$ alkyl, $CO_2H$, $CO_2(C_{1-4}$alkyl), $C(=O)H$, $C(=O)(C_{1-4}$alkyl), halogen, cyano, hydroxy, $(C_{1-4})$alkoxy, $(C_{1-4})$haloalkyl, $(C_{1-4})$haloalkoxy, $NH_2$, $NH(C_{1-4}$alkyl), $N(C_{1-4}$alkyl)$_2$, $N(C_{1-4}$alkyl)$_3{}^+$, $-C(=O)(CH_2)NH_2$, $-NHCO_2(C_{1-4}$alkyl), $-C(=O)NHSO_2(C_{1-4}$alkyl), $SO_2(C_{1-4}$alkyl), ), thienyl, tetrazolyl, triazolyl, pyrazolyl, and imidazolyl;

f is 0, 1, 2 or 3; and n is 0 or 1.

19. A compound according to claim 17, having the formula,

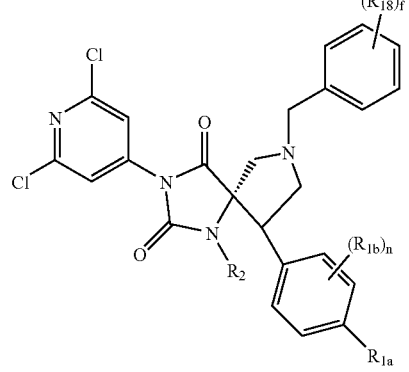

or a pharmaceutically-acceptable salt, hydrate, prodrug, or enantiomer thereof, in which:

$R_{1a}$ is halogen, cyano, nitro, trifluoromethyl, $OCF_3$, aryl or heteroaryl;

$R_{1b}$ is halogen, $C_{1-4}$alkyl, cyano, nitro, —$CO_2H$, —C(=O)H, —$CO_2$alkyl, or —C(=O)alkyl;

$R_2$ is hydrogen, $C_{1-6}$alkyl, or $C_{1-6}$alkyl substituted with $CO_2H$ or $CO_2(C_{1-4}$alkyl);

$R_{18}$ is selected from $(C_{1-4})$ alkyl, $CO_2H$, $CO_2(C_{1-4}$alkyl), C(=O)H, C(=O)($C_{1-4}$alkyl), halogen, cyano, hydroxy, $(C_{1-4})$alkoxy, $(C_{1-4})$haloalkyl, $(C_{1-4})$haloalkoxy, $NH_2$, $NH(C_{1-4}$alkyl), $N(C_{1-4}$alkyl$)_2$, $N(C_{1-4}$alkyl$)_3^+$, —C(=O)($CH_2$)$NH_2$, —$NHCO_2(C_{1-4}$alkyl), —C(=O)$NHSO_2(C_{1-4}$alkyl), $SO_2(C_{1-4}$alkyl), thienyl, tetrazolyl, triazolyl, pyrazolyl, and imidazolyl;

f is 0, 1, 2 or 3; and n is 0 or 1.

20. A pharmaceutical composition comprising at least one compound according to claim 1 and a pharmaceutically acceptable carrier or diluent.

21. A pharmaceutical composition comprising at least one compound according to claim 13 and a pharmaceutically acceptable carrier or diluent.

22. A compound according to claim 7, or a pharmaceutically-acceptable salt, hydrate, salt, hydrate, prodrug, or enantiomer thereof, wherein $R_9$ is selected from:

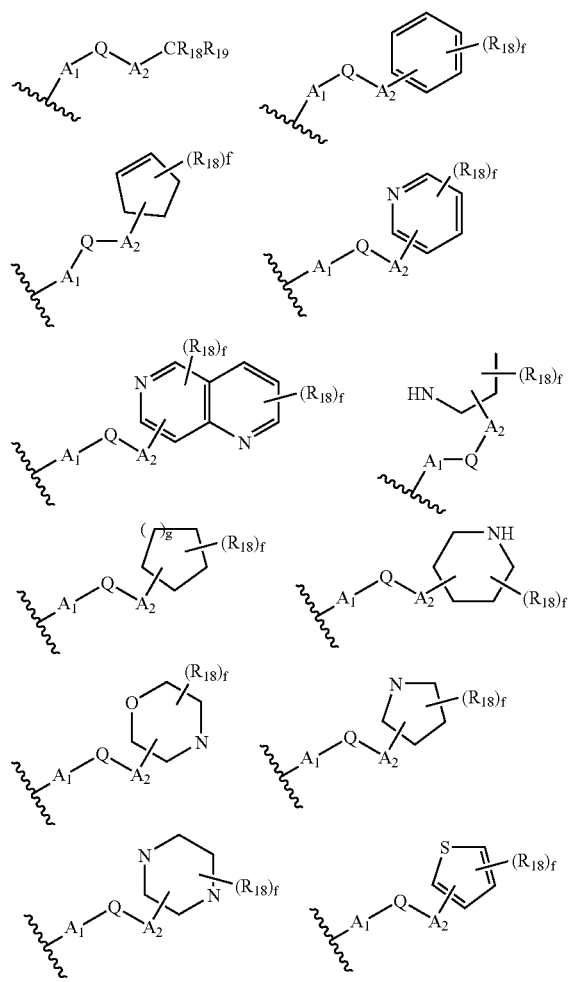

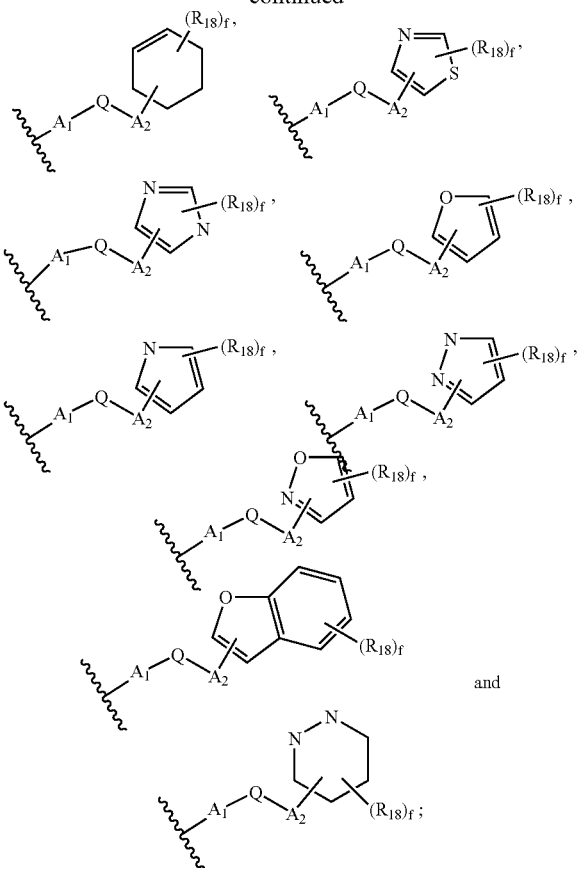

$A_1$ is a bond, $C_{1-2}$alkylene, or $C_{2-3}$alkenylene;

Q is a bond, —C(=O)—, —C(=O)$NR_{17}$—, —$SO_2$—, —$CO_2$—, or —$NR_{17}CO_2$—;

$A_2$ is a bond, $C_3$alkylene, $C_{2-3}$alkenylene, —$C_{1-4}$alkylene-$NR_{17}$—, —$C_{1-4}$alkylene-$NR_{17}C$(=O)—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted with a group selected from —$CO_2H$, —$CO_2(C_{1-4}$alkyl), —S($C_{1-4}$alkyl), $NH_2$, —$NH(C_{1-4}$alkyl), or —$N(C_{1-4}$alkyl$)_2$;

$R_{17}$ is hydrogen or alkyl;

$R_{18}$ and $R_{19}$ are selected from hydrogen, $(C_{1-6})$ alkyl, $(C_{2-6})$ alkenyl, $CO_2H$, $CO_2(C_{1-6}$alkyl), C(=O)H, C(=O)($C_{1-6}$alkyl), halogen, cyano, hydroxy, $(C_{1-4})$alkoxy, $(C_{1-4})$haloalkyl, $(C_{1-4})$haloalkoxy, $NH_2$, $NH(C_{1-4}$alkyl), $N(C_{1-4}$alkyl$)_2$, $N(C_4$alkyl$)_3^+$, —C(=O)($CH_2$)$NH_2$, —$NHCO_2(C_{1-4}$alkyl), —C(=O)$NHSO_2$($C_{1-4}$alkyl), $SO_2(C_{1-4}$alkyl), phenyl, $C_{3-7}$cycloalkyl, five to six membered heteroaryl, and four to seven membered heterocyclo, wherein each group $R_{18}$ and $R_{19}$ in turn is optionally substituted with one to two of $(C_{1-4})$ alkyl, $(C_{2-4})$ alkenyl, $CO_2H$, $CO_2(C_{1-4}$alkyl), C(=O)H, C(=O)($C_{1-4}$alkyl), halogen, cyano, hydroxy, $(C_{1-4})$alkoxy, trifluoromethyl, trifluoromethoxy, $NH_2$, $NH(C_{1-4}$alkyl), $N(C_{1-4}$alkyl$)_2$, $N(C_{1-4}$alkyl$)_3^+$, —C(=O)($CH_2$)$NH_2$, —$NHCO_2(C_{1-4}$alkyl), and/or $SO_2(C_{1-4}$alkyl);

f is 0, 1, 2 or 3; and g is −1, 0, 1, or 2.

* * * * *

UNITED STATES PATENT AND TRADEMARK OFFICE
CERTIFICATE OF CORRECTION

PATENT NO. : 7,078,420 B2
APPLICATION NO. : 10/852576
DATED : July 18, 2006
INVENTOR(S) : T. G. Murali Dhar et al.

It is certified that error appears in the above-identified patent and that said Letters Patent is hereby corrected as shown below:

In the Claims:

Claim 1:
   Column 220, line 18, after "-$C_{1-4}$alkylene-$SO_2$-", insert -- or --.

Claim 3:
   Column 220, line 61, change "$NR_2OR_{21}$" to -- $NR_{20}R_{21}$ --.
   Column 220, line 64, change "$SO_2NR_2OR_{21}$" to -- $SO_2NR_{20}R_{21}$ --.

Claim 7:
   Column 222, line 24, change "-$C(=O)NH(CH_2)_{14}CO_2(alkyl)$" to
-- -$C(=O)NH(CH_2)_{1-4}CO_2(alkyl)$ --.

Claim 8:
   Column 222, lines 47 to 48, change "-$(CH_2)_nC_{3-6}$cycloalkyl" to -- -$(CH_2)_sC_{3-6}$cycloalkyl --.
   Column 223, line 18, change "-$(CH_2)_tC(=O)N(C_4alkyl)(thiazolyl)$" to
-- -$(CH_2)_tC(=O)N(C_{1-4}alkyl)(thiazolyl)$ --.

In the Claims:

Claim 9:
   Column 224, lines 42 to 47, change

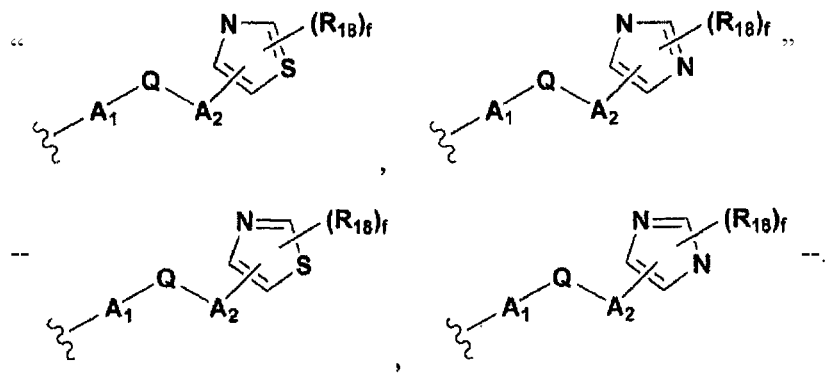

to

CERTIFICATE OF CORRECTION (continued)  Page 2 of 4
U.S. Pat. No. 7,078,420 B2

In the Claims:

Claim 10:
  Column 225, line 60, after "one of:", insert -- H, --.
  Column 228, lines 53 to 59, change

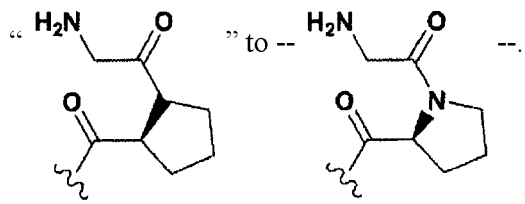

Column 236, lines 48 to 53, change

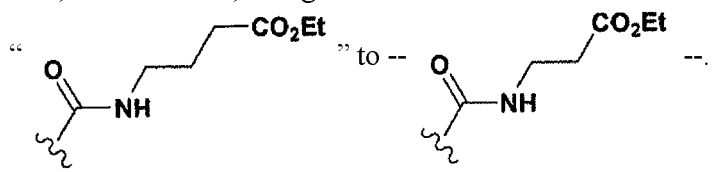

Column 236, lines 54 to 59, change

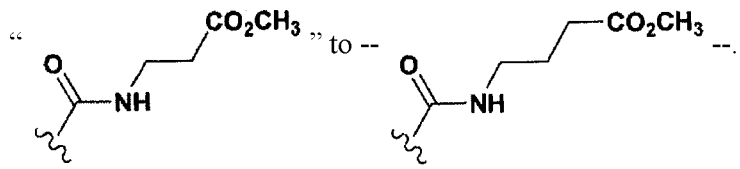

Claim 12:
  Column 239, lines 37 to 48, change

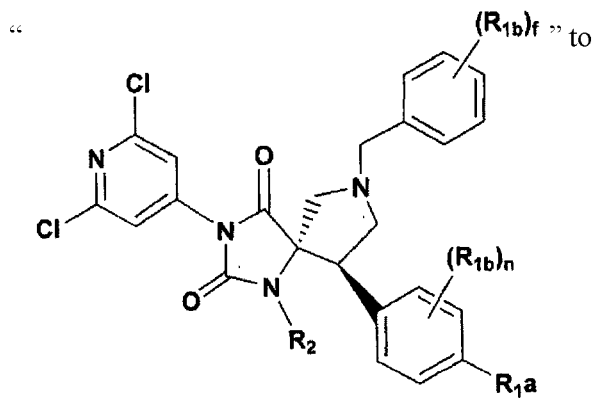

CERTIFICATE OF CORRECTION (continued)
U.S. Pat. No. 7,078,420 B2

In the Claims:

Claim 12 (continued):

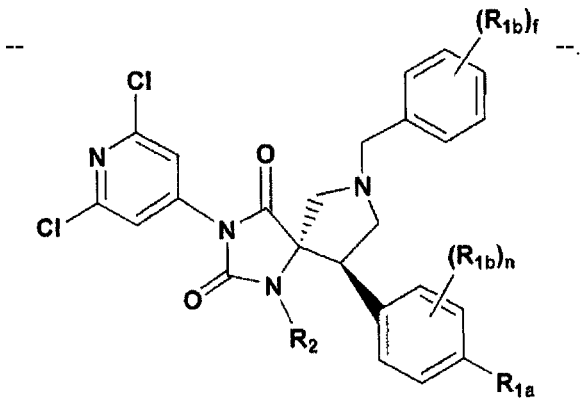

Column 239, line 61, change "(C$_4$)alkoxy" to -- (C$_{1-4}$)alkoxy --.

Claim 13:
Column 240, line 19, change "R$_1$ b" to -- R$_{1b}$ --.
Column 240, line 21, change "R, $_1$," to -- R$_{11}$ --.
Column 240, line 56, change "NR$_2$OR$_{21}$" to -- NR$_{20}$R$_{21}$ --.
Column 240, line 57, change "C(=O)NR$_2$OR$_{21}$" to -- C(=O)NR$_{20}$R$_{21}$ --.
Column 240, line 60, change "SO$_2$NR$_2$OR$_{21}$" to -- SO$_2$NR$_{20}$R$_{21}$ --.

Claim 16:
Column 241, line 29, change "15" to --13 --.

Claim 17:
Column 241, line 56, change "R$_{9c}$" to -- R$_9$ --.

Claim 22:
Column 243, lines 43 to 48, change

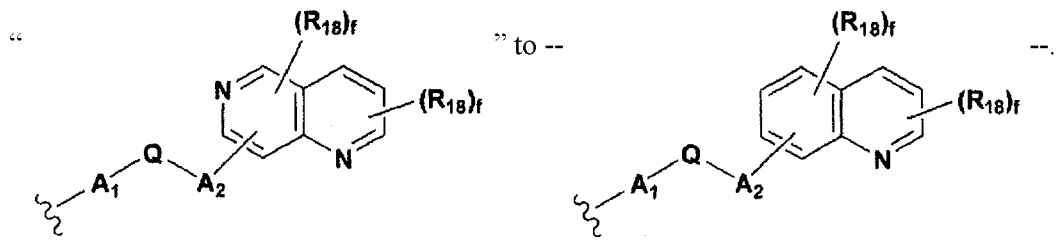

CERTIFICATE OF CORRECTION (continued)
U.S. Pat. No. 7,078,420 B2

In the Claims:

Claim 22 (continued):
Column 244, lines 15 to 24, change

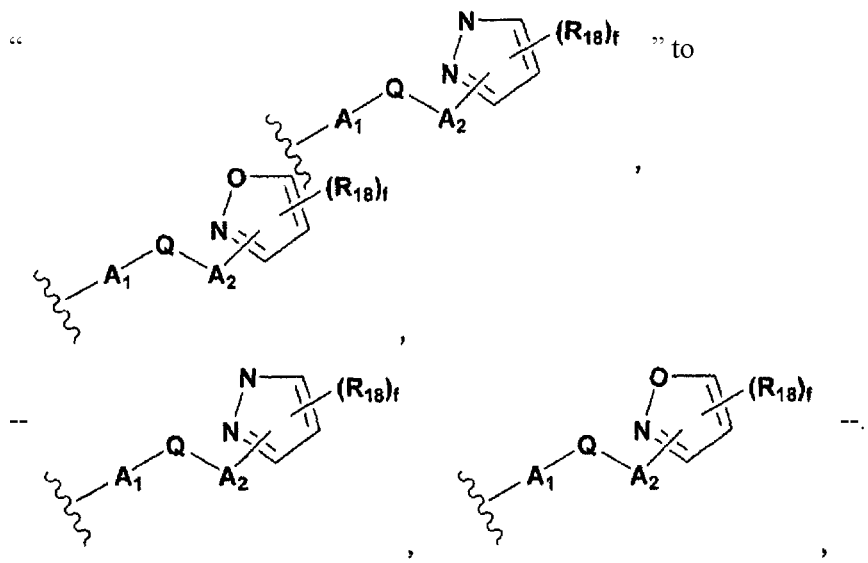

Column 244, line 40, change "C$_3$alkylene" to -- C$_{1-3}$alkylene --.
Column 244, line 53, change "N(C$_4$alkyl)$_3^+$" to -- N(C$_{1-4}$alkyl)$_3^+$ --.

Signed and Sealed this

Ninth Day of February, 2010

David J. Kappos
*Director of the United States Patent and Trademark Office*